US009845464B2

United States Patent
Zha et al.

(10) Patent No.: US 9,845,464 B2
(45) Date of Patent: Dec. 19, 2017

(54) SURFACE DISPLAY OF RECOMBINANT PROTEINS IN LOWER EUKARYOTES

(71) Applicant: GLYCOFI, INC., Lebanon, NH (US)

(72) Inventors: Dongxing Zha, Etna, NH (US); Stefan Wildt, New York, NY (US)

(73) Assignee: GlycoFi, Inc., Lebanon, NH (US)

( * ) Notice: Subject to any disclaimer, the term of this patent is extended or adjusted under 35 U.S.C. 154(b) by 248 days.

(21) Appl. No.: 14/517,223

(22) Filed: Oct. 17, 2014

(65) Prior Publication Data

US 2015/0211000 A1    Jul. 30, 2015

Related U.S. Application Data

(62) Division of application No. 12/863,911, filed as application No. PCT/US2009/034631 on Feb. 20, 2009, now Pat. No. 8,877,686.

(60) Provisional application No. 61/067,965, filed on Mar. 3, 2008.

(51) Int. Cl.

| | |
|---|---|
| C40B 40/08 | (2006.01) |
| C12N 15/10 | (2006.01) |
| C07K 16/00 | (2006.01) |
| C07K 16/28 | (2006.01) |
| C07K 16/32 | (2006.01) |
| C07K 16/40 | (2006.01) |
| C40B 40/02 | (2006.01) |
| C40B 50/06 | (2006.01) |

(52) U.S. Cl.
CPC ........ *C12N 15/1037* (2013.01); *C07K 16/005* (2013.01); *C07K 16/2887* (2013.01); *C07K 16/32* (2013.01); *C07K 16/40* (2013.01); *C12N 15/1055* (2013.01); *C40B 40/02* (2013.01); *C40B 50/06* (2013.01); *C07K 2317/51* (2013.01); *C07K 2317/55* (2013.01); *C40B 40/08* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 4,888,281 | A | 12/1989 | Schochetman et al. |
| 5,037,750 | A | 8/1991 | Schochetman et al. |

(Continued)

FOREIGN PATENT DOCUMENTS

| | | |
|---|---|---|
| EP | 1 743 938 | 1/2007 |
| JP | 2007130520 A | 5/2007 |

(Continued)

OTHER PUBLICATIONS

Bidlingmaier, et al., Molecular & Cellular Proteomics, 2006, pp. 533-540, vol. 5, No. 3.

(Continued)

*Primary Examiner* — Christian Boesen
(74) *Attorney, Agent, or Firm* — John David Reilly; Gloria Fuentes

(57) ABSTRACT

Methods for display of recombinant proteins or protein libraries on the surface of lower eukaryotes such as yeast and filamentous fungi are described. The methods are useful for screening libraries of recombinant proteins in lower eukaryotes to identify particular proteins with desired properties from the array of proteins in the libraries. The methods are particularly useful for constructing and screening antibody libraries in lower eukaryotes.

13 Claims, 33 Drawing Sheets

Plasmid map of cell wall anchor protein–coiled coil peptide–*Pichia pastoris* signal sequence fusion.

(56) References Cited

U.S. PATENT DOCUMENTS

| | | | |
|---|---|---|---|
| 5,700,678 | A | 12/1997 | Toyoshima et al. |
| 5,714,377 | A | 2/1998 | Tanner et al. |
| 5,733,757 | A | 3/1998 | Barbas, III et al. |
| 5,843,708 | A | 12/1998 | Hardman et al. |
| 5,874,247 | A | 2/1999 | Toyoshima et al. |
| 5,985,626 | A | 11/1999 | Barbas, III et al. |
| 6,114,147 | A | 9/2000 | Frenken et al. |
| 6,180,370 | B1 | 1/2001 | Queen et al. |
| 6,300,065 | B1 | 10/2001 | Kieke et al. |
| 6,368,839 | B1 | 4/2002 | Barbas, III et al. |
| 6,423,538 | B1 | 7/2002 | Wittrup et al. |
| 6,632,927 | B2 | 10/2003 | Adair et al. |
| 6,699,658 | B1 | 3/2004 | Wittrup et al. |
| 6,872,392 | B2 | 3/2005 | Nakamura et al. |
| 6,919,183 | B2 | 7/2005 | Fandl et al. |
| 6,949,372 | B2 | 9/2005 | Betenbaugh et al. |
| 7,029,872 | B2 | 4/2006 | Gerngross |
| 7,105,554 | B2 | 9/2006 | Orchard et al. |
| 7,117,096 | B2 | 10/2006 | Luo et al. |
| 7,132,273 | B1 | 11/2006 | Choi et al. |
| 7,166,423 | B1 | 1/2007 | Miltenyi et al. |
| 7,175,983 | B2 | 2/2007 | Wang et al. |
| 7,198,921 | B2 | 4/2007 | Miura et al. |
| 7,205,136 | B1 | 4/2007 | Schochetman et al. |
| 7,259,007 | B2 | 8/2007 | Bobrowicz et al. |
| 2002/0068325 | A1 | 6/2002 | Ng et al. |
| 2003/0104355 | A1 | 6/2003 | Wang et al. |
| 2003/0186374 | A1 | 10/2003 | Hufton et al. |
| 2004/0018590 | A1 | 1/2004 | Gerngross et al. |
| 2004/0074458 | A1 | 4/2004 | Nakamura et al. |
| 2004/0219611 | A1 | 11/2004 | Racher |
| 2004/0230042 | A1 | 11/2004 | Hamilton |
| 2005/0142562 | A1 | 6/2005 | Zhu et al. |
| 2005/0170452 | A1 | 8/2005 | Wildt et al. |
| 2005/0196406 | A1 | 9/2005 | Daugherty et al. |
| 2005/0216958 | A1 | 9/2005 | Yamane et al. |
| 2005/0260729 | A1 | 11/2005 | Hamilton |
| 2006/0040353 | A1 | 2/2006 | Davidson et al. |
| 2006/0211085 | A1 | 9/2006 | Bobrowicz |
| 2007/0020260 | A1 | 1/2007 | Presta |
| 2007/0037248 | A1 | 2/2007 | Bobrowicz et al. |
| 2007/0072262 | A1 | 3/2007 | Nett et al. |
| 2008/0032399 | A1 | 2/2008 | Harney et al. |
| 2009/0163379 | A1 | 6/2009 | Wang et al. |

FOREIGN PATENT DOCUMENTS

| | | |
|---|---|---|
| WO | 03012069 A2 | 2/2003 |
| WO | 2004/057002 | 7/2004 |
| WO | 2007/061631 | 5/2007 |
| WO | 2007130520 A2 | 11/2007 |
| WO | 2008/006554 | 1/2008 |
| WO | 2009/105357 | 8/2009 |

OTHER PUBLICATIONS

Bidlingmaier, et al., Molecular & Cellular Proteomics, 2007, pp. 2012-2020, vol. 6, No. 11.

Boder, E. et al. "Yeast surface display for screening combinatorial polypeptide libraries", Nature Biotechnology, vol. 15, pp. 553-557, Jun. 1997.

Holler, "In vitro evolution of a T cell receptor . . . ", PNAS (2000), vol. 97, pp. 5387-5392.

Heyman, "Feedback regulaton by IgG antibodies", Immunol. Letters (2003). vol. 88, pp. 157-161.

Hamilton, "Humanization of yeast to produce complex terminally . . . ", Science (2006), vol. 313, pp. 1441-1443.

Hamilton, "Production of complex human glycoproteins . . . ", Science (2003), vol. 301, pp. 1244-1246.

Jacobs, "Pichia surface display: Display of proteins on the surface . . . ", Pichia Protein Expression Conference (2006), San Diego, CA, Abstract T23, pp. 1-9 and 37.

Huo, "Co-expression of human protein disulfide isomerase . . . ", Protein Exp. and Purif. (2007), vol. 54, pp. 234-239.

Inan, "Enhancement of protein secretion in Pichia pastoris . . . ", Biotech. and Bioeng. (2006). vol. 93, pp. 771-778.

Jabet, "NMR studies of the Pbx1 TALE homeodomain protein . . . ", J. Mol. Biol. (1999), vol. 291, pp. 521-530.

Jacobs, "Pichia surface display: Display of proteins on the surface . . . ", Biotech. Letters (2008), vol. 30, pp. 2173-2181.

Jordan, "G-protein-coupled receptor heterodimerization . . . ", Nature (1999), vol. 399, pp. 697-700.

Kammerer, "Heterodimerization of a functional GABA . . . ", Biochemistry (1999), vol. 38, pp. 13263-13269.

Kanda, "Comparison of biological activity among nonfucosylated . . . ", Glycobiology (2006), vol. 17, pp. 104-118.

Kanda, "Comparison of cell lines for stable production . . . ", Biotech. and Bioeng. (2006), vol. 94, pp. 680-688.

Keizer-Gunnink, "Accumulation of properly folded human type III . . . ", Matrix Biology (2000), vol. 19, pp. 29-36.

Kennard, "GPI-anchored fusion proteins", Methods in Biotech. (1999), vol. 8, pp. 187-200.

Kohler, "Continuous cultures of fused cells . . . ", Nature (1975), vol. 256, pp. 495-497.

Kuner, "Role of heteromer formation in GABA . . . ", Science (1999), vol. 283, pp. 74-77.

Ladner, "Constrained peptides as binding entities", Trends in Biotech. (1995), vol. 13, pp. 426-430.

Li, "Optimization of humanized IgGs in glycoengineered . . . ", Nature Biotech. (2006), vol. 24, pp. 210-215.

Lowman, "Selecting high-affinity binding proteins by monovalent . . . ", Biochemistry (1991), vol. 30, pp. 10832-10838.

Maras, "Filamentous fungi as production organisms . . . ", Glycoconjugate Journal (1999), vol. 16, pp. 99-107.

Markland, "Selection for protease inhibitors using bacteriophage . . . ", Methods in Enzymology (1996), vol. 267, pp. 28-51.

Marks, "Human antibodies from V-gene libraries . . . ", J. Mol. Biol. (1991), vol. 222, pp. 581-597.

Matthews, "Substrate phage: Selection of protease subtrates . . . ", Science (1993), vol. 260, pp. 1113-1117.

Mille, "Identification of a new family of genes involved in . . . ", J. Biol, Chem. (2008), vol. 283, pp. 9724-9736.

Nakabeppu, "DNA binding activities of three murine Jun proteins: . . . ", Cell (1988), vol. 55, pp. 907-915.

Nett, "Cloning and disruption of the PpURA5 gene and construction . . . ", Yeast (2003), vol. 20, pp. 1279-1290.

Nett, "Cloning and disruption of the Pichia pastoris ARG1 . . . ", Yeast (2005), vol. 22, pp. 295-304.

Phizicky, "Protein-protein interactions: Methods for detection . . . ", Microbiol. Rev. (1995), vol. 59, pp. 94-123.

Piper, "Structure of a HoxB1-Pbx1 heterodimer bound to DNA: . . . ", Cell (1999), vol. 96, pp. 587-597.

Rehberg, "Specific molecular activities of recombinant . . . ", J. Biol. Chem. (1982), vol. 257, pp. 11497-11502.

Ravetch, "Fc receptors", Curr. Opin. Immunol. (1997), vol. 9, pp. 121-125.

Riechmann, "Phage display and selection of a site-directed randomized . . . ", Biochemistry (1993), vol. 32, pp. 8848-8855.

Ren, "Display of adenoregulin with a novel Pichia pastoris . . . ", Molecular Biotech. (2007), vol. 35, pp. 103-108.

Roberts, "The biochemistry and genetics of capsular polysaccharide . . . ", Ann. Rev. Microbiol. (1996), vol. 50, pp. 285-315.

Sblattero, "Exploiting recombination in single bacteria . . . ", Nature Biotech. (2000), vol. 18, pp. 75-80.

Smeal, "Different requirements for formation of Jun: . . . ", Genes and Develop. (1989) vol. 3, pp. 2091-2100.

Slugg, "Baclofen Inhibits guinea pig magnocellular neurones . . . ", J. Physiol. (2003), vol. 551.1, pp. 295-308.

Waterhouse, "Combinatorial infection and in vivo recombination: . . . ", Nucleic Acid Res., (1993), vol. 21, pp. 2265-2266.

Ryckaert, "Fishing for lectins for diverse sequence libraries: . . . ", Abstracts BVBMB Meeting (2005), 191st meeting of the Belgian Society of Biochemistry and Molecular Biology, Brussels, Belgium.

Abel, "Action of leucine zippers," Nature (1989), vol. 341, pp. 24-25.

(56) References Cited

OTHER PUBLICATIONS

Belshaw, "Controlling protein association and subcellular localization . . . ", PNAS (1996), vol. 93, pp. 4604-4607.
Berens, "Gene regulation by tetracylines", Eur. J. Biochem. (2003), vol. 270, pp. 3109-3121.
Bobrowicz, "Isolation of three contiguous genes . . . ", Yeast (1997), vol. 13, pp. 819-828.
Bobrowicz, "Engineering of an artificial glycosylation pathway . . . ", Glycobiology (2004), vol. 14, pp. 757-766.
Boder, "Directed evolution of antibody fragments with monovalent . . . ", PNAS (2000), vol. 97, pp. 10701-10705.
Frank, "A distinct seven-residue trigger sequence . . . ", J. Biol. Chem. (2000), vol. 275, pp. 11672-11677.
Caldas, "Design and synthesis of germline-based hemi-humanized . . . ", Protein Engineering (2000), vol. 13, pp. 353-360.
Songyang, "SH2 domains recognize specific phosphopeptide sequences", Cell (1993), vol. 72, pp. 767-778.
Chiba, "Production of human compatible high mannose-type . . . ", J. Biol. Chem. (1998), vol. 273, pp. 26298-26304.
Choi, "Use of combinatorial genetic libraries to humanize . . . ", PNAS (2003), vol. 100, pp. 5022-5027.
Choo, "Designing DNA-binding proteins on the surface . . . ", Curr. Opin. in Biotech. (1995), vol. 6, pp. 431-436.
Cohen, "The product of a fos-related gene, fra-1, binds cooperatively . . . ". Genes & Develop. (1989), vol. 3, pp. 173-184.
Cox, "Phagocytic signaling strategies: . . . ", Immunology (2001), vol. 13, pp. 339-345.
Daeron, "Fc receptor biology", Ann. Rev. Immunol. (1997), vol. 15, pp. 203-234.
Damasceno, "Cooverexpression of chaperones for enhanced secretion . . . ", Appl. Microbiol. Biotechnol. (2007), vol. 74, pp. 381-389.
Mergler, "Development of a bisphenol A-adsorbing yeast by surface display . . . ", Appl. Microbiol. Biotechnol. (2004), vol. 63, pp. 418-421.
Daugherty, "Quantitative analysis of the effect of the mutation . . . ", PNAS (2000), vol. 97, pp. 2029-2034.
De Groot, "Genome-wide identification of fungal GPI proteins", Yeast (2003), vol. 20, pp. 781-796.
DiRienzo, "The outer membrane proteins of gram-negative bacteria: . . . ", Ann. Rev. Biochem. (1978). vol. 47, pp. 481-532.
Ellman, "Combinatorial thinking in chemistry and biology", PNAS (1997), vol. 94, pp. 2779-2782.
Francisco, "Production and fluorescence-activated cell sorting . . . ", PNAS (1993), vol. 90, pp, 10444-10448.
Gentz, "Parallel association of Fos and Jun leucine zippers . . . ", Science (1989), vol. 243, pp. 1695-1699.
Geoffroy, "A new phage display system to construct multicombinatorial . . . ", Gene (1994), vol. 15, pp. 109-113.
Georgiou, "Display of heterologous proteins on the surface . . . ", Nature Biotech. (1997), vol. 15, pp. 29-34.
Gomes, "Heterodimerization of mu and beta opioid receptors: . . . ", J. of Neuroscience (2000), vol. 20, pp. 1-5.

Hoogenboom, "Designing and optimizing library selection strategies . . . ", Trends in Biotech. (1997), vol. 15, pp. 62-70.
Songyang, "A single point mutation switches the specificity . . . ", J. Biol. Chem, (1995), vol. 270, pp. 26029-26032.
Stemmer, "Rapid evolution of a protein in vitro by DNA shuffling", Nature (1994), vol. 370, pp. 389-391.
Stemmer, "DNA shuffling by random fragmentation and reassembly: . . . ", PNAS (1994), vol. 91, 10747-10751.
Streuli, "Target cell specificity of two species of human interferon-alpha . . . ", PNAS (1981), vol. 78, pp. 2848-2852.
Swers, "Shuffled antibody libraries created by in vivo homologous . . . ", Nucleic Acid Res. (2004), vol. 32, pp. 1-8.
Tanino, "Construction of a Pichia pastoris cell-surface display . . . ", Biotechnol. Prog. (2006), vol. 22, pp. 989-993.
Toman, "Production of recombinant human Type I procollagen . . . ", J. Biol. Chem. (2000), vol. 275, pp. 23303-23309.
Ulrich, "Expression studies of catalytic antibodies", PNAS (1995), vol. 92, pp. 11907-11911.
Vad, "Engineering of a Pichia pastoris expression system for secretion . . . ", J. of Biotech. (2005), vol. 116, pp. 251-260.
Walker, "Effect of redox environment on the in vitro and in vivo . . . ", J. Biol. Chem, (1994), vol. 269, pp. 28487-28493.
Wang, "Phage display of proteases and macromolecular inhibitors", Methods in Enzymology (1996), vol. 267, pp. 52-68.
Wang, "A new yeast display vector permitting free scFv amino . . . ", Protein Engineering, Design & Selection (2005), vol. 18, pp. 337-343.
White, "Heterodlmerization is required for the formation . . . ", Nature (1998), vol. 396, pp. 679-682.
Wildt, "The humanization of N-glycosylation pathways in yeast", Nature Rev. (2005), p. 119-128.
Wolf, MultiCoil: A program for predicting two- and three-stranded coiled coils, Protein Science (1997), vol. 6, pp. 1179-1189.
Wysocki, "The *Saccharomyces cerevisiae* ACR3 gene encodes . . . ", J. Biol. Chem. (1997), vol. 272, pp. 30061-30066.
Yamane-Ohnuki, "Establishment of FUT8 knockout Chinese hamster . . . ", Biotech. and Bioeng. (2004), vol. 87, pp. 614-622.
Zhang, "Enhanced secretion of heterologous proteins in Pichia pastoris . . . ", Biotech. Prog. (2006), vol. 22, pp. 1090-1095.
Ward, "The effector functions of immunoglobulins: . . . ", Therapeutic Immunol. (1995), vol. 2, p. 77-94.
Knappik, "Engineered turns of a recombinant antibody . . . ", Protein Engineering (1995), vol. 8, pp. 81-89.
Weaver-Feldhaus JM, Miller KD, Feldhaus MJ, Siegel RW. Directed evolution for the development of conformation-specific affinity reagents using yeast display.Protein Eng Des Sel. Nov. 2005;18(11):527-36. Epub Sep. 26, 2005.
Van der Vaart JM, te Biesebeke R, Chapman JW, Toschka HY, Klis FM, Verrips CT. Comparison of cell wall proteins of *Saccharomyces cerevisiae* as anchors for cell surface expression of heterologous proteins. Appl Environ Microbiol. Feb. 1997;63(2):615-20.
Feldhaus, et al., Flow-cytometric isolation of human antibodies from a nonimmune Saccharomyces cerevisiae surface display library, Nature Biotechnology, Feb. 2003, 163-170, v. 21.

A yeast cell expresses a potential cell wall anchor-coiled coil peptide fusion protein dimerized with a gene of interest-coiled coil peptide fusion and locked by an artificial disulfide bond.

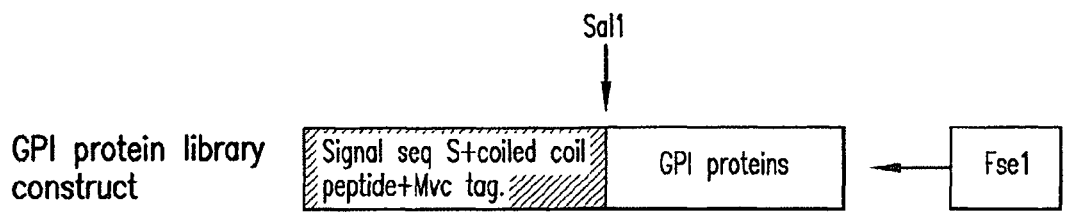

GPI anchoring protein expression constructs.

FIG.2A (SEQ ID NO:20)

MVAWWSLFLYGLQVAAPALATSRLEGLQSENHRLRMKITELDKDLEEVTM
QLQDVGGC*EQKLISEEDL*VDQFSNSTSASSTDVTSSSSISTSSGSVTITSSEAPES
DNGTSTAAPTETSTEAPTTAIPTNGTSTEAPTTAIPTNGTSTEAPTDTTTEAPTTA
LPTNGTSTEAPTDTTTEAPTTGLPTNGTTSAFPPTTSLPPSNTTTTPPYNPSTDYT
TDYTVVTEYTTYCPEPTTFTTNGKTYTVTEPTTLTITDCPCTIEKPTTTSTTEYTV
VTEYTTYCPEPTTFTTNGKTYTVTEPTTLTITDCPCTIEKSEAPESSVPVTESKGT
TTKETGVTTKOTTQTTANPSLTVSTVVPVSSSASSHSVVINSNGANVVPGALGLAG
VAMLFL

FIG.2B

Plasmid map of cell wall anchor protein–coiled coil peptide–*Pichia pastoris* signal sequence fusion.

Monoclonal antibody or antibody fragment fused to coiled coil peptide GR1 for displaying the antibody fragment on the host glycoengineered yeast.

Map of Fab display plasmid. The heavy chain fused with GR1 and the light chains are under the control of the AOX1 promoter and both chains contain alpha amylase signal sequence. The plasmid uses Zeocin selection marker. The constructs were integrated by a single crossover event at the *Pichia pastoris* Trp2 site.

Whole antibody display plasmid. Full-length heavy chain is fused to GR1 and HA tags (explain what these are) under control of the AOX1 promoter and alpha MF-pre signal sequence. The light chain was expressed in separate cassette under control of the AOX1 promoter and alpha MF pre signal sequence.

Schematic diagram of detection of the displayed antibody or antibody fragment by goat anti-human H+L IgGs Alexa 488 or fluorophor conjugated antigen.

YGLY4102/pGLY3015
ScCWP2

YGLY4102/pGLY3033
ScSED1

YGLY4102/pGLY3034
ScSED1 Truncation

YGLY4102/pGLY3035
PpSPI1

YGLY4102/pGLY3036
PpGAS1

YGLY4102/pGLY3037
ScGAS1

YGLY4102/pGLY3038
ScGAS1 Truncation

YGLY4102/pGLY3039
HpTIP

YGLY4102/pGLY3040
HpTIP Truncation

YGLY4102
Control

YGLY5149 (YGLY5079/pGLY3916)
15 second exposure

YGLY5152 (YGLY5079/pGLY3917)
15 second exposure

YGLY6693 (YGLY5079/pGLY3918)
30 second exposure

YGLY6694 (YGLY5079/pGLY3919)
30 second exposure

SEQUENCE LISTING

<160> NUMBER OF SEQ ID NOS: 74

<210> SEQ ID NO 1
<211> LENGTH: 29
<212> TYPE: PRT
<213> ORGANISM: Artificial Sequence
<220> FEATURE:
<223> OTHER INFORMATION: c-fos zipper

<400> SEQUENCE: 1

Leu Gln Ala Glu Thr Asp Gln Leu Glu Asp Glu Lys Ser Ala Leu Gln
1               5                   10                  15

Thr Glu Ile Ala Asn Leu Leu Lys Glu Lys Glu Lys Leu
            20                  25

<210> SEQ ID NO 2
<211> LENGTH: 29
<212> TYPE: PRT
<213> ORGANISM: Artificial Sequence
<220> FEATURE:
<223> OTHER INFORMATION: c-jun zipper

<400> SEQUENCE: 2

Leu Glu Glu Lys Val Lys Thr Leu Lys Ala Gln Asn Ser Glu Leu Ala
1               5                   10                  15

Ser Thr Ala Asn Met Leu Arg Glu Gln Val Ala Gln Leu
            20                  25

<210> SEQ ID NO 3
<211> LENGTH: 38
<212> TYPE: PRT
<213> ORGANISM: Artificial Sequence
<220> FEATURE:
<223> OTHER INFORMATION: c-fos zipper

<400> SEQUENCE: 3

Leu Thr Asp Thr Leu Gln Ala Glu Thr Asp Gln Leu Glu Asp Glu Lys
1               5                   10                  15

Ser Ala Leu Gln Thr Glu Ile Ala Asn Leu Leu Lys Glu Lys Glu Lys
            20                  25                  30

Leu Glu Phe Ile Leu Ala
        35

<210> SEQ ID NO 4
<211> LENGTH: 39
<212> TYPE: PRT
<213> ORGANISM: Artificial Sequence
<220> FEATURE:
<223> OTHER INFORMATION: c-jun zipper

<400> SEQUENCE: 4

Arg Ile Ala Arg Leu Glu Glu Lys Val Lys Thr Leu Lys Ala Gln Asn
1               5                   10                  15

Ser Glu Leu Ala Ser Thr Ala Asn Met Leu Arg Glu Gln Val Ala Gln
            20                  25                  30

Leu Lys Gln Lys Val Met Asn
        35

<210> SEQ ID NO 5
<211> LENGTH: 29
<212> TYPE: PRT
<213> ORGANISM: Artificial Sequence
<220> FEATURE:
<223> OTHER INFORMATION: c-jun zipper -continued

```
<400> SEQUENCE: 5

Leu Glu Glu Lys Val Lys Thr Leu Lys Ala Gln Asn Ser Glu Leu Ala
1               5                   10                  15

Ser Thr Phe Asn Met Leu Arg Glu Gln Phe Ala Gln Leu
            20                  25

<210> SEQ ID NO 6
<211> LENGTH: 29
<212> TYPE: PRT
<213> ORGANISM: Artificial Sequence
<220> FEATURE:
<223> OTHER INFORMATION: c-jun zipper

<400> SEQUENCE: 6

Leu Glu Glu Lys Val Lys Thr Leu Lys Ala Gln Asn Ser Glu Leu Ala
1               5                   10                  15

Ser Thr Ala Asn Met Leu Arg Glu Gln Val Ala Gln Phe
            20                  25

<210> SEQ ID NO 7
<211> LENGTH: 29
<212> TYPE: PRT
<213> ORGANISM: Artificial Sequence
<220> FEATURE:
<223> OTHER INFORMATION: c-jun zipper

<400> SEQUENCE: 7

Leu Glu Glu Lys Val Lys Thr Phe Lys Ala Gln Asn Ser Glu Leu Ala
1               5                   10                  15

Ser Thr Ala Asn Met Leu Arg Glu Gln Val Ala Gln Phe
            20                  25

<210> SEQ ID NO 8
<211> LENGTH: 29
<212> TYPE: PRT
<213> ORGANISM: Artificial Sequence
<220> FEATURE:
<223> OTHER INFORMATION: c-jun zipper

<400> SEQUENCE: 8

Leu Glu Glu Lys Val Lys Ser Phe Lys Ala Gln Asn Ser Glu His Ala
1               5                   10                  15

Ser Thr Ala Asn Met Leu Arg Glu Gln Val Ala Gln Leu
            20                  25

<210> SEQ ID NO 9
<211> LENGTH: 74
<212> TYPE: PRT
<213> ORGANISM: Artificial Sequence
<220> FEATURE:
<223> OTHER INFORMATION: S.cerevisiae CWP2

<400> SEQUENCE: 9

Val Asp Glu Ser Ala Ala Ala Ile Ser Gln Ile Thr Asp Gly Gln Ile
1               5                   10                  15

Gln Ala Thr Thr Thr Ala Thr Thr Glu Ala Thr Thr Thr Ala Ala Pro
            20                  25                  30

Ser Ser Thr Val Glu Thr Val Ser Pro Ser Ser Thr Glu Thr Ile Ser
                35                  40                  45

Gln Gln Thr Glu Asn Gly Ala Ala Lys Ala Ala Val Gly Met Gly Ala
        50                  55                  60

Gly Ala Leu Ala Ala Ala Ala Met Leu Leu
```

```
                            65                  70

<210> SEQ ID NO 10
<211> LENGTH: 54
<212> TYPE: PRT
<213> ORGANISM: Artificial Sequence
<220> FEATURE:
<223> OTHER INFORMATION: S.cerevisiae CWP2 truncated version

<400> SEQUENCE: 10

Val Asp Thr Thr Glu Ala Thr Thr Ala Ala Pro Ser Ser Thr Val
 1               5                  10                  15

Glu Thr Val Ser Pro Ser Ser Thr Glu Thr Ile Ser Gln Gln Thr Glu
            20                  25                  30

Asn Gly Ala Ala Lys Ala Ala Val Gly Met Gly Ala Gly Ala Leu Ala
        35                  40                  45

Ala Ala Ala Met Leu Leu
    50

<210> SEQ ID NO 11
<211> LENGTH: 322
<212> TYPE: PRT
<213> ORGANISM: Artificial Sequence
<220> FEATURE:
<223> OTHER INFORMATION: S. cerevisiae SED1

<400> SEQUENCE: 11

Val Asp Gln Phe Ser Asn Ser Thr Ser Ala Ser Ser Thr Asp Val Thr
 1               5                  10                  15

Ser Ser Ser Ser Ile Ser Thr Ser Ser Gly Ser Val Thr Ile Thr Ser
            20                  25                  30

Ser Glu Ala Pro Glu Ser Asp Asn Gly Thr Ser Thr Ala Ala Pro Thr
        35                  40                  45

Glu Thr Ser Thr Glu Ala Pro Thr Thr Ala Ile Pro Thr Asn Gly Thr
    50                  55                  60

Ser Thr Glu Ala Pro Thr Thr Ala Ile Pro Thr Asn Gly Thr Ser Thr
65                  70                  75                  80

Glu Ala Pro Thr Asp Thr Thr Thr Glu Ala Pro Thr Thr Ala Leu Pro
                85                  90                  95

Thr Asn Gly Thr Ser Thr Glu Ala Pro Thr Asp Thr Thr Thr Glu Ala
            100                 105                 110

Pro Thr Thr Gly Leu Pro Thr Asn Gly Thr Thr Ser Ala Phe Pro Pro
        115                 120                 125

Thr Thr Ser Leu Pro Pro Ser Asn Thr Thr Thr Thr Pro Pro Tyr Asn
    130                 135                 140

Pro Ser Thr Asp Tyr Thr Thr Asp Tyr Thr Val Val Thr Glu Tyr Thr
145                 150                 155                 160

Thr Tyr Cys Pro Glu Pro Thr Thr Phe Thr Thr Asn Gly Lys Thr Tyr
                165                 170                 175

Thr Val Thr Glu Pro Thr Thr Leu Thr Ile Thr Asp Cys Pro Cys Thr
            180                 185                 190

Ile Glu Lys Pro Thr Thr Thr Ser Thr Thr Glu Tyr Thr Val Val Thr
        195                 200                 205

Glu Tyr Thr Thr Tyr Cys Pro Glu Pro Thr Thr Phe Thr Thr Asn Gly
    210                 215                 220

Lys Thr Tyr Thr Val Thr Glu Pro Thr Thr Leu Thr Ile Thr Asp Cys
225                 230                 235                 240
```

```
Pro Cys Thr Ile Glu Lys Ser Glu Ala Pro Glu Ser Val Pro Val
                245                 250                 255

Thr Glu Ser Lys Gly Thr Thr Thr Lys Glu Thr Gly Val Thr Thr Lys
        260                 265                 270

Gln Thr Thr Ala Asn Pro Ser Leu Thr Val Ser Thr Val Val Pro Val
            275                 280                 285

Ser Ser Ser Ala Ser Ser His Ser Val Val Ile Asn Ser Asn Gly Ala
        290                 295                 300

Asn Val Val Val Pro Gly Ala Leu Gly Leu Ala Gly Val Ala Met Leu
305                 310                 315                 320

Phe Leu
```

<210> SEQ ID NO 12
<211> LENGTH: 45
<212> TYPE: PRT
<213> ORGANISM: Artificial Sequence
<220> FEATURE:
<223> OTHER INFORMATION: S. cerevisiae SED1 truncated version

<400> SEQUENCE: 12

```
Val Asp Leu Thr Val Ser Thr Val Val Pro Val Ser Ser Ser Ala Ser
1               5                   10                  15

Ser His Ser Val Val Ile Asn Ser Asn Gly Ala Asn Val Val Val Pro
            20                  25                  30

Gly Ala Leu Gly Leu Ala Gly Val Ala Met Leu Phe Leu
        35                  40                  45
```

<210> SEQ ID NO 13
<211> LENGTH: 131
<212> TYPE: PRT
<213> ORGANISM: Artificial Sequence
<220> FEATURE:
<223> OTHER INFORMATION: Pichia pastoris SPI1

<400> SEQUENCE: 13

```
Val Asp Leu Val Ser Asn Ser Ser Ser Val Ile Val Val Pro Ser
1               5                   10                  15

Ser Asp Ala Thr Ile Ala Gly Asn Asp Thr Ala Thr Pro Ala Pro Glu
            20                  25                  30

Pro Ser Ser Ala Ala Pro Ile Phe Tyr Asn Ser Thr Ala Thr Ala Thr
        35                  40                  45

Gln Tyr Glu Val Val Ser Glu Phe Thr Thr Tyr Cys Pro Glu Pro Thr
    50                  55                  60

Thr Phe Val Thr Asn Gly Ala Thr Phe Thr Val Thr Ala Pro Thr Thr
65                  70                  75                  80

Leu Thr Ile Thr Asn Cys Pro Cys Thr Ile Glu Lys Pro Thr Ser Glu
                85                  90                  95

Thr Ser Val Ser Ser Thr His Asp Val Glu Thr Asn Ser Asn Ala Ala
            100                 105                 110

Asn Ala Arg Ala Ile Pro Gly Ala Leu Gly Leu Ala Gly Ala Val Met
        115                 120                 125

Met Leu Leu
    130
```

<210> SEQ ID NO 14
<211> LENGTH: 538
<212> TYPE: PRT
<213> ORGANISM: Artificial Sequence
<220> FEATURE:

<223> OTHER INFORMATION: S. cerevisiae GAS1

<400> SEQUENCE: 14

```
Val Asp Asp Val Pro Ala Ile Glu Val Val Gly Asn Lys Phe Phe Tyr
 1               5                  10                  15
Ser Asn Asn Gly Ser Gln Phe Tyr Ile Arg Gly Val Ala Tyr Gln Ala
                20                  25                  30
Asp Thr Ala Asn Glu Thr Ser Gly Ser Thr Val Asn Asp Pro Leu Ala
            35                  40                  45
Asn Tyr Glu Ser Cys Ser Arg Asp Ile Pro Tyr Leu Lys Lys Leu Asn
        50                  55                  60
Thr Asn Val Ile Arg Val Tyr Ala Ile Asn Thr Thr Leu Asp His Ser
 65                 70                  75                  80
Glu Cys Met Lys Ala Leu Asn Asp Ala Asp Ile Tyr Val Ile Ala Asp
                85                  90                  95
Leu Ala Ala Pro Ala Thr Ser Ile Asn Arg Asp Asp Pro Thr Trp Thr
            100                 105                 110
Val Asp Leu Phe Asn Ser Tyr Lys Thr Val Val Asp Thr Phe Ala Asn
        115                 120                 125
Tyr Thr Asn Val Leu Gly Phe Phe Ala Gly Asn Glu Val Thr Asn Asn
    130                 135                 140
Tyr Thr Asn Thr Asp Ala Ser Ala Phe Val Lys Ala Ala Ile Arg Asp
145                 150                 155                 160
Val Arg Gln Tyr Ile Ser Asp Lys Asn Tyr Arg Lys Ile Pro Val Gly
                165                 170                 175
Tyr Ser Ser Asn Asp Asp Glu Asp Thr Arg Val Lys Met Thr Asp Tyr
            180                 185                 190
Phe Ala Cys Gly Asp Asp Val Lys Ala Asp Phe Tyr Gly Ile Asn
        195                 200                 205
Met Tyr Glu Trp Cys Gly Lys Ser Asp Phe Lys Thr Ser Gly Tyr Ala
    210                 215                 220
Asp Arg Thr Ala Glu Phe Lys Asn Leu Ser Ile Pro Val Phe Phe Ser
225                 230                 235                 240
Glu Tyr Gly Cys Asn Glu Val Thr Pro Arg Leu Phe Thr Glu Val Glu
                245                 250                 255
Ala Leu Tyr Gly Ser Asn Met Thr Asp Val Trp Ser Gly Gly Ile Val
            260                 265                 270
Tyr Met Tyr Phe Glu Glu Thr Asn Lys Tyr Gly Leu Val Ser Ile Asp
        275                 280                 285
Gly Asn Asp Val Lys Thr Leu Asp Asp Phe Asn Asn Tyr Ser Ser Glu
    290                 295                 300
Ile Asn Lys Ile Ser Pro Thr Ser Ala Asn Thr Lys Ser Tyr Ser Ala
305                 310                 315                 320
Thr Thr Ser Asp Val Ala Cys Pro Ala Thr Gly Lys Tyr Trp Ser Ala
                325                 330                 335
Ala Thr Glu Leu Pro Pro Thr Pro Asn Gly Gly Leu Cys Ser Cys Met
            340                 345                 350
Asn Ala Ala Asn Ser Cys Val Val Ser Asp Asp Val Asp Ser Asp Asp
        355                 360                 365
Tyr Glu Thr Leu Phe Asn Trp Ile Cys Asn Glu Val Asp Cys Ser Gly
    370                 375                 380
Ile Ser Ala Asn Gly Thr Ala Gly Lys Tyr Gly Ala Tyr Ser Phe Cys
385                 390                 395                 400
```

```
Thr Pro Lys Glu Gln Leu Ser Phe Val Met Asn Leu Tyr Tyr Glu Lys
                405                 410                 415

Ser Gly Gly Ser Lys Ser Asp Cys Ser Phe Ser Gly Ser Ala Thr Leu
            420                 425                 430

Gln Thr Ala Thr Thr Gln Ala Ser Cys Ser Ser Ala Leu Lys Glu Ile
        435                 440                 445

Gly Ser Met Gly Thr Asn Ser Ala Ser Gly Ser Val Asp Leu Gly Ser
    450                 455                 460

Gly Thr Glu Ser Ser Thr Ala Ser Ser Asn Ala Ser Gly Ser Ser Ser
465                 470                 475                 480

Lys Ser Asn Ser Gly Ser Ser Gly Ser Ser Ser Ser Ser Ser Ser Ser
                485                 490                 495

Ser Ala Ser Ser Ser Ser Ser Lys Lys Asn Ala Ala Thr Asn Val
            500                 505                 510

Lys Ala Asn Leu Ala Gln Val Val Phe Thr Ser Ile Ile Ser Leu Ser
            515                 520                 525

Ile Ala Ala Gly Val Gly Phe Ala Leu Val
            530                 535

<210> SEQ ID NO 15
<211> LENGTH: 521
<212> TYPE: PRT
<213> ORGANISM: Artificial Sequence
<220> FEATURE:
<223> OTHER INFORMATION: Pichia pastoris GAS1

<400> SEQUENCE: 15

Val Asp Ala Asp Phe Pro Thr Ile Glu Val Thr Gly Asn Lys Phe Phe
1               5                   10                  15

Tyr Ser Asn Asn Gly Ser Gln Phe Tyr Ile Lys Gly Val Ala Tyr Gln
            20                  25                  30

Lys Asp Thr Ser Gly Leu Ser Ser Asp Ala Thr Phe Val Asp Pro Leu
        35                  40                  45

Ala Asp Lys Ser Thr Cys Glu Arg Asp Ile Pro Tyr Leu Glu Glu Leu
    50                  55                  60

Gly Thr Asn Val Ile Arg Val Tyr Ala Val Asp Ala Asp Ala Asp His
65                  70                  75                  80

Asp Asp Cys Met Gln Met Leu Gln Asp Ala Gly Ile Tyr Val Ile Ala
                85                  90                  95

Asp Leu Ser Gln Pro Asn Asn Ser Ile Ile Thr Thr Asp Pro Glu Trp
            100                 105                 110

Thr Val Asp Leu Tyr Asp Gly Tyr Thr Ala Val Leu Asp Asn Leu Gln
        115                 120                 125

Lys Tyr Asp Asn Ile Leu Gly Phe Phe Ala Gly Asn Glu Val Ile Thr
    130                 135                 140

Asn Lys Ser Asn Thr Asp Thr Ala Pro Phe Val Lys Ala Ala Ile Arg
145                 150                 155                 160

Asp Met Lys Thr Tyr Met Glu Asp Lys Gly Tyr Arg Ser Ile Pro Val
                165                 170                 175

Gly Tyr Ser Ala Asn Asp Asp Glu Leu Thr Arg Val Ala Ser Ala Asp
            180                 185                 190

Tyr Phe Ala Cys Gly Asp Ser Asp Val Lys Ala Asp Phe Tyr Gly Ile
        195                 200                 205

Asn Met Tyr Glu Trp Cys Gly Lys Ala Thr Phe Ser Asn Ser Gly Tyr
    210                 215                 220
```

Lys Asp Arg Thr Ala Glu Phe Lys Asn Leu Ser Ile Pro Val Phe Phe
225                 230                 235                 240

Ser Glu Tyr Gly Cys Asn Glu Val Gln Pro Arg Leu Phe Thr Glu Val
            245                 250                 255

Gln Ser Leu Tyr Gly Asp Asp Met Thr Asp Val Trp Ser Gly Gly Ile
        260                 265                 270

Val Tyr Met Tyr Phe Glu Glu Thr Asn Asn Tyr Gly Leu Val Thr Ile
    275                 280                 285

Lys Ser Asp Gly Asp Val Ser Thr Leu Glu Asp Phe Asn Asn Leu Lys
290                 295                 300

Thr Glu Leu Ala Ser Ile Ser Pro Ser Ile Ala Thr Gln Ser Glu Val
305                 310                 315                 320

Ser Ala Thr Ala Thr Glu Ile Asp Cys Pro Ala Thr Gly Ser Asn Trp
            325                 330                 335

Lys Ala Ser Thr Asp Leu Pro Pro Val Pro Glu Gln Ala Ala Cys Gln
        340                 345                 350

Cys Met Ala Asp Ala Leu Ser Cys Val Val Ser Glu Asp Val Asp Thr
    355                 360                 365

Asp Asp Tyr Ser Asp Leu Phe Ser Tyr Val Cys Glu Asn Val Ser Ser
370                 375                 380

Cys Asp Gly Val Ser Ala Asp Ser Glu Ser Gly Glu Tyr Gly Ser Tyr
385                 390                 395                 400

Ser Phe Cys Ser Ser Lys Glu Lys Leu Ser Phe Leu Leu Asn Leu Tyr
            405                 410                 415

Tyr Ser Glu Asn Gly Ala Lys Ser Ser Ala Cys Asp Phe Ser Gly Ser
        420                 425                 430

Ala Thr Leu Val Ser Gly Thr Thr Ala Ser Glu Cys Ser Ser Ile Leu
    435                 440                 445

Ser Ala Ala Gly Thr Ala Gly Thr Gly Ser Ile Thr Gly Ile Thr Gly
450                 455                 460

Ser Val Glu Ala Ala Thr Gln Ser Gly Ser Asn Ser Gly Ser Ser Lys
465                 470                 475                 480

Ser Ser Ser Ala Ser Gln Ser Ser Ser Ser Asn Ala Gly Val Gly Gly
            485                 490                 495

Gly Ala Ser Gly Ser Ser Trp Ala Met Thr Gly Leu Val Ser Ile Ser
        500                 505                 510

Val Ala Leu Gly Met Ile Met Ser Phe
    515                 520

<210> SEQ ID NO 16
<211> LENGTH: 78
<212> TYPE: PRT
<213> ORGANISM: Artificial Sequence
<220> FEATURE:
<223> OTHER INFORMATION: Pichia pastoris GAS1 truncated version

<400> SEQUENCE: 16

Val Asp Ser Ile Leu Ser Ala Ala Gly Thr Ala Gly Thr Gly Ser Ile
1               5                   10                  15

Thr Gly Ile Thr Gly Ser Val Glu Ala Ala Thr Gln Ser Gly Ser Asn
            20                  25                  30

Ser Gly Ser Ser Lys Ser Ser Ser Ala Ser Gln Ser Ser Ser Ser Asn
        35                  40                  45

Ala Gly Val Gly Gly Gly Ala Ser Gly Ser Ser Trp Ala Met Thr Gly
    50                  55                  60

```
Leu Val Ser Ile Ser Val Ala Leu Gly Met Ile Met Ser Phe
 65                  70                  75

<210> SEQ ID NO 17
<211> LENGTH: 159
<212> TYPE: PRT
<213> ORGANISM: Artificial Sequence
<220> FEATURE:
<223> OTHER INFORMATION: H. polymorpha TIP1

<400> SEQUENCE: 17

Val Asp Ala Ala Ala Thr Ser Ser Val Ala Ala Ala Ala Ser Glu Val
 1               5                  10                  15

Ser Ser Ser Ser Ala Ala Ala Ser Ser Thr Gln Ala Ala Ala Ala
             20                  25                  30

Ser Thr Ser Ala Ala Ala Ser Thr Glu Ala Thr Thr Ser Ala Ala Ala
             35                  40                  45

Ala Ala Thr Ser Ser Ser Glu Ala Ala Ser Ser Ser Ala His Val His
             50                  55                  60

Ser His Ala Ala Glu Ser Thr Ser Ala Val Glu Ser Thr Ser Ala Ala
 65                  70                  75                  80

His Ser His Ala Ala Glu Ser Ser Ala Ala His Ser His Ala Val
             85                  90                  95

Glu Ser Ser Ser Ala Ala His Val His Ser His Ala Ala Glu Ser Ser
             100                 105                 110

Ser Ala Ala His Ser His Ala Ala Gly Ser Ser Ser Ala Ala Ser Asn
         115                 120                 125

Ser Ser Gly His Ile Ser Thr Phe Ser Gly Ala Gly Ala Lys Leu Ala
         130                 135                 140

Val Gly Ala Gly Ala Gly Ile Val Gly Leu Ala Ala Leu Leu Met
145                 150                 155

<210> SEQ ID NO 18
<211> LENGTH: 74
<212> TYPE: PRT
<213> ORGANISM: Artificial Sequence
<220> FEATURE:
<223> OTHER INFORMATION: H. polymorpha TIP1 truncated version

<400> SEQUENCE: 18

Val Asp Ser Ser Ala Ala His Ser His Ala Val Glu Ser Ser Ser Ala
 1               5                  10                  15

Ala His Val His Ser His Ala Ala Glu Ser Ser Ser Ala Ala His Ser
             20                  25                  30

His Ala Ala Gly Ser Ser Ser Ala Ala Ser Asn Ser Ser Gly His Ile
             35                  40                  45

Ser Thr Phe Ser Gly Ala Gly Ala Lys Leu Ala Val Gly Ala Gly Ala
             50                  55                  60

Gly Ile Val Gly Leu Ala Ala Leu Leu Met
 65                  70

<210> SEQ ID NO 19
<211> LENGTH: 38
<212> TYPE: PRT
<213> ORGANISM: Artificial Sequence
<220> FEATURE:
<223> OTHER INFORMATION: Human GR2 coiled coil peptide sequence

<400> SEQUENCE: 19

Thr Ser Arg Leu Glu Gly Leu Gln Ser Glu Asn His Arg Leu Arg Met
```

```
                  1               5              10              15
         Lys Ile Thr Glu Leu Asp Lys Asp Leu Glu Glu Val Thr Met Gln Leu
                         20              25              30
         Gln Asp Val Gly Gly Cys
                         35

<210> SEQ ID NO 20
<211> LENGTH: 390
<212> TYPE: PRT
<213> ORGANISM: Artificial Sequence
<220> FEATURE:
<223> OTHER INFORMATION: SED 1 Fusion
      Leader GR2 cMyc SED1

<400> SEQUENCE: 20

Met Val Ala Trp Trp Ser Leu Phe Leu Tyr Gly Leu Gln Val Ala Ala
         1               5                  10                  15

Pro Ala Leu Ala Thr Ser Arg Leu Glu Gly Leu Gln Ser Glu Asn His
                         20                  25                  30

Arg Leu Arg Met Lys Ile Thr Glu Leu Asp Lys Asp Leu Glu Glu Val
                     35                  40                  45

Thr Met Gln Leu Gln Asp Val Gly Gly Cys Glu Gln Lys Leu Ile Ser
             50                  55                  60

Glu Glu Asp Leu Val Asp Gln Phe Ser Asn Ser Thr Ser Ala Ser Ser
         65                  70                  75                  80

Thr Asp Val Thr Ser Ser Ser Ile Ser Thr Ser Ser Gly Ser Val
                         85                  90                  95

Thr Ile Thr Ser Ser Glu Ala Pro Glu Ser Asp Asn Gly Thr Ser Thr
                         100                 105                 110

Ala Ala Pro Thr Glu Thr Ser Thr Glu Ala Pro Thr Thr Ala Ile Pro
                     115                 120                 125

Thr Asn Gly Thr Ser Thr Glu Ala Pro Thr Thr Ala Ile Pro Thr Asn
             130                 135                 140

Gly Thr Ser Thr Glu Ala Pro Thr Asp Thr Thr Glu Ala Pro Thr
         145                 150                 155                 160

Thr Ala Leu Pro Thr Asn Gly Thr Ser Thr Glu Ala Pro Thr Asp Thr
                         165                 170                 175

Thr Thr Glu Ala Pro Thr Thr Gly Leu Pro Thr Asn Gly Thr Thr Ser
                     180                 185                 190

Ala Phe Pro Pro Thr Thr Ser Leu Pro Pro Ser Asn Thr Thr Thr Thr
             195                 200                 205

Pro Pro Tyr Asn Pro Ser Thr Asp Tyr Thr Thr Asp Tyr Thr Val Val
         210                 215                 220

Thr Glu Tyr Thr Thr Tyr Cys Pro Glu Pro Thr Thr Phe Thr Thr Asn
         225                 230                 235                 240

Gly Lys Thr Tyr Thr Val Thr Glu Pro Thr Thr Leu Thr Ile Thr Asp
                         245                 250                 255

Cys Pro Cys Thr Ile Glu Lys Pro Thr Thr Ser Thr Thr Glu Tyr
                         260                 265                 270

Thr Val Val Thr Glu Tyr Thr Thr Tyr Cys Pro Glu Pro Thr Thr Phe
                     275                 280                 285

Thr Thr Asn Gly Lys Thr Tyr Thr Val Thr Glu Pro Thr Thr Leu Thr
             290                 295                 300

Ile Thr Asp Cys Pro Cys Thr Ile Glu Lys Ser Glu Ala Pro Glu Ser
         305                 310                 315                 320
```

```
Ser Val Pro Val Thr Glu Ser Lys Gly Thr Thr Lys Glu Thr Gly
            325                 330                 335

Val Thr Thr Lys Gln Thr Thr Ala Asn Pro Ser Leu Thr Val Ser Thr
            340                 345                 350

Val Val Pro Val Ser Ser Ala Ser Ser His Ser Val Val Ile Asn
            355                 360                 365

Ser Asn Gly Ala Asn Val Val Val Pro Gly Ala Leu Gly Leu Ala Gly
    370                 375                 380

Val Ala Met Leu Phe Leu
385                 390

<210> SEQ ID NO 21
<211> LENGTH: 38
<212> TYPE: PRT
<213> ORGANISM: Artificial Sequence
<220> FEATURE:
<223> OTHER INFORMATION: Human GR1 coiled coil peptide sequence

<400> SEQUENCE: 21

Glu Glu Lys Ser Arg Leu Leu Glu Lys Glu Asn Arg Glu Leu Glu Lys
1               5                   10                  15

Ile Ile Ala Glu Lys Glu Glu Arg Val Ser Glu Leu Arg His Gln Leu
            20                  25                  30

Gln Ser Val Gly Gly Cys
        35

<210> SEQ ID NO 22
<211> LENGTH: 450
<212> TYPE: PRT
<213> ORGANISM: Artificial Sequence
<220> FEATURE:
<223> OTHER INFORMATION: mAb1 (anti-her2) Heavy chain

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 23
<211> LENGTH: 214
<212> TYPE: PRT
<213> ORGANISM: Artificial Sequence
<220> FEATURE:
<223> OTHER INFORMATION: mAb1 (anti-her2) Light chain

<400> SEQUENCE: 23

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 438
<212> TYPE: PRT
<213> ORGANISM: Artificial Sequence
<220> FEATURE:
<223> OTHER INFORMATION: mAb2 (anti-DKK1) Heavy chain

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile His Ser Asn Ser Gly Ala Thr Thr Tyr Ala Gln Lys Phe
    50                  55                  60

Gln Ala Arg Val Thr Met Ser Arg Asp Thr Ser Ser Ser Thr Ala Tyr
65                  70                  75                  80

Met Glu Leu Ser Arg Leu Glu Ser Asp Asp Thr Ala Met Tyr Phe Cys
                85                  90                  95

Ser Arg Glu Asp Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Thr Ser Ser Asn Phe Gly Thr Gln Thr
            180                 185                 190

Tyr Thr Cys Asn Val Asp His Lys Pro Ser Asn Thr Lys Val Asp Lys
        195                 200                 205

Thr Val Glu Arg Lys Cys Cys Val Glu Cys Pro Pro Cys Pro Ala Pro
    210                 215                 220

Pro Val Ala Gly Pro Ser Val Phe Leu Phe Pro Pro Lys Pro Lys Asp
225                 230                 235                 240
```

```
Thr Leu Met Ile Ser Arg Thr Pro Glu Val Thr Cys Val Val Val Asp
            245                 250                 255

Val Ser Gln Glu Asp Pro Glu Val Gln Phe Asn Trp Tyr Val Asp Gly
        260                 265                 270

Val Glu Val His Asn Ala Lys Thr Lys Pro Arg Glu Glu Gln Phe Asn
    275                 280                 285

Ser Thr Phe Arg Val Val Ser Val Leu Thr Val Leu His Gln Asp Trp
290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Thr Lys Gly Gln Pro Arg Glu
                325                 330                 335

Pro Gln Val Tyr Thr Leu Pro Pro Ser Arg Glu Glu Met Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Met Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
            435

<210> SEQ ID NO 25
<211> LENGTH: 216
<212> TYPE: PRT
<213> ORGANISM: Artificial Sequence
<220> FEATURE:
<223> OTHER INFORMATION: mAb2 (anti-DKK1) Light Chain

<400> SEQUENCE: 25

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Tyr Ser Asn Arg Pro Ser Gly Val Pro Asp Arg Phe
    50                  55                  60

Ser Gly Ser Lys Ser Gly Ala Ser Ala Ser Leu Ala Ile Thr Gly Leu
65                  70                  75                  80

Arg Pro Asp Asp Glu Ala Asp Tyr Tyr Cys Gln Ser Tyr Asp Asn Ser
                85                  90                  95

Leu Ser Ser Tyr Val Phe Gly Gly Gly Thr Gln Leu Thr Val Leu Ser
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160
```

```
Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys
    210                 215

<210> SEQ ID NO 26
<211> LENGTH: 451
<212> TYPE: PRT
<213> ORGANISM: Artificial Sequence
<220> FEATURE:
<223> OTHER INFORMATION: mAb3 (anti-CD20, C2B8) Heavy chain

<400> SEQUENCE: 26

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 27
<211> LENGTH: 213
<212> TYPE: PRT
<213> ORGANISM: Artificial Sequence
<220> FEATURE:
<223> OTHER INFORMATION: mAb3 (anti-CD20, C2B8) Light chain

<400> SEQUENCE: 27

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 28
<211> LENGTH: 451
<212> TYPE: PRT
<213> ORGANISM: Artificial Sequence
<220> FEATURE:
<223> OTHER INFORMATION: mAb4 (anti-CD20, Frame grafted Heavy chain

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

-continued

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 29
<211> LENGTH: 213
<212> TYPE: PRT
<213> ORGANISM: Artificial Sequence
<220> FEATURE:
<223> OTHER INFORMATION: mAb4 (anti-CD20, Frame grafted) Light chain

<400> SEQUENCE: 29

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Ser Ser Val Ser Tyr Ile
                 20                  25                  30

His Trp Tyr Gln Gln Lys Pro Gly Gln Ala Pro Arg Leu Leu Ile Tyr
             35                  40                  45

Ala Thr Ser Asn Leu Ala Ser Gly Ile Pro Ala Arg Phe Ser Gly Ser
         50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Trp Thr Ser Asn Pro Pro Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 30
<211> LENGTH: 453
<212> TYPE: PRT
<213> ORGANISM: Artificial Sequence
<220> FEATURE:
<223> OTHER INFORMATION: mAb5 (anti-CD20, Genmab) Heavy chain

<400> SEQUENCE: 30

```
Ala Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Gly Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Asp Asn Gln Tyr Gly Ser Gly Ser Thr Tyr Gly Leu Gly Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 31
<211> LENGTH: 214
<212> TYPE: PRT
<213> ORGANISM: Artificial Sequence
<220> FEATURE:
<223> OTHER INFORMATION: mAb5 (anti-CD20, Genmab) Light chain

<400> SEQUENCE: 31

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 514
<212> TYPE: PRT
<213> ORGANISM: Artificial Sequence
<220> FEATURE:
<223> OTHER INFORMATION: Anti-Her2 mAb heavy chain readthrough coiled
      coil peptide
<221> NAME/KEY: VARIANT
<222> LOCATION: 451
<223> OTHER INFORMATION: Xaa=unkown amino acid inserted by readthrough
      of the stop codon at 1408-1410 of SEQ ID NO:60
      translated in presence of antibiotic
<221> NAME/KEY: DOMAIN
```

<222> LOCATION: (475)...(514)
<223> OTHER INFORMATION: GR1 coiled coil

<400> SEQUENCE: 32

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Xaa Ala Ala Ala Tyr Pro Tyr Asp Val Pro Asp Tyr Ala Gly
    450                 455                 460

Gly His His His His His His His Gly Gly Glu Glu Lys Ser
465                 470                 475                 480

Arg Leu Leu Glu Lys Glu Asn Arg Glu Leu Glu Lys Ile Ile Ala Glu
                485                 490                 495

Lys Glu Glu Arg Val Ser Glu Leu Arg His Gln Leu Gln Ser Val Gly
            500                 505                 510

Gly Cys

<210> SEQ ID NO 33
<211> LENGTH: 60
<212> TYPE: DNA
<213> ORGANISM: Artificial Sequence
<220> FEATURE:
<223> OTHER INFORMATION: Encodes alpha amylase signal sequence (from
      Aspergillus niger -amylase) (DNA)

<400> SEQUENCE: 33
atggttgctt ggtggtcctt gttcttgtac ggattgcaag ttgctgctcc agctttggct    60

<210> SEQ ID NO 34
<211> LENGTH: 20
<212> TYPE: PRT
<213> ORGANISM: Artificial Sequence
<220> FEATURE:
<223> OTHER INFORMATION: Alpha amylase signal sequence (from Aspergillus
      niger -amylase) (DNA)

<400> SEQUENCE: 34

Met Val Ala Trp Trp Ser Leu Phe Leu Tyr Gly Leu Gln Val Ala Ala
1               5                   10                  15

Pro Ala Leu Ala
            20

<210> SEQ ID NO 35
<211> LENGTH: 30
<212> TYPE: DNA
<213> ORGANISM: Artificial Sequence
<220> FEATURE:
<223> OTHER INFORMATION: PCR primer hPDI/UP1

<400> SEQUENCE: 35
agcgctgacg ccccgagga ggaggaccac                                       30

<210> SEQ ID NO 36
<211> LENGTH: 42
<212> TYPE: DNA
<213> ORGANISM: Artificial Sequence
<220> FEATURE:
<223> OTHER INFORMATION: PCR primer hPDI/LP-PacI

<400> SEQUENCE: 36
ccttaattaa ttacagttca tcatgcacag ctttctgatc at                        42
```

-continued

```
<210> SEQ ID NO 37
<211> LENGTH: 1476
<212> TYPE: DNA
<213> ORGANISM: Artificial Sequence
<220> FEATURE:
<223> OTHER INFORMATION: DNA encoding relevant portion of human PDI

<400> SEQUENCE: 37 gacgccccg aggaggagga ccacgtcttg gtgctgcgga aaagcaactt cgcggaggcg      60
ctggcggccc acaagtaccc gccggtggag ttccatgccc cctggtgtgg ccactgcaag    120
gctctggccc ctgagtatgc caaagccgct gggaagctga aggcagaagg ttccgagatc    180
aggttggcca aggtggacgc cacggaggag tctgacctag cccagcagta cggcgtgcgc    240
ggctatccca ccatcaagtt cttcaggaat ggagacacgg cttcccccaa ggaatataca    300
gctggcagag aggctgatga catcgtgaac tggctgaaga gcgcacggg cccggctgcc     360 accaccctgc tgacggcgc agctgcagag tccttggtgg agtccagcga ggtggccgtc     420
atcggcttct tcaaggacgt ggagtcggac tctgccaagc agttttttgca ggcagcagag   480 gccatcgatg acataccatt tgggatcact tccaacagtg acgtgttctc caaataccag    540
ctcgacaaag atggggttgt cctctttaag aagtttgatg aaggccggaa caactttgaa    600
ggggaggtca ccaaggagaa cctgctggac tttatcaaac acaaccagct gccccttgtc    660
atcgagttca ccgagcagac agccccgaag attttttggag gtgaaatcaa gactcacatc    720
ctgctgttct tgcccaagag tgtgtctgac tatgacggca aactgagcaa cttcaaaaca    780
gcagccgaga gcttcaaggg caagatcctg ttcatcttca tcgacagcga ccacaccgac    840
aaccagcgca tcctcgagtt cttttggcctg aagaaggaag agtgcccggc cgtgcgcctc    900
atcaccttgg aggaggagat gaccaagtac aagcccgaat cggaggagct gacggcagag    960
aggatcacag agttctgcca ccgcttcctg gagggcaaaa tcaagcccca cctgatgagc   1020
caggagctgc cggaggactg ggacaagcag cctgtcaagg tgcttgttgg gaagaacttt   1080
gaagacgtgg cttttgatga aaaaaaac gtctttgtgg agttctatgc ccatggtgt     1140 ggtcactgca acagttggc tcccattttgg gataaactgg agagacgta caaggaccat    1200 gagaacatcg tcatcgccaa gatggactcg actgccaacg aggtggaggc cgtcaaagtg   1260
cacggcttcc ccacactcgg gttctttcct gccagtgccg acaggacggt cattgattac    1320
aacggggaac gcacgctgga tggttttaag aaattcctag agagcggtgg ccaagatggg   1380 gcagggatg ttgacgacct cgaggacctc gaagaagcag aggagccaga catggaggaa    1440
gacgatgacc agaaagctgt gaaagatgaa ctgtaa                             1476

<210> SEQ ID NO 38
<211> LENGTH: 491
<212> TYPE: PRT
<213> ORGANISM: Artificial Sequence
<220> FEATURE:
<223> OTHER INFORMATION: Relevant portion of human PDI

<400> SEQUENCE: 38

Asp Ala Pro Glu Glu Glu Asp His Val Leu Val Leu Arg Lys Ser Asn
  1               5                  10                  15

Phe Ala Glu Ala Leu Ala Ala His Lys Tyr Pro Val Glu Phe His
             20                  25                  30

Ala Pro Trp Cys Gly His Cys Lys Ala Leu Ala Pro Glu Tyr Ala Lys
         35                  40                  45

Ala Ala Gly Lys Leu Lys Ala Glu Gly Ser Glu Ile Arg Leu Ala Lys
```

```
                50                  55                  60
Val Asp Ala Thr Glu Glu Ser Asp Leu Ala Gln Gln Tyr Gly Val Arg
 65                  70                  75                  80

Gly Tyr Pro Thr Ile Lys Phe Phe Arg Asn Gly Asp Thr Ala Ser Pro
                     85                  90                  95

Lys Glu Tyr Thr Ala Gly Arg Glu Ala Asp Asp Ile Val Asn Trp Leu
                100                 105                 110

Lys Lys Arg Thr Gly Pro Ala Ala Thr Thr Leu Pro Asp Gly Ala Ala
                115                 120                 125

Ala Glu Ser Leu Val Glu Ser Ser Glu Val Ala Val Ile Gly Phe Phe
            130                 135                 140

Lys Asp Val Glu Ser Asp Ser Ala Lys Gln Phe Leu Gln Ala Ala Glu
145                 150                 155                 160

Ala Ile Asp Asp Ile Pro Phe Gly Ile Thr Ser Asn Ser Asp Val Phe
                165                 170                 175

Ser Lys Tyr Gln Leu Asp Lys Asp Gly Val Val Leu Phe Lys Lys Phe
                180                 185                 190

Asp Glu Gly Arg Asn Asn Phe Glu Gly Glu Val Thr Lys Glu Asn Leu
                195                 200                 205

Leu Asp Phe Ile Lys His Asn Gln Leu Pro Leu Val Ile Glu Phe Thr
            210                 215                 220

Glu Gln Thr Ala Pro Lys Ile Phe Gly Gly Glu Ile Lys Thr His Ile
225                 230                 235                 240

Leu Leu Phe Leu Pro Lys Ser Val Ser Asp Tyr Asp Gly Lys Leu Ser
                245                 250                 255

Asn Phe Lys Thr Ala Ala Glu Ser Phe Lys Gly Lys Ile Leu Phe Ile
                260                 265                 270

Phe Ile Asp Ser Asp His Thr Asp Asn Gln Arg Ile Leu Glu Phe Phe
            275                 280                 285

Gly Leu Lys Lys Glu Glu Cys Pro Ala Val Arg Leu Ile Thr Leu Glu
            290                 295                 300

Glu Glu Met Thr Lys Tyr Lys Pro Glu Ser Glu Glu Leu Thr Ala Glu
305                 310                 315                 320

Arg Ile Thr Glu Phe Cys His Arg Phe Leu Glu Gly Lys Ile Lys Pro
                325                 330                 335

His Leu Met Ser Gln Glu Leu Pro Glu Asp Trp Asp Lys Gln Pro Val
                340                 345                 350

Lys Val Leu Val Gly Lys Asn Phe Glu Asp Val Ala Phe Asp Glu Lys
            355                 360                 365

Lys Asn Val Phe Val Glu Phe Tyr Ala Pro Trp Cys Gly His Cys Lys
            370                 375                 380

Gln Leu Ala Pro Ile Trp Asp Lys Leu Gly Glu Thr Tyr Lys Asp His
385                 390                 395                 400

Glu Asn Ile Val Ile Ala Lys Met Asp Ser Thr Ala Asn Glu Val Glu
                405                 410                 415

Ala Val Lys Val His Gly Phe Pro Thr Leu Gly Phe Phe Pro Ala Ser
                420                 425                 430

Ala Asp Arg Thr Val Ile Asp Tyr Asn Gly Glu Arg Thr Leu Asp Gly
            435                 440                 445

Phe Lys Lys Phe Leu Glu Ser Gly Gly Gln Asp Gly Ala Gly Asp Val
450                 455                 460

Asp Asp Leu Glu Asp Leu Glu Glu Ala Glu Glu Pro Asp Met Glu Glu
465                 470                 475                 480
```

Asp Asp Asp Gln Lys Ala Val His Asp Glu Leu
            485                 490

<210> SEQ ID NO 39
<211> LENGTH: 1554
<212> TYPE: DNA
<213> ORGANISM: Pichia pastoris

<400> SEQUENCE: 39

```
atgcaattca actggaatat taaaactgtg gcaagtattt tgtccgctct cacactagca      60
caagcaagtg atcaggaggc tattgctcca gaggactctc atgtcgtcaa attgactgaa     120
gccactttg agtctttcat caccagtaat cctcacgttt tggcagagtt ttttgcccct     180
tggtgtggtc actgtaagaa gttgggccct gaacttgttt ctgctgccga gatcttaaag    240
gacaatgagc aggttaagat tgctcaaatt gattgtacgg aggagaagga attatgtcaa    300
ggctacgaaa ttaaagggta tcctactttg aaggtgttcc atggtgaggt tgaggtccca    360
agtgactatc aaggtcaaag acagagccaa agcattgtca gctatatgct aaagcagagt    420
ttaccccctg tcagtgaaat caatgcaacc aaagatttag acgacacaat cgccgaggca    480
aaagagcccg tgattgtgca agtactaccg gaagatgcat ccaacttgga atctaacacc    540
acattttacg gagttgccgg tactctcaga gagaaattca cttttgtctc cactaagtct    600
actgattatg ccaaaaaata cactagcgac tcgactcctg cctatttgct tgtcagacct    660
ggcgaggaac ctagtgttta ctctggtgag gagttagatg agactcattt ggtgcactgg    720
attgatattg agtccaaacc tctatttgga gacattgacg gatccacctt caaatcatat    780
gctgaagcta acatcccttt agcctactat ttctatgaga acgaagaaca acgtgctgct    840
gctgccgata ttattaaacc ttttgctaaa gagcaacgtg gcaaaattaa ctttgttggc    900
ttagatgccg ttaaattcgg taagcatgcc aagaacttaa acatggatga agagaaactc    960
cctctatttg tcattcatga tttggtgagc aacaagaagt tggagttcc tcaagaccaa    1020
gaattgacga acaaagatgt gaccgagctg attgagaaat tcatcgcagg agaggcagaa   1080
ccaattgtga atcagagcc aattccagaa attcaagaag agaaagtctt caagctagtc   1140
ggaaaggccc acgatgaagt tgtcttcgat gaatctaaag atgttctagt caagtactac   1200
gccccttggt gtggtcactg taagagaatg gctcctgctt atgaggaatt ggctactctt   1260
tacgccaatg atgaggatgc ctcttcaaag gttgtgattg caaaacttga tcacactttg   1320
aacgatgtcg acaacgttga tattcaaggt tatcctactt tgatcccttta tccagctggt   1380
gataaatcca atcctcaact gtatgatgga tctcgtgacc tagaatcatt ggctgagttt   1440
gtaaaggaga gaggaaccca caagtggat gccctagcac tcagaccagt cgaggaagaa    1500
aaggaagctg aagaagaagc tgaaagtgag gcagacgctc acgacgagct ttaa          1554
```

<210> SEQ ID NO 40
<211> LENGTH: 517
<212> TYPE: PRT
<213> ORGANISM: Pichia pastoris

<400> SEQUENCE: 40

Met Gln Phe Asn Trp Asn Ile Lys Thr Val Ala Ser Ile Leu Ser Ala
  1               5                  10                  15

Leu Thr Leu Ala Gln Ala Ser Asp Gln Glu Ala Ile Ala Pro Glu Asp
             20                  25                  30

Ser His Val Val Lys Leu Thr Glu Ala Thr Phe Glu Ser Phe Ile Thr

-continued

```
                35                  40                  45
Ser Asn Pro His Val Leu Ala Glu Phe Phe Ala Pro Trp Cys Gly His
 50                  55                  60

Cys Lys Lys Leu Gly Pro Glu Leu Val Ser Ala Ala Glu Ile Leu Lys
 65                  70                  75                  80

Asp Asn Glu Gln Val Lys Ile Ala Gln Ile Asp Cys Thr Glu Glu Lys
                 85                  90                  95

Glu Leu Cys Gln Gly Tyr Glu Ile Lys Gly Tyr Pro Thr Leu Lys Val
                100                 105                 110

Phe His Gly Glu Val Glu Val Pro Ser Asp Tyr Gln Gly Gln Arg Gln
                115                 120                 125

Ser Gln Ser Ile Val Ser Tyr Met Leu Lys Gln Ser Leu Pro Pro Val
                130                 135                 140

Ser Glu Ile Asn Ala Thr Lys Asp Leu Asp Thr Ile Ala Glu Ala
145                 150                 155                 160

Lys Glu Pro Val Ile Val Gln Val Leu Pro Glu Asp Ala Ser Asn Leu
                165                 170                 175

Glu Ser Asn Thr Thr Phe Tyr Gly Val Ala Gly Thr Leu Arg Glu Lys
                180                 185                 190

Phe Thr Phe Val Ser Thr Lys Ser Thr Asp Tyr Ala Lys Lys Tyr Thr
                195                 200                 205

Ser Asp Ser Thr Pro Ala Tyr Leu Leu Val Arg Pro Gly Glu Pro
210                 215                 220

Ser Val Tyr Ser Gly Glu Glu Leu Asp Glu Thr His Leu Val His Trp
225                 230                 235                 240

Ile Asp Ile Glu Ser Lys Pro Leu Phe Gly Asp Ile Asp Gly Ser Thr
                245                 250                 255

Phe Lys Ser Tyr Ala Glu Ala Asn Ile Pro Leu Ala Tyr Tyr Phe Tyr
                260                 265                 270

Glu Asn Glu Glu Gln Arg Ala Ala Ala Asp Ile Ile Lys Pro Phe
                275                 280                 285

Ala Lys Glu Gln Arg Gly Lys Ile Asn Phe Val Gly Leu Asp Ala Val
290                 295                 300

Lys Phe Gly Lys His Ala Lys Asn Leu Asn Met Asp Glu Glu Lys Leu
305                 310                 315                 320

Pro Leu Phe Val Ile His Asp Leu Val Ser Asn Lys Lys Phe Gly Val
                325                 330                 335

Pro Gln Asp Gln Glu Leu Thr Asn Lys Asp Val Thr Glu Leu Ile Glu
                340                 345                 350

Lys Phe Ile Ala Gly Glu Ala Glu Pro Ile Val Lys Ser Glu Pro Ile
                355                 360                 365

Pro Glu Ile Gln Glu Glu Lys Val Phe Lys Leu Val Gly Lys Ala His
                370                 375                 380

Asp Glu Val Val Phe Asp Glu Ser Lys Asp Val Leu Val Lys Tyr Tyr
385                 390                 395                 400

Ala Pro Trp Cys Gly His Cys Lys Arg Met Ala Pro Ala Tyr Glu Glu
                405                 410                 415

Leu Ala Thr Leu Tyr Ala Asn Asp Glu Asp Ala Ser Ser Lys Val Val
                420                 425                 430

Ile Ala Lys Leu Asp His Thr Leu Asn Asp Val Asp Asn Val Asp Ile
                435                 440                 445

Gln Gly Tyr Pro Thr Leu Ile Leu Tyr Pro Ala Gly Asp Lys Ser Asn
450                 455                 460
```

```
Pro Gln Leu Tyr Asp Gly Ser Arg Asp Leu Glu Ser Leu Ala Glu Phe
465                 470                 475                 480

Val Lys Glu Arg Gly Thr His Lys Val Asp Ala Leu Ala Leu Arg Pro
                485                 490                 495

Val Glu Glu Lys Glu Ala Glu Glu Ala Glu Ser Glu Ala Asp
            500                 505                 510

Ala His Asp Glu Leu
        515

<210> SEQ ID NO 41
<211> LENGTH: 47
<212> TYPE: DNA
<213> ORGANISM: Artificial Sequence
<220> FEATURE:
<223> OTHER INFORMATION: PCR primer PB248

<400> SEQUENCE: 41
atgaattcag gccatatcgg ccattgttta ctgtgcgccc acagtag          47

<210> SEQ ID NO 42
<211> LENGTH: 35
<212> TYPE: DNA
<213> ORGANISM: Artificial Sequence
<220> FEATURE:
<223> OTHER INFORMATION: PCR primer PB249

<400> SEQUENCE: 42
atgtttaaac gtgaggatta ctggtgatga aagac                       35

<210> SEQ ID NO 43
<211> LENGTH: 34
<212> TYPE: DNA
<213> ORGANISM: Artificial Sequence
<220> FEATURE:
<223> OTHER INFORMATION: PCR primer PB250

<400> SEQUENCE: 43
agactagtct atttggagac attgacggat ccac                        34

<210> SEQ ID NO 44
<211> LENGTH: 46
<212> TYPE: DNA
<213> ORGANISM: Artificial Sequence
<220> FEATURE:
<223> OTHER INFORMATION: PCR primer PB251

<400> SEQUENCE: 44
atctcgagag gccatgcagg ccaaccacaa gatgaatcaa attttg           46

<210> SEQ ID NO 45
<211> LENGTH: 37
<212> TYPE: DNA
<213> ORGANISM: Artificial Sequence
<220> FEATURE:
<223> OTHER INFORMATION: PCR primer hGRP94/UP1

<400> SEQUENCE: 45
agcgctgacg atgaagttga tgtggatggt acagtag                     37

<210> SEQ ID NO 46
<211> LENGTH: 38
<212> TYPE: DNA
<213> ORGANISM: Artificial Sequence
<220> FEATURE:
```

<223> OTHER INFORMATION: PCR primer hGRP94/LP1

<400> SEQUENCE: 46

```
ggccggcctt acaattcatc atgttcagct gtagattc                              38
```

<210> SEQ ID NO 47
<211> LENGTH: 2349
<212> TYPE: DNA
<213> ORGANISM: Artificial Sequence
<220> FEATURE:
<223> OTHER INFORMATION: Encodes relevant portion of GRP94

<400> SEQUENCE: 47

```
gatgatgaag ttgacgttga cggtactgtt gaagaggact tgggaaagtc tagagagggt      60
tccagaactg acgacgaagt tgttcagaga gaggaagagg ctattcagtt ggacggattg     120
aacgcttccc aaatcagaga gttgagagag aagtccgaga gttcgctttc caagctgag     180
gttaacagaa tgatgaaatt gattatcaac tccttgtaca gaacaaaga gattttcttg     240
agagagttga tctctaacgc ttctgacgct ttggacaaga tcagattgat ctccttgact     300
gacgaaaacg cttttgtccgg taacgaagag ttgactgtta agatcaagtg tgacaaagag     360
aagaacttgt tgcacgttac tgacactggt gttggaatga ctagaagaa gttggttaag     420
aacttgggta ctatcgctaa gtctggtact tccgagttct tgaacaagat gactgaggct     480
caagaagatg gtcaatccac ttccgagttg attggtcagt cggtgttgg tttctactcc     540
gctttcttgg ttgctgacaa ggttatcgtt acttccaagc acaacaacga cactcaacac     600
atttgggaat ccgattccaa cgagttctcc gttattgctg acccaagagg taacactttg     660
ggtagaggta ctactatcac tttggttttg aaagaagagg cttccgacta cttggagttg     720
gacactatca gaacttggt taagaagtac tcccagttca tcaacttccc aatctatgtt     780
tggtcctcca agactgagac tgttgaggaa ccaatggaag aagaagaggc tgctaaagaa     840
gagaaagagg aatctgacga cgaggctgct gttgaagaag aggaagaaga aaagaagcca     900
aagactaaga aggttgaaaa gactgtttgg gactgggagc ttatgaacga catcaagcca     960
atttggcaga gaccatccaa agaggttgag gaggacgagt acaaggcttt ctacaagtcc    1020
ttctccaaag aatccgatga cccaatggct acatccact tcactgctga gggtgaagtt    1080
actttcaagt ccatcttgtt cgttccaact tctgctccaa gaggattgtt cgacgagtac    1140
ggttctaaga gtccgactat catcaaactt tatgttagaa gagttttcat cactgacgac    1200
ttccacgata tgatgccaaa gtacttgaac ttcgttaagg gtgttgttga ttccgatgac    1260
ttgccattga acgtttccag agagactttg cagcagcaca gttgttgaa ggttatcaga    1320
aagaaacttg ttagaaagac tttggacatg atcaagaaga tcgctgacga caagtacaac    1380
gacactttct ggaaagagtt cggaactaac atcaagttgg gtgttattga ggaccactcc    1440
aacagaacta gattggctaa gttgttgaga ttccagtcct ctcatcaccc aactgacatc    1500
acttccttgg accagtacgt tgagagaatg aaagagaagc aggacaaaat ctacttcatg    1560
gctggttcct ctagaaaaga ggctgaatcc tccccattcg ttgagagatt gttgaagaag    1620
ggttacgagg ttatctactt gactgagcca gttgacgagt actgtatcca ggctttgcca    1680
gagtttgacg aaagagatt ccagaacgtt gctaagagg gtgttaagtt cgacgaatcc    1740
gaaaagacta agaatccag agaggctgtt gagaaagagt tcgagccatt gttgaactgg    1800
atgaaggaca aggctttgaa ggacaagatc gagaggctg ttgtttccca gagattgact    1860
gaatccccat gtgctttggt tgcttcccaa tacggatgga gtggtaacat ggaaagaatc    1920
```

-continued

```
atgaaggctc aggcttacca aactggaaag gacatctcca ctaactacta cgcttcccag    1980
aagaaaactt tcgagatcaa cccaagacac ccattgatca gagacatgtt gagaagaatc    2040
aaagaggacg aggacgacaa gactgttttg gatttggctg ttgttttgtt cgagactgct    2100
actttgagat ccggttactt gttgccagac actaaggctt acggtgacag aatcgagaga    2160
atgttgagat tgtccttgaa cattgaccca gacgctaagg ttgaagaaga accagaagaa    2220
gagccagagg aaactgctga agatactact gaggacactg aacaagacga ggacgaagag    2280
atggatgttg gtactgacga agaggaagag acagcaaagg aatccactgc tgaacacgac    2340
gagttgtaa                                                             2349
```

<210> SEQ ID NO 48
<211> LENGTH: 782
<212> TYPE: PRT
<213> ORGANISM: Artificial Sequence
<220> FEATURE:
<223> OTHER INFORMATION: Relevant portion of GPR94

<400> SEQUENCE: 48

```
Asp Asp Glu Val Asp Val Asp Gly Thr Val Glu Glu Asp Leu Gly Lys
  1               5                  10                  15

Ser Arg Glu Gly Ser Arg Thr Asp Asp Glu Val Val Gln Arg Glu Glu
             20                  25                  30

Glu Ala Ile Gln Leu Asp Gly Leu Asn Ala Ser Gln Ile Arg Glu Leu
         35                  40                  45

Arg Glu Lys Ser Glu Lys Phe Ala Phe Gln Ala Glu Val Asn Arg Met
     50                  55                  60

Met Lys Leu Ile Ile Asn Ser Leu Tyr Lys Asn Lys Glu Ile Phe Leu
 65                  70                  75                  80

Arg Glu Leu Ile Ser Asn Ala Ser Asp Ala Leu Asp Lys Ile Arg Leu
                 85                  90                  95

Ile Ser Leu Thr Asp Glu Asn Ala Leu Ser Gly Asn Glu Glu Leu Thr
            100                 105                 110

Val Lys Ile Lys Cys Asp Lys Glu Lys Asn Leu Leu His Val Thr Asp
        115                 120                 125

Thr Gly Val Gly Met Thr Arg Glu Glu Leu Val Lys Asn Leu Gly Thr
    130                 135                 140

Ile Ala Lys Ser Gly Thr Ser Glu Phe Leu Asn Lys Met Thr Glu Ala
145                 150                 155                 160

Gln Glu Asp Gly Gln Ser Thr Ser Glu Leu Ile Gly Gln Phe Gly Val
                165                 170                 175

Gly Phe Tyr Ser Ala Phe Leu Val Ala Asp Lys Val Ile Val Thr Ser
            180                 185                 190

Lys His Asn Asn Asp Thr Gln His Ile Trp Glu Ser Asp Ser Asn Glu
        195                 200                 205

Phe Ser Val Ile Ala Asp Pro Arg Gly Asn Thr Leu Gly Arg Gly Thr
    210                 215                 220

Thr Ile Thr Leu Val Leu Lys Glu Glu Ala Ser Asp Tyr Leu Glu Leu
225                 230                 235                 240

Asp Thr Ile Lys Asn Leu Val Lys Lys Tyr Ser Gln Phe Ile Asn Phe
                245                 250                 255

Pro Ile Tyr Val Trp Ser Ser Lys Thr Glu Thr Val Glu Glu Pro Met
            260                 265                 270

Glu Glu Glu Glu Ala Ala Lys Glu Glu Lys Glu Glu Ser Asp Asp Glu
```

```
              275                 280                 285
Ala Ala Val Glu Glu Glu Glu Lys Lys Pro Lys Thr Lys Lys
    290                 295                 300

Val Glu Lys Thr Val Trp Asp Trp Glu Leu Met Asn Asp Ile Lys Pro
305                 310                 315                 320

Ile Trp Gln Arg Pro Ser Lys Glu Val Glu Asp Glu Tyr Lys Ala
                325                 330                 335

Phe Tyr Lys Ser Phe Ser Lys Glu Ser Asp Pro Met Ala Tyr Ile
            340                 345                 350

His Phe Thr Ala Glu Gly Glu Val Thr Phe Lys Ser Ile Leu Phe Val
        355                 360                 365

Pro Thr Ser Ala Pro Arg Gly Leu Phe Asp Glu Tyr Gly Ser Lys Lys
    370                 375                 380

Ser Asp Tyr Ile Lys Leu Tyr Val Arg Val Phe Ile Thr Asp Asp
385                 390                 395                 400

Phe His Asp Met Met Pro Lys Tyr Leu Asn Phe Val Lys Gly Val Val
                405                 410                 415

Asp Ser Asp Asp Leu Pro Leu Asn Val Ser Arg Glu Thr Leu Gln Gln
            420                 425                 430

His Lys Leu Leu Lys Val Ile Arg Lys Lys Leu Val Arg Lys Thr Leu
        435                 440                 445

Asp Met Ile Lys Lys Ile Ala Asp Asp Lys Tyr Asn Asp Thr Phe Trp
    450                 455                 460

Lys Glu Phe Gly Thr Asn Ile Lys Leu Gly Val Ile Glu Asp His Ser
465                 470                 475                 480

Asn Arg Thr Arg Leu Ala Lys Leu Leu Arg Phe Gln Ser Ser His His
                485                 490                 495

Pro Thr Asp Ile Thr Ser Leu Asp Gln Tyr Val Glu Arg Met Lys Glu
            500                 505                 510

Lys Gln Asp Lys Ile Tyr Phe Met Ala Gly Ser Ser Arg Lys Glu Ala
        515                 520                 525

Glu Ser Ser Pro Phe Val Glu Arg Leu Leu Lys Lys Gly Tyr Glu Val
    530                 535                 540

Ile Tyr Leu Thr Glu Pro Val Asp Glu Tyr Cys Ile Gln Ala Leu Pro
545                 550                 555                 560

Glu Phe Asp Gly Lys Arg Phe Gln Asn Val Ala Lys Glu Gly Val Lys
                565                 570                 575

Phe Asp Glu Ser Glu Lys Thr Lys Glu Ser Arg Glu Ala Val Glu Lys
            580                 585                 590

Glu Phe Glu Pro Leu Leu Asn Trp Met Lys Asp Lys Ala Leu Lys Asp
        595                 600                 605

Lys Ile Glu Lys Ala Val Val Ser Gln Arg Leu Thr Glu Ser Pro Cys
    610                 615                 620

Ala Leu Val Ala Ser Gln Tyr Gly Trp Ser Gly Asn Met Glu Arg Ile
625                 630                 635                 640

Met Lys Ala Gln Ala Tyr Gln Thr Gly Lys Asp Ile Ser Thr Asn Tyr
                645                 650                 655

Tyr Ala Ser Gln Lys Lys Thr Phe Glu Ile Asn Pro Arg His Pro Leu
            660                 665                 670

Ile Arg Asp Met Leu Arg Arg Ile Lys Glu Asp Glu Asp Lys Thr
        675                 680                 685

Val Leu Asp Leu Ala Val Val Leu Phe Glu Thr Ala Thr Leu Arg Ser
    690                 695                 700
```

```
Gly Tyr Leu Leu Pro Asp Thr Lys Ala Tyr Gly Asp Arg Ile Glu Arg
705                 710                 715                 720

Met Leu Arg Leu Ser Leu Asn Ile Asp Pro Asp Ala Lys Val Glu Glu
                725                 730                 735

Glu Pro Glu Glu Glu Pro Glu Glu Thr Ala Glu Asp Thr Thr Glu Asp
            740                 745                 750

Thr Glu Gln Asp Glu Asp Glu Glu Met Asp Val Gly Thr Asp Glu Glu
        755                 760                 765

Glu Glu Thr Ala Lys Glu Ser Thr Ala Glu His Asp Glu Leu
        770                 775                 780

<210> SEQ ID NO 49
<211> LENGTH: 57
<212> TYPE: DNA
<213> ORGANISM: Artificial Sequence
<220> FEATURE:
<223> OTHER INFORMATION: Encodes Saccharomyces cerevisiae mating factor
      pre-signal peptide

<400> SEQUENCE: 49
atgagattcc catccatctt cactgctgtt ttgttcgctg cttcttctgc tttggct        57

<210> SEQ ID NO 50
<211> LENGTH: 19
<212> TYPE: PRT
<213> ORGANISM: Artificial Sequence
<220> FEATURE:
<223> OTHER INFORMATION: Saccharomyces cerevisiae mating factor
      pre-signal peptide

<400> SEQUENCE: 50

Met Arg Phe Pro Ser Ile Phe Thr Ala Val Leu Phe Ala Ala Ser Ser
1               5                   10                  15

Ala Leu Ala

<210> SEQ ID NO 51
<211> LENGTH: 966
<212> TYPE: DNA
<213> ORGANISM: Artificial Sequence
<220> FEATURE:
<223> OTHER INFORMATION: Encodes Fab Anti-Her2 HC-GR1 fusion with
      Pre-pro alpha- mating factor signal peptide
      (ScalphaMTprepro)
<221> NAME/KEY: sig_peptide
<222> LOCATION: (1)...(57)
<223> OTHER INFORMATION: Encodes Pre-pro alpha- mating factor signal
      peptide
<221> NAME/KEY: misc_feature
<222> LOCATION: (847)...(966)
<223> OTHER INFORMATION: Encodes GR1 coiled coil

<400> SEQUENCE: 51
atgagattcc catccatctt cactgctgtt ttgttcgctg cttcttctgc tttggctgag      60
gttcagttgg ttgaatctgg aggaggattg gttcaacctg gtggttcttt gagattgtcc    120
tgtgctgctt ccggtttcaa catcaaggac acttacatcc actgggttag acaagctcca    180
ggaaagggat tggagtgggt tgctagaatc tacccaacta acggttacac aagatacgct    240
gactccgtta agggaagatt cactatctct gctgacactt ccaagaacac tgcttacttg    300
cagatgaact ccttgagagc tgaggatact gctgtttact actgttccag atgggggtggt    360 gatggtttct acgctatgga ctactggggt caaggaactt tggttactgt ttcctccgct    420
tctactaagg gaccatctgt tttcccattg gctccatctt ctaagtctac ttccggtggt    480
```

```
actgctgctt tgggatgttt ggttaaagac tacttcccag agccagttac tgtttcttgg      540
aactccggtg ctttgacttc tggtgttcac actttcccag ctgttttgca atcttccggt      600
ttgtactctt tgtcctccgt tgttactgtt ccatcctctt ccttgggtac tcagacttac      660
atctgtaacg ttaaccacaa gccatccaac actaaggttg acaagaaggt tgagccaaag      720
tcctgtggtg gtggtggtag tggaggtggt ggaagtggtg gcggtggttc tgcggccgct      780
tatccatatg atgttccaga ctacgctgga ggtcatcatc atcaccacca tcaccatcat      840
ggtggtgaag agaagtccag attgttggag aaagagaaca gagagttgga agatcatc       900 gctgagaaag aagagagagt ttccgagttg agacaccaat gcaatccgt tggtggttgt      960 taatag                                                                966

<210> SEQ ID NO 52
<211> LENGTH: 705
<212> TYPE: DNA
<213> ORGANISM: Artificial Sequence
<220> FEATURE:
<223> OTHER INFORMATION: Encodes Anti-Her2 LC with Pre-pro alpha- mating
      factor signal peptide (ScalphaMTprepro)
<221> NAME/KEY: sig_peptide
<222> LOCATION: (1)...(57)
<223> OTHER INFORMATION: Encodes Pre-pro alpha- mating factor signal
      peptide

<400> SEQUENCE: 52
atgagattcc catccatctt cactgctgtt tgttcgctg cttcttctgc tttggctgac       60
atccaaatga ctcaatcccc atcttctttg tctgcttccg ttggtgacag agttactatc     120
acttgtagag cttcccagga cgttaatact gctgttgctt ggtatcaaca gaagccagga     180
aaggctccaa agttgttgat ctactccgct tccttcttgt actctggtgt tccatccaga     240
ttctctggtt ccagatccgg tactgacttc actttgacta tctcctcctt gcaaccagaa     300
gatttcgcta cttactactg tcagcagcac tacactactc caccaacttt cggacagggt     360
actaaggttg agatcaagag aactgttgct gctccatccg tttttcatttt cccaccatcc    420 gacgaacagt tgaagtctgg tacagcttcc gttgtttgtt tgttgaacaa cttctaccca    480
agagaggcta aggttcagtg gaaggttgac aacgctttgc aatccggtaa ctcccaagaa    540
tccgttactg agcaagactc taaggactcc acttactcct tgtcctccac tttgactttg    600
tccaaggctg attacgagaa gcacaaggtt tacgcttgtg aggttacaca tcagggtttg    660
tcctccccag ttactaagtc cttcaacaga ggagagtgtt aatag                    705

<210> SEQ ID NO 53
<211> LENGTH: 943
<212> TYPE: DNA
<213> ORGANISM: Artificial Sequence
<220> FEATURE:
<223> OTHER INFORMATION: Encodes Fab Anti-DKK1 HC-GR1 fusion with Alpha
      amylase signal peptide (from Aspergillus niger
      alpha-amylase)
<221> NAME/KEY: sig_peptide
<222> LOCATION: (1)...(60)
<223> OTHER INFORMATION: Encodes Alpha amylase signal peptide
<221> NAME/KEY: misc_feature
<222> LOCATION: (823)...(943)
<223> OTHER INFORMATION: Encodes GR coiled coil

<400> SEQUENCE: 53
atggtcgctt ggtggtcttt gtttctgtac ggtcttcagg tcgctgcacc tgctttggct       60
gaggttcagt tggttcaatc tggtgctgag gttaagaaac tggtgcttc cgttaaggtt     120
```

```
tcctgtaagg cttccggtta cactttcact gactactaca tccactgggt tagacaagct    180
ccaggtcaag gattggaatg gatgggatgg attcactcta actccggtgc tactacttac    240
gctcagaagt tccaggctag agttactatg tccagagaca cttcttcttc cactgcttac    300
atggaattgt ccagattgga atccgatgac actgctatgt acttttgttc agagaggac     360 tactggggac agggaacttt ggttactgtt tcctccgctt ctactaaagg ccctctgtt     420 tttccattgg ctccatgttc tagatccact tccgaatcca ctgctgcttt gggatgtttg    480
gttaaggact acttcccaga gccagttact gtttcttgga actccggtgc tttgacttct    540
ggtgttcaca ctttcccagc tgttttgcaa tcttccggtt tgtactcctt gtcctccgtt    600
gttactgtta cttcctccaa cttcggtact cagacttaca cttgtaacgt tgaccacaag    660
ccatccaaca ctaaggttga caagactgtt gagagaaagt gtggtggtgg tggtagtgga    720
ggtggtggaa gtggtggcgg tggttctgcg ccgcttatc catatgatgt tccagactac    780
gctggaggtc atcatcatca ccaccatcac catcatggtg gtgaagagaa gtccagattg    840
ttggagaaag agaacagaga gttggagaag atcatcgctg agaagaaga gagagtttcc    900 gagttgagac accaattgca atccgttggt ggttgttaat agg                      943

<210> SEQ ID NO 54
<211> LENGTH: 718
<212> TYPE: DNA
<213> ORGANISM: Artificial Sequence
<220> FEATURE:
<223> OTHER INFORMATION: Encodes Fab Anti-DKK1 LC with Alpha amylase
      signal peptide (from Aspergillus niger alpha -amylase)
<221> NAME/KEY: sig_peptide
<222> LOCATION: (1)...(60)
<223> OTHER INFORMATION: Encodes Alpha-amylase signal peptide

<400> SEQUENCE: 54
atggtcgctt ggtggtcttt gtttctgtac ggtcttcagg tcgctgcacc tgctttggct     60
cagtccgttt tgacacaacc accatctgtt tctggtgctc aggacagag agttactatc    120 tcctgtactg gttcctcttc caacattggt gctggttacg atgttcactg gtatcaacag    180
ttgccaggta ctgctccaaa gttgttgatc tacggttact ccaacagacc atctggtgtt    240
ccagacagat ctctctggttc taagtctggt gcttctgctt ccttggctat cactggattg    300
agaccagatg acgaggctga ctactactgt caatcctacg acaactcctt gtcctcttac    360
gttttcggtg tggtactca gttgactgtt ttgtcccagc caaaggctaa tccaactgtt    420
actttgttcc caccatcttc cgaagaactg caggctaata ggctacttt ggtttgtttg    480 atctccgact ctacccagg tgctgttact gttgcttgga aggctgatgg ttctccagtt    540
aaggctggtt tgagactac taagccatcc aagcagtcca ataacaagta cgctgctagc    600
tcttacttgt ccttgacacc agaacaatgg aagtcccaca gatcctactc ttgtcaggtt    660
acacacgagg ttctactgt tgaaaagact gttgctccaa ctgagtgttc ctaatgag      718

<210> SEQ ID NO 55
<211> LENGTH: 972
<212> TYPE: DNA
<213> ORGANISM: Artificial Sequence
<220> FEATURE:
<223> OTHER INFORMATION: Encodes Fab Anti-CD20, C2B8 HC with Alpha
      amylase signal peptide (from Aspergillus niger alpha -amylase)
<221> NAME/KEY: sig_peptide
<222> LOCATION: (1)...(60)
<223> OTHER INFORMATION: Encodes Alpha amylase signal peptide
<221> NAME/KEY: misc_feature
```

```
<222> LOCATION: (876)...(972)
<223> OTHER INFORMATION: Encodes GR1 coiled coil

<400> SEQUENCE: 55
atggttgctt ggtggtcttt gttcttgtac ggattgcaag ttgctgctcc agctttggct      60
caagttcagc tgcaacaacc aggtgctgaa ttggttaagc ctggtgcttc tgttaagatg     120
tcttgtaagg cttctggtta cactttcact cctacaaca tgcactgggt taagcaaact      180
ccaggtagag gattggaatg gattggtgct atctacccag gtaacggtga cacttcttat     240
aaccaaaagt tcaagggaaa ggctactttg actgctgaca atcttcttc tactgcttac      300 atgcaattgt cctccttgac ttctgaagat tctgctgttt actactgtgc tagatccact     360
tactacggtg gtgactggta ctttaatgtt tggggtgctg gtactactgt tactgtctcg     420
agtgcttcta ctaagggacc atctgttttc ccattggctc catcttctaa gtctacttcc     480
ggtggtaccg ctgctttggg atgtttggtt aaagactact cccagagcc agttactgtt      540 tcttggaact ccggtgcttt gacttctggt gttcacactt cccagctgt tttgcaatct      600 tccggtttgt actctttgtc ctccgttgtt actgttccat cctcttcctt gggtactcag     660
acttacatct gtaacgttaa ccacaagcca tccaacacta aggttgacaa gaaggttgag     720
ccaaagtcct gtggtggtgg tggtagtgga ggtggtggaa gtggtggcgg tggttctgcg     780
gccgcttatc catatgatgt tccagactac gctggaggtc atcatcatca ccaccatcac     840
catcatggtg gtgaagagaa gtccagattg ttggagaaag agaacagaga gttggagaag     900
atcatcgctg agaaagaaga gagagtttcc gagttgagac accaattgca atccgttggt     960
ggttgttaat ag                                                          972

<210> SEQ ID NO 56
<211> LENGTH: 702
<212> TYPE: DNA
<213> ORGANISM: Artificial Sequence
<220> FEATURE:
<223> OTHER INFORMATION: Encodes Anti-CD20, C28B LC with Alpha amylase
      signal peptide (from Aspergillus niger alpha
      -amylase)
<221> NAME/KEY: sig_peptide
<222> LOCATION: (1)...(60)
<223> OTHER INFORMATION: Encodes Alpha amylase signal peptide

<400> SEQUENCE: 56
atggttgctt ggtggtcctt gttcttgtac ggattgcaag ttgctgctcc agctttggct      60
gagatcgttt tgacacagtc cccagctact ttgtctttgt ccccaggtga agagctaca      120 ttgtcctgta gagcttcctc ttccgtttcc tacatccact ggtatcaaca aaagccagga     180
caggctccaa gattgttgat ctacgctact tccaacttgg cttccggtat tccagctaga     240
ttctctggtt ctggttccgg tactgacttc actttgacta tctcttcctt ggaaccagag     300
gacttcgctg tttactactg tcaacagtgg acttctaacc caccaacttt cggacaaggt     360
actaaggttg agatcaagcg tacggttgct gctccttccg tttttcatttt cccaccatcc     420 gacgaacaat tgaagtctgg taccgcttcc gttgtttgtt tgttgaacaa cttctaccca     480
cgtgaggcta aggttcagtg gaaggttgac aacgctttgc aatccggtaa ctcccaagaa     540
tccgttactg agcaggattc taaggattcc acttactcat tgtcctccac tttgactttg     600
tccaaggctg attacgagaa gcacaaggtt tacgcatgcg aggttacaca tcagggtttg     660
tcctccccag ttactaagtc cttcaacaga ggagagtgtt aa                         702
```

<210> SEQ ID NO 57
<211> LENGTH: 972
<212> TYPE: DNA
<213> ORGANISM: Artificial Sequence
<220> FEATURE:
<223> OTHER INFORMATION: Encodes Fab Anti-CD20 frame grafted HC-GR1 with
      Alpha amylase signal peptide (from Aspergillus
      niger alpha -amylase)
<221> NAME/KEY: sig_peptide
<222> LOCATION: (1)...(60)
<223> OTHER INFORMATION: Encodes Alpha amylase signal peptide
<221> NAME/KEY: misc_feature
<222> LOCATION: (853)...(972)
<223> OTHER INFORMATION: Encodes GR1 coiled coil

<400> SEQUENCE: 57

```
atggttgctt ggtggtcctt gttcttgtac ggattgcaag ttgctgctcc agctttggct      60
caagttcagc tggttcaatc tggtgctgag gttaagaagc ctggttcctc cgttaaggtt     120
tcctgtaagg cttccggtta cactttcact cctacaaca tgcactgggt tagacaagct     180
ccaggtcaag gattggaatg gatgggtgct atctacccag gtaacggtga cacttcttac     240
aaccagaagt tcaagggtag agttactatc actgctgacg aatccacttc cactgcttac     300
atggaattgt cctcattgag atccgaggac actgctgttt actactgtgc tagatccact     360
tactacggtg gtgactggta ctttaatgtt tggggacagg aactttggt tactgtctcg      420 agtgcttcta ctaagggacc atccgttttt ccattggctc catcctctaa gtctacttcc     480
ggtggtaccg ctgctttggg atgtttggtt aaagactact cccagagcc agttactgtt      540 tcttggaact ccggtgcttt gacttctggt gttcacactt cccagctgt tttgcaatct     600 tccggtttgt actctttgtc ctccgttgtt actgttccat cctcttcctt gggtactcag     660
acttacatct gtaacgttaa ccacaagcca tccaacacta aggttgacaa gaaggttgag     720
ccaaagtcct gtggtggtgg tggtagtgga ggtggtggaa gtggtggcgg tggttctgcg     780
gccgcttatc catatgatgt tccagactac gctggaggtc atcatcatca ccaccatcac     840
catcatggtg gtgaagagaa gtccagattg ttggagaaag agaacagaga gttggagaag     900
atcatcgctg agaagaagaa gagagttcc gagttgagac accaattgca atccgttggt     960
ggttgttaat ag                                                         972
```

<210> SEQ ID NO 58
<211> LENGTH: 702
<212> TYPE: DNA
<213> ORGANISM: Artificial Sequence
<220> FEATURE:
<223> OTHER INFORMATION: Encodes Anti-CD20 frame grafted LC with Alpha
      amylase signal peptide (from Aspergillus niger
      alpha -amylase)
<221> NAME/KEY: sig_peptide
<222> LOCATION: (1)...(60)
<223> OTHER INFORMATION: Encodes Alpha amylase signal peptide

<400> SEQUENCE: 58

```
atggttgctt ggtggtcctt gttcttgtac ggattgcaag ttgctgctcc agctttggct      60
gagatcgttt tgacacagtc cccagctact ttgtctttgt ccccaggtga aagagctaca     120
ttgtcctgta gagcttcctc ttccgtttcc tacatccact ggtatcaaca aaagccagga     180
caggctccaa gattgttgat ctacgctact tccaacttgg cttccggtat tccagctaga     240
ttctctggtt ctggttccgg tactgacttc actttgacta tctcttcctt ggaaccagag     300
gacttcgctg tttactactg tcaacagtgg acttctaacc caccaacttt cggacaaggt     360
actaaggttg agatcaagcg tacggttgct gctccttccg ttttcatttt cccaccatcc     420
```

```
gacgaacaat tgaagtctgg taccgcttcc gttgtttgtt tgttgaacaa cttctaccca      480
cgtgaggcta aggttcagtg aaggttgac aacgctttgc aatccggtaa ctcccaagaa       540
tccgttactg agcaggattc taaggattcc acttactcat tgtcctccac tttgactttg      600
tccaaggctg attacgagaa gcacaaggtt tacgcatgcg aggttacaca tcagggtttg      660
tcctccccag ttactaagtc cttcaacaga ggagagtgtt aa                         702
```

<210> SEQ ID NO 59
<211> LENGTH: 1602
<212> TYPE: DNA
<213> ORGANISM: Artificial Sequence
<220> FEATURE:
<223> OTHER INFORMATION: Encodes Anti-Her2 full length HC with GR1 ORF
      and Pre-pro alpha- mating factor signal peptide
      (ScalphaMTprepro)
<221> NAME/KEY: sig_peptide
<222> LOCATION: (1)...(57)
<223> OTHER INFORMATION: Encodes Signal peptide
<221> NAME/KEY: misc_feature
<222> LOCATION: (1483)...(1602)
<223> OTHER INFORMATION: Encodes GR1 coiled coil

<400> SEQUENCE: 59

```
atgagattcc catccatctt cactgctgtt ttgttcgctg cttcttctgc tttggctgag      60
gttcagttgg ttaatctgg aggaggattg gttcaacctg gtggttcttt gagattgtcc       120
tgtgctgctt ccggtttcaa catcaaggac acttacatcc actgggttag acaagctcca     180
ggaaagggat tggagtgggt tgctagaatc tacccaacta acggttacac aagatacgct     240
gactccgtta agggaagatt cactatctct gctgacactt ccaagaacac tgcttacttg     300
cagatgaact ccttgagagc tgaggatact gctgtttact actgtccag atggggtggt     360 gatggttct acgctatgga ctactggggt caaggaactt tggttactgt ttcctccgct     420
tctactaagg gaccatctgt tttcccattg gctccatctt ctaagtctac ttccggtggt     480
actgctgctt tgggatgttt ggttaaagac tacttcccag agccagttac tgtttcttgg    540
aactccggtg ctttgacttc tggtgttcac acttcccag ctgttttgca atcttccggt      600
ttgtactctt tgtcctccgt tgttactgtt ccatcctctt ccttgggtac tcagacttac    660
atctgtaacg ttaaccacaa gccatccaac actaaggttg acaagaaggt tgagccaaag    720
tcctgtgaca gactcatac ttgtccacca tgtccagctc cagaattgtt gggtggtcct      780
tccgtttttt tgttcccacc aaagccaaag gacactttga tgatctccag aactccagag    840
gttacatgtg ttgttgttga cgtttctcac gaggacccag aggttaagtt caactggtac    900
gttgacggtg ttgaagttca caacgctaag actaagccaa gagaggagca gtacaactcc    960
acttacagag ttgtttccgt tttgactgtt ttgcaccagg attggttgaa cggaaaggag   1020
tacaagtgta aggttccaa caaggctttg ccagctccaa tcgaaaagac tatctccaag   1080
gctaagggtc aaccaagaga gccacaggtt tacactttgc caccatccag agatgagttg   1140
actaagaacc aggtttcctt gacttgtttg gttaagggat tctacccatc cgacattgct   1200
gttgaatggg agtctaacgg tcaaccagag aacaactaca agactactcc acctgttttg   1260
gactctgacg gttccttttt cttgtactcc aagttgactg ttgacaagtc cagatggcaa   1320
cagggtaacg ttttctcctg ttccgttatg catgaggctt gcacaaccaa ctacactcaa   1380
aagtccttgt cttgtccccc tggtaaggcg ccgcttatc catatgatgt tccagactac   1440
gctggaggtc atcatcatca ccaccatcac catcatggtg tgaagagaa gtccagattg   1500
```

```
ttggagaaag agaacagaga gttggagaag atcatcgctg agaaagaaga gagagtttcc    1560
gagttgagac accaattgca atccgttggt ggttgttaat ag                       1602
```

<210> SEQ ID NO 60
<211> LENGTH: 1619
<212> TYPE: DNA
<213> ORGANISM: Artificial Sequence
<220> FEATURE:
<223> OTHER INFORMATION: Encodes Anti-Her2 full length HC with Pre-pro
      alpha- mating factor signal peptide
      (ScalphaMTprepro) and GR1 with single stop codon
      between
<221> NAME/KEY: sig_peptide
<222> LOCATION: (1)...(57)
<223> OTHER INFORMATION: Encodes signal peptide
<221> NAME/KEY: terminator
<222> LOCATION: (1408)...(1410)
<223> OTHER INFORMATION: stop codon
<221> NAME/KEY: misc_feature
<222> LOCATION: (1486)...(1619)
<223> OTHER INFORMATION: Encodes GR1 coiled coil

<400> SEQUENCE: 60

```
atgagattcc catccatctt cactgctgtt tgttcgctg cttcttctgc tttggctgag    60
gttcagttgg ttgaatctgg aggaggattg gttcaacctg gtggttcttt gagattgtcc   120
tgtgctgctt ccggtttcaa catcaaggac acttacatcc actgggttag acaagctcca   180
ggaaagggat tggagtgggt tgctagaatc tacccaacta acggttacac aagatacgct   240
gactccgtta agggaagatt cactatctct gctgacactt ccaagaacac tgcttacttg   300
cagatgaact ccttgagagc tgaggatact gctgtttact actgttccag atggggtggt   360
gatggtttct acgctatgga ctactggggt caaggaactt tggttactgt tcctccgct    420 tctactaagg gaccatctgt tttcccattg gctccatctt ctaagtctac ttccggtggt   480
actgctgctt tgggatgttt ggttaaagac tacttcccag agccagttac tgtttcttgg   540
aactccggtg ctttgacttc tggtgttcac actttcccag ctgttttgca atcttccggt   600
ttgtactctt tgtcctccgt tgttactgtt ccatcctctt ccttgggtac tcagacttac   660
atctgtaacg ttaaccacaa gccatccaac actaaggttg acaagaaggt tgagccaaag   720
tcctgtgaca gactcatac ttgtccacca tgtccagctc cagaattgtt gggtggtcct   780 tccgttttttt tgttcccacc aaagccaaag gacactttga tgatctccag aactccagag   840
gttacatgtg ttgttgttga cgtttctcac gaggacccag aggttaagtt caactggtac   900
gttgacggtg ttgaagttca caacgctaag actaagccaa gagaggagca gtacaactcc   960
acttacagag ttgtttccgt tttgactgtt ttgcaccagg attggttgaa cggaaaggag  1020
tacaagtgta aggtttccaa caaggctttg ccagctccaa tcgaaaagac tatctccaag  1080
gctaagggtc aaccaagaga gccacaggtt tacactttgc caccatccag agatgagttg  1140
actaagaacc aggtttcctt gacttgtttg gttaagggat tctacccatc cgacattgct  1200
gttgaatggg agtctaacgg tcaaccagag aacaactaca agactactcc acctgttttg  1260
gactctgacg gttccttttt cttgtactcc aagttgactg ttgacaagtc cagatggcaa  1320
cagggtaacg tttctcctg ttccgttatg catgaggctt gcacaaccac tacactcaa   1380 aagtccttgt ctttgtcccc tggtaagtag gcggccgctt atccatatga tgttccagac  1440
tacgctggag tcatcatca tcaccaccat caccatcatg gtggtgaaga aagtccaga   1500 ttgttggaga aagagaacag agagttggag aagatcatcg ctgagaaaga agagagagtt   1560
tccgagttga gacaccaatt gcaatccgtt ggtggttgtt aatagggccg ccatttaa    1619
```

<210> SEQ ID NO 61
<211> LENGTH: 1611
<212> TYPE: DNA
<213> ORGANISM: Artificial Sequence
<220> FEATURE:
<223> OTHER INFORMATION: Encodes Anti-CD20 C2B8 full length HC with
      Alpha amylase signal peptide (from Aspergillus niger
      alpha-amylase) (DNA) and GR1 with single stop
      codon between
<221> NAME/KEY: sig_peptide
<222> LOCATION: (1)...(60)
<223> OTHER INFORMATION: Encodes Signal peptide
<221> NAME/KEY: terminator
<222> LOCATION: (1414)...(1416)
<223> OTHER INFORMATION: stop codon
<221> NAME/KEY: misc_feature
<222> LOCATION: (1491)...(1611)
<223> OTHER INFORMATION: Encodes GR1 coiled coil

<400> SEQUENCE: 61

| | |
|---|---|
| atggttgctt ggtggtcttt gttcttgtac ggattgcaag ttgctgctcc agctttggct | 60 |
| caagttcagc tgcaacaacc aggtgctgaa ttggttaagc ctggtgcttc tgttaagatg | 120 |
| tcttgtaagg cttctggtta cactttcact tcctacaaca tgcactgggt taagcaaact | 180 |
| ccaggtagag gattggaatg gattggtgct atctacccag gtaacggtga cacttcttat | 240 |
| aaccaaaagt tcaagggaaa ggctactttg actgctgaca atcttcttc tactgcttac | 300 |
| atgcaattgt cctccttgac ttctgaagat tctgctgttt actactgtgc tagatccact | 360 |
| tactacggtg gtgactggta ctttaatgtt tggggtgctg gtactactgt tactgtctcg | 420 |
| agtgcttcta ctaagggacc atctgttttc ccattggctc catcttctaa gtctacttcc | 480 |
| ggtggtaccg ctgctttggg atgtttggtt aaagactact ccccagagcc agttactgtt | 540 |
| tcttggaact ccggtgcttt gacttctggt gttcacactt cccagctgt tttgcaatct | 600 |
| tccggtttgt actctttgtc ctccgttgtt actgttccat cctcttcctt gggtactcag | 660 |
| acttacatct gtaacgttaa ccacaagcca tccaacacta aggttgacaa gaaggttgag | 720 |
| ccaaagtcct gtgacaagac tcatacttgt ccaccatgtc cagctccaga attgttgggt | 780 |
| ggtccttccg ttttttttgtt cccaccaaag ccaaaggaca ctttgatgat ctccagaact | 840 |
| ccagaggtta catgtgttgt tgttgacgtt tctcacgagg acccagaggt taagttcaac | 900 |
| tggtacgttg acggtgttga agttcacaac gctaagacta gccaagaga ggagcagtac | 960 |
| aactccactt acagagttgt ttccgttttg actgttttgc accaggattg gttgaacgga | 1020 |
| aaggagtaca gtgtaaggt ttccaacaag gctttgccag ctccaatcga aaagactatc | 1080 |
| tccaaggcta agggtcaacc aagagagcca caggtttaca ctttgccacc atccagagat | 1140 |
| gagttgacta gaaccaggt ttccttgact tgtttggtta agggattcta cccatccgac | 1200 |
| attgctgttg aatgggagtc taacggtcaa ccagagaaca actacaagac tactccacct | 1260 |
| gttttggact ctgacggttc ctttttcttg tactccaagt tgactgttga caagtccaga | 1320 |
| tggcaacagg gtaacgtttt ctcctgttcc gttatgcatg aggctttgca caaccactac | 1380 |
| actcaaaagt ccttgtcttt gtcccctggt aagtaggcgg ccgcttatcc atatgatgtt | 1440 |
| ccagactacg ctggaggtca tcatcatcac caccatcacc atcatggtgg tgaagagaag | 1500 |
| tccagattgt tggagaaaga gaacagagag ttggagaaga tcatcgctga aaagaagag | 1560 |
| agagtttccg agttgagaca ccaattgcaa tccgttggtg ttgttaata g | 1611 |

<210> SEQ ID NO 62

```
<211> LENGTH: 1617
<212> TYPE: DNA
<213> ORGANISM: Artificial Sequence
<220> FEATURE:
<223> OTHER INFORMATION: Encodes Anti-CD20 Genmab full length HC with
      with Alpha amylase signal peptide (from Aspergillus
      niger alpha-amylase) and GR1 with single stop
      codon between
<221> NAME/KEY: sig_peptide
<222> LOCATION: (1)...(60)
<223> OTHER INFORMATION: Encodes signal peptide
<221> NAME/KEY: terminator
<222> LOCATION: (1420)...(1422)
<223> OTHER INFORMATION: Stop codon
<221> NAME/KEY: misc_feature
<222> LOCATION: (1498)...(1617)
<223> OTHER INFORMATION: Encodes GR1 coiled coil

<400> SEQUENCE: 62
atggttgctt ggtggtcctt gttcttgtac ggattgcaag ttgctgctcc agctttggct      60
gctgttcagc tggttgaatc tggtggtgga ttggttcaac ctggtagatc cttgagattg     120
tcctgtgctg cttccggttt tactttcggt gactacacta tgcactgggt tagacaagct     180
ccaggaaagg gattgaatg ggtttccggt atttcttgga actccggttc cattggttac      240
gctgattccg ttaagggaag attcactatc tccagagaca cgctaagaa ctccttgtac      300 ttgcagatga ctccttgag agctgaggat actgctttgt actactgtac taaggacaac     360
caatacggtt ctggttccac ttacggattg ggagtttggg acagggaac tttggttact     420 gtctcgagtg cttctactaa gggaccatcc gttttccat ggctccatc ctctaagtct      480 acttccggtg gtaccgctgc tttgggatgt ttggttaaag actacttccc agagccagtt     540
actgtttctt ggaactccgg tgctttgact tctggtgttc acactttccc agctgttttg     600
caatcttccg gtttgtactc tttgtcctcc gttgttactg ttccatcctc ttccttgggt     660
actcagactt acatctgtaa cgttaaccac aagccatcca acactaaggt tgacaagaag     720
gttgagccaa agtcctgtga caagactcat acttgtccac catgtccagc tccagaattg     780
ttgggtggtc cttccgtttt tttgttccca ccaaagccaa aggacacttt tgatgatctcc     840 agaactccag aggttacatg tgttgttgtt gacgtttctc acgaggaccc agaggttaag     900
ttcaactggt acgttgacgg tgttgaagtt cacaacgcta agactaagcc aagagaggag     960
cagtacaact ccacttacag agttgtttcc gttttgactg ttttgcacca ggattggttg    1020
aacggaaagg agtacaagtg taaggtttcc aacaaggctt gccagctcc aatcgaaaag    1080 actatctcca aggctaaggg tcaaccaaga gagccacagg tttacacttt gccaccatcc    1140
agagatgagt tgactaagaa ccaggtttcc ttgacttgtt tggttaaggg attctaccca    1200
tccgacattg ctgttgaatg ggagtctaac ggtcaaccag agaacaacta caagactact    1260
ccacctgttt tggactctga cggttccttt ttcttgtact ccaagttgac tgttgacaag    1320
tccagatggc aacagggtaa cgtttttctc tgttccgtta tgcatgaggc tttgcacaac    1380
cactacactc aaaagtcctt gtctttgtcc cctggtaagt aggcggccgc ttatccatat    1440
gatgttccag actacgctgg aggtcatcat catcaccacc atcaccatca tggtggtgaa    1500
gagaagtcca gattgttgga aaagagaaac agagagttgg agaagatcat cgctgagaaa    1560
gaagagagag tttccgagtt gagacaccaa ttgcaatccg ttggtggttg ttaatag      1617

<210> SEQ ID NO 63
<211> LENGTH: 705
<212> TYPE: DNA
<213> ORGANISM: Artificial Sequence
```

```
<220> FEATURE:
<223> OTHER INFORMATION: Encodes Anti-CD20 Genmab LC with with Alpha
      amylase signal peptide (from Aspergillus niger
      alpha-amylase)
<221> NAME/KEY: sig_peptide
<222> LOCATION: (1)...(60)
<223> OTHER INFORMATION: Encodes signal peptide

<400> SEQUENCE: 63
atggttgctt ggtggtcctt gttcttgtac ggattgcaag ttgctgctcc agctttggct    60
gagatcgttt tgacacagtc cccagctact ttgtctttgt ccccaggtga aagagctaca   120
ttgtcctgta gagcttccca atctgtttcc tcctacttgg cttggtatca acaaaagcca   180
ggacaggctc caagattgtt gatctacgac gcttccaata gagctactgg tatcccagct   240
agattctctg gttctggttc cggtactgac ttcactttga ctatctcttc cttggaacca   300
gaggacttcg ctgtttacta ctgtcagcag agatccaatt ggccattgac tttcggtggt   360
ggtactaagg ttgagatcaa gcgtacggtt gctgctcctt ccgttttcat tttcccacca   420
tccgacgaac aattgaagtc tggtaccgct tccgttgttt gtttgttgaa caacttctac   480
ccacgtgagg ctaaggttca gtggaaggtt gacaacgctt tgcaatccgg taactcccaa   540
gaatccgtta ctgagcagga ttctaaggat tccacttact cattgtcctc cactttgact   600
ttgtccaagg ctgattacga gaagcacaag gtttacgcat gcgaggttac acatcagggt   660
ttgtcctccc cagttactaa gtccttcaac agaggagagt gttaa               705

<210> SEQ ID NO 64
<211> LENGTH: 1611
<212> TYPE: DNA
<213> ORGANISM: Artificial Sequence
<220> FEATURE:
<223> OTHER INFORMATION: Encodes Anti-CD20 full length HC with Alpha
      amylase signal peptide (from Aspergillus niger
      alpha-amylase) and GR1 and stop codon between
<221> NAME/KEY: sig_peptide
<222> LOCATION: (1)...(60)
<223> OTHER INFORMATION: Encodes signal peptide
<221> NAME/KEY: terminator
<222> LOCATION: (1414)...(1416)
<223> OTHER INFORMATION: Stop codon
<221> NAME/KEY: misc_feature
<222> LOCATION: (142)...(1611)
<223> OTHER INFORMATION: Encodes GR1 coiled coil

<400> SEQUENCE: 64
atggttgctt ggtggtcctt gttcttgtac ggattgcaag ttgctgctcc agctttggct    60
caagttcagc tggttcaatc tggtgctgag gttaagaagc tggttcctc cgttaaggtt   120 tcctgtaagg cttccggtta cactttcact tcctacaaca tgcactgggt tagacaagct   180
ccaggtcaag gattggaatg gatgggtgct atctacccag gtaacggtga cacttcttac   240
aaccagaagt tcaagggtag agttactatc actgctgacg aatccacttc cactgcttac   300
atggaattgt cctcattgag atccgaggac actgctgttt actactgtgc tagatccact   360
tactacggtg gtgactggta ctttaatgtt tggggacagg gaactttggt tactgtctcg   420
agtgcttcta ctaagggacc atccgttttt ccattggctc catcctctaa gtctacttcc   480
ggtggtaccg ctgctttggg atgtttggtt aaagactact ccccagagcc agttactgtt   540
tcttggaact ccggtgcttt gacttctggt gttcacactt tcccagctgt tttgcaatct   600
tccggtttgt actctttgtc ctccgttgtt actgttccat cctcttcctt gggtactcag   660
acttacatct gtaacgttaa ccacaagcca tccaacacta ggttgacaa gaaggttgag   720
```

```
ccaaagtcct gtgacaagac tcatacttgt ccaccatgtc cagctccaga attgttgggt    780
ggtccttccg ttttttgtt cccaccaaag ccaaaggaca ctttgatgat ctccagaact    840
ccagaggtta catgtgttgt tgttgacgtt tctcacgagg acccagaggt taagttcaac    900
tggtacgttg acggtgttga agttcacaac gctaagacta agccaagaga ggagcagtac    960
aactccactt acagagttgt tccgttttg actgttttgc accaggattg gttgaacgga   1020
aaggagtaca agtgtaaggt ttccaacaag gctttgccag ctccaatcga aaagactatc   1080
tccaaggcta agggtcaacc aagagagcca caggtttaca ctttgccacc atccagagat   1140
gagttgacta gaaccaggt ttccttgact gttggtta agggattcta cccatccgac   1200
attgctgttg aatgggagtc taacggtcaa ccagagaaca actacaagac tactccacct   1260
gttttggact ctgacggttc cttttcttg tactccaagt tgactgttga caagtccaga   1320
tggcaacagg gtaacgtttt ctcctgttcc gttatgcatg aggctttgca caaccactac   1380
actcaaaagt ccttgtcttt gtcccctggt aagtaggcgg ccgcttatcc atatgatgtt   1440
ccagactacg ctggaggtca tcatcatcac caccatcacc atcatggtgg tgaagagaag   1500
tccagattgt tggagaaaga gaacagagag ttggagaaga tcatcgctga gaaagaagag   1560
agtttccg agttgagaca ccaattgcaa tccgttggtg gttgttaata g             1611

<210> SEQ ID NO 65
<211> LENGTH: 702
<212> TYPE: DNA
<213> ORGANISM: Artificial Sequence
<220> FEATURE:
<223> OTHER INFORMATION: Encodes Anti-CD20 LC with Alpha amylase signal
      peptide (from Aspergillus niger alpha-amylase)
<221> NAME/KEY: sig_peptide
<222> LOCATION: (1)...(60)
<223> OTHER INFORMATION: Encodes signal peptide

<400> SEQUENCE: 65
atggttgctt ggtggtcctt gttcttgtac ggattgcaag ttgctgctcc agctttggct    60
gagatcgttt tgacacagtc cccagctact ttgtctttgt ccccaggtga agagctaca   120
ttgtcctgta gagcttcctc ttccgttcc tacatccact ggtatcaaca aaagccagga   180
caggctccaa gattgttgat ctacgctact tccaacttgg cttccggtat tccagctaga   240
ttctctggtt ctggttccgg tactgacttc actttgacta ctcttccctt ggaaccagag   300
gacttcgctg tttactactg tcaacagtgg acttctaacc caccaacttt cggacaaggt   360
actaaggttg agatcaagcg tacggttgct gctccttccg ttttcatttt cccaccatcc   420
gacgaacaat tgaagtctgg taccgcttcc gttgtttgtt tgttgaacaa cttctaccca   480
cgtgaggcta aggttcagtg gaaggttgac aacgctttgc aatccggtaa ctcccaagaa   540
tccgttactg agcaggattc taaggattcc acttactcat tgtcctccac tttgactttg   600
tccaaggctg attacgagaa gcacaaggtt tacgcatgcg aggttacaca tcagggtttg   660
tcctccccag ttactaagtc cttcaacaga ggagagtgtt aa                      702

<210> SEQ ID NO 66
<211> LENGTH: 993
<212> TYPE: DNA
<213> ORGANISM: Artificial Sequence
<220> FEATURE:
<223> OTHER INFORMATION: Encodes 1D05 Heavy chain with Saccharomyces
      cerevisiae mating factor pre-signal peptide and
      GR1
<221> NAME/KEY: sig_peptide
<222> LOCATION: (1)...(57)
```

<223> OTHER INFORMATION: Encodes signal peptide
<221> NAME/KEY: misc_feature
<222> LOCATION: (874)...(993)
<223> OTHER INFORMATION: Encodes GR1 coiled coil

<400> SEQUENCE: 66

```
atgagattcc catccatctt cactgctgtt ttgttcgctg cttcttccgc tttggctcag      60
gttcaattgg ttcaatccgg tgctgaagtt aagaagcctg gttcctccgt taaggtttcc     120
tgtaaggctt ctggtggtac ttttaactcc cacgctatct ctgggttag acaagctcca      180
ggtcaaggat tggaatggat gggtggtatc aacccaattt gggtatcgc taactacgct      240
caaaagttcc agggtagagt tactattact gctgacgaat ccacttccac tgcttacatg     300
gaattgtcct cattgagatc cgaggacact gctgtttact actgtgctag acactacgag     360
atccagatcg gtagatacgg aatgaacgtt tactacttga tgtacagatt cgcttcttgg     420
ggacagggaa ctttggttac tgtctcgagt gcttctacta aggggccctc tgttttcca     480
ttggctccat gttctagatc cacttccgaa tccactgctg ctttgggatg tttggttaag     540
gactacttcc cagagccagt tactgtttct ggaactccg gtgctttgac ttctggtgtt     600
cacactttcc cagctgtttt gcaatcttcc ggtttgtact ccttgtcctc cgttgttact     660
gttacttcct ccaacttcgg tactcagact tacacttgta acgttgacca caagccatcc     720
aacactaagg ttgacaagac tgttgagaga aagggtggtg gtggtagtgg aggtggtgga     780
agtggtggcg gtggttctgc ggccgcttat ccatatgatg ttccagacta cgctggaggt     840
catcatcatc accaccatca ccatcatggt ggtgaagaga agtccagatt gttggagaaa     900
gagaacagag agttggagaa gatcatcgct gagaagaag agagagtttc cgagttgaga      960
caccaattgc aatccgttgg tggttgttaa tag                                  993
```

<210> SEQ ID NO 67
<211> LENGTH: 251
<212> TYPE: PRT
<213> ORGANISM: Artificial Sequence
<220> FEATURE:
<223> OTHER INFORMATION: 1D05 Heavy chain with Saccharomyces cerevisiae mating factor pre-signal peptide
<221> NAME/KEY: SIGNAL
<222> LOCATION: (1)...(19)
<223> OTHER INFORMATION: Signal peptide

<400> SEQUENCE: 67

```
Met Arg Phe Pro Ser Ile Phe Thr Ala Val Leu Phe Ala Ala Ser Ser
            -15                 -10                  -5

Ala Leu Ala Gln Val Gln Leu Val Gln Ser Gly Ala Glu Val Lys Lys
     -1   1               5                  10

Pro Gly Ser Ser Val Lys Val Ser Cys Lys Ala Ser Gly Gly Thr Phe
         15                  20                  25

Asn Ser His Ala Ile Ser Trp Val Arg Gln Ala Pro Gly Gln Gly Leu
 30                  35                  40                  45

Glu Trp Met Gly Gly Ile Asn Pro Ile Leu Gly Ile Ala Asn Tyr Ala
                 50                  55                  60

Gln Lys Phe Gln Gly Arg Val Thr Ile Thr Ala Asp Glu Ser Thr Ser
             65                  70                  75

Thr Ala Tyr Met Glu Leu Ser Ser Leu Arg Ser Glu Asp Thr Ala Val
         80                  85                  90

Tyr Tyr Cys Ala Arg His Tyr Glu Ile Gln Ile Gly Arg Tyr Gly Met
     95                 100                 105
```

| | | | | | | | | | | | | |
|---|---|---|---|---|---|---|---|---|---|---|---|---|
| Asn | Val | Tyr | Tyr | Leu | Met | Tyr | Arg | Phe | Ala | Ser | Trp | Gly | Gln | Gly | Thr |
| 110 | | | | | 115 | | | | | 120 | | | | | 125 |

Leu Val Thr Val Ser Ser Ala Ser Thr Lys Gly Pro Ser Val Phe Pro
                130                 135                 140

Leu Ala Pro Cys Ser Arg Ser Thr Ser Glu Ser Thr Ala Ala Leu Gly
            145                 150                 155

Cys Leu Val Lys Asp Tyr Phe Pro Glu Pro Val Thr Val Ser Trp Asn
        160                 165                 170

Ser Gly Ala Leu Thr Ser Gly Val His Thr Phe Pro Ala Val Leu Gln
    175                 180                 185

Ser Ser Gly Leu Tyr Ser Leu Ser Ser Val Val Thr Val Thr Ser Ser
190                 195                 200                 205

Asn Phe Gly Thr Gln Thr Tyr Thr Cys Asn Val Asp His Lys Pro Ser
                210                 215                 220

Asn Thr Lys Val Asp Lys Thr Val Glu Arg Lys
            225                 230

<210> SEQ ID NO 68
<211> LENGTH: 702
<212> TYPE: DNA
<213> ORGANISM: Artificial Sequence
<220> FEATURE:
<223> OTHER INFORMATION: Encodes 1D05 light chain with Saccharomyces
      cerevisiae mating factor pre-signal peptide
<221> NAME/KEY: sig_peptide
<222> LOCATION: (1)...(57)
<223> OTHER INFORMATION: Encodes signal peptide

<400> SEQUENCE: 68

```
atgagattcc catccatctt cactgctgtt ttgttcgctg cttcttctgc tttggctgac     60
atccaaatga cacaatcccc atcttccttg tctgcttccg ttggtgacag agttactatc    120
acttgtagag cttcccaagg tatcagatcc gctttgaact ggtatcaaca gaagccagga    180
aaggctccaa agttgttgat ctacaacggt tccactttgc aatctggtgt tccatctaga    240
ttctctggtt ccggttctgg tactgacttc actttgacta tctcttcctt gcaaccagag    300
gacttcgctg tttactactg tcaacagttc gatggtgacc caacttttgg acagggtact    360
aaggttgaga tcaagagaac tgttgctgct ccatccgttt tcattttccc accatccgac    420
gaacaattga gtctggtac cgcttccgtt gtttgtttgt tgaacaactt ctacccacgt    480
gaggctaagg ttcagtggaa ggttgacaac gctttgcaat ccggtaactc ccaagaatcc    540
gttactgagc aggattctaa ggattccact tactcattgt cctccacttt gactttgtcc    600
aaggctgatt acgagaagca caaggtttac gcttgcgagg ttacacatca gggtttgtcc    660
tccccagtta ctaagtcctt caacagagga gagtgttaat ag                      702
```

<210> SEQ ID NO 69
<211> LENGTH: 232
<212> TYPE: PRT
<213> ORGANISM: Artificial Sequence
<220> FEATURE:
<223> OTHER INFORMATION: 1D05 LC with Saccharomyces cerevisiae mating
      factor pre-signal peptide
<221> NAME/KEY: SIGNAL
<222> LOCATION: (1)...(19)
<223> OTHER INFORMATION: Signal peptide

<400> SEQUENCE: 69

Met Arg Phe Pro Ser Ile Phe Thr Ala Val Leu Phe Ala Ala Ser Ser
            -15                 -10                  -5

Ala Leu Ala Asp Ile Gln Met Thr Gln Ser Pro Ser Ser Leu Ser Ala
        -1   1               5                  10

Ser Val Gly Asp Arg Val Thr Ile Thr Cys Arg Ala Ser Gln Gly Ile
        15                  20                  25

Arg Ser Ala Leu Asn Trp Tyr Gln Gln Lys Pro Gly Lys Ala Pro Lys
30                  35                  40                  45

Leu Leu Ile Tyr Asn Gly Ser Thr Leu Gln Ser Gly Val Pro Ser Arg
            50                  55                  60

Phe Ser Gly Ser Gly Ser Gly Thr Asp Phe Thr Leu Thr Ile Ser Ser
            65                  70                  75

Leu Gln Pro Glu Asp Phe Ala Val Tyr Tyr Cys Gln Gln Phe Asp Gly
        80                  85                  90

Asp Pro Thr Phe Gly Gln Gly Thr Lys Val Glu Ile Lys Arg Thr Val
        95                  100                 105

Ala Ala Pro Ser Val Phe Ile Phe Pro Pro Ser Asp Glu Gln Leu Lys
110                 115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
            145                 150                 155

Ser Gln Glu Ser Val Thr Glu Gln Asp Ser Lys Asp Ser Thr Tyr Ser
            160                 165                 170

Leu Ser Ser Thr Leu Thr Leu Ser Lys Ala Asp Tyr Glu Lys His Lys
        175                 180                 185

Val Tyr Ala Cys Glu Val Thr His Gln Gly Leu Ser Ser Pro Val Thr
190                 195                 200                 205

Lys Ser Phe Asn Arg Gly Glu Cys
                210

<210> SEQ ID NO 70
<211> LENGTH: 945
<212> TYPE: DNA
<213> ORGANISM: Artificial Sequence
<220> FEATURE:
<223> OTHER INFORMATION: Encodes 1H23 heavy chain with Aspergillus
      amylase signal sequence and GR1
<221> NAME/KEY: sig_peptide
<222> LOCATION: (1)...(60)
<223> OTHER INFORMATION: Encodes ignal peptide
<221> NAME/KEY: misc_feature
<222> LOCATION: (826)...(945)
<223> OTHER INFORMATION: Encodes GR1 coiled coil

<400> SEQUENCE: 70
atggttgctt ggtggtcctt gttcttgtac ggattgcaag ttgctgctcc agctttggct     60
caagttcagt tggttgaatc cggtggtgga ttggttcaac tggtggttc tttgagattg    120 tcctgtgctg cttccggttt tactttctcc gactactaca tgcactgggt tagacaagca    180
cctggaaagg gattgaatg ggtttccaac atttctggtt ccggttccac tacttactac    240
gctgattccg ttaagggaag attcactatc tccagagaca actccaagaa cactttgtac    300
ttgcagatga actccttgag agctgaggat actgctgttt actactgtgc tagaggaatg    360
tttgacttct ggggacaggg aactttggtt actgtctcga gtgcttctac taagggccc    420 tctgtttttc cattggctcc atgttctaga tccacttccg aatccactgc tgctttggga    480
tgtttggtta aggactactt cccagagcca gttactgttt cttggaactc cggtgctttg    540
acttctggtg ttcacacttt cccagctgtt ttgcaatctt ccggttttgta ctccttgtcc    600

```
tccgttgtta ctgttacttc ctccaacttc ggtactcaga cttacacttg taacgttgac    660
cacaagccat ccaacactaa ggttgacaag actgttgaga gaaagggtgg tggtggtagt    720
ggaggtggtg aagtggtgg cggtggttct gcggccgctt atccatatga tgttccagac     780
tacgctggag gtcatcatca tcaccaccat caccatcatg gtggtgaaga gaagtccaga    840
ttgttggaga aagagaacag agagttggag aagatcatcg ctgagaaaga agagagagtt    900
tccgagttga gacaccaatt gcaatccgtt ggtggttgtt aatag                    945
```

<210> SEQ ID NO 71
<211> LENGTH: 234
<212> TYPE: PRT
<213> ORGANISM: Artificial Sequence
<220> FEATURE:
<223> OTHER INFORMATION: 1H23 heavy chain with Aspergillus amylase
    signal sequence
<221> NAME/KEY: SIGNAL
<222> LOCATION: (1)...(19)
<223> OTHER INFORMATION: Signal peptide

<400> SEQUENCE: 71

```
Met Arg Phe Pro Ser Ile Phe Thr Ala Val Leu Phe Ala Ala Ser Ser
            -15                 -10                  -5

Ala Leu Ala Gln Val Gln Leu Val Glu Ser Gly Gly Gly Leu Val Gln
     -1   1               5                  10

Pro Gly Gly Ser Leu Arg Leu Ser Cys Ala Ala Ser Gly Phe Thr Phe
         15                  20                  25

Ser Asp Tyr Tyr Met His Trp Val Arg Gln Ala Pro Gly Lys Gly Leu
 30                  35                  40                  45

Glu Trp Val Ser Asn Ile Ser Gly Ser Gly Ser Thr Thr Tyr Tyr Ala
                 50                  55                  60

Asp Ser Val Lys Gly Arg Phe Thr Ile Ser Arg Asp Asn Ser Lys Asn
             65                  70                  75

Thr Leu Tyr Leu Gln Met Asn Ser Leu Arg Ala Glu Asp Thr Ala Val
         80                  85                  90

Tyr Tyr Cys Ala Arg Gly Met Phe Asp Phe Trp Gly Gln Gly Thr Leu
 95                  100                 105

Val Thr Val Ser Ser Ala Ser Thr Lys Gly Pro Ser Val Phe Pro Leu
110                 115                 120                 125

Ala Pro Cys Ser Arg Ser Thr Ser Glu Ser Thr Ala Ala Leu Gly Cys
                130                 135                 140

Leu Val Lys Asp Tyr Phe Pro Glu Pro Val Thr Val Ser Trp Asn Ser
            145                 150                 155

Gly Ala Leu Thr Ser Gly Val His Thr Phe Pro Ala Val Leu Gln Ser
        160                 165                 170

Ser Gly Leu Tyr Ser Leu Ser Ser Val Val Thr Val Ser Ser Asn
    175                 180                 185

Phe Gly Thr Gln Thr Tyr Thr Cys Asn Val Asp His Lys Pro Ser Asn
190                 195                 200                 205

Thr Lys Val Asp Lys Thr Val Glu Arg Lys
                210                 215
```

<210> SEQ ID NO 72
<211> LENGTH: 717
<212> TYPE: DNA
<213> ORGANISM: Artificial Sequence
<220> FEATURE:
<223> OTHER INFORMATION: Encodes 1H23 light chain with Aspergillus
    amylase signal sequence <221> NAME/KEY: sig_peptide
<222> LOCATION: (1)...(60)
<223> OTHER INFORMATION: Encodes signal peptide

<400> SEQUENCE: 72

```
atggttgctt ggtggtcctt gttcttgtac ggattgcaag ttgctgctcc agctttggct      60
gacatcgttt tgacacagtc cccagctact ttgtctttgt ccccaggtga agagctaca     120
ttgtcctgta gagcttccca atccgttaac tccaactact ggcttggta tcaacaaaag     180
ccaggacagg ctccaagatt gttgatctac ggtgcttctt ctagagctac tggtgttcca     240
gctagattct ctggttctgg ttccggtact gacttcactt tgactatctc ttccttggaa     300
ccagaggact cgctgttta ctactgtcaa cagtggggtg acgttccaat tactttcgga     360
cagggtacta aggttgagat caagagaact gttgctgctc cttccgtttt catttcccca     420
ccatccgacg aacaattgaa gtctggtacc ggtaccgctt ccgttgtttg tttgttgaac     480
aacttctacc cacgtgaggc taaggttcag tggaaggttg acaacgcttt gcaatccggt     540
aactcccaag aatccgttac tgagcaggat tctaaggatt ccacttactc attgtcctcc     600
actttgactt tgtccaaggc tgattacgag aagcacaagg tttacgcttg cgaggttaca     660
catcagggtt tgtcctcccc agttactaag tccttcaaca gaggagagtg ttaatag        717
```

<210> SEQ ID NO 73
<211> LENGTH: 237
<212> TYPE: PRT
<213> ORGANISM: Artificial Sequence
<220> FEATURE:
<223> OTHER INFORMATION: 1H23 light chain
<221> NAME/KEY: SIGNAL
<222> LOCATION: (1)...(20)
<223> OTHER INFORMATION: Signal peptide

<400> SEQUENCE: 73

```
Met Val Ala Trp Trp Ser Leu Phe Leu Tyr Gly Leu Gln Val Ala Ala
-20             -15                 -10                  -5

Pro Ala Leu Ala Asp Ile Val Leu Thr Gln Ser Pro Ala Thr Leu Ser
            -1   1               5                  10

Leu Ser Pro Gly Glu Arg Ala Thr Leu Ser Cys Arg Ala Ser Gln Ser
        15                  20                  25

Val Asn Ser Asn Tyr Leu Ala Trp Tyr Gln Gln Lys Pro Gly Gln Ala
    30                  35                  40

Pro Arg Leu Leu Ile Tyr Gly Ala Ser Ser Arg Ala Thr Gly Val Pro
45                  50                  55                  60

Ala Arg Phe Ser Gly Ser Gly Ser Gly Thr Asp Phe Thr Leu Thr Ile
                65                  70                  75

Ser Ser Leu Glu Pro Glu Asp Phe Ala Val Tyr Tyr Cys Gln Gln Trp
            80                  85                  90

Gly Asp Val Pro Ile Thr Phe Gly Gln Gly Thr Lys Val Glu Ile Lys
        95                  100                 105

Arg Thr Val Ala Ala Pro Ser Val Phe Ile Phe Pro Pro Ser Asp Glu
    110                 115                 120

Gln Leu Lys Ser Gly Thr Gly Thr Ala Ser Val Val Cys Leu Leu Asn
125                 130                 135                 140

Asn Phe Tyr Pro Arg Glu Ala Lys Val Gln Trp Lys Val Asp Asn Ala
                145                 150                 155

Leu Gln Ser Gly Asn Ser Gln Glu Ser Val Thr Glu Gln Asp Ser Lys
            160                 165                 170
```

```
Asp Ser Thr Tyr Ser Leu Ser Ser Thr Leu Thr Leu Ser Lys Ala Asp
            175                 180                 185

Tyr Glu Lys His Lys Val Tyr Ala Cys Glu Val Thr His Gln Gly Leu
        190                 195                 200

Ser Ser Pro Val Thr Lys Ser Phe Asn Arg Gly Glu Cys
205                 210                 215

<210> SEQ ID NO 74
<211> LENGTH: 662
<212> TYPE: PRT
<213> ORGANISM: Artificial Sequence
<220> FEATURE:
<223> OTHER INFORMATION: PCSK9

<400> SEQUENCE: 74

Gln Glu Asp Glu Asp Gly Asp Tyr Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
            85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
            115                 120                 125

Glu Arg Ile Thr Pro Pro Arg Tyr Arg Ala Asp Glu Tyr Gln Pro Pro
        130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
305                 310                 315                 320
```

```
Leu Gly Thr Asn Phe Gly Arg Cys Val Asp Leu Phe Ala Pro Gly Glu
            325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
            355                 360                 365

Met Leu Ser Ala Glu Pro Glu Leu Thr Leu Ala Glu Leu Arg Gln Arg
            370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                    405                 410                 415

Ser Thr His Gly Ala Gly Trp Gln Leu Phe Cys Arg Thr Val Trp Ser
                    420                 425                 430

Ala His Ser Gly Pro Thr Arg Met Ala Thr Ala Ile Ala Arg Cys Ala
            435                 440                 445

Pro Asp Glu Glu Leu Leu Ser Cys Ser Ser Phe Ser Arg Ser Gly Lys
450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                    485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
            515                 520                 525

Leu Thr Gly Cys Ser Ser His Trp Glu Val Glu Asp Leu Gly Thr His
            530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                    565                 570                 575

Glu Cys Lys Val Lys Glu His Gly Ile Pro Ala Pro Gln Glu Gln Val
                    580                 585                 590

Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys
            610                 615                 620

Val Val Arg Ser Arg Asp Val Ser Thr Thr Gly Ser Thr Ser Glu Glu
625                 630                 635                 640

Ala Val Thr Ala Val Ala Ile Cys Cys Arg Ser Arg His Leu Ala Gln
                    645                 650                 655

Ala Ser Gln Glu Leu Gln
            660
```

SURFACE DISPLAY OF RECOMBINANT PROTEINS IN LOWER EUKARYOTES

This Application is a Divisional of U.S. patent application Ser. No. 12/863,911, filed Jul. 21, 2010; which is the national stage application, filed under 35 U.S.C. §371, of International Patent Application No. PCT/US09/34631, filed Feb. 20, 2009; which claims the benefit of U.S. Provisional Patent Application No. 61/067,965, filed Mar. 3, 2008; each of which is herein incorporated by reference in its entirety.

BACKGROUND OF THE INVENTION (1) Field of the Invention

The present invention relates to methods for display of recombinant proteins or protein libraries on the surface of lower eukaryotes such as yeast and filamentous fungi. The methods are useful for screening libraries of recombinant proteins in lower eukaryotes to identify particular proteins with desired properties from the array of proteins in the libraries. The methods are particularly useful for constructing and screening antibody libraries in lower eukaryotes.

(2) Description of Related Art

The discovery of monoclonal antibodies has evolved from hybridoma technology for producing the antibodies to direct selection of antibodies from human cDNA or synthetic DNA libraries. This has been driven in part by the desire to engineer improvements in binding affinity and specificity of the antibodies to improve efficacy of the antibodies. Thus, combinatorial library screening and selection methods have become a common tool for altering the recognition properties of proteins (Ellman et al., Proc. Natl. Acad. Sci. USA 94: 2779-2782 (1997): Phizicky & Fields, Microbiol. Rev. 59: 94-123 (1995)). The ability to construct and screen antibody libraries in vitro promises improved control over the strength and specificity of antibody-antigen interactions.

The most widespread technique for constructing and screening antibody libraries is phage display, whereby the protein of interest is expressed as a polypeptide fusion to a bacteriophage coat protein and subsequently screened by binding to immobilized or soluble biotinylated ligand. Fusions are made most commonly to a minor coat protein, called the gene III protein (pIII), which is present in three to five copies at the tip of the phage. A phage constructed in this way can be considered a compact genetic "unit", possessing both the phenotype (binding activity of the displayed antibody) and genotype (the gene coding for that antibody) in one package. Phage display has been successfully applied to antibodies, DNA binding proteins, protease inhibitors, short peptides, and enzymes (Choo & Klug, Curr. Opin. Biotechnol. 6: 431-436 (1995); Hoogenboom, Trends Biotechnol. 15: 62-70 (1997); Ladner, Trends Biotechnol. 13: 426-430 (1995); Lowman et al., Biochemistry 30: 10832-10838 (1991); Markland et al., Methods Enzymol. 267: 28-51 (1996); Matthews & Wells, Science 260: 1113-1117 (1993); Wang et al., Methods Enzymol. 267: 52-68 (1996)).

Antibodies possessing desirable binding properties are selected by binding to immobilized antigen in a process called "panning." Phage bearing nonspecific antibodies are removed by washing, and then the bound phage are eluted and amplified by infection of E. coli. This approach has been applied to generate antibodies against many antigens.

Nevertheless, phage display possesses several shortcomings. Although panning of antibody phage display libraries is a powerful technology, it possesses several intrinsic difficulties that limit its wide-spread successful application. For example, some eukaryotic secreted proteins and cell surface proteins require post-translational modifications such as glycosylation or extensive disulfide isomerization, which are unavailable in bacterial cells. Furthermore, the nature of phage display precludes quantitative and direct discrimination of ligand binding parameters. For example, very high affinity antibodies (K d≤1 nM) are difficult to isolate by panning, since the elution conditions required to break a very strong antibody-antigen interaction are generally harsh enough (e.g., low pH, high salt) to denature the phage particle sufficiently to render it non-infective. Additionally, the requirement for physical immobilization of an antigen to a solid surface produces many artifactual difficulties. For example, high antigen surface density introduces avidity effects which mask true affinity. Also, physical tethering reduces the translational and rotational entropy of the antigen, resulting in a smaller DS upon antibody binding and a resultant overestimate of binding affinity relative to that for soluble antigen and large effects from variability in mixing and washing procedures lead to difficulties with reproducibility. Furthermore, the presence of only one to a few antibodies per phage particle introduces substantial stochastic variation, and discrimination between antibodies of similar affinity becomes impossible. For example, affinity differences of 6-fold or greater are often required for efficient discrimination (Riechmann & Weill, '93). Finally, populations can be overtaken by more rapidly growing wild-type phage. In particular, since pIII is involved directly in the phage life cycle, the presence of some antibodies or bound antigens will prevent or retard amplification of the associated phage.

Several bacterial cell surface display methods have been developed (Francisco, et al., Proc. Natl. Acad. Sci. USA 90: 10444-10448 (1993); Georgiou et al., Nat. Biotechnol. 15: 29-34 (1997)). However, use of a prokaryotic expression system occasionally introduces unpredictable expression biases (Knappik & Pluckthun, Prot. Eng. 8: 81-89 (1995); Ulrich et al., Proc. Natl. Acad. Sci. USA 92: 11907-11911 (1995); Walker & Gilbert, J. Biol. Chem 269: 28487-28493 (1994)) and bacterial capsular polysaccharide layers present a diffusion barrier that restricts such systems to small molecule ligands (Roberts, Annu. Rev. Microbiol. 50: 285-315 (1996)). E. coli possesses a lipopolysaccharide layer or capsule that may interfere sterically with macromolecular binding reactions. In fact, a presumed physiological function of the bacterial capsule is restriction of macromolecular diffusion to the cell membrane, in order to shield the cell from the immune system (DiRienzo et al., Ann. Rev. Blochem. 47: 481-532, (1978)). Since the periplasm of E. coli has not evolved as a compartment for the folding and assembly of antibody fragments, expression of antibodies in E. coli has typically been very clone dependent, with some clones expressing well and others not at all. Such variability introduces concerns about equivalent representation of all possible sequences in an antibody library expressed on the surface of E. coli. Moreover, phage display does not allow some important posttranslational modifications such as glycosylation that can affect specificity or affinity of the antibody. About a third of circulating monoclonal antibodies contain one or more N-linked glycans in the variable regions. In some cases it is believed that these N-glycans in the variable region may play a significant role in antibody function.

The discovery of novel therapeutics would be facilitated by the development of alternative selection systems that relied upon eukaryotic cells, such as yeast cells. The structural similarities between B-cells displaying antibodies and yeast cells displaying antibodies provide a closer analogy to in vivo affinity maturation than is available with filamentous phage. Moreover, the ease of growth culture and facility of genetic manipulation available with yeast will enable large populations to be mutagenized and screened rapidly. By contrast with conditions in the mammalian body, the physicochemical conditions of binding and selection can be altered for a yeast culture within a broad range of pH, temperature, and ionic strength to provide additional degrees of freedom in antibody engineering experiments. The development of yeast surface display system for screening combinatorial protein libraries has been described.

U.S. Pat. Nos. 6,300,065 and 6,699,658 describe the development of a yeast surface display system for screening combinatorial antibody libraries and a screen based on antibody-antigen dissociation kinetics. The system relies on transforming yeast with vectors that express an antibody or antibody fragment fused to a yeast cell surface anchoring protein, using mutagenesis to produce a variegated population of mutants of the antibody or antibody fragment and then screening and selecting those cells that produce the antibody or antibody fragment with the desired enhanced phenotypic properties. U.S. Pat. No. 7,132,273 discloses various yeast cell wall anchor proteins and a surface expression system that uses them to immobilize foreign enzymes or polypeptides on the cell wall.

U.S. Published Application No. 2005/0142562 discloses Compositions, kits and methods are provided for generating highly diverse libraries of proteins such as antibodies via homologous recombination in vivo, and screening these libraries against protein, peptide and nucleic acid targets using a two-hybrid method in yeast. The method for screening a library of tester proteins against a target protein or peptide comprises expressing a library of tester proteins in yeast cells, each tester protein being a fusion protein comprised of a first polypeptide subunit whose sequence varies within the library, a second polypeptide subunit whose sequence varies within the library independently of the first polypeptide, and a linker peptide which links the first and second polypeptide subunits; expressing one or more target fusion proteins in the yeast cells expressing the tester proteins, each of the target fusion proteins comprising a target peptide or protein; and selecting those yeast cells in which a reporter gene is expressed, the expression of the reporter gene being activated by binding of the tester fusion protein to the target fusion protein.

Of interest are Tanino et al, Biotechnol. Prog. 22: 989-993 (2006), which discloses construction of a *Pichia pastoris* cell surface display system using Flo1p anchor system; Ren et al., Molec. Biotechnol. 35:103-108 (2007), which discloses the display of adenoregulin in a *Pichia pastoris* cell surface display system using the Flo1p anchor system; Mergler et al., Appl. Microbiol. Biotechnol. 63:418-421 (2004), which discloses display of *K. lactis* yellow enzyme fused to the C-terminus half of *S. cerevisiae* α-agglutinin; Jacobs et al., Abstract T23, *Pichia* Protein expression Conference, San Diego, Calif. (Oct. 8-11, 2006), which discloses display of proteins on the surface of *Pichia pastoris* using α-agglutinin; Ryckaert et al., Abstracts BVBMB Meeting, Vrije Universiteit Brussel, Belgium (Dec. 2, 2005), which discloses using a yeast display system to identify proteins that bind particular lectins; U.S. Pat. No. 7,166,423, which discloses a method for identifying cells based on the product secreted by the cells by coupling to the cell surface a capture moiety that binds the secreted product, which can then be identified using a detection means; U.S. Published Application No. 2004/0219611, which discloses a biotin-avidin system for attaching protein A or G to the surface of a cell for identifying cells that express particular antibodies; U.S. Pat. No. 6,919,183, which discloses a method for identifying cells that express a particular protein by expressing in the cell a surface capture moiety and the protein wherein the capture moiety and the protein form a complex which is displayed on the surface of the cell; U.S. Pat. No. 6,114,147, which discloses a method for immobilizing proteins on the surface of a yeast or fungal using a fusion protein consisting of a binding protein fused to a cell surface anchoring protein which is expressed in the cell.

The potential applications of engineering antibodies for the diagnosis and treatment of human disease such as cancer therapy, tumor imaging, sepsis are far-reaching. For these applications, antibodies with high affinity (i.e., K d≤10 nM) and high specificity are highly desirable. Anecdotal evidence, as well as the a priori considerations discussed previously, suggest that phage display or bacterial display systems are unlikely to consistently produce antibodies of sub-nanomolar affinity. To date, yeast display will fill this gap and as such should be a key technology of tremendous commercial and medical significance.

Development of further protein expression systems for yeasts and filamentous fungi, such as *Pichia pastoris*, based on improved vectors and host cell lines in which effective protein display facilitates development of genetically enhanced yeast strains for recombinant production of proteins, and in particular, for recombinant production of monoclonal antibodies, is a desirable objective.

BRIEF SUMMARY OF THE INVENTION

The present invention provides a method for expressing and displaying proteins on the surface of a lower eukaryote in a form that is accessible for detection. Combining this method with fluorescence-activated cell sorting (FACS) provides a means for selecting cells that express proteins with increased or decreased affinity for another molecule, catalytic activity, altered specificity, or conditional binding. The method is particularly useful for constructing and screening antibody libraries in lower eukaryotes such as yeast or filamentous fungi.

In a further aspect, there is provided a method of genetic fusion of a lower eukaryote cell surface anchoring protein to a first binding moiety and genetic fusion of a polypeptide of interest to a second binding moiety that is capable of pairwise binding to the first binding moiety. Nucleic acids comprising the genetic fusions are transformed into host cells. Expression of the genetic fusions provides a cell surface anchoring protein wherein the first binding moiety binds the second binding moiety and at the cell surface presents the protein of interest. When the protein of interest is an antibody, one effectively can mimic the cell surface display of antibodies by B cells in the immune system.

In further aspects, the first and second binding moieties are adapter peptide are derived from the sequences of homodimeric or heterodimeric proteins that are involved in the formation of stable protein complexes. In particular embodiments, these peptides are coiled coil peptides that are capable of forming a dimeric complex such as the coiled coil peptides comprising the GABAB-R1/GABA-R2 receptors.

In one aspect of the present invention, provided is a method for selecting proteins with desirable binding properties comprising: transforming lower eukaryote host cells with nucleic acids expressing a host cell wall binding protein fused at its N- or C-terminus to a first adapter peptide and a protein to be tested fused at its C-terminus to a second adapter peptide capable of pairwise binding to the first adapter peptide; labeling the host cells with a first label, wherein the first label associates with or binds to host cells expressing the protein to be tested and does not associate with or bind to host cells which do not express the protein to be tested; selecting for the host cells with which the first label is associated; and quantitating said first label, wherein a high occurrence of the first label indicates the protein to be tested has desirable binding properties and wherein a low occurrence of the first label indicates the protein to be tested does not have desirable binding properties.

A further embodiment of the present invention further includes the steps of: labeling the host cells with a second label, wherein the second label associates with or binds to host cells expressing an epitope tag fused to the protein to be tested and encoded by the nucleic acid and does not associate with or bind to host cells which do not express the epitope tag encoded by the nucleic acid; quantitating the second label, wherein an occurrence of the second label indicates a number of expressed copies of the epitope-tagged protein to be tested on the host cell surface: and comparing said quanititation of the first label to the quantitation of the second label to determine the occurrence of the first label normalized for the occurrence of the second label, wherein a high occurrence of the first label relative to the occurrence of the second label indicates the protein to be tested has desirable binding properties.

Another further embodiment of the present invention includes the steps of: labeling the host cells with a third label that competes with the first label for binding to the protein to be tested; labeling the yeast cells with the first label; quantitating said first label; labeling the host cells with the second label; quantitating the second label; and comparing the quantitation of the first label to the quantitation of the second label to determine the occurrence of the first label normalized for the occurrence of the second label, wherein a low occurrence of the first label relative to the occurrence of the second label indicates the protein to be tested has desirable binding properties.

In one embodiment of the present invention, the first label is a fluorescent label attached to a ligand and the second label is a fluorescent label attached to an antibody. When the labels are fluoresceit, the quantitation step is performed by flow cytometry or confocal fluorescence microscopy.

Another aspect of the present invention provides vectors for performing the method of the present invention, a vector comprising a nucleic acid encoding a cell wall binding protein fused to a first adapter peptide and a vector comprising a nucleic acid encoding a protein of interest fused at its C-terminus to a second adapter peptide capable of pairwise binding to the first adapter peptide. Further embodiments of this aspect include means for expressing a polypeptide epitope tag fused to the protein of interest in the host cells. Further still embodiments provide that the cell wall binding protein is GPI-anchored cell surface anchoring protein, in particular embodiments, a SED1 protein.

Further provided is a method for selecting antibodies and fragments thereof with desirable binding properties, performed as described above using a vector in which a single stop codon is place between the nucleic acid encoding the antibody sequence and the nucleic acid encoding the second adapter peptide. The vector is transformed into lower eukaryote host cells comprising nucleic acids expressing a host cell wall binding protein fused at its N- or C-terminus to a first adapter peptide that is capable of pairwise binding to the second adapter peptide. Translation of mRNA transcribed from the vector is performed under conditions that increases translational readthrough through the stop codon thereby resulting in the production of antibodies that are fused to the second adapter. Labeling the host cells with a first label, wherein the first label associates with or binds to host cells expressing the desired antibodies and does not associate with or bind to host cells which do not express the desired antibodies enables identification and selection of those host cells that produce the desired antibodies. After the host cells that produce the desired antibodies have been selected and isolated, the host cells are grown under conditions that do result in an increase in translational readthrough through the stop codon. Under the second conditions, the host cells produce antibodies or fragments thereof that are not fused to the second adapter peptide.

Therefore, in particular aspects, provided is a method for selecting proteins for displayability on a lower eukaryote host cell surface, comprising: (a) providing a host cell that expresses a capture moiety comprising a cell surface anchoring protein fused to a first binding moiety; (b) transforming the host cell with a nucleic acid encoding a protein fused to a second binding moiety that is capable of specifically interacting with the first binding moiety fused to the cell surface anchoring protein, wherein mutagenesis is used to generate a plurality of host cells encoding a variegated population of mutants of the proteins; (c) contacting the plurality of host cells with a detection means that specifically binds to proteins that are displayed on the surface of the host cell and does not bind to proteins that are not displayed on the surface of the host cell; and (d) isolating the host cells with which the detection means is bound, wherein the presence of the detection means bound to a protein on the surface of the host cells indicates the protein is displayable on the lower eukaryote cell surface.

In a further aspect, provided is a method for selecting a recombinant lower eukaryote host cell that displays a desired protein on the surface of the host cell, comprising: (a) providing host cells that expresses a capture moiety comprising a cell surface anchoring protein fused to a first binding moiety; (b) transforming the host cells with nucleic acids encoding proteins, each fused to a second binding moiety that is capable of specifically interacting with the first binding moiety fused to the cell surface anchoring protein, to produce a plurality of host cells wherein at least one host cell is suspected of displaying the desired protein on the cell surface; (c) contacting the transformed host cells with a detection means that specifically binds to the desired proteins that are displayed on the cell surface; and (d) isolating the host cells with which the detection means is bound to select the host cell that displays the desired protein.

In a further aspect, provided is a method for producing an antibody comprising: (a) providing a host cell that expresses a capture moiety comprising a cell surface anchoring protein fused to a first binding moiety; (b) transforming the host cell with a nucleic acid encoding the heavy and light chains of an antibody wherein the heavy chain (HC) is fused to a second binding moiety that is capable of specifically interacting with the first binding moiety fused to the cell surface anchoring protein, wherein mutagenesis is used to generate a plurality of host cells encoding a variegated population of mutants of the antibodies; (c) contacting the plurality of host cells with a detection means that specifically binds to antibodies that are displayed on the surface of the host cell and does not bind to antibodies that are not displayed on the surface of the host cell; and (d) isolating the host cells with which the detection means is bound, wherein the presence of the detection means bound to an antibody on the surface of the host cell indicates the host cell produces the antibody.

In a further aspect, provided is a method for selecting a recombinant lower eukaryote host cell that displays a desired antibody on the surface of the host cell, comprising: (a) providing host cells that expresses a capture moiety comprising a cell surface anchoring protein fused to a first binding moiety; (b) transforming the host cell with nucleic acids encoding the heavy chain and light chain (LC) of antibodies wherein the heavy chains are fused to a second binding moiety that is capable of specifically interacting with the first binding moiety fused to the cell surface anchoring protein, to produce a plurality of host cells wherein at least one host cell is suspected of displaying the desired antibody on the cell surface; (c) contacting the transformed host cells with a detection means that specifically binds to the desired antibody that is displayed on the cell surface; and (d) isolating the host cell with which the detection means is bound to select the host cell that displays the desired antibody.

Further provided is a method of producing a member of a specific binding pair, wherein the specific binding pair member is an antibody or antibody fragment, comprising an antibody VH domain and an antibody VL domain, and having an antigen binding site with binding specificity for an antigen of interest, the method comprising (a) providing a library of lower eukaryote host cells displaying on their surface a specific binding pair member, which specific binding pair member is an antibody or antibody fragment comprising a synthetic human antibody VH domain and a human antibody VL domain, wherein the library is created by: (i) providing lower eukaryote host cells that express a capture moiety comprising a cell surface anchoring protein fused to a first binding moiety; (ii) providing a library of nucleic acid sequences encoding a genetically diverse population of the specific binding pair member, wherein the VH domains of the genetically diverse population of the specific binding pair member are biased for one or more VH gene families and wherein the specific binding pair member includes a second binding moiety that is capable of specifically interacting with the first binding moiety fused to the cell surface anchoring protein; (iii) expressing the library of nucleic acid sequences in the lower eukaryote host cells, whereby each specific binding pair member is displayed at the surface of a lower eukaryote host cell; (b) selecting one or more specific binding pair members having a binding specificity for the antigen of interest, by binding the one or more specific binding pair members with the antigen of interest, each thus selected specific binding pair member being displayed on the lower eukaryote host cell.

The further aspects, the specific binding pair member comprises a synthetic human antibody VH domain and a synthetic human antibody VL domain and wherein the synthetic human antibody VH domain and the synthetic human antibody VL domain comprise framework regions and hypervariable loops, wherein the framework regions and first two hypervariable loops of both the VH domain and VL domain are essentially human germ line, and wherein the VH domain and VL domain have altered CDR3 loops. In further still aspects in addition to having altered CDR3 loops, the human synthetic antibody VH and VL domains contain mutations in other CDR loops. In further aspects, each human synthetic antibody VH domain CDR loop is of random sequence. In further still aspects, the human synthetic antibody VH domain CDR loops are of known canonical structures and incorporate random sequence elements. The binding pari member can be a full-sized or whole antibody or a fragment such as a single-chain Fv antibody fragment.

In further aspects of any one of the aforementioned methods, the first binding moiety is a first adapter peptide and the second binding moiety is a second adapter peptide wherein the first and second adapter peptides are capable of a specific pairwise interaction. In particular aspects, the first and second adapter peptides are coiled coil peptides that capable of the specific pairwise interaction. In further aspects, the coiled coil peptides are GABAB-R1 and GABAB-R2 subunits that are capable of the specific pairwise interaction.

In further aspects of any one of the aforementioned methods, the cell surface anchoring protein is a GPI protein, for example, a GPI protein selected from the group consisting of α-agglutinin, Cwp1p, Cwp2p, Gas1p, Yap3p, Flo1p, Crh2p, Pir1p, Pir4p, Sed1p, Tip1p, Wpip, Hpwp1p, Als3p, and Rbt5p. In particular aspects, the cell surface anchoring protein is Sed1p.

In further still aspects, the lower eukaryote is a yeast, including but not limited to, *Pichia pastoris*.

In further aspects of any one of the aforementioned methods, expression of the nucleic acids encoding the capture moiety and proteins is constitutive or the expression of the nucleic acids encoding the capture moiety and the proteins is induced simultaneously, or the expression of the nucleic acids encoding the capture moiety and the mutants of the proteins are induced sequentially.

In further aspects of any one of the aforementioned methods, O-glycosylation of glycoproteins in the host cell is controlled. That is, O-glycan occupancy and mannose chain length are reduced. In lower eukaryote host cells such as yeast, O-glycosylation can be controlled by deleting the genes encoding one or more protein O-mannosyltransferases (Dol-P-Man:Protein (Ser/Thr) Mannosyl Transferase genes) (PMTs) or by growing the host in a medium containing one or more Pmtp inhibitors. In further aspects, the host cell includes a deletion of one or more of the genes encoding PMTs and the host cell is cultivated in a medium that includes one or more Pmtp inhibitors. Pmtp inhibitors include but are not limited to a benzylidene thiazolidinedione. Examples of benzylidene thiazolidinediones that can be used are 5-[[3,4-bis(phenylmethoxy)phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo-3-thiazolidineacetic Acid. In further still aspects, the host cell further includes a nucleic acid that encodes an alpha-1,2-mannosidase that has a signal peptide that directs it for secretion. In another aspect, genes encoding one or more endogenous mannosyltransferase enzymes are deleted. This deletion(s) can be in combination with providing the secreted alpha-1,2-mannosidase and/or PMT inhibitors or can be in lieu of providing the secreted alpha-1,2-mannosidase and/or PMT inhibitors.

In further aspects of any one of the aforementioned methods, host cells further include lower eukaryote cells (e.g., yeast such as *Pichia pastoris*) that are genetically engineered to eliminate glycoproteins having α-mannosidase-resistant N-glycans by deleting or disrupting one or more of the β-mannosyltransferase genes (e.g., BMT1, BMT2, BMT3, and BMT4)(See, U.S. Published Patent Application No. 2006/0211085) or abrogating translation of RNAs encoding one or more of the β-mannosyltransferases using interfering RNA, antisense RNA, or the like.

In further aspects of any one of the methods herein, the host cells can further include lower eukaryote cells (e.g., yeast such as *Pichia pastoris*) that are genetically engineered to eliminate glycoproteins having phosphomannose residues by deleting or disrupting one or both of the phosphomannosyl transferase genes PNO1 and MNN4B (See for example, U.S. Pat. Nos. 7,198,921 and 7,259,007), which in further aspects can also include deleting or disrupting the MNN4A gene or abrogating translation of RNAs encoding one or more of the phosphomannosyltransferases using interfering RNA, antisense RNA, or the like.

In further still aspects, the host cell has been genetically modified to produce glycoproteins that have predominantly an N-glycan selected from the group consisting of complex N-glycans, hybrid N-glycans, and high mannose N-glycans wherein complex N-glycans are selected from the group consisting of $Man_3GlcNAc_2$, $GlcNAC_{(1-4)}Man_3GlcNAc_2$, $Gal_{(1-4)}GlcNAc_{(1-4)}Man_3GlcNAc_2$, and $NANA_{(1-4)}Gal_{(1-4)}Man_3GlcNAc_2$; hybrid N-glycans are selected from the group consisting of $Man_5GlcNAc_2$, $GlcNAcMan_5GlcNAc_2$, $GalGlcNAcMan_5GlcNAc_2$, and $NANAGalGlcNAcMan_5GlcNAc_2$; and high Mannose N-glycans are selected from the group consisting of $Man_6GlcNAc_2$, $Man_7GlcNAc_2$, $Man_8GlcNAc_2$, and $Man_9GlcNAc_2$.

DEFINITIONS

Unless otherwise defined herein, scientific and technical terms and phrases used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999).

All publications, patents and other references mentioned herein are hereby incorporated by reference in their entireties.

The following terms, unless otherwise indicated, shall be understood to have the following meanings:

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetylneuraminic acid (NANA)). The processing of the sugar groups occurs cotranslationally in the lumen of the ER and continues in the Golgi apparatus for N-linked glycoproteins.

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("Man3") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

Abbreviations used herein are of common usage in the art, see, e.g., abbreviations of sugars, above. Other common abbreviations include "PNGase", or "glycanase" or "glucosidase" which all refer to peptide N-glycosidase F (EC 3.2.2.18).

The term "operably linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "eukaryotic" refers to a nucleated cell or organism, and includes insect cells, plant cells, mammalian cells, animal cells and lower eukaryotic cells.

The term "lower eukaryotic cells" includes yeast and filamentous fungi. Yeast and filamentous fungi include, but are not limited to *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha*, any *Kluyveromyces* sp., *Candida albicans*, any *Aspergillus* sp., *Trichoderma reesei, Chrysosoporium lucknowense*, any *Fusarium* sp. and *Neurospora crassa*.

The term "specific binding pair" refers to a pair of molecules (each being a member of a specific binding pair) which are naturally derived or synthetically produced. One of the pair of molecules, has an area on its surface, or a cavity which specifically binds to, and is therefore, defined as complementary with a particular spatial and polar organisation of the other molecule, so that the pair have the property of binding specifically to each other. Examples of types of specific binding pairs are antigen-antibody, biotin-avidin, hormone-hormone receptor, receptor-ligand, enzyme-substrate, IgG-protein A.

As used herein, the terms "antibody," "immunoglobulin," "immunoglobulins" and "immunoglobulin molecule" are used interchangeably. Each immunoglobulin molecule has a unique structure that allows it to bind its specific antigen, but all immunoglobulins have the same overall structure as described herein. The basic immunoglobulin structural unit is known to comprise a tetramer of subunits. Each tetramer has two identical pairs of polypeptide chains, each pair having one "light" chain (LC) (about 25 kDa) and one "heavy" chain (HC) (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Light chains (LCs) are classified as either kappa or lambda. Heavy chains (HCs) are classified as gamma, mu, alpha, delta, or epsilon, and define the antibody's isotype as IgG, IgM, IgA, IgD and IgE, respectively.

The light and heavy chains are subdivided into variable regions and constant regions (See generally, Fundamental Immunology (Paul, W., ed., 2nd ed. Raven Press, N.Y., 1989), Ch. 7. The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. The terms include naturally occurring forms, as well as fragments and derivatives. Included within the scope of the term are classes of immunoglobulins (Igs), namely, IgG, IgA, IgE, IgM, and IgD. Also included within the scope of the terms are the subtypes of IgGs, namely, IgG1, IgG2, IgG3 and IgG4. The term is used in the broadest sense and includes single monoclonal antibodies (including agonist and antagonist antibodies) as well as antibody compositions which will bind to multiple epitopes or antigens. The terms specifically cover monoclonal antibodies (including full length monoclonal antibodies), polyclonal antibodies, multispecific antibodies (for example, bispecific antibodies), and antibody fragments so long as they contain or are modified to contain at least the portion of the $C_H2$ domain of the heavy chain immunoglobulin constant region which comprises an N-linked glycosylation site of the $C_H2$ domain, or a variant thereof. Included within the terms are molecules comprising only the Fc region, such as immunoadhesins (U.S. Published Patent Application No. 20040136986), Fc fusions, and antibody-like molecules. Alternatively, these terms can refer to an antibody fragment of at least the Fab region that at least contains an N-linked glycosylation site.

The term "Fc" fragment refers to the 'fragment crystallized' C-terminal region of the antibody containing the $C_H2$ and $C_H3$ domains (FIG. 1). The term "Fab" fragment refers to the 'fragment antigen binding' region of the antibody containing the $V_H$, $C_H1$, $V_L$ and $C_L$ domains (See FIG. 1).

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, monoclonal antibodies are advantageous in that they can be synthesized by hybridoma culture, uncontaminated by other immunoglobulins. The term "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature, 256:495, or may be made by recombinant DNA methods (See, for example, U.S. Pat. No. 4,816,567 to Cabilly et al.).

The term "fragments" within the scope of the terms "antibody" or "immunoglobulin" include those produced by digestion with various proteases, those produced by chemical cleavage and/or chemical dissociation and those produced recombinantly, so long as the fragment remains capable of specific binding to a target molecule. Among such fragments are Fc, Fab, Fab', Fv, F(ab')$_2$, and single chain Fv (scFv) fragments. Hereinafter, the term "immunoglobulin" also includes the term "fragments" as well.

Immunoglobulins further include immunoglobulins or fragments that have been modified in sequence but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (See, for example, Intracellular Antibodies: Research and Disease Applications, (Marasco, ed., Springer-Verlag New York, Inc., 1998).

The term "catalytic antibody" refers to immunoglobulin molecules that are capable of catalyzing a biochemical reaction. Catalytic antibodies are well known in the art and have been described in U.S. Pat. Nos. 7,205,136; 4,888,281; 5,037,750 to Schochetman et al., U.S. Pat. Nos. 5,733,757; 5,985,626; and 6,368,839 to Barbas, III et al.

As used herein, the term "consisting essentially of" will be understood to imply the inclusion of a stated integer or group of integers; while excluding modifications or other integers which would materially affect or alter the stated integer. With respect to species of N-glycans, the term "consisting essentially of" a stated N-glycan will be understood to include the N-glycan whether or not that N-glycan is fucosylated at the N-acetylglucosamine (GlcNAc) which is directly linked to the asparagine residue of the glycoprotein.

As used herein, the term "predominantly" or variations such as "the predominant" or "which is predominant" will be understood to mean the glycan species that has the highest mole percent (%) of total neutral N-glycans after the glycoprotein has been treated with PNGase and released glycans analyzed by mass spectroscopy, for example, MALDI-TOF MS or HPLC. In other words, the phrase "predominantly" is defined as an individual entity, such as a specific glycoform, is present in greater mole percent than any other individual entity. For example, if a composition consists of species A in 40 mole percent, species B in 35 mole percent and species C in 25 mole percent, the composition comprises predominantly species A, and species B would be the next most predominant species. Some host cells may produce compositions comprising neutral N-glycans and charged N-glycans such as mannosylphosphate. Therefore, a composition of glycoproteins can include a plurality of charged and uncharged or neutral N-glycans. In the present invention, it is within the context of the total plurality of neutral N-glycans in the composition in which the predominant N-glycan determined. Thus, as used herein, "predominant N-glycan" means that of the total plurality of neutral N-glycans in the composition, the predominant N-glycan is of a particular structure.

As used herein, the term "essentially free of" a particular sugar residue, such as fucose, or galactose and the like, is used to indicate that the glycoprotein composition is substantially devoid of N-glycans which contain such residues. Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent. Thus, substantially all of the N-glycan structures in a glycoprotein composition according to the present invention are free of fucose, or galactose, or both.

As used herein, a glycoprotein composition "lacks" or "is lacking" a particular sugar residue, such as fucose or galactose, when no detectable amount of such sugar residue is present on the N-glycan structures at any time. For example, in preferred embodiments of the present invention, the glycoprotein compositions are produced by lower eukaryotic organisms, as defined above, including yeast (for example, *Pichia* sp.; *Saccharomyces* sp.; *Kluyveromyces* sp.; *Aspergillus* sp.), and will "lack fucose," because the cells of these organisms do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

The interaction of antibodies and antibody-antigen complexes with cells of the immune system and the variety of responses, including antibody-dependent cell-mediated cytotoxicity (ADCC) and complement-dependent cytotoxicity (CDC), clearance of immunocomplexes (phagocytosis), antibody production by B cells and IgG serum half-life are defined respectively in the following: Daeron et al., 1997, Annu. Rev. Immunol. 15: 203-234; Ward and Ghetie, 1995, Therapeutic Immunol. 2:77-94; Cox and Greenberg, 2001, Semin. Immunol. 13: 339-345; Heyman, 2003, Immunol. Lett. 88:157-161; and Ravetch, 1997, Curr. Opin. Immunol. 9: 121-125.

BRIEF DESCRIPTION OF THE DRAWINGS

FIG. 2A illustrates the fusion protein expression construct consisting of a signal sequence, GR2 coiled coil peptide, Myc tag, and GPI anchor fusion protein.

FIG. 2B shows the amino acid sequences of the SED1 fusion protein (SEQ ID NO:20) wherein the alpha amylase signal peptide is underlined, the GR2 coiled coil peptide sequence is in bold-faced type, the myc-tag sequence in italics, and the *S. cerevisiae* SED1 sequence in normal font.

FIG. 9A, *Pichia pastoris* GS2.0anti-DKK1 Fab fragment displaying cell; FIG. 9B, *Pichia pastoris* GS2.0 anti-Her2 secreted Fab fragment without overexpression of the SED1 GPI-protein cell wall anchor; FIG. 9C, *Pichia pastoris* GS2.0 anti-Her2 Fab fragment displaying cell. All these cells were labeled with anti-human H&L Alexa 488 and photographed using the same exposure time.

FIG. 12A: Cells were isolated from five areas of decreasing fluorescence (C1 through C5). FIG. 12B shows two population of cells with different fluorescent intensity when we mix anti-Her2 and anti-DKK1 as 1:1 ratio. FIG. 12C: Cells were plated and analyzed by colony PCR to determine their identity.

FIGS. 14A-E shows fluorescence microscopy of samples A-E in the FACS analysis shown in FIG. 14F.

FIG. 17A YGLY7762 cells (1D05); FIG. 17B YGLY7764 cells (1H23).

FIG. 19A shows FACS sorting of cells displaying binding Fab fragment (1D05) from cells displaying non-binding Fab fragment (α-CD20) when using fluorophore-labeled PCSK-9 antigen. The cells were mixed at a 1 D05: α-CD20 ratio of 1:1,000; 1:10,000; and 1:100,000 and then sorted for up to two rounds. FIG. 19B shows FACS sorting of cells displaying high affinity binding Fab fragment (1D05) from cells displaying low affinity Fab fragment (1H23) when using fluorophore-labeled PCSK-9 antigen. The cells were mixed at a 1D05:1H23 ratio of 1:10,000 and 1:100,000 and sorted two rounds.

DETAILED DESCRIPTION OF THE INVENTION

The present invention provides a protein display system that is capable of displaying diverse libraries of proteins on the surface of a eukaryote host cell such as a lower eukaryote host cell (e.g., yeast or filamentous fungal cells). The compositions and methods are particularly useful for the display of collections of proteins in the context of discovery (that is, screening) or molecular evolution protocols. A salient feature of the method is that it provides a display system in which proteins of interest can be displayed on the surface of a host cell without having to express the protein of interest as a fusion protein in which the protein of interest is fused to a surface anchor protein.

In general, provided is a method for selecting proteins for displayability on a lower eukaryote cell surface, comprising providing a host cell that expresses a capture moiety comprising a cell surface anchoring protein fused to a first binding moiety; transforming the host cell with a nucleic acid encoding proteins fused to a second binding moiety that is capable of specifically interacting with the first binding moiety fused to the cell surface anchoring protein, wherein mutagenesis is used to generate a plurality of host cells encoding a variegated population of mutants of the proteins; contacting the plurality of host cells with a detection means that specifically binds to proteins that are displayed on the surface of the host cell and does not bind to proteins that are not displayed on the surface of the host cell; and isolating the host cells with which the detection means is bound, wherein the presence of the detection means bound to a protein on the surface of the host cells indicates the proteins are displayable on the lower eukaryote cell surface.

Further provided is a method for selecting recombinant lower eukaryote host cells that display a desired protein on the surface of the host cells, comprising providing host cells that expresses a capture moiety comprising a cell surface anchoring protein fused to a first binding moiety; transforming the host cells with nucleic acids encoding proteins fused to a second binding moiety that is capable of specifically interacting with the first binding moiety fused to the cell surface anchoring protein to produce a plurality of host cells wherein at least one host cell is suspected of displaying the desired protein on the cell surface; contacting the transformed host cells with a detection means that specifically binds to the desired proteins that are displayed on the cell surface; and isolating the host cells with which the detection means is bound to select the host cells that display the desired protein.

Figure 1:
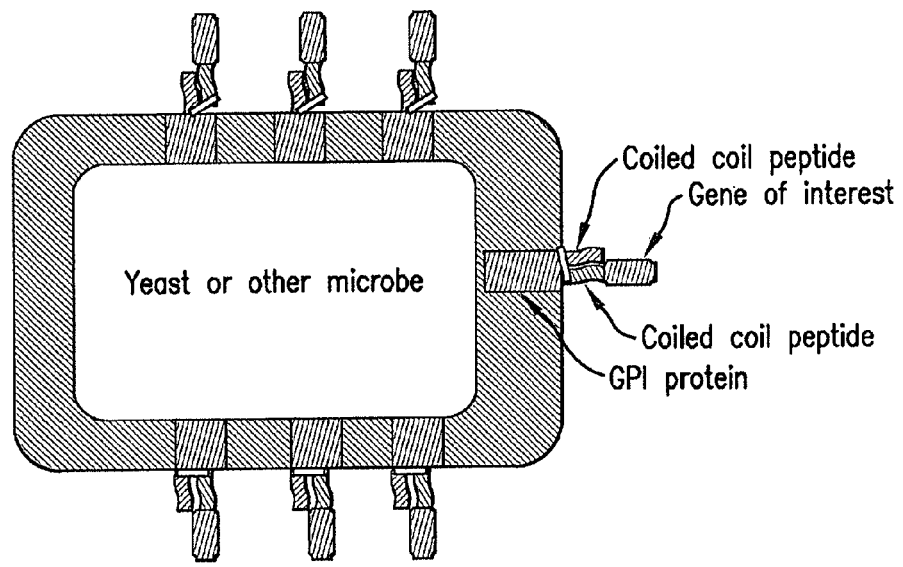
FIG. 1 illustrates a yeast cell engineered to express a potential cell wall anchor-coiled coil peptide fusion protein that dimerizes with a gene of interest-coiled coil peptide fusion. The two fusion protein heterodimers are locked by an artificial disulfide bond.

Thus, as shown in FIG. 1, the system comprises at least two components. The first component is a helper vector that expresses a capture moiety that in particular embodiments comprises a cell surface anchoring protein that is capable of binding or integrating to the surface of the host cell fused to a first binding moiety, which in particular aspects comprises an adapter peptide that is capable of pairwise binding to the second adapter peptide. The first binding moiety or adapter peptide is located at the end of the cell surface anchoring protein that is exposed to the extracellular environment such that the first adapter peptide is capable of interacting with the second adapter peptide. The second component is a vector that expresses a protein of interest or libraries of which the protein of interest is to be selected (for example, a library of vectors expressing antibodies or fragments thereof). The vector expresses the proteins of interest as fusion proteins in which a second adapter peptide is fused to the N- or C-terminus of the proteins of interest.

Both of the components can be provided in vectors which integrate the nucleic acids into the genome of the host cell by homologous recombination. Homologous recombination can be double crossover or single crossover homologous recombination. Roll-in single crossover homologous recombination has been described in Nett et al., Yeast 22: 295-304 (2005). Each component can be integrated in the same locus in the genome or in separate loci in the genome. Alternatively, one or both components can be transiently expressed in the host cell.

The method enables selection of proteins with desirable binding properties including but not limited to antibodies or fragments thereof (e.g., Fab fragments) of a desired affinity or avidity, enzymes with a particular enzymatic activity or substrate specificity, including catalytic antibodies, receptors with a particular specificity for particular ligands, and fusion proteins including but not limited to those comprising the Fc region of antibody fused to a heterologous protein. In general, the method comprises transforming lower eukaryote host cells with a first nucleic acid expressing a host cell wall binding protein fused at its N- or C-terminus to a first binding moiety such as an adapter peptide capable of pairwise binding to the second adapter peptide and a second nucleic acid expressing a protein to be tested fused at its N- or C-terminus to a second binding moiety such as an adapter peptide capable of pairwise binding to the first adapter peptide. The first and second nucleic acids can be operably linked to the same promoter or to different promoters that are separately inducible. Preferably, the protein of interest is fused to a cellular signal peptide that facilitates shuttle of the fusion protein through the secretory pathway to the cell surface. Expression of first nucleic acids results in the production of the cell wall binding fusion protein, which is transported to the cell surface where it then binds to the surface of the cell with the first binding moiety exposed to the extracellular environment. Expression of the second nucleic acid results in the production of the protein of interest fusion protein, which is transported through the secretory pathway and secreted from the cell. However, as the protein of interest fusion protein is secreted, it is retained on the cell surface because the second binding moiety fused to the protein of interest forms a specific interaction with the first binding moiety fused to the cell wall binding protein.

Further provided is a library method for identifying and selecting cells that produce a particular member of a specific binding pair including but not limited to antibodies and Fab fragments. Therefore, in further aspects, a method of producing a protein that is a member of a specific binding pair, wherein the specific binding pair member is an antibody or antibody fragment, comprising an antibody VH domain and an antibody VL domain, and having an antigen binding site with binding specificity for an antigen of interest. The method comprises providing a library of lower eukaryote host cells displaying on their surface a specific binding pair member, which specific binding pair member is an antibody or antibody fragment comprising a synthetic human antibody VH domain and a human antibody VL domain. The library is created by providing lower eukaryote host cells that express a capture moiety comprising a cell surface anchoring protein fused to a first binding moiety and providing a library of nucleic acid sequences encoding a genetically diverse population of the specific binding pair member, wherein the VH domains of the genetically diverse population of the specific binding pair member are biased for one or more VH gene families and wherein the specific binding pair member includes a second binding moiety that is capable of specifically interacting with the first binding moiety fused to the cell surface anchoring protein. The library of nucleic acid sequences is expressed in the lower eukaryote host cells so that each specific binding pair member is displayed at the surface of a lower eukaryote host cell. Then, cells that produce one or more specific binding pair members having a binding specificity for the antigen of interest are selected by binding the one or more specific binding pair members with the antigen of interest.

The further aspects, the specific binding pair member comprises a synthetic human antibody VH domain and a synthetic human antibody VL domain and wherein the synthetic human antibody VH domain and the synthetic human antibody VL domain comprise framework regions and hypervariable loops, wherein the framework regions and first two hypervariable loops of both the VH domain and VL domain are essentially human germ line, and wherein the VH domain and VL domain have altered CDR3 loops. In further still aspects in addition to having altered CDR3 loops, the human synthetic antibody VH and VL domains contain mutations in other CDR loops. In further aspects, each human synthetic antibody VH domain CDR loop is of random sequence. In further still aspects, the human synthetic antibody VH domain CDR loops are of known canonical structures and incorporate random sequence elements.

The binding pair member can be a full-sized or whole antibody or a fragment such as a single-chain Fv antibody fragment.

Detection of host cells that express the desired protein of interest can be achieved by labeling the host cells with a first label, wherein the first label associates with or binds to the protein of interest and does not associate with or bind to host cells which do not express the protein of interest. For example, in the case when the protein of interest is an antibody, the first label can be an antigen that is specifically recognized by the antibody of interest. The host cells with which the first label is associated are selected and the amount of first label associated with the host cell is quantitated. A high occurrence of the first label indicates the protein of interest has desirable binding properties and a low occurrence of the first label indicates the protein of interest does not have desirable binding properties.

A further aspect includes the steps of labeling the above host cells with a second label, wherein the second label associates with or binds to host cells expressing an epitope tag fused to the protein of interest and does not associate with or bind to host cells which do not express the epitope tag. The amount of second label associated with the host cells is quantitated. The amount of the second label associated with the host cell indicates a number of expressed copies of the epitope-tagged protein of interest on the host cell surface and by comparing the quanitation of the first label to the quantitation of the second label enables the amount of the first label normalized for the amount of the second label, wherein a high occurrence of first label relative to the occurrence of the second label indicates the protein to be tested has desirable binding properties.

Another aspect includes the steps of labeling the above host cells with a third label that competes with the first label for binding to the protein of interest. In this aspect, the host cells are labeled with the first label and the amount of first label associated with host cells is quantitated. Then the host cells are labeled with the second label and the amount of second label associated with host cells is quantitated. Comparing the quantitation of the first label to the quantitation of the second label is performed to determine the occurrence of the first label normalized for the occurrence of the second label, wherein a low occurrence of the first label relative to the occurrence of the second label indicates the protein of interest has desirable binding properties.

In further aspects, the first label is a fluorescent label attached to a ligand specific for the protein of interest and the second label is a fluorescent label attached to an antibody specific for the protein of interest. When the labels are fluorescent, the quantitation step is performed by flow cytometry or confocal fluorescence microscopy. In a further still aspect, the first label is a fluorescent label attached to a ligand specific for the protein of interest and fluorescence-activated cell sorting (FACS) is used to separate the host that express the protein of interest from host cells that do not produce the protein of interest.

Further provided is a method for selecting antibodies and fragments thereof with desirable binding properties, performed as described above using a vector in which a single stop codon is place between the nucleic acid encoding the antibody sequence and the nucleic acid encoding the second adapter peptide. The vector is transformed into lower eukaryote host cells comprising nucleic acids expressing a host cell wall binding protein fused at its N- or C-terminus to a first adapter peptide that is capable of pairwise binding to the second adapter peptide. Translation of mRNAs encoded by the vector is performed under conditions that increases translational readthrough through the stop codon thereby producing antibodies that are fused to the second adapter. Labeling the host cells with a first label, wherein the first label associates with or binds to host cells expressing the desired antibodies and does not associate with or bind to host cells Which do not express the desired antibodies enables identification and selection of those host cells that produce the desired antibodies. After the host cells that produce the desired antibodies have been selected and isolated, the host cells are grown under conditions that do result in an increase in translational readthrough through the stop codon. Under the second conditions, the host cells produce antibodies or fragments thereof that are not fused to the second adapter peptide.

Figure 4:
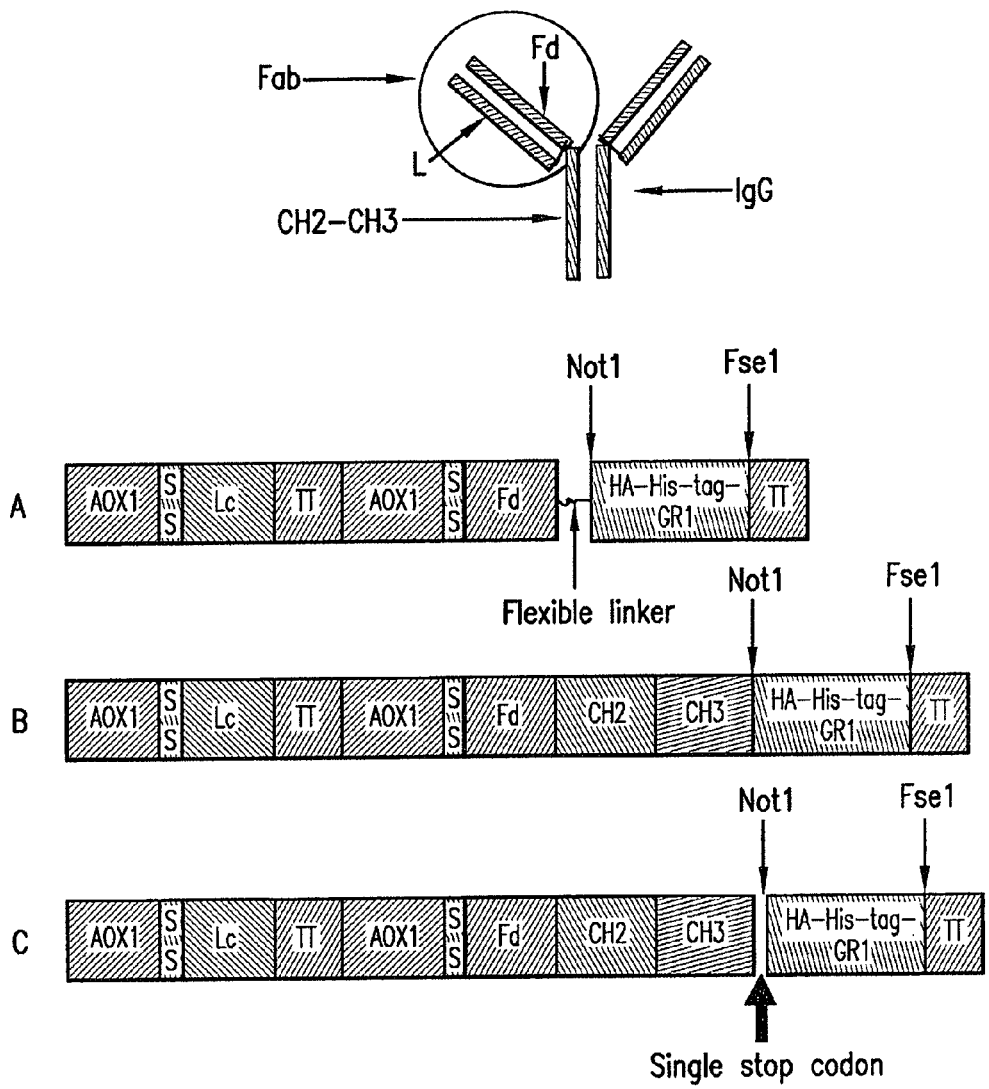
FIG. 4 illustrates three different constructs that can be used to create a monoclonal antibody or antibody fragment fused to coiled coil peptide GR1 for displaying the antibody or antibody fragment on the host glycoengineered yeast. Construct A is a Fab fragment display format, Construct B is a full-length antibody display format, and Construct C contains a stop codon between the antibody heavy chain and the coiled coil (GR1). AOX1 is the AOX1 promoter, SS is signal peptide, Lc is light chain, TT is transcription termination sequence, Fd is heavy chain variable fragment, CH2 and CH3 are heavy chain constant domains, HA is haemaglutinin, His is poly histidine, GR1 is coiled coil peptide.

FIG. 4 shows expression cassette C, which had been designed for use in lower eukaryotes such as yeast such that when introduced into a host cell and the host cell is grown under appropriate conditions, the host cell is capable of producing full-length antibodies that include a second adapter peptide fused to the heavy chain for selection of a desired full-length antibody. However, under production conditions, the construct enables production of antibodies in which the heavy chain is not fused to the second adapter peptide. Thus, expression cassette C avoids the need to reclone the nucleic acid encoding the antibody to remove the nucleic acid that encodes the second adapter peptide. In expression cassette C, the second ORF that encodes a fusion protein comprising the heavy chain fused at the C-terminus to the N-terminus of the second adapter peptide further includes a single stop codon between the end of the nucleic acid sequence encoding the heavy chain and the nucleic acid encoding the second adapter peptide, in which readthrough of the stop codon is inducible. Under most conditions, translation of an mRNA transcribed from the construct predominantly terminates at the single stop codon and thus results in the production of a full-length antibody that is not fused to the second adapter peptide. However, in the presence of the antibiotic G418, translational readthrough through the stop codon is increased; however, even in the presence of the antibiotic, expression of full-length antibody not fused to the GR1 coiled coil peptide is the predominant species. In general, the mistranslation results in the insertion of a random amino acid. This proportional readthrough can reflect the expressability of the full-length antibody; by monitoring both the secreted full-length antibody and the full-length antibody fusion captured at the cell surface, one can screen for high producing host cells. Thus, in the presence of the antibiotic, a population of the full-length antibodies will include the heavy chain-adapter peptide fusion protein. Therefore, when screening a library of antibodies for a desired antibody, the host cells are grown in the presence of the antibiotic. The full-length antibodies comprising the heavy chain-adapter peptide fusion protein are captured at the cell surface by heterodimerization to the first adapter peptide fused to the cell surface anchoring protein on the surface of the cell. Desired antibodies can then be detected by a suitable detection means. However, for production of full-length antibodies in which the heavy chain is not fused to the adapter peptide, host cells that have been identified to produce the desired antibody are grown in the absence of the antibiotic. The premise behind expression cassette C can be adapted to produce Fab fragments that are not fused to the GR1 coiled coil peptide and can be adapted to use with other protein species such as enzymes and receptor proteins.

I. General Characteristics of the Adapters

A further consideration in constructing the display system is to select a pair of adapter peptides that encode two adapters capable of pairwise interaction. Whereas a nucleic acid encoding one of the adapter peptides is inserted in-frame with the nucleic acid encoding an exogenous protein of interest carried by the vector, a nucleic encoding the other is fused in-frame with a nucleic acid encoding a cell surface anchoring protein capable of attaching to the outer wall or membrane of the host cell. By "pairwise interaction" is meant that the two adapters can interact with and bind to each other to form a stable complex. The stable complex must be sufficiently long-lasting to permit detecting the protein of interest on the outer surface of the host cell. The complex or dimer must be able to withstand whatever conditions exist or are introduced between the moment of formation and the moment of detecting the displayed polypeptide, these conditions being a function of the assay or reaction which is being performed. The stable complex or dimer may be irreversible or reversible as long as it meets the other requirements of this definition. Thus, a transient complex or dimer may form in a reaction mixture, but it does not constitute a stable complex if it dissociates spontaneously and yields no detectable polypeptide displayed on the outer surface of a genetic package.

The pairwise interaction between the first and second adapters may be covalent or non-covalent interactions. Non-covalent interactions encompass every exiting stable linkage that do not result in the formation of a covalent bond. Non-limiting examples of noncovalent interactions include electrostatic bonds, hydrogen bonding, Van der Waal's forces, steric interdigitation of amphiphilic peptides. By contrast, covalent interactions result in the formation of covalent bonds, including but not limited to disulfide bond between two cysteine residues, C—C bond between two carbon-containing molecules, C—O or C—H between a carbon and oxygen- or hydrogen-containing molecules respectively, and O—P bond between an oxygen- and phosphate-containing molecule.

Adapter peptides applicable for constructing the expression and helper vectors of the display system can be derived from a variety of sources. Generally, any protein sequences involved in the formation of stable multimers are candidate adapter peptides. As such, these peptides may be derived from any homomultimeric or heteromultimeric protein complexes. Representative homomultimeric proteins are homodimeric receptors (e.g., platelet-derived growth factor homodimer BB (PDGF), homodimeric transcription factors (e.g. Max homodimer, NF-kappaB p65 (RelA) homodimer), and growth factors (e.g., neurotrophin homodimers). Non-limiting examples of heteromultimeric proteins are complexes of protein kinases and SH2-domain-containing proteins (Cantley et al., Cell 72: 767-778 (1993); Cantley et al., J. Biol. Chem. 270: 26029-26032 (1995)), heterodimeric transcription factors, and heterodimeric receptors.

Currently used heterodimeric transcription factors are α-Pal/Max complexes and Hox/Pbx complexes. Hox represents a large family of transcription factors involved in patterning the anterior-posterior axis during embryogenesis. Hox proteins bind DNA with a conserved three alpha helix homeodomain. In order to bind to specific DNA sequences, Hox proteins require the presence of hetero-partners such as the Pbx homeodomain. Wolberger et al. solved the 2.35 Å crystal structure of a HoxB1-Pbx1-DNA ternary complex in order to understand how Hox-Pbx complex formation occurs and how this complex binds to DNA. The structure shows that the homeodomain of each protein binds to adjacent recognition sequences on opposite sides of the DNA. Heterodimerization occurs through contacts formed between a six amino acid hexapeptide N-terminal to the homeodomain of HoxB1 and a pocket in Pbx1 formed between helix 3 and helices 1 and 2. A C-terminal extension of the Pbx1 homeodomain forms an alpha helix that packs against helix 1 to form a larger four helix homeodomain (Wolberger et al., Cell 96: 587-597 (1999); Wolberger et al., J Mol Biol. 291: 521-530).

A vast number of heterodimeric receptors have also been identified. They include but are not limited to those that bind to growth factors (e.g. heregulin), neurotransmitters (e.g. γ-Aminobutyric acid), and other organic or inorganic small molecules (e.g. mineralocorticoid, glucocorticoid). Currently used heterodimeric receptors are nuclear hormone receptors (Belshaw et al., Proc. Natl. Acad. Sci. U.S.A 93:4604-4607 (1996)), erbB3 and erbB2 receptor complex, and G-protein-coupled receptors including but not limited to opioid (Gomes et al., J. Neuroscience 20: RC110 (2000)); Jordan et al. Nature 399: 697-700 (1999)), muscarinic, dopamine, serotonin, adenosine/dopamine, and $GABA_B$ families of receptors. For majority of the known heterodimeric receptors, their C-terminal sequences are found to mediate heterodimer formation.

Peptides derived from antibody chains that are involved in dimerizing the L and H chains can also be used as adapters for constructing the subject display systems. These peptides include but are not limited to constant region sequences of an L or H chain. Additionally, adapter peptides can be derived from antigen-binding site sequences and its binding antigen. In such case, one adapter of the pair contains antigen-binding site amino acid residues that is recognized (i.e. being able to stably associate with) by the other adapter containing the corresponding antigen residues.

Based on the wealth of genetic and biochemical data on vast families of genes, one of ordinary skill will be able to select and obtain suitable adapter peptides for constructing the subject display system without undue experimentation.

Where desired, sequences from novel hetermultimeric proteins can be employed as adapters. In such situation, the identification of candidate peptides involved in formation of heteromultimers can be determined by any genetic or biochemical assays without undue experimentation. Additionally, computer modeling and searching technologies further facilitates detection of heteromultimeric peptide sequences based on sequence homologies of common domains appeared in related and unrelated genes. Non-limiting examples of programs that allow homology searches are Blast (http://www.ncbi.nlm.nih.gov/BLAST/), Fasta (Genetics Computing Group package, Madison, Wis.), DNA Star, Clustlaw, TOFFEE, COBLATH, Genthreader, and MegAlign. Any sequence databases that contains DNA sequences corresponding to a target receptor or a segment thereof can be used for sequence analysis. Commonly employed databases include but are not limited to GenBank, EMBL, DDBJ, PDB, SWISS-PROT, EST, STS, GSS, and HTGS.

The subject adapters that are derived from heterodimerization sequences can be further characterized based on their physical properties. Current heterodimerization sequences exhibit pairwise affinity resulting in predominant formation of heterodimers to a substantial exclusion of homodimers. Preferably, the predominant formation yields a heteromultimeric pool that contains at least 60% heterodimers, more preferably at least 80% heterodimers, more preferably between 85-90% heterodimers, and more preferably between 90-95% heterodimers, and even more preferably between 96-99% heterodimers that are allowed to form under physiological buffer conditions and/or physiological body temperatures. In certain embodiments of the present invention, at least one of the heterodimerization sequences of the adapter pair is essentially incapable of forming a homodimer in a physiological buffer and/or at physiological body temperature. By "essentially incapable" is meant that the selected heterodimerization sequences when tested alone do not yield detectable amounts of homodimers in an in vitro sedimentation experiment as detailed in Kammerer et al., Biochemistry 38: 13263-13269 (1999)), or in the in vivo two-hybrid yeast analysis (see e.g. White et al., Nature 396: 679-682 (1998)). In addition, individual heterodimerization sequences can be expressed in a host cell and the absence of homodimers in the host cell can be demonstrated by a variety of protein analyses including but not limited to SDS-PAGE, Western blot, and immunoprecipitation. The in vitro assays must be conducted under a physiological buffer conditions, and/or preferably at physiological body temperatures. Generally, a physiological buffer contains a physiological concentration of salt and at adjusted to a neutral pH ranging from about 6.5 to about 7.8, and preferably from about 7.0 to about 7.5.

An illustrative adapter pair exhibiting the above-mentioned physical properties is $GABA_B$-R1/$GABA_B$-R2 receptors. These two receptors are essentially incapable of forming homodimers under physiological conditions (e.g. in vivo) and at physiological body temperatures. Research by Kuner et al. and White et al. (Science 283: 74-77 (1999); Nature 396: 679-682 (1998)) has demonstrated the heterodimerization specificity of $GABA_B$-R1 and $GABA_B$-R2 in vivo. In fact, White et al. were able to clone $GABA_B$-R2 from yeast cells based on the exclusive specificity of this heterodimeric receptor pair. In vitro studies by Kammerer et al. supra has shown that neither $GABA_B$-R1 nor $GABA_B$-R2 C-terminal sequence is capable of forming homodimers in physiological buffer conditions when assayed at physiological body temperatures. Specifically, Kammerer et al. have demonstrated by sedimentation experiments that the heterodimerization sequences of $GABA_B$ receptor 1 and 2, when tested alone, sediment at the molecular mass of the monomer under physiological conditions and at physiological body temperatures (e.g., at 37° C.). When mixed in equimolar amounts, $GABA_B$ receptor 1 and 2 heterodimerization sequences sediment at the molecular mass corresponding to the heterodimer of the two sequences (see Table 1 of Kammerer et al.). However, when the $GABA_B$-R1 and $GABA_B$-R2 C-terminal sequences are linked to a cysteine residue, homodimers may occur via formation of disulfide bond.

Adapters can be further characterized based on their secondary structures. Current adapters consist of amphiphilic peptides that adopt a coiled-coil helical structure. The helical coiled coil is one of the principal subunit oligomerization sequences in proteins. Primary sequence analysis reveals that approximately 2-3% of all protein residues form coiled coils (Wolf et al., Protein Sci. 6: 1179-1189 (1997)). Well-characterized coiled-coil-containing proteins include members of the cytoskeletal family (e.g., α-keratin, vimentin), cytoskeletal motor family (e.g., myosine, kinesins, and dyneins), viral membrane proteins (e.g. membrane proteins of Ebola or HIV), DNA binding proteins, and cell surface receptors (e.g. $GABA_B$ receptors 1 and 2). Coiled-coil adapters of the present invention can be broadly classified into two groups, namely the left-handed and right-handed coiled coils. The left-handed coiled coils are characterized by a heptad repeat denoted "abcdefg" with the occurrence of apolar residues preferentially located at the first (a) and fourth (d) position. The residues at these two positions typically constitute a zig-zag pattern of "knobs and holes" that interlock with those of the other stand to form a tight-fitting hydrophobic core. In contrast, the second (b), third (c) and sixth (f) positions that cover the periphery of the coiled coil are preferably charged residues. Examples of charged amino acids include basic residues such as lysine, arginine, histidine, and acidic residues such as aspartate, glutamate, asparagine, and glutamine. Uncharged or apolar amino-acids suitable for designing a heterodimeric coiled coil include but are not limited to glycine, alanine, valine, leucine, isoleucine, serine and threonine. While the uncharged residues typically form the hydrophobic core, inter-helical and intra-helical salt-bridge including charged residues even at core positions may be employed to stabilize the overall helical coiled-coiled structure (Burkhard et al (2000) J. Biol. Chem. 275:11672-11677). Whereas varying lengths of coiled coil may be employed, the subject coiled coil adapters preferably contain two to ten heptad repeats. More preferably, the adapters contain three to eight heptad repeats, even more preferably contain four to five heptad repeats.

In designing optimal coiled-coil adapters, a variety of existing computer software programs that predict the secondary structure of a peptide can be used. An illustrative computer analysis uses the COILS algorithm which compares an amino acid sequence with sequences in the database of known two-stranded coiled coils, and predicts the high probability coiled-coil stretches (Kammerer et al., Biochemistry 38:13263-13269 (1999)).

While a diverse variety of coiled coils involved in multimer formation can be employed as the adapters in the subject display system. Currentcoiled coils are derived from heterodimeric receptors. Accordingly, the present invention encompasses coiled-coil adapters derived from $GABA_B$ receptors 1 and 2. In one aspect, the subject coiled coils adapters comprise the C-terminal sequences of $GABA_B$ receptor 1 and $GABA_B$ receptor 2. In another aspect, the subject adapters are composed of two distinct polypeptides of at least 30 amino acid residues, one of which is essentially identical to a linear sequence of comparable length depicted in SEQ ID NO:13 (GR1), and the other is essentially identical to a linear peptide sequence of comparable length depicted in SEQ ID NO:11 (GR2).

Another class of current coiled coil adapters are leucine zippers. The leucine zipper have been defined in the art as a stretch of about 35 amino acids containing 4-5 leucine residues separated from each other by six amino acids (Maniatis and Abel, Nature 341:24 (1989)). The leucine zipper has been found to occur in a variety of eukaryotic DNA-binding proteins, such as GCN4, C/EBP, c-fos gene product (Fos), c-jun gene product (Jun), and c-Myc gene product. In these proteins, the leucine zipper creates a dimerization interface wherein proteins containing leucine zippers may form stable homodimers and/or heterodimers. Molecular analysis of the protein products encoded by two proto-oncogenes, c-fos and c-jun, has revealed such a case of preferential heterodimer formation (Gentz et al., Science 243: 1695 (1989); Nakabeppu et al., Cell 55: 907 (1988); Cohen et al., Genes Dev. 3: 173 (1989)). Synthetic peptides comprising the leucine zipper regions of Fos and Jun have also been shown to mediate heterodimer formation, and, where the amino-termini of the synthetic peptides each include a cysteine residue to permit intermolecular disulfide bonding, heterodimer formation occurs to the substantial exclusion of homodimerization.

The leucine-zipper adapters of the present invention have the general structural formula known as the heptad repeat (Leucine-$X_1$-$X_2$-$X_3$-$X_4$-$X_5$-$X_6$)$_n$, where X may be any of the conventional 20 amino acids, but are most likely to be amino acids with alpha-helix forming potential, for example, alanine, valine, aspartic acid, glutamic acid, and lysine, and n may be 2 or greater, although typically n is 3 to 10, preferably 4 to 8, more preferably 4 to 5. Currently, the sequences are the Fos or Jun leucine zippers.

As used herein, a linear sequence of peptide is "essentially identical" to another linear sequence, if both sequences exhibit substantial amino acid or nucleotide sequence homology. Generally, essentially identical sequences are at least about 60% identical with each other, after alignment of the homologous regions. Generally, the sequences are at least about 70% identical; more specifically, they are at least about 80% identical; more specifically, they are at least about 90% identical; more specifically, the sequences are at least about 95% identical; still more specifically, the sequences are 100% identical.

In determining whether polypeptide sequences are essentially identical, a sequence that preserves the functionality of the polypeptide with which it is being compared is particularly preferred. Functionality may be established by different criteria, such as ability to form a stable complex with a pairing adapter, and ability to facilitate display of polypeptides fused in-frame with the adapter.

The subject adapters include modified leucine zippers and $GABA_B$ heterodimerization peptide sequences which are functionally equivalent to the polypeptide sequences exemplified herein. In particular embodiments, modified polypeptides providing improved stability to the paired adapters and/or display efficiency are used. Examples of modified polypeptides include those with conservative substitutions of amino acid residues, and one or more deletions or additions of amino acids which do not significantly deleteriously alter the heterodimerization specificity. Substitutions can range from changing or modifying one or more amino acid residues to complete redesign of a region as long as the pairwise interaction is maintained. Amino acid substitutions, if present, are preferably conservative substitutions that do not deleteriously affect folding or functional properties of the peptide. Groups of functionally related amino acids within which conservative substitutions can be made are glycine/alanine; valine/isoleucine/leucine; asparagine/glutamine; aspartic acid/glutamic acid; serine/threonine/methionine; lysine/arginine; and phenylalanine/tryosine/tryptophan. Polypeptides of this invention can be in glycosylated or unglycosylated form, can be modified post-translationally (e.g., acetylation, and phosphorylation) or can be modified synthetically (e.g., the attachment of a labeling group).

One c-fos zipper is: LQAETDQLEDEKSALQTEIANLLKEKEKL (SEQ ID NO: 1). One c-Jun zipper is LEEKVKTLKAQNSELASTANMLREQVAQL (SEQ ID NO: 2). Longer forms of these zippers are as follows: c-fos: LTDTLQAETDQLEDEKSALQ TEIANLLKEKEKLEFILA (SEQ ID NO: 3). c-Jun: RIARLEEKVKTLKAQNSELAS TANMLREQVAQLKQKVMN (SEQ ID NO: 4).

Alternative c-Jun zippers may also be used. These zippers have reduced ability to form homodimers, but still heterodimerize with c-Fos (Smeal et al. (1989) Genes & Development 3:2091-2100).

Some c-Jun zippers with reduced heterodimerization ability include:

```
LEEKVKTLKAQNSELASTFNMLREQFAQL;   (SEQ ID NO: 5)
LEEKVKTLKAQNSELASTANMLREQVAQF;   (SEQ ID NO: 6)
LEEKVKTFKAQNSELASTANMLREQVAQF;   (SEQ ID NO: 7)
LEEKVKSFKAQNSEHASTANMLREQVAQL    (SEQ ID NO: 8)
```

The adapter sequences of the present invention can be obtained using conventional recombinant cloning methods and/or by chemical synthesis. Using well-established restriction and ligation techniques, the appropriate adapter sequences can be excised from various DNA sources and integrated in-frame with the exogenous gene sequences and the outer-surface sequences to generate the expression and helper vectors, respectively.

Preferably, the second adapter sequence is inserted into the expression vector in such a way to minimize structural interference, if any, on the resulting exogenous fusion polypeptide. Whereas the first adapter can be fused to the 5' or 3' of the exogenous gene sequence, FIG. 4 depicts a construct in which the adapter peptide sequence (i.e., hererodimerization sequence derived from $GABA_B$ receptor 1) is fused in-frame to the 3' end of the exogenous gene sequence.

Similarly, the first adapter peptide sequence is inserted into the second vector in a position where the integrity of the cell surface anchoring protein is not undermined. The adapter sequence can be fused to the 5' or 3' end of an outer-surface sequence without disrupting the coding region. FIG. 2 depicts a vector in which the adapter sequence (i.e. heterodimerizeration sequence derived from $GABA_B$ receptor 2) is placed in-frame to the 5' end of the cell surface anchoring protein SED1.

II. Host Cells

In general, lower eukaryotes such as yeast are used for expression of the proteins, particularly glycoproteins because they can be economically cultured, give high yields, and when appropriately modified are capable of suitable glycosylation. Yeast particularly offers established genetics allowing for rapid transformations, tested protein localization strategies and facile gene knock-out techniques. Suitable vectors have expression control sequences, such as promoters, including 3-phosphoglycerate kinase or other glycolytic enzymes, and an origin of replication, termination sequences and the like as desired.

While the invention has been demonstrated herein using the methylotrophic yeast *Pichia pastoris*, other useful lower eukaryote host cells include *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum* and *Neurospora crassa*. Various yeasts, such as *K. lactis, Pichia pastoris, Pichia methanolica*, and *Hansenula polymorpha* are particularly suitable for cell culture because they are able to grow to high cell densities and secrete large quantities of recombinant protein. Likewise, filamentous fungi, such as *Aspergillus niger, Fusarium* sp, *Neurospora crassa* and others can be used to produce glycoproteins of the invention at an industrial scale. In the case of lower eukaryotes, cells are routinely grown from between about 1.5 to 3 days under conditions that induce expression of the capture moiety. The induction of immunoglobulin expression while inhibiting expression of the capture moiety is for about 1 to 2 days. Afterwards, the cells are analyzed for those cells that display the immunoglobulin of interest.

Lower eukaryotes, particularly yeast and filamentous fungi, can be genetically modified so that they express glycoproteins in which the glycosylation pattern is human-like or humanized. In this manner, glycoprotein compositions can be produced in which a specific desired glycoform is predominant in the composition. Such can be achieved by eliminating selected endogenous glycosylation enzymes and/or genetically engineering the host cells and/or supplying exogenous enzymes to mimic all or part of the mammalian glycosylation pathway as described in US 2004/0018590. If desired, additional genetic engineering of the glycosylation can be performed, such that the glycoprotein can be produced with or without core fucosylation. Use of lower eukaryotic host cells is further advantageous in that these cells are able to produce highly homogenous compositions of glycoprotein, such that the predominant glycoform of the glycoprotein may be present as greater than thirty mole percent of the glycoprotein in the composition. In particular aspects, the predominant glycoform may be present in greater than forty mole percent, fifty mole percent, sixty mole percent, seventy mole percent and, most preferably, greater than eighty mole percent of the glycoprotein present in the composition.

Lower eukaryotes, particularly yeast, can be genetically modified so that they express glycoproteins in which the glycosylation pattern is human-like or humanized. Such can be achieved by eliminating selected endogenous glycosylation enzymes and/or supplying exogenous enzymes as described by Gemgross et al., US 20040018590. For example, a host cell can be selected or engineered to be depleted in 1,6-mannosyl transferase activities, which would otherwise add mannose residues onto the N-glycan on a glycoprotein.

In one embodiment, the host cell further includes an α1,2-mannosidase catalytic domain fused to a cellular targeting signal peptide not normally associated with the catalytic domain and selected to target the α1,2-mannosidase activity to the ER or Golgi apparatus of the host cell. Passage of a recombinant glycoprotein through the ER or Golgi apparatus of the host cell produces a recombinant glycoprotein comprising a $Man_5GlcNAc_2$ glycoform, for example, a recombinant glycoprotein composition comprising predominantly a $Man_5GlcNAc_2$ glycoform. For example, U.S. Pat. No. 7,029,872 and U.S. Published Patent Application Nos. 2004/0018590 and 2005/0170452 disclose lower eukaryote host cells capable of producing a glycoprotein comprising a $Man_5GlcNAc_2$ glycoform.

In a further embodiment, the immediately preceding host cell further includes a GlcNAc transferase I (GnT I) catalytic domain fused to a cellular targeting signal peptide not normally associated with the catalytic domain and selected to target GlcNAc transferase I activity to the ER or Golgi apparatus of the host cell. Passage of the recombinant glycoprotein through the ER or Golgi apparatus of the host cell produces a recombinant glycoprotein comprising a $GlcNAcMan_5GlcNAc_2$ glycoform, for example a recombinant glycoprotein composition comprising predominantly a $GlcNAcMan_5GlcNAc_2$ glycoform. U.S. Pat. No. 7,029,872 and U.S. Published Patent Application Nos. 2004/0018590 and 2005/0170452 disclose lower eukaryote host cells capable of producing a glycoprotein comprising a $GlcNAcMan_5GlcNAc_2$ glycoform. The glycoprotein produced in the above cells can be treated in vitro with a hexaminidase to produce a recombinant glycoprotein comprising a $Man_5GlcNAc_2$ glycoform.

In a further embodiment, the immediately preceding host cell further includes a mannosidase II catalytic domain fused to a cellular targeting signal peptide not normally associated with the catalytic domain and selected to target mannosidase II activity to the ER or Golgi apparatus of the host cell. Passage of the recombinant glycoprotein through the ER or Golgi apparatus of the host cell produces a recombinant glycoprotein comprising a $GlcNAcMan_3GlcNAc_2$ glycoform, for example a recombinant glycoprotein composition comprising predominantly a $GlcNAcMan_3GlcNAc_2$ glycoform. U.S. Pat. No. 7,029,872 and U.S. Published Patent Application No. 2004/0230042 discloses lower eukaryote host cells that express mannosidase II enzymes and are capable of producing glycoproteins having predominantly a $GlcNAc_2Man_3GlcNAc_2$ glycoform. The glycoprotein produced in the above cells can be treated in vitro with a hexaminidase to produce a recombinant glycoprotein comprising a $Man_3GlcNAc_2$ glycoform.

In a further embodiment, the immediately preceding host cell further includes GlcNAc transferase II (GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a $GlcNAc_2Man_3GlcNAc_2$ glycoform, for example a recombinant glycoprotein composition comprising predominantly a $GlcNAc_2Man_3GlcNAc_2$ glycoform. U.S. Pat. No. 7,029,872 and U.S. Published Patent Application Nos. 2004/0018590 and 2005/0170452 disclose lower eukaryote host cells capable of producing a glycoprotein comprising a $GlcNAc_2Man_3GlcNAc_2$ glycoform. The glycoprotein produced in the above cells can be treated in vitro with a hexaminidase to produce a recombinant glycoprotein comprising a $Man_3GlcNAc_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a $GalGlcNAc_2Man_3GlcNAc_2$ or $Gal_2GlcNAc_2Man_3GlcNAc_2$ glycoform, or mixture thereof for example a recombinant glycoprotein composition comprising predominantly a $GalGlcNAc_2Man_3GlcNAc_2$ glycoform or $Gal_2GlcNAc_2Man_3GlcNAc_2$ glycoform or mixture thereof. U.S. Pat. No. 7,029,872 and U.S. Published Patent Application No. 2006/0040353 discloses lower eukaryote host cells capable of producing a glycoprotein comprising a $Gal_2GlcNAc_2Man_3GlcNAc_2$ glycoform. The glycoprotein produced in the above cells can be treated in vitro with a galactosidase to produce a recombinant glycoprotein comprising a $GlcNAc_2Man_3GlcNAc_2$ glycoform, for example a recombinant glycoprotein composition comprising predominantly a $GlcNAc_2Man_3GlcNAc_2$ glycoform.

In a further embodiment, the immediately preceding host cell further includes a sialyltransferase catalytic domain fused to a cellular targeting signal peptide not normally associated with the catalytic domain and selected to target sialytransferase activity to the ER or Golgi apparatus of the host cell. Passage of the recombinant glycoprotein through the ER or Golgi apparatus of the host cell produces a recombinant glycoprotein comprising predominantly a NANA$_2$Gal$_2$GlcNAc$_2$Man$_3$GlcNAc$_2$ glycoform or NANAGal$_2$GlcNAc$_2$Man$_3$GlcNA$_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729 discloses a method for genetically engineering lower eukaryotes to have a CMP-sialic acid synthesis pathway and U.S. Published Patent Application No. 2006/0286637 discloses a method for genetically engineering lower eukaryotes to produce sialylated glycoproteins. The glycoprotein produced in the above cells can be treated in vitro with a neuraminidase to produce a recombinant glycoprotein comprising predominantly a Gal$_2$GlcNAc$_2$Man$_3$GlcNAc$_2$ glycoform or GalGlcNAc$_2$Man$_3$GlcNAc$_2$ glycoform or mixture thereof.

Any one of the preceding host cells can further include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX) N-glycan structures such as disclosed in U.S. Published Patent Application Nos. 2004/074458 and 2007/0037248.

In further embodiments, the host cell that produces glycoproteins that have predominantly GlcNAcMan$_5$GlcNAc$_2$ N-glycans further includes a galactosyltransferase catalytic domain fused to a cellular targeting signal peptide not normally associated with the catalytic domain and selected to target Galactosyltransferase activity to the ER or Golgi apparatus of the host cell. Passage of the recombinant glycoprotein through the ER or Golgi apparatus of the host cell produces a recombinant glycoprotein comprising predominantly the GalGlcNAcMan$_5$GlcNAc$_2$ glycoform.

In a further embodiment, the immediately preceding host cell that produced glycoproteins that have predominantly the GalGlcNAcMan$_5$GlcNAc$_2$ N-glycans further includes a sialyltransferase catalytic domain fused to a cellular targeting signal peptide not normally associated with the catalytic domain and selected to target sialytransferase activity to the ER or Golgi apparatus of the host cell. Passage of the recombinant glycoprotein through the ER or Golgi apparatus of the host cell produces a recombinant glycoprotein comprising a NANAGalGlcNAcMan$_5$GlcNAc$_2$ glycoform.

Various of the preceding host cells further include one or more sugar transporters such as UDP-GlcNAc transporters (for example, Kluyveromyces lactis and Mus musculus UDP-GlcNAc transporters), UDP-galactose transporters (for example, Drosophila melanogaster UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

Host cells further include lower eukaryote cells (e.g., yeast such as Pichia pastoris) that are genetically engineered to eliminate glycoproteins having α-mannosidase-resistant N-glycans by deleting or disrupting one or more of the β-mannosyltransferase genes (e.g., BMT1, BMT2, BMT3, and BMT4)(See, U.S. Published Patent Application No. 2006/0211085) and glycoproteins having phosphomannose residues by deleting or disrupting one or both of the phosphomannosyl transferase genes PNO1 and MNN4B (See for example, U.S. Pat. Nos. 7,198,921 and 7,259,007), which in further aspects can also include deleting or disrupting the MNN4A gene. Disruption includes disrupting the open reading frame encoding the particular enzymes or disrupting expression of the open reading frame or abrogating translation of RNAs encoding one or more of the α-mannosyltransferases and/or phosphomannosyltransferases using interfering RNA, antisense RNA, or the like. The host cells can further include any one of the aforementioned host cells modified to produce particular N-glycan structures.

Host cells further include lower eukaryote cells (e.g., yeast such as Pichia pastoris) that are genetically modified to control O-glycosylation of the glycoprotein by deleting or disrupting one or more of the protein O-mannosyltransferase (Dol-P-Man:Protein (Ser/Thr) Mannosyl Transferase genes) (PMTs) (See U.S. Pat. No. 5,714,377) or grown in the presence of Pmtp inhibitors and/or an alpha-mannosidase as disclosed in Published International Application No. WO 2007061631, or both. Disruption includes disrupting the open reading frame encoding the Pmtp or disrupting expression of the open reading frame or abrogating translation of RNAs encoding one or more of the Pmtps using interfering RNA, antisense RNA, or the like. The host cells can further include any one of the aforementioned host cells modified to produce particular N-glycan structures.

Pmtp inhibitors include but are not limited to a benzylidene thiazolidinediones.

Examples of benzylidene thiazolidinediones that can be used are 5-[[3,4-bis(phenylmethoxy)phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo-3-thiazolidineacetic Acid.

In particular embodiments, the function or expression of at least one endogenous PMT gene is reduced, disrupted, or deleted. For example, in particular embodiments the function or expression of at least one endogenous PMT gene selected from the group consisting of the PMT1, PMT2, PMT3, and PMT4 genes is reduced, disrupted, or deleted; or the host cells are cultivated in the presence of one or more PMT inhibitors. In further embodiments, the host cells include one or more PMT gene deletions or disruptions and the host cells are cultivated in the presence of one or more Pmtp inhibitors. In particular aspects of these embodiments, the host cells also express a secreted alpha-1,2-mannosidase.

PMT deletions or disruptions and/or Pmtp inhibitors control O-glycosylation by reducing O-glycosylation occupancy, that is by reducing the total number of O-glycosylation sites on the glycoprotein that are glycosylated. The further addition of an alpha-1,2-mannsodase that is secreted by the cell controls O-glycosylation by reducing the mannose chain length of the O-glycans that are on the glycoprotein. Thus, combining PMT deletions or disruptions and/or Pmtp inhibitors with expression of a secreted alpha-1,2-mannosidase controls O-glycosylation by reducing occupancy and chain length. In particular circumstances, the particular combination of PMT deletions or disruptions, Pmtp inhibitors, and alpha-1,2-mannosidase is determined empirically as particular heterologous glycoproteins (Fabs and antibodies, for example) may be expressed and transported through the Golgi apparatus with different degrees of efficiency and thus may require a particular combination of PMT deletions or disruptions, Pmtp inhibitors, and alpha-1,2-mannosidase. In another aspect, genes encoding one or emore endogenous mannosyltransferase enzymes are deleted. This deletion(s) can be in combination with providing the secreted alpha-1,2-mannosidase and/or PMT inhibitors or can be in lieu of providing the secreted alpha-1,2-mannosidase and/or PMT inhibitors.

Thus, the control of O-glycosylation can be useful for producing particular glycoproteins in the host cells disclosed herein in better total yield or in yield of properly assembled glycoprotein. The reduction or elimination of O-glycosylation appears to have a beneficial effect on the assembly and transport of whole antibodies and Fab fragments as they traverse the secretory pathway and are transported to the cell surface. Thus, in cells in which O-glycosylation is controlled, the yield of properly assembled antibodies or Fab fragments is increased over the yield obtained in host cells in which O-glycosylation is not controlled.

In addition, O-glycosylation may have an effect on an antibody or Fab fragment's affinity and/or avidity for an antigen. This can be particularly significant when the ultimate host cell for production of the antibody or Fab is not the same as the host cell that was used for selecting the antibody. For example, O-glycosylation might interfere with an antibody's or Fab fragment's affinity for an antigen, thus an antibody or Fab fragment that might otherwise have high affinity for an antigen might not be identified because O-glycosylation may interfere with the ability of the antibody or Fab fragment to bind the antigen. In other cases, an antibody or Fab fragment that has high avidity for an antigen might not be identified because O-glycosylation interferes with the antibody's or Fab fragment's avidity for the antigen. In the preceding two cases, an antibody or Fab fragment that might be particularly effective when produced in a mammalian cell line might not be identified because the host cells for identifying and selecting the antibody or Fab fragment was of another cell type, for example, a yeast or fungal cell (e.g., a *Pichia pastoris* host cell). It is well known that O-glycosylation in yeast can be significantly different from O-glycosylation in mammalian cells. This is particularly relevant when comparing wild type yeast o-glycosylation with mucin-type or dystroglycan type O-glycosylation in mammals. In particular cases, O-glycosylation might enhance the antibody or Fab fragments affinity or avidity for an antigen instead of interfere. This effect is undesirable when the production host cell is to be different from the host cell used to identify and select the antibody or Fab fragment (for example, identification and selection is done in yeast and the production host is a mammalian cell) because in the production host the O-glycosylation will no longer be of the type that caused the enhanced affinity or avidity for the antigen. Therefore, controlling O-glycosylation can enable use of the materials and methods herein to identify and select antibodies or Fab fragments with specificity for a particular antigen based upon affinity or avidity of the antibody or Fab fragment for the antigen without identification and selection of the antibody or Fab fragment being influenced by the O-glycosylation system of the host cell. Thus, controlling O-glycosylation further enhances the usefulness of yeast or fungal host cells to identify and select antibodies or Fab fragments that will ultimately be produced in a mammalian cell line.

Yield of antibodies and Fabs can in some situations be improved by overexpressing nucleic acid molecules encoding mammalian or human chaperone proteins or replacing the genes encoding one or more endogenous chaperone proteins with nucleic acid molecules encoding one or more mammalian or human chaperone proteins. In addition, the expression of mammalian or human chaperone proteins in the host cell may control O-glycosylation in the cell. Thus, further included are the host cells herein wherein the function of at least one endogenous gene encoding a chaperone protein has been reduced or eliminated, and a vector encoding at least one mammalian or human homolog of the chaperone protein is expressed in the host cell. Also included are host cells in which the endogenous host cell chaperones and the mammalian or human chaperone proteins are expressed. In further aspects, the lower eukaryotic host cell is a yeast or filamentous fungi host cell. Examples of the use of chaperones of host cells in which human chaperone proteins are introduced to improve the yield and reduce or control O-glycosylation of recombinant proteins has been disclosed in U.S. Provisional Application Nos. 61/066,409 filed Feb. 20, 2008 and 61/188,723 filed Aug. 12, 2008. Like above, further included are lower eukaryotic host cells wherein, in addition to replacing the genes encoding one or more of the endogenous chaperone proteins with nucleic acid molecules encoding one or more mammalian or human chaperone proteins or overexpressing one or more mammalian or human chaperone proteins as described above, the function or expression of at least one endogenous gene encoding a protein O-mannosyltransferase (PMT) protein is reduced, disrupted, or deleted. In particular embodiments, the function of at least one endogenous PMT gene selected from the group consisting of the PMT1, PMT2, PMT3, and PMT4 genes is reduced, disrupted, or deleted.

Therefore, the methods disclosed herein can use any host cell that has been genetically modified to produce glycoproteins that have no N-glycan compositions wherein the predominant N-glycan is selected from the group consisting of complex N-glycans, hybrid N-glycans, and high mannose N-glycans wherein complex N-glycans are selected from the group consisting of $Man_3GlcNAc_2$, $GlcNAC_{(1-4)}Man_3GlcNAc_2$, $Gal_{(1-4)}GlcNAc_{(1-4)}Man_3GlcNAc_2$, and $NANA_{(1-4)}Gal_{(1-4)}Man3GlcNAc_2$; hybrid N-glycans are selected from the group consisting of $GlcNAcMan_5GlcNAc_2$, $GalGlcNAcMan_5GlcNAc_2$, and $NANAGalGlcNAcMan_5GlcNAc_2$; and high Mannose N-glycans are selected from the group consisting of $Man_5GlcNAc_2$, $Man_6GlcNAc_2$, $Man_7GlcNAc_2$, $Man_8GlcNAc_2$, and $Man_9GlcNAc_2$. In particular aspects, the composition of N-glycans comprises about 39% $GlcNAC_2Man_3GlcNAc_2$; 40% $Gal_1GlcNAC_2Man_3GlcNAc_2$; and 6% $Gal_2GlcNAC_2Man_3GlcNAc_2$ or about 60% $GlcNAC_2Man_3GlcNAc_2$; 17% $Gal_1GlcNAC_2Man_3GlcNAc_2$; and 5% $Gal_2GlcNAC_2Man_3GlcNAc_2$, or mixtures in between.

In the above embodiments in which the yeast cell does not display 1,6-mannosyl transferase activity (that is, the OCH1 gene encoding och1p has been disrupted or deleted or the activity of Och1p has been disabled), the host cell is not capable of mating. Thus, depending on the efficiency of transformation, the potential library diversity of light chains and heavy chains appears to be limited to a heavy chain library of between about 103 to $10^6$ diversity and a light chain library of about $10^3$ to $10^6$ diversity. However, in a yeast host cell that is capable of mating, the diversity can be increased to about $10^6$ to $10^{12}$ because the host cells expressing the heavy chain library can be mated to host cells expressing the light chain library to produce host cells that express heavy chain/light chain library. Therefore, in particular embodiments, the host cell is a yeast cell such as *Pichia pastoris* that displays 1,6-mannosyl transferase activities (that is, has an OCH1 gene encoding a functional och1p) but which is modified as described herein to display antibodies or fragments thereof on the cell surface. In these embodiments, the host cell can be a host cell with its native glycosylation pathway.

In embodiments that express whole antibodies or the Fc region of an antibody heavy chain (e.g., Fab fragments), the nucleic acid molecule encoding the antibody or heavy chain fragment thereof is modified to replace the codon encoding an asparagine residue at position 297 of the molecule (the glycosylation site) with a codon encoding any other amino acid residue. Common replacements include but are not limited to alanine, glutamine, and aspartate. Thus, the antibody or fragment thereof that is produced in the host cell is not glycosylated at asparagine-297. In this embodiment, the host cell displaying the heavy chain library is mated to the host cell displaying the light chain library and the resulting combinatorial library is screened as taught herein. Because the antibodies or fragments thereof lack N-glycosylation at asparagine-297, the non-human yeast N-glycans of the host cell linked to asparagine-297 which might interfere with antibody affinity for a desired antigen are not present on the recombinant antibodies or fragments thereof. Cells producing antibodies or fragments that have desired affinity for an antigen of interest are selected. The nucleic acid molecules encoding the heavy and light chains of the antibody or fragments thereof are removed from the cells and the nucleic acid molecule encoding the heavy chain is modified to reintroduce an asparagine residue at position 297. This enables appropriate human-like glycosylation at position 297 of the antibody or fragment thereof when the nucleic acid molecule encoding the antibody or fragment thereof is introduced into a mammalian cell line (e.g., CHO or the like) or lower eukaryote (e.g., *Pichia pastoris*) host cell that has been engineered to make glycoproteins that have human-like N-glycans (e.g., high mannose, hybrid, or complex N-glycans as discussed previously.

While in general the host cells used to practice the present invention are lower eukaryote host cells (e.g., yeast or filamentous fungal cells), it is envisioned that the methods herein can be adapted to use higher eukaryote cells. Thus, in particular embodiments, the cell systems used for recombinant expression and display of the immunoglobulin can also be any higher eukaryote cell, tissue, organism from the animal kingdom, for example transgenic goats, transgenic rabbits, CHO cells, insect cells, and human cell lines. Examples of animal cells include, but are not limited to, SC-I cells, LLC-MK cells, CV-I cells, CHO cells, COS cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0, NSO cells, and derivatives thereof. Insect cells include cells of *Drosophila melanogaster* origin. In addition, these cells can be genetically engineered to render the cells capable of making immunoglobulins that have particular N-glycans or predominantly particular N-glycans. For example, U.S. Pat. No. 6,949,372 discloses methods for making glycoproteins in insect cells that are sialylated. Yamane-Ohnuki et al. Biotechnol. Bioeng. 87: 614-622 (2004), Kanda et al., Biotechnol. Bioeng. 94: 680-688 (2006), Kanda et al., Glycobiol. 17: 104-118 (2006), and U.S. Pub. Application Nos. 2005/0216958 and 2007/0020260 disclose mammalian cells that are capable of producing immunoglobulins in which the N-glycans thereon lack fucose or have reduced fucose.

In particular embodiments, the higher eukaryote cell, tissue, organism can also be from the plant kingdom, for example, wheat, rice, corn, tobacco, and the like. Alternatively, bryophyte cells can be selected, for example from species of the genera *Physcomitrella, Funaria, Sphagnum, Ceratodon, Marchantia*, and *Sphaerocarpos*. Exemplary of plant cells is the bryophyte cell of *Physcomitrella patens*, which has been disclosed in WO 2004/057002 and WO2008/006554. Expression systems using plant cells can further manipulated to have altered glycosylation pathways to enable the cells to produce immunoglobulins that have predominantly particular N-glycans. For example, the cells can be genetically engineered to have a dysfunctional or no core fucosyltransferase and/or a dysfunctional or no xylosyltransferase, and/or a dysfunctional or no β1,4-galactosyltransferase. Alternatively, the galactose, fucose and/or xylose can be removed from the immunoglobulin by treatment with enzymes removing the residues. Any enzyme resulting in the release of galactose, fucose and/or xylose residues from N-glycans which are known in the art can be used, for example α-galactosidase, β-xylosidase, and α-fucosidase. Alternatively an expression system can be used which synthesizes modified N-glycans which can not be used as substrates by 1,3-fucosyltransferase and/or 1,2-xylosyltransferase, and/or 1,4-galactosyltransferase. Methods for modifying glycosylation pathways in plant cells has been disclosed in U.S. Published Application No. 2004/0018590.

The methods disclosed herein can be adapted for use in mammalian, insect, and plant cells. The regulatable promoters selected for regulating expression of the expression cassettes in mammalian, insect, or plant cells should be selected for functionality in the cell-type chosen. Examples of suitable regulatable promoters include but are not limited to the tetracycline-regulatable promoters (See for example, Berens & Hillen, Eur. J. Biochem. 270: 3109-3121 (2003)), RU 486-inducible promoters, ecdysone-inducible promoters, and kanamycin-regulatable systems. These promoters can replace the promoters exemplified in the expression cassettes described in the examples. The capture moiety can be fused to a cell surface anchoring protein suitable for use in the cell-type chosen. Cell surface anchoring proteins including GPI proteins are well known for mammalian, insect, and plant cells. GPI-anchored fusion proteins has been described by Kennard et al., Methods Biotechnol. Vo. 8: Animal Cell Biotechnology (Ed. Jenkins. Human Press, Inc., Totowa, N.J.) pp. 187-200 (1999). The genome targeting sequences for integrating the expression cassettes into the host cell genome for making stable recombinants can replace the genome targeting and integration sequences exemplified in the examples. Transfection methods for making stable and transiently transfected mammalian, insect, plant host cells are well known in the art. Once the transfected host cells have been constructed as disclosed herein, the cells can be screened for expression of the immunoglobulin of interest and selected as disclosed herein.

III. Glycosylphosphatidylinositol-Anchored (GPI) Proteins

Lower eukaryotic cells have systems of GPI proteins that are involved in anchoring or tethering expressed proteins to the cell wall so that they are effectively displayed on the cell wall of the cell from which they were expressed. For example, 66 putative GPI proteins have been identified in *Saccharomyces cerevisiae* (See, de Groot et al., Yeast 20: 781-796 (2003)). GPI proteins which may be used in the methods herein include, for example *Saccharomyces cerevisiae* CWP1; CWP2; SED1; GAS1; *Pichia pastoris* SP1; GAS1; and *H. polymorpha* TIP1. Additional GPI proteins may also be useful. Suitable GPI proteins Can be identified using the methods and materials of the invention described and exemplified herein.

The selection of the appropriate GPI protein will depend on the particular recombinant protein to be produced in the host cell and the particular post-translation modifications to be performed on the recombinant protein. For example, production of antibodies or fragments thereof with particular glycosylation patterns will entail the use of recombinant host cells that produce glycoproteins having particular glycosylation patterns. The GPI protein most suitable in a system for producing antibodies or fragments thereof that have predominantly $Man_5GlcNAc_2$ N-glycosylation many not necessarily be the GPI protein most suitable in a system for producing antibodies or thereof having predominantly $Gal_2GlcNAc_2Man_3GlcNAc_2$ N-glycosylation. In addition, the GPI most suitable in a system for producing antibodies or fragments thereof specific for one epitope or antigen may not necessarily be the most suitable GPI protein in a system for producing antibodies or fragments thereof specific for another epitope or antigen. Furthermore, the GPI most suitable in a system for producing antibody fragments such as scFv or the like may not necessarily be the most suitable GPI protein in a system for producing full-length antibodies.

Therefore, further provided is a library method for constructing the host cell that is to be used for producing a particular recombinant protein. In general, the host that is desired to produce the recombinant proteins is selected based on the desired characteristics that will be imparted to the recombinant protein produced by the host cell. For example, a host cell that produces glycoproteins having predominantly $Man_5GlcNAc_2$ or $Gal_2GlcNAc_2Man_3GlcNAc_2$ N-glycosylation is selected. A library of vectors encoding GPI proteins fused to one or more adapters is then provided. A library of host cells is then constructed wherein each host cell to make up the library is transfected with one of the vectors in the library of vectors encoding GPI-adapter fusion proteins such that each host cell species in the library will express one particular GPI-adapter fusion protein. Each host cell species of the library is then transformed with a vector encoding the desired protein or a protein similar in function or structure to the desired protein. The host cell that results in the best presentation of recombinant protein on the surface of the host cell is selected as the host cell for producing the desired recombinant protein.

In general, the GPI protein used in the methods disclosed herein is a chimeric protein or fusion protein comprising the GPI protein fused at its N-terminus to the C-terminus of a binding moiety or adapter peptide. The N-terminus of the binding moiety or adapter peptide is fused to the C-terminus of a signal sequence that enables the GPI fusion protein to be transported through the secretory pathway to the cell surface where the GPI fusion protein is secreted and then bound to the cell surface. In some aspects, the GPI fusion protein comprises the entire GPI protein and in other aspects, the GPI fusion protein comprises the portion of the GPI protein that is capable of binding to the cell surface.

V. Regulatory Sequences

Regulatory sequences which may be used in the practice of the methods disclosed herein include signal sequences, promoters, and transcription terminator sequences. It is generally preferred that the regulatory sequences used be from a species or genus that is the same as or closely related to that of the host cell or is operational in the host cell type chosen. Examples of signal sequences include those of *Saccharomyces cerevisiae* invertase; the *Aspergillus niger* amylase and glucoamylase; human serum albumin; *Kluyveromyces maxianus* inulinase; and *Pichia pastoris* mating factor and Kar2. Signal sequences shown herein to be useful in yeast and filamentous fungi include, but are not limited to, the alpha mating factor presequence and preprosequence from *Saccharomyces cerevisiae*; and signal sequences from numerous other species.

Examples of promoters include promoters from numerous species, including but not limited to alcohol-regulated promoter, tetracycline-regulated promoters, steroid-regulated promoters (e.g., glucocorticoid, estrogen, ecdysone, retinoid, thyroid), metal-regulated promoters, pathogen-regulated promoters, temperature-regulated promoters, and light-regulated promoters. Specific examples of regulatable promoter systems well known in the art include but are not limited to metal-inducible promoter systems (e.g., the yeast copper-metallothionein promoter), plant herbicide safner-activated promoter systems, plant heat-inducible promoter systems, plant and mammalian steroid-inducible promoter systems, Cym repressor-promoter system (Krackeler Scientific, Inc. Albany, N.Y.), RheoSwitch System (New England Biolabs, Beverly Mass.), benzoate-inducible promoter systems (See WO2004/043885), and retroviral-inducible promoter systems. Other specific regulatable promoter systems well-known in the art include the tetracycline-regulatable systems (See for example, Berens & Hillen, Eur J Biochem 270: 3109-3121 (2003)), RU 486-inducible systems, ecdysone-inducible systems, and kanamycin-regulatable system. Lower eukaryote-specific promoters include but are not limited to the *Saccharomyces cerevisiae* TEF-1 promoter, *Pichia pastoris* GAPDH promoter, *Pichia pastoris* GUT1 promoter, PMA-1 promoter, *Pichia pastoris* PCK-1 promoter, and *Pichia pastoris* AOX-1 and AOX-2 promoters. For temporal expression of the GPI-IgG capture moiety and the immunoglobulins, the *Pichia pastoris* GUT1 promoter operably linked to the nucleic acid molecule encoding the GPI-IgG capture moiety and the *Pichia pastoris* GAPDH promoter operably linked to the nucleic acid molecule encoding the immunoglobulin are shown in the examples herein to be useful.

Examples of transcription terminator sequences include transcription terminators from numerous species and proteins, including but not limited to the *Saccharomyces cerevisiae* cytochrome C terminator; and *Pichia pastoris* ALG3 and PMA1 terminators.

VI. Nucleic Acid Sequences Encoding the Protein of Interest

The methods of the present invention can be employed with any gene of interest for further study. Because of the particular advantages afforded by the methods disclosed herein, the methods and materials will utilize genes encoding glycoproteins. Of particular interest are human glycoproteins with known therapeutic utility, including but not limited to monoclonal antibodies and functional fragments thereof such as Fab fragments; immunoglobulins including but not limited to IgG, IgM, IgD, antibody fragments such as scFv, Fab fragments, or the like; Fc fusion proteins; catalytic antibodies, camel or lama antibodies; erythropoietin; cytokines such as interferon-alpha, interferon-beta, interferon-gamma, interferon-omega, and granulocyte-CSF; coagulation factors such as factor VIII, factor IX, and human protein C; soluble IgE receptor alpha-chain; urokinase; chymase and urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; and osteoprotegerin.

Nucleic acids encoding desired glycoproteins can be obtained from several sources. cDNA sequences can be amplified from cell lines known to express the glycoprotein using primers to conserved regions (See, e.g., Marks et al., J. Mol. Biol. 581-596 (1991)). Nucleic acids can also be synthesized de novo based on sequences in the scientific literature. Nucleic acids can also be synthesized by extension of overlapping oligonucleotides spanning a desired sequence (See, e.g., Caldas et al., Protein Engineering, 13: 353-360 (2000)). Production of active glycoproteins requires proper folding of the protein when it is produced and secreted by the cells. The presence of effective molecular chaperone proteins may be required, or may enhance the ability of the cell to produce and secrete properly folded proteins.

Nucleic acid molecules encoding immunoglobulins can be obtained from any suitable source including spleen and liver cells and antigen-stimulated antibody producing cells, obtained from either in vivo or in vitro sources. Regardless of source, the cellular VH and VL mRNAs are reverse transcribed into VH and VL cDNA sequences. Reverse transcription may be performed in a single step or in an optional combined reverse transcription/PCR procedure to produce cDNA libraries containing a plurality of immunoglobulin-encoding DNA molecules. (See, for example, Marks et al., J. Mol. Biol. 222: 581-596 (1991)). Nucleic acid molecules can also be synthesized de novo based on sequences in the scientific literature. Nucleic acid molecules can also be synthesized by extension of overlapping oligonucleotides spanning a desired sequence (See, e.g., Caldas et al., Protein Engineering, 13: 353-360 (2000)). Humanized immunoglobulin-encoding cDNA libraries can be constructed by PCR amplifying the complementary-determining regions (CDR) from the cDNAs in one or more libraries from any source and integrating the PCR amplified CDR-encoding nucleic acid molecules into nucleic acid molecules encoding a human immunoglobulin framework to produce a cDNA library encoding a plurality of humanized immunoglobulins (See, for example, U.S. Pat. Nos. 6,180,370; 6,632,927; and, 6,872,392). Chimeric immunoglobulin-encoding cDNA libraries can be constructed by PCR amplifying the variable regions from the cDNAs in the cDNA library from one species and integrating the nucleic acid molecules encoding the PCR-amplified variable regions onto nucleic acid molecules encoding immunoglobulin constant regions from another species to produce a cDNA library encoding a plurality of chimeric immunoglobulins (See, for example, U.S. Pat. No. 5,843,708). Various methods that have been developed for the creation of diversity within protein libraries, including random mutagenesis (Daugherty et al., Proc. Natl Acad. Sci. USA, 97: 2029-2034 (2000); Boder et al., Proc. Natl Acad. Sci. USA, 97: 10701-10705 (2000); Holler et al., Proc. Natl Acad. Sci. USA, 97: 5387-5392 (2000)), in vitro DNA shuffling (Stemmer, Nature, 370: 389-391 (1994); Stemmer, Proc. Natl Acad. Sci. USA, 91: 10747-10751 (1994)), in vivo DNA shuffling (Swers et al., Nucl. Acid Res. 32: e36 (2004)), and site-specific recombination (Rehberg et al., J. Biol. Chem., 257: 11497-11502 (1982); Streuli et al., Proc. Natl Acad. Sci. USA, 78: 2848-2852 (1981); Waterhouse et al., (1993) Nucl. Acids Res., 21: 2265-2266 (1993); Sblattero & Bradbury, Nat. Biotechnol., 18: 75-80 (2000)) can be used or adapted to produce the plurality of host cells disclosed herein that express immunoglobulins and the capture moiety comprising a cell surface anchoring protein fused to a binding moiety that is capable of specifically binding an immunoglobulin.

Production of active immunoglobulins requires proper folding of the protein when it is produced and secreted by the cells. In E. coli, the complexity and large size of an antibody presents an obstacle to proper folding and assembly of the expressed light and heavy chain polypeptides, resulting in poor yield of intact antibody. The presence of effective molecular chaperone proteins may be required, or may enhance the ability of the cell to produce and secrete properly folded proteins. The use of molecular chaperone proteins to improve production of immunoglobulins in yeast has been disclosed in U.S. Pat. No. 5,772,245; U.S. Pat. Nos. 5,700,678 and 5,874,247; U.S. Application Publication No. 2002/0068325; Toman et al., J. Biol. Chem. 275: 23303-23309 (2000); Keizer-Gunnink et al., Martix Biol. 19: 29-36 (2000); Vad et al., J. Biotechnol. 116: 251-260 (2005); Inana et al., Biotechnol. Bioengineer. 93: 771-778 (2005); Zhang et al., Biotechnol. Prog. 22: 1090-1095 (2006); Damasceno et al., Appl. Microbiol. Biotechnol. 74: 381-389 (2006); Huo et al., Protein Express. Purif. 54: 234-239 (2007); and copending application Ser. No. 61/066,409, filed 20 Feb. 2008.

As used herein, the methods can use host cells from any kind of cellular system which can be modified to express a capture moiety comprising a cell surface anchoring protein fused to a binding moiety capable of binding an immunoglobulin and whole, intact immunoglobulins. Within the scope of the invention, the term "cells" means the cultivation of individual cells, tissues, organs, insect cells, avian cells, reptilian cells, mammalian cells, hybridoma cells, primary cells, continuous cell lines, stem cells, plant cells, yeast cells, filamentous fungal cells, and/or genetically engineered cells, such as recombinant cells expressing and displaying a glycosylated immunoglobulin.

VII. Uses of the Adapter-Directed Display Systems

The adapter-directed display systems disclosed herein allows the display of monomeric and multimeric polypeptides on the surface of suitable lower eukaryote host cells. The subject display systems also can be used to create libraries of random or predetermined polypeptides, full-length proteins, and protein domains for a variety of purposes. For instance, the displayed libraries can be employed for mapping epitopes and mimotopes, identifying antagonists and agonists of various target proteins, engineering antibodies, optimizing antibody specificities and creating novel binding activities.

Accordingly, provided is a method of detecting the presence of a specific interaction between a test agent and an exogenous polypeptide that is displayed on the surface of a suitable lower eukaryote host cell. The method involves the steps of: (a) providing a lower eukaryote host cell of the subject display system that presents the exogenous polypeptide; (b) contacting the lower eukaryote host cell with the test agent under conditions suitable to produce a stable polypeptide-agent complex; and (c) detecting the formation of the stable polypeptide-agent complex on the surface of the lower eukaryote host cell, thereby detecting the presence of the specific interaction.

The term "test agent" is intended to include, but not be limited to a biological or chemical compound such as a simple or complex organic or inorganic molecule, a protein, carbohydrate, lipid, polynucleotide or combinations thereof. A vast array of compounds can be synthesized, for example oligomers, such as oligopeptides and oligonucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen. In particular embodiments, the agents are candidate diagnostics and/or therapeutics, such as those capable of modulating the signal transduction pathways of a cell.

In a separate embodiment, the present invention provides a method of obtaining a polypeptide with desired property. The method comprises the steps of (a) providing a selectable library of the subject display system; and (b) screening the selectable library to obtain at least one lower eukaryote host cell displaying a polypeptide on its surface with the desired property. The method may further comprise the step of isolating the lower eukaryote host cell that displays a polypeptide having the desired property. Such isolation of the lower eukaryote host cell may involve obtaining a nucleotide sequence from the lower eukaryote host cell that encodes the desired polypeptide. The desired property encompasses the ability of the polypeptide to specifically bind to an agent of interest. The selected polypeptide with the desired property may fall within one or more classes of the following molecules, namely antigen-binding unit, cell surface receptor, receptor ligand, cytosolic protein, secreted protein, nuclear protein, and functional motif thereof. The choice of specific agent to be tested and the libraries of exogenous polypeptides to by displayed will depend on the intended purpose of the screening assay.

VIII. Isolating Antibodies Exhibiting Desired Binding Specificity or Affinity

One of the most powerful applications of display system herein is its use in the arena of antibody engineering. It has been shown that scFv antigen-binding units can be expressed on the surface of lower eukaryote host cells with no apparent loss of binding specificity and affinity (See for example, U.S. Pat. No. 6,300,065). It has also been shown that full-length antibodies can be captured and bound to the surface of hybridomas and CHO cells, for example (See U.S. Pat. Nos. 6,919,183 and 7,166,423). While antibodies and fragments thereof to many diverse antigens have been successfully isolated using phage display technology, there is still a need for a robust display system for producing antibodies and fragments thereof in lower eukaryotic host cell. It is particularly desirable to have a robust display system for producing antibodies and fragments thereof that have human-like glycosylation patterns. Genetically engineered lower eukaryotes that produce glycoproteins that have various human-like glycosylation patterns has been described in U.S. Pat. No. 7,029,872 and for example in Choi et al., Hamilton, et al., Science 313; 1441 1443 (2006); Wildt and Gerngross, Nature Rev. 3: 119-128 (2005); Bobrowicz et al., Glyco Biol. 757-766 (2004); Li et al., nature Biotechnol. 24: 210-215 (2006); Chiba et al., J. Biol. Chem. 273: 26298-26304 (1998); and, Mara et al., Glycoconjugate J. 16: 99-107 (1999).

The subject display system is particularly suited for this application because the system allows presentation of a vast diverse repertoire of antibodies having particular glycosylation patterns. In many respects the subject display system mimics the natural immune system. Antigen-driven stimulation can be achieved by selecting for high-affinity binders from a display library of cloned antibody H and L chains. The large number of chain permutations that occur during recombination of H and L chain genes in developing B cells can be mimicked by shuffling the cloned H and L chains as DNA, and protein and through the use of site-specific recombination (Geoffory et al. Gene 151: 109-113 (1994)). The somatic mutation can also be matched by the introduction of mutations in the CDR regions of the H and L chains.

Antibodies or fragments thereof with desired binding specificity or affinity can be identified using a form of affinity selection known as "panning" (Parmley and Smith (1988) Gene 73:305-318). The library of Antibodies or fragments thereof is first incubated with an antigen of interest followed by the capture of the antigen with the bound antibodies or fragments thereof. The antibodies or fragments thereof recovered in this manner can then be amplified and again gain selected for binding to the antigen, thus enriching for those antibodies or fragments thereof that bind the antigen of interest. After one or more rounds of selection isolation will enable isolation of antibodies or fragments thereof with the desired specificity or avidity. Thus, rare host cells expressing a desired antibody or fragment thereof can easily be selected from greater than $10^4$ different individuals in one experiment. The primary structure of the binding Antibody or fragment thereof is then deduced by nucleotide sequence of the individual host cell clone. When human $V_H$ and $V_L$ regions are employed in the displayed antibodies or fragments thereof, the subject display systems allow selection of human antibodies without further manipulation of a non-human antibodies or fragments thereof.

IX. Generating Novel Proteins Including Antibodies and Fragments Thereof with Improved Binding Specificity or Affinity Using the subject display systems, one can obtain a replicable host cells that displays a polypeptide, such as an antibody or fragment thereof, having high affinity and specificity for a target protein. Such a host cells carries a first polynucleotide encoding the antibody or fragment thereof fused to a second adapter peptide and a second polynucleotide encoding the cell surface anchoring protein fused to a first adapter peptide that is capable of pairwise interaction with the second adapter peptide. The presence of the first polynucleotide facilitates recombinant expression and subsequent manipulation of the binding protein. For instance, the first polynucleotide can be mutagenized by cassette mutagenesis, error-prone PCR, or shuffling to generate a refined repertoire of altered sequences that resemble the parent polynucleotide. Upon screening the refined repertoire of novel antibodies or fragments thereof, those exhibiting improved binding specificity or affinity can be identified.

X. Mapping Antigenic Epitopes

Traditionally, epitope mapping of an antigen has relied heavily on physical chemical analysis. These approaches have included: (1) fragmenting the purified antigen with various proteases, identifying reactive fragments, and sequencing them; (2) chemical modification experiments in which residues interaction with the antigen-binding unit are protected from modification; (3) synthesizing a series of peptides corresponding to the primary structure of the antigen; and (4) direct physical characterization using NMR or X-ray crystallography. All of these methods are labor intensive and generally not amenable to high-throughput analyses. Lower eukaryote display as disclosed herein provides a highly efficient and robust alternative for localizing the antigenic epitope. Fragments of DNA that encode portions of the antigen can be expressed as the exogenous polypeptides by the subject expression vectors. The lower eukaryote host cells can then be tested with the antibody to determine which displayed fragments react with the antibody. This application of display technology has been widely used in the art and has been shown to be successful for determining the antigenic epitopes of a variety of molecules.

XI. Mapping Binding Epitopes

The subject display system also can be used to present random peptide libraries for mapping the specificity of the antigen-binding sites. Random peptide libraries represent a source of sequences from which epitopes and mimotopes can be operationally defined. With such a library, one can identify and obtain peptide competitors for antigen-antibody interactions, and thus map accessible and/or functional sites of numerous antibodies or fragments thereof.

XII. Kits Comprising the Vectors of the Present Invention

The present invention also encompasses kits containing the expression and helper vectors of this invention in suitable packaging. Each kit necessarily comprises the reagents which render the delivery of vectors into a host cell possible. The selection of reagents that facilitate delivery of the vectors may vary depending on the particular transfection or infection method used. The kits may also contain reagents useful for generating labeled polynucleotide probes or proteinaceous probes for detection of exogenous sequences and the protein product. Each reagent can be supplied in a solid form or dissolved/suspended in a liquid buffer suitable for inventory storage, and later for exchange or addition into the reaction medium when the experiment is performed. Suitable packaging is provided. The kit can optionally provide additional components that are useful in the procedure. These optional components include, but are not limited to, buffers, capture reagents, developing reagents, labels, reacting surfaces, means for detection, control samples, instructions, and interpretive information.

In the following examples, heterologous human proteins are expressed in host cells of the species *Pichia pastoris*. The following examples are intended to promote a further understanding of the present invention.

Example 1

The objective was to develop a novel yeast display method especially designed for *Pichia pastoris* strains genetically engineered to produce glycoproteins with various mammalian glycosylation patterns. In this example, a nucleic acid encoding the N-terminus of a cell surface anchoring protein that inherently contains an attached glycophosphotidylinositol (GPI) post-translational modification that anchors the protein in the cell wall was linked to a nucleic acid that encodes a first coiled coil peptide that is capable of forming a heterodimer with a second coiled coil peptide fused to a test protein. The specific cell surface anchoring protein that was used was Sed1p, which had been identified by screening a panel of cell wall or plasma membrane proteins that had been identified using GPI protein prediction software.

Expression cassettes encoding the GPI protein and the test antibodies and Fab fragments were constructed using as the adapter peptides the coiled coil peptides GABAB-R2 (AEQ ID NO:19) fused to the N-terminus of the GPI protein and the GABAB-R1 (SEQ ID NO:21) fused to the C-terminus of the antibody or Fab fragment. GABAB-R1 (GR1) and GABAB-R2 (GR2) are derived from the γ-Aminobutyric acid (GABA) receptors GABAB-R1 and GABAB-R2. Heterodimerization of GABAB-R1 and GABAB-R2 subunits is a prerequisite for the formation of a functional GABAB receptor. Each individual subunit contains one stretch of 30 amino acid residues within its intracellular C-terminal domain that mediates heterodimer formation. (Kammerer et al., J. Biochem. 38:13263-9 (1999)). Heterodimerization of a functional GABAB receptor is mediated by parallel coiled-coil alpha-helices. Three additional amino acid residues, Gly, Gly, and Cys were attached at the end of GR1. The Cys at the end of the GR1 creates a disulfide bond with the Cys at the end of GR2, which is fused at the C-terminal of the display Fab fragment CH1. The two Glys are believed to increase the flexibility of the heterodimer.

Construction of expression cassettes encoding the cell surface anchoring protein library was as follows. Candidate cell surface anchoring proteins were selected from *S. cerevisiae*, *P. pastoris* and *H. polymorpha* according to the literature and further identified as cell surface anchoring proteins using GPI protein prediction software available at IMP (Research Institute of Molecular Pathology), Bioinformatics Group, Dr. Bohr-Gasse 7, 1030 Vienna, Austria. Ten proteins were selected for analysis.

Table 1 below shows the amino acid sequences for the relevant portion of ten GPI proteins and truncated variants of the proteins that were selected for analysis. Because highly expressed genes are desirable, truncation of the 3' end of the candidate nucleic acid sequences was made for several of the proteins in an attempt to improve expression. For all of the GPI proteins, the nucleic acid encoding the endogenous signal sequence for the GPI protein was removed. Therefore, the amino acid sequences shown in Table 1 do not include the amino acid sequences for the endogenous signal peptides. The bold-faced amino acids in the amino acid sequences shown in Table 1 signify the omega site. The omega site is the region at which GPI is attached to the protein. The GPI proteins were separated into two types based upon site of anchoring: GPI-anchored plasma membrane proteins (GPI-PMP) and GPI-dependent cell surface anchoring proteins (GPI-CWP).

TABLE 1

| GPI protein | Source | Type | Sequence | SEQ ID NO: |
|---|---|---|---|---|
| CWP2 | S. cerevisiae | CWP | VDESAAAISQITDGQIQATTTATT EATTTAAPSSTVETVSPS STETI SQQTE NGAAKAAVGMGAGALAAA AMLL | 9 |
| CWP2* | S. cerevisiae Truncated | CWP | VDTTEATTTAAPSSTVETVSPSST ETISQQTENGAAKAAVGMGAGALA AAAMLL | 10 |
| SED1 | S. cerevisiae | CWP | VDQFSNSTSASSTDVTSSSSISTS SGSVTITSSEAPESDNGTSTAAPT ETSTEAPTTAIPTNGTSTEAPTTA IPTNGTSTEAPTDTTTEAPTTALP TNGTSTEAPTDTTTEAPTTGLPTN GTTSAFPPTTSLPPSNTTTTPPYN PSTDYTTDYTVVTEYTTYCPEPTT FTTNGKTYTVTEPTTLTITDCPCT IEKPTTTSTTEYTVVTEYTTYCPE PTTFTTNGKTYTVTEPTTLTITDC PCTIEKSEAPESSVPVTESKGTTT KETGVTTKQTTANPSLTVSTVVPV SSSASSHSVVINSNGANVVVPGAL GLAGVAMLFL | 11 |
| SED1* | S. cerevisiae Truncated | CWP | VDLTVSTVVPVSSSASSHSVVINS NGANVVVPGALGLAGVAMLFL | 12 |
| SPI1 | P.pastoris | CWP | VDLVSNSSSSVIVVPSSDATIAGN DTATPAPEPSSAAPIFYNSTATAT QYEVVSEFTTYCPEPTTFVTNGAT FTVTAPTTLTITNCPCTIEKPTSE TSVSSTHDVETNSNAANARAIPGA LGLAGAVMMLL | 13 |
| GAS1 | S. cerevisiae | PMP | VDDVPAIEVVGNKFFYSNNGSQFY IRGVAYQADTANETSGSTVNDPLA NYESCSRDIPYLKKLNTNVIRVYA INTTLDHSECMKALNDADIYVIAD LAAPATSINRDDPTWTVDLFNSYK | 14 |

TABLE 1-continued

| GPI protein | Source | Type | Sequence | SEQ ID NO: |
|---|---|---|---|---|
| | | | TVVDTFANYTNVLGFFAGNEVTNN YTNTDASAFVKAAIRDVRQYISDK NYRKIPVGYSSNDDEDTRVKMTDY FACGDDDVKADFYGINMYEWCGKS DFKTSGYADRTAEFKNLSIPVFFS EYGCNEVTPRLFTEVEALYGSNMT DVWSGGIVYMYFEET NKYGLVSIDGNDVKTLDDFNNYSS EINKISPTSANTKSYSATTSDVAC PATGKYWSAATELPPTPNGGLCSC MNAANSCVVSDDVDSDDYETLFNW ICNEVDCSGISANGTAGKYGAYSF CTPKEQLSFVMNLYYEKSGGSKSD CSFSGSATLQTATTQASCSSALKE IGSMGTNSASGSVDLGSGTESSTA SSNASGSSSKSNSGSSGSSSSSSS SSASSSSSKKNAATNVKANLAQV VFTSIISLSIAAGVGFALV | |
| GAS1 | P. pastoris | CWP | VDADFPTIEVTGNKFFYSNNGSQF YIKGVAYQKDTSGLSSDATFVDPL ADKSTCERDIPYLEELGTNV1RVY AVDADADHDDCMQMLQDAGIYVIA DLSQPNNSIITTDPEWTVDLYDGY TAVLDNLQKYDNILGFFAGNEVIT NKSNTDTAPFVKAAIRDMKTYMED KGYRSIPVGYSANDDELTRVASAD YFACGDSDVKADFYGINMYEWCGK ATFSNSGYKDRTAEFKNLSIPVFF SEYGCNEVQPRLFTEVQSLYGDDM TDVWSGGIVYMYFEETNNYGLVTI KSDGDVSTLEDFNNLKTELASISP SIATQSEVSATATEIDCPATGSNW KASTDLPPVPEQAACQCMADALSC VVSEDVDTDDYSDLFSYVCENVSS CDGVSADSESGEYGSYSFCSSKEK LSFLLNLYYSENGAKSSACDFSGS ATLVSGTTASECSSILSAAGTAGT GSITGITGSVEAATQSGSNSGSSK SSSASQSSSSNAGVGGGASGSSWA MTGLVSISVALGMIMSF | 15 |
| GAS1* | P. pastoris Truncated | CWP | VDSILSAAGTAGTGSITGITGSVE AATQSGSNSGSSKSSSASQSSSSN AGVGGGASGSSWAMTGLVSISVAL GMIMSF | 16 |
| TIP1 | H. polymorpha | CWP | VDAAATSSVAAAASEVSSSSAAAS STQAAAAASTSAAASTEATTSAAA AATSSSEAASSSAHVHSHAAESTS AVESTSAAHSHAAESSSAAHSHAV ESSSAAHVHSHAAESSSAAHSHAA GSSSAASNSSGHISTFSGAGAKLA VGAGAGIVGLAALLM | 17 |
| TIP1 | H. polymorpha Truncated | CWP | VDSSAAHSHAVESSSAAHVHSHAA ESSSAAHSHAAGSSSAASNSSGHI STFSGAGAKLAVGAGAGIVGLAAL LM | 18 |

The nucleic acids encoding each of the anchoring proteins was codon-optimized according to *Pichia pastoris* codon usage. A nucleic acid encoding a valine and aspartic acid dipeptide (VD) was added to the 5' end of the nucleic acid encoding the proteins to create a SalI restriction site at the 5' end of the nucleic acid. The endogenous signal peptides of each of these GPI proteins was replaced with the *Aspergillus niger* alpha-amylase signal peptide. The DNA encoding the signal peptide is ATGGTTGCTT GGTGGTCCTT GTTCTTGTAC GGATTGCAAG TTGCTGCTCC AGCTTTGGCT (SEQ ID NO:33) and the signal peptide has the amino acid sequence MVAWWSLFLY GLQVAAPALA (SEQ ID NO:34).

Further optimization of anchor protein expression and cell surface localization may be achieved through screening a library of N-terminal signal peptides fused to the n-terminus of the anchoring proteins to identify signal peptides that best localize the GPI protein to the cell surface. For each construct, a nucleic acid encoding a GR2 coiled coil peptide having the amino acid sequence TSRLEGLQSE NHRLRM-KITE LDKDLEEVTM QLQDVGGC (SEQ ID NO:19) was inserted between the nucleic acid encoding the signal peptide and the nucleic acid encoding the GPI protein. The cassettes further included a nucleic acid encoding a myc epitope which was inserted between the nucleic acid encoding the GR2 coiled coil peptide and the GPI protein. The myc epitope is optional but had been included in the expression cassettes in order to provide an epitope to facilitate detecting the expressed GPI protein attached to the cell surface using a commercially available anti-myc antibody.

Figure 3:
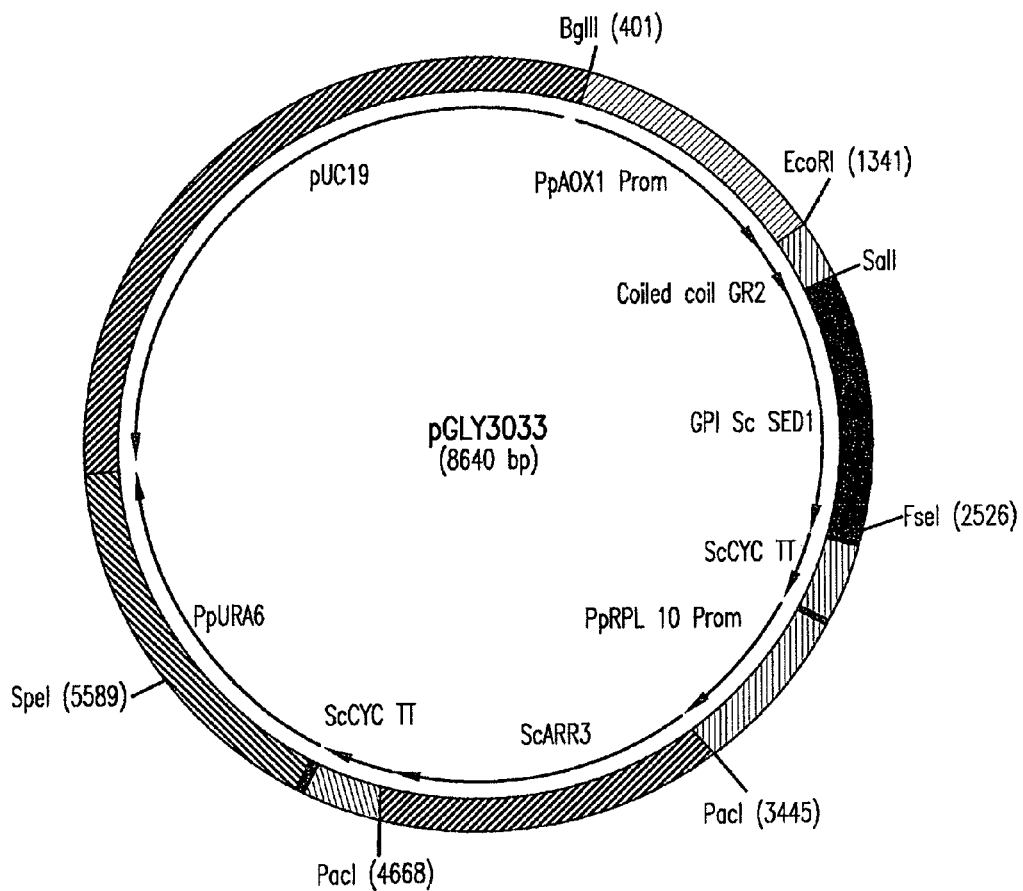
FIG. 3 shows a map of pGLY3033 expressing a fusion protein consisting of a *Pichia pastoris* signal sequence, a myc tag, the GR2 coiled coil peptide, and the cell wall anchor protein SED under the control of the AOX1 promoter.

FIG. 2A shows an example of the *S. cerevisiae* SED1 GPI protein fused to the GR2 coiled coil peptide. The fusion protein consists of the *Aspergillus niger* alpha-amylase signal peptide followed by the GR2 coiled coil peptide followed by a Myc tag, and ending with the SED1 GFP anchor protein (without its endogenous signal peptide). FIG. 2B shows the amino acid sequence of the fusion protein (SEQ ID NO:20). FIG. 3 shows a representative plasmid map encoding the SED1 fusion protein. The SED1 fusion protein when expressed in the cell is transported to the surface of the cell where it is bound at the cell wall such that the GR2 coiled coil peptide is oriented extracellularly and rendered accessible to binding any protein in the extracellular environment that contains a GR1 coiled coil peptide accessible to the GR2 coiled coil peptide. All of the above nucleic acid sequences were codon optimized according to *Pichia pastoris* codon usages and synthesized by GeneArt AG. Table 2 shows a representative number of plasmids containing cell surface anchoring expression cassettes in which the GPI protein was fused to GR2 that were constructed.

The *Pichia pastoris* URA6 locus was chosen as an integrating site for the GPI anchoring protein expression cassettes. The URA6 gene was PCR amplified from *Pichia pastoris* genomic DNA and cloned into pCR2.1 TOPO to produce plasmid pGLY1849. The Bgl2 and EcoR1 sites within the gene were mutated by silent mutation for cloning purposes. The TRP2 targeting nucleic acid of plasmid pGLY2184 was replaced with the *Pichia pastoris* URA6 gene from pGLY1849. In addition, the *Pichia pastoris* ARG1 selection marker was replaced with the with Arsenite marker cassette from plasmid pGF18. The final plasmid was named pGF130t and was used to make the plasmids shown in Table 2.

TABLE 2

Plasmids Containing Cell Surface Anchoring Expression Cassettes

| Plasmid | Description |
|---|---|
| pGLY3015 | *S. cerevisiae* CWP2-GR2 fusion protein |
| pGLY3033 | *S. cerevisiae* SED1-GR2 fusion protein |
| pGLY3034 | *S. cerevisiae* SED1 truncated-GR2 fusion protein |
| pGLY3035 | *P. pastoris* SPI1-GR2 fusion protein |
| pGLY3036 | *P. pastoris* GAS1-GR2 fusion protein |
| pGLY3037 | *S. cerevisiae* GAS1-GR2 fusion protein |
| pGLY3038 | *S. cerevisiae* GAS1 truncated-GR2 fusion protein |
| pGLY3039 | *H. polymorpha* TIP1-GR2 fusion protein |
| PGLY3040 | *H. polymorpha* TIPI truncated-GR2 fusion protein |

Figure 5:
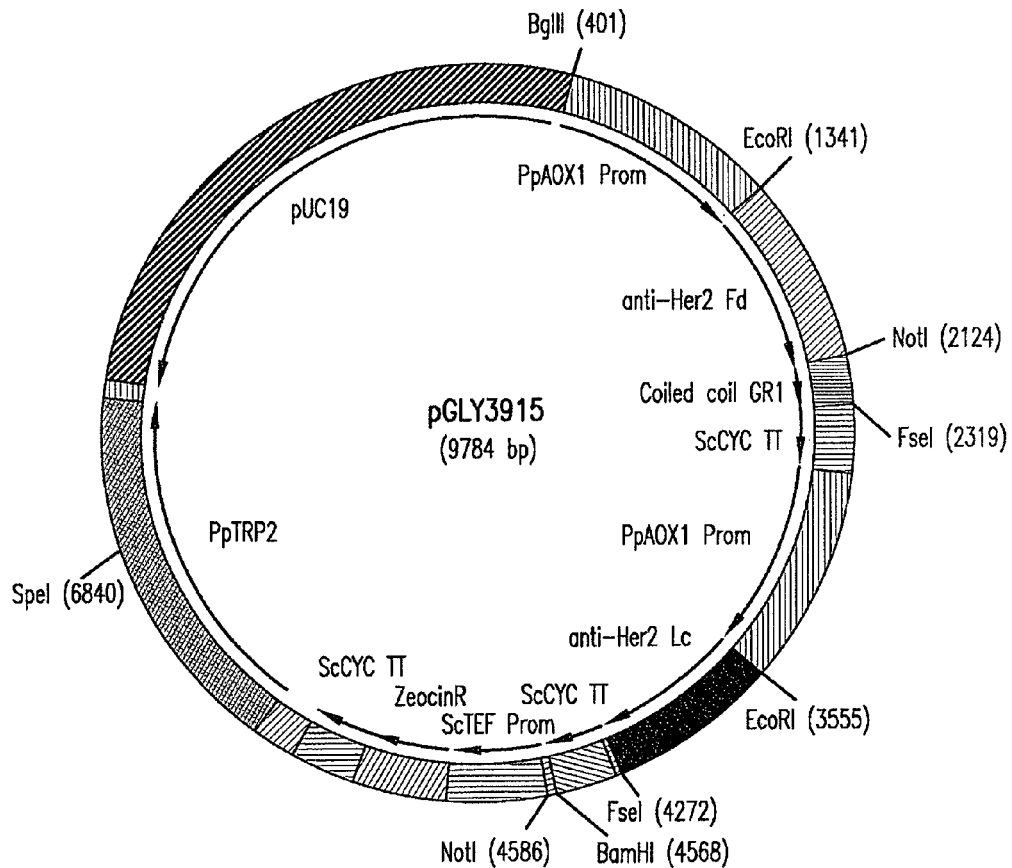
FIG. 5 shows a map of Fab fragment display plasmid pGLY3915.

The antibody and Fab fragment expression cassettes were constructed as follows. FIG. 4 illustrates three different antibody expression cassettes that have been constructed for producing antibodies or fragments thereof. Expression cassette A comprises two separately expressed open reading frames (ORFs). The first ORF encodes the light chain and the second ORF encodes a fusion protein comprising the Fd region of the heavy chain fused at the C-terminus to the GR1 coiled coil peptide. Each ORF is operably linked to an AOX1 promoter, which enables expression of the fusion proteins to be inducibly expressed. When expression is induced, this expression cassette is capable of producing an Fab fragment consisting of the light chain and Fd fragment fused at its C-terminus to a GR1 coiled coil peptide. The Fab fragment can be captured by heterodimerization by the GR2 coiled coil peptide fused to the GPI protein, which is on the surface of the cell. Desired Fab fragments can then be detected by a suitable detection means. FIG. 5 shows a plasmid map of a plasmid that was constructed in which expression cassette A encodes an Fab that is specific for Her2 antigen.

Expression cassette B is capable of producing a full-length antibody fused to a GR1 coiled coil peptide. The first ORF encodes the light chain and the second ORF encodes a fusion protein comprising the heavy chain fused at the C-terminus to the GR1 coiled coil protein. Each ORF is operably linked to an AOX1 promoter. When expression is induced, this expression cassette is capable of producing full-length antibody consisting of the light chain and heavy chain fused at its C-terminus to a GR1 coiled coil peptide. The full-length antibody can be captured by heterodimerization by the GR2 coiled coil peptide fused to the GPI protein, which is on the surface of the cell. Desired antibodies can then be detected by a suitable detection means.

The limitation of expression cassette B is that the full-length antibodies produced will always include the GR1 coiled coil peptide fused to the heavy chain. This limitation may not be desirable for antibodies that are intended for therapeutic purposes. Thus, a new expression cassette must be constructed by isolating from the host cell that produces the desired antibody the nucleic acid that encodes the desired antibody and recloning the nucleic in an expression cassette that does not include the nucleic acid encoding the GR1 coiled *coli* peptide and which, therefore, produces the full-length antibody without the GR1 coiled *coli* peptide fused to the C-terminus of the heavy chain. To get around the limitation, expression cassette C was designed.

Figure 6:
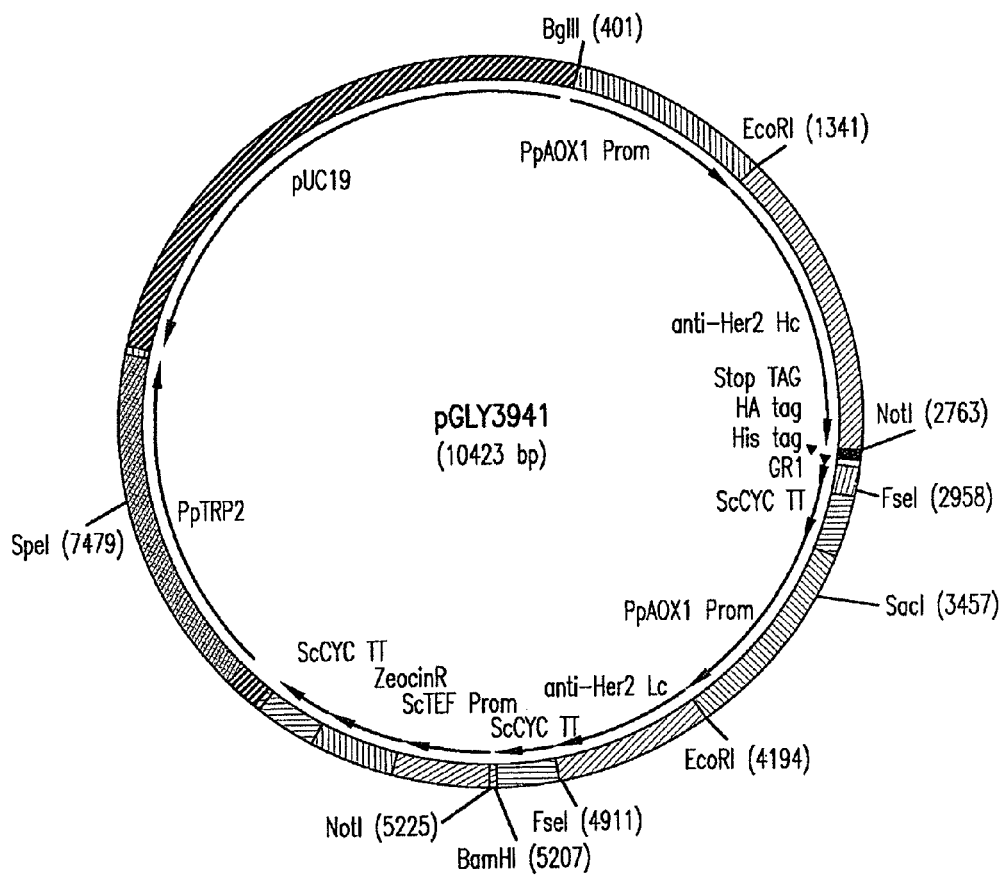
FIG. 6 shows a map of full-length antibody display plasmid pGLY3941.

Expression cassette C under appropriate conditions is capable of producing full-length antibodies that include the GR1 coiled coil peptide fused to the heavy chain for selection of a desired full-length antibody; however, under production conditions, the expression cassette produces the desired antibody in which the heavy chain is not fused to the GR1 coiled coil peptide. Thus, expression cassette C avoids the need to reclone the nucleic acid encoding the desired antibody. In expression cassette C, the second ORF that encodes a fusion protein comprising the heavy chain fused at the C-terminus to the N-terminus of the GR1 coiled coil peptide further includes a single stop codon between the end of the nucleic acid sequence encoding the heavy chain and the nucleic acid encoding the GR1 coiled coil peptide, in which readthrough of the stop codon is inducible. Normally, stop codons signal the ribosome to terminate the decoding of an mRNA template. In yeast, inefficient termination will allow translation to continue; the frequency of read-through varies depending on the yeast strain and stop codon chosen. The cassette is designed with a stop codon in frame with the nucleic acid encoding the full length antibody and separating it from the nucleic acid encoding the coiled coil peptide GR1. therefore, under most conditions, translation of an mRNA transcribed from the expression cassette predominantly terminates at the single stop codon and thus results in production of a full-length antibody that is not fused to the GR1 coiled coil peptide. However, in the presence of the antibiotic G418, translation readthrough through the stop codon is increased, which results in the production of full-length antibodies fused to GR1 coiled coil peptide; however, even in the presence of the antibiotic, expression of full-length antibody not fused to the GR1 coiled coil peptide is the predominant species. This proportional readthrough can reflect the expressability of the full-length antibody; by monitoring both the secreted full-length antibody and the full-length antibody fusion captured at the cell surface, one can screen for high producing host cells. Thus, in the presence of the antibiotic, a population of the full-length antibodies will include the heavy chain-GR1 coiled coil peptide fusion protein. Therefore, when screening a library of antibodies for a desired antibody, the host cells are grown in the presence of the antibiotic. The full-length antibodies comprising the heavy chain GR1 fusion protein are captured at the cell surface by heterodimerization to the GR2 coiled coil peptide fused to the GPI protein on the surface of the cell. Desired antibodies can then be detected by a suitable detection means. However, for production of full-length antibodies in which the heavy chain is not fused to the GR1 coiled coil peptide, host cells that have been identified to produce the desired antibody are grown in the absence of the antibiotic. The premise behind expression cassette C can be adapted to produce Fab fragments that are not fused to the GR1 coiled coil peptide. FIG. 6 shows a map of a plasmid that was constructed in which expression cassette C encodes a full-length antibody that is specific for Her2. Table 3 shows representative number of plasmids that were constructed that contain expression cassettes encoding Fabs (A) or antibodies (B) fused to GR1. Also shown in Table 3 are plasmids comprising expression cassette C.

TABLE 3

Plasmid Containing Antibody or Fab Expression Cassettes

| Plasmid | Cassette Type | Description |
| --- | --- | --- |
| pGLY3028 | A | Anti-Her2 Fab-GR1 fusion protein |
| pGLY3915 | A | Anti-Her2 Fab-GR1 fusion protein |
| pGLY3026 | A | Anti-DKK1 Fab-GR1 fusion protein |
| pGLY3916 | A | Anti-CD20, C2B8 Fab-GR1 fusion protein |
| pGLY3917 | A | Anti-CD20, Frame grafted Fab-GR1 fusion protein |
| pGLY3918 | A | Anti-CD20, Frame grafted Fab-GR1 fusion protein |
| pGLY3919 | A | Anti-CD20, Frame grafted Fab-GR1 fusion protein |
| pGLY3920 | A | Anti-CD20, Frame grafted Fab-GR1 fusion protein |
| pGLY3939 | B | Anti-Her2 full-length antibody-GR1 fusion protein |
| pGLY3941 | C | Anti-her2 full-length antibody-GR1 fusion protein with single stop codon between antibody ORF and GR1 ORF |
| pGLY3942 | C | Anti CD20 C2B8 full length antibody-GR1 fusion protein single stop codon between antibody ORF and GR1 ORF |
| pGLY3943 | C | Anti-CD20 Genmab antibody-GR1 fusion protein single stop codon between antibody ORF and GR1 ORF |
| pGLY3944 | C | Anti-CD20 full length antibody-GR1 fusion protein single stop codon between antibody ORF and GR1 ORF |

Plasmids pGLY3028 and pGLY3915. The amino acid sequences for the heavy and light chains of the anti-her2 antibody are shown in SEQ ID NOs:22 and 23, respectively. The nucleic acid sequence encoding the anti-her2 Fab heavy chain fused to GR1 and the ScαMTprepro signal sequence is shown in SEQ ID NO:51. The nucleic acid sequence encoding the anti-her2 light chain fused to the ScαMTprepro signal sequence (SEQ ID NO:49) is shown in SEQ ID NO:52.

Plasmid pGLY3926. The amino acid sequences for the heavy and light chains of the anti-DKK1 antibody are shown in SEQ ID NOs:24 and 25, respectively. The nucleic acid sequence encoding the anti-DKK1 Fab heavy chain fused to GR1 and the *Aspergillus niger* alpha amylase signal sequence is shown in SEQ ID NO:53. The nucleic acid sequence encoding the anti-DKK1 light chain fused to the *Aspergillus niger* alpha amylase signal sequence (SEQ ID NO:33) is shown in SEQ ID NO:54.

Plasmid pGLY3916. The amino acid sequences for the heavy and light chains of the anti-CD20 antibody are shown in SEQ ID NOs:26 and 27, respectively. The nucleic acid sequence encoding the anti-CD20, C2B8, Fab heavy chain fused to GR1 and the *Aspergillus niger* alpha amylase signal sequence is shown in SEQ ID NO:55. The nucleic acid sequence encoding the anti-CD20, C2B8, light chain fused to the *Aspergillus niger* alpha amylase signal sequence is shown in SEQ ID NO:56.

Plasmids pGLY3917-3920. The amino acid sequences for frame-grafted heavy and light chains of the anti-C20 Fab antibody are shown in SEQ ID NOs:28 and 29, respectively. The nucleic acid sequence encoding the anti-CD20, frame-grafted, Fab heavy chain fused to GR1 and the *Aspergillus niger* alpha amylase signal sequence is shown in SEQ ID NO:57. The nucleic acid sequence encoding the anti-CD20, frame-grafted, light chain fused to the *Aspergillus niger* alpha amylase signal sequence is shown in SEQ ID NO:58.

Plasmids pGLY3939 and 41. The amino acid sequences for the heavy and light chains of the anti-her2 antibody are shown in SEQ ID NOs:22 and 23, respectively. The nucleic acid sequence encoding the anti-her2 full length heavy chain fused to GR1 and the ScαMTprepro signal sequence is shown in SEQ ID NO:59 (pGLY3939). The nucleic acid sequence encoding the anti-her2 full length heavy chain with single stop codon between the heavy chain-encoding ORF and GR1 encoding ORF fused to GR1 and the ScαMTprepro signal sequence is shown in SEQ ID NO:60 (pGLY3941). The nucleic acid sequence encoding the anti-her2 light chain fused to the ScαMTprepro signal sequence in both plasmids is shown in SEQ ID NO:52. Plasmid pGLY3942. The amino acid sequences for the heavy and light chains of the anti-CD20 antibody are shown in SEQ ID NOs:26 and 27, respectively. The nucleic acid sequence encoding the anti-CD-20, C2B8, full length heavy chain with single stop codon between the heavy chain-encoding ORF and GR1 encoding ORF fused to GR1 and the *Aspergillus niger* alpha amylase signal sequence is shown in SEQ ID NO:61. The nucleic acid sequence encoding the anti-CD20, C2B8, light chain fused to the *Aspergillus niger* alpha amylase signal sequence is shown in SEQ ID NO:56.

Plasmid pGLY3943. The amino acid sequences for Genmab heavy and light chains of the anti-CD20 antibody are shown in SEQ ID NOs:30 and 31, respectively. The nucleic acid sequence encoding the anti-CD-20, Genmab, full length heavy chain with single stop codon, between the heavy chain-encoding ORF and GR1 encoding ORF fused to GR1 and the *Aspergillus niger* alpha amylase signal sequence is shown in SEQ ID NO:62. The nucleic acid sequence encoding the anti-CD20, Genmab, light chain fused to the *Aspergillus niger* alpha amylase signal sequence is shown in SEQ ID NO:63.

Plasmid pGLY3944. The nucleic acid sequence encoding the anti-CD-20 full length heavy chain with single stop codon between the heavy chain-encoding ORF and GR1 encoding ORF fused to GR1 and the *Aspergillus niger* alpha amylase signal sequence is shown in SEQ ID NO:64. The nucleic acid sequence encoding the anti-CD20 light chain fused to the *Aspergillus niger* alpha amylase signal sequence is shown in SEQ ID NO:65.

Co-Expression of Fab- and Antibody-GR1 Fusion Protein Expression Cassettes and GPI Protein-GR2 Fusion Protein Expression Cassettes in Yeast.

Two different methods were used for transforming the plasmids containing expression cassettes encoding the GPI protein-GR2 fusion proteins and Fab- or antibody-GR1 fusion proteins into glycoengineered yeast.

In the first approach, plasmid vectors containing the GPI protein-GR2 fusion protein expression cassettes and containing a first selection marker is transformed into *P. pastoris* and plated on medium with the selection means to select for colonies carrying the GPI protein-GR2 expression cassettes. Then, colony PCR is used to screen the positive colonies for the presence of the GPI protein-GR2 fusion proteins. Finally, these cells are transformed with plasmids containing the Fab- or antibody-GR1 fusion expression cassette and containing a gene for conferring a second selection marker and recombinant cells identified by growing the cells in the presence of a second selection means. In the second approach, the plasmids containing the antibody or Fab-GR1 fusion protein expression cassettes are transformed first into the glycoengineered *Pichia pastoris* followed by transformation with plasmids containing the GPI protein-GR2 fusion protein expression cassettes.

FIG. 3 shows plasmid pGLY3033, which is an example of a plasmid vector that contains a GPI protein-GR2 expression cassette and the *S. cerevisiae* ARR3 gene as the marker gene. The ARR3 gene from *S. cerevisiae* confers arsenite resistance to cells that are grown in the presence of arsenite (Bobrowicz et al., Yeast, 13:819-828 (1997); Wysocki et al., J. Biol. Chem. 272:30061-066 (1997)). FIGS. 5 and 6 show examples of plasmids that contain Fab-GR1 (FIG. 5) or antibody-GR1 (FIG. 6) fusion protein expression cassettes. The plasmids shown in FIGS. 5 and 6 containing the Fab-GR1 or whole antibody-GR1 fusion expression cassette also contain a nucleic acid homologous to a portion of the TRP2 locus in *Pichia pastoris* to target the vector for integration into the TRP2 locus and a gene that confers resistance to the antibiotic Zeocin. When the vector is linearized within this nucleic acid, the plasmid vector is capable of single crossover homologous recombination into the TRP2 locus. Thus, the vectors shown in FIGS. 5 and 6 enable recombinant *Pichia pastoris* strains to be made with the Fab- or antibody-GR1 fusion expression cassette integrated into the genome of the cell.

Table 4 shows a representative number of yeast strains that were made. All the strains were in a GS2.0 background. GS2.0 strains are glycoengineered *Pichia pastoris* strains that produce glycoproteins having predominantly $Man_5GlcNAc_2$ N-glycans (strains YGLY638 and YGLY2696. Strains that produce glycoproteins that have predominantly $Man_5GlcNAc_2$ N-glycans have been described in for example, U.S. Pat. No. 7,029,872 and in Choi et al., Proc. Natl. Acad. Sci. USA 100: 5022-5027 (2003). Strain YGLY2696 is a GS2.0 strain that further has the gene encoding the endogenous chaperone protein PD1 deleted and expresses a nucleic acid encoding a human PD1 chaperone protein and further includes a nucleic acid encoding the human GRP94 protein inserted into the PEP4 locus (See Example 6 below).

TABLE 4

Yeast Strains

| Strain | Description |
|---|---|
| YGLY638 | GS2.0 glycoengineered *Pichia pastoris* |
| YGLY2696 | GS2.0 glycoengineered and humanized chaperones *Pichia pastoris* |
| YGLY2966 | YGLY638/pGLY3026 - expresses anti-DKK1 Fab |
| YGLY4105 | YGLY638/pGLY3028 - expresses anti-Her2 Fab |
| YGLY4145 | YGLY4102/pGLY3033 - expresses anti Her2 Fab and SED1 anchor |
| YGLY4146 | YGLY2966/pGLY3033 - expresses anti-DKK1 Fab and SED1 anchor |
| YGLY5079 | YGLY2696/SED1pGLY3033 #1 SED1 anchor |
| YGLY5147 | YGLY2696/pGLY3916 Patch #1 - expresses anti-CD20 Fab |
| YGLY5148 | YGLY2696/pGLY3917 Patch #4 - expresses anti-CD20 Fab |
| YGLY5149 | YGLY5079/pGLY3916 Patch #16 - expresses anti-CD20 Fab and SED1 anchor |
| YGLY5150 | YGLY5079/pGLY3916 Patch #18 - expresses anti-CD20 Fab and SED1 anchor |
| YGLY5151 | YGLY5079/pGLY3917 Patch #19 - expresses anti-CD20 Fab and SED1 anchor |
| YGLY5152 | YGLY5079/pGLY3917 Patch #20 - expresses anti-CD20 Fab and SED1 anchor |
| YGLY5153 | YGLY5079/pGLY3918 Patch #22 - expresses anti-CD20 Fab and SED1 anchor |
| YGLY6693 | YGLY5079/pGLY3918 Patch #23 - expresses anti-CD20 Fab and SED1 anchor |
| YGLY6694 | YGLY5079/pGLY3919 Patch #25 - expresses anti-CD20 Fab and SED1 anchor |

The above *Pichia pastoris* strains are grown in 50 mL BMGY media until OD 600=2. The cells are washed three times with 1 M sorbitol and resuspended in 1 mL 1 M sorbitol. About 1 to 2 μg linearized plasmid are mixed with these competent cells. Transformation is performed with a BioRad electroporation apparatus using the manufacturer's program specific for electroporation of nucleic acids into *Pichia pastoris*. One mL recovery media is added to the cells, which are then plated out on MG with 300 μg/mL zeocin or YPG with 50 μg/mL arsenite.

Growth and Induction of Fab Displaying Yeast.

Glycoengineered yeast transformed with both Fab-GR1 fusion protein expression cassette and GPI protein-GR2 expression cassette was inoculated using 600 μL BMGY in a 96 deep well plate or 50 mL BMGY in a 250 mL shake flask for two days. The cells were collected by centrifugation and the supernatant was discarded. The cells are induced by incubation in 300 μL or 25 mL BMMY with Pmti-3 inhibitor overnight following the methods taught in WO2007/061631. Pmti-3 is 3-hydroxy-4-(2-phenylethoxyl)benzaldehyde; 3-(1-phenylethoxy)-4-(2-phenylethoxy)-benzaldehyde, which as been described in U.S. Pat. No. 7,105,554 and Published International Application No. WO 2007061631.

Figure 7:
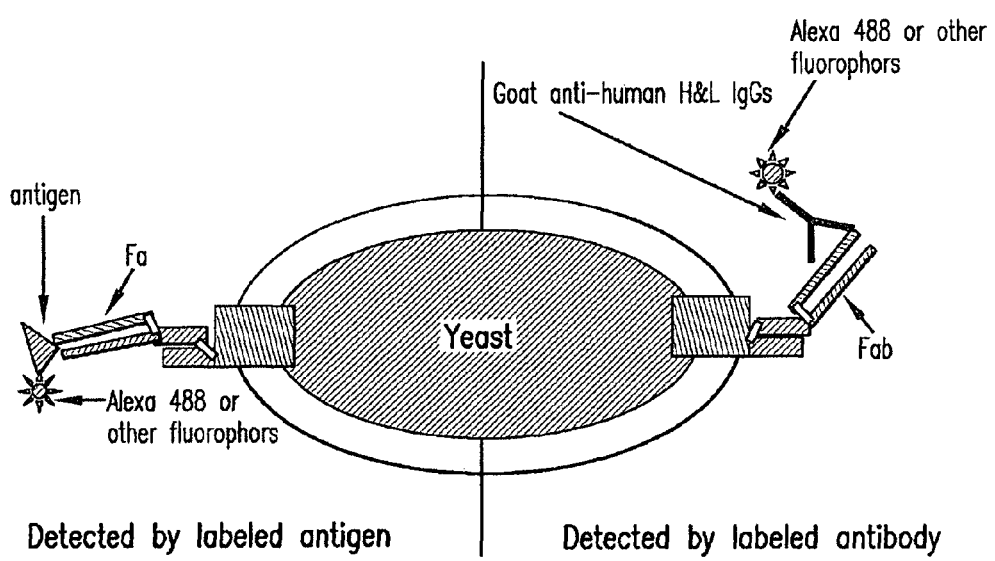
FIG. 7 illustrates detection of a displayed antibody or antibody fragment on the yeast cell surface by goat anti-human H+L IgGs Alexa 488 or fluorophor conjugated antigen.
Figure 8A:
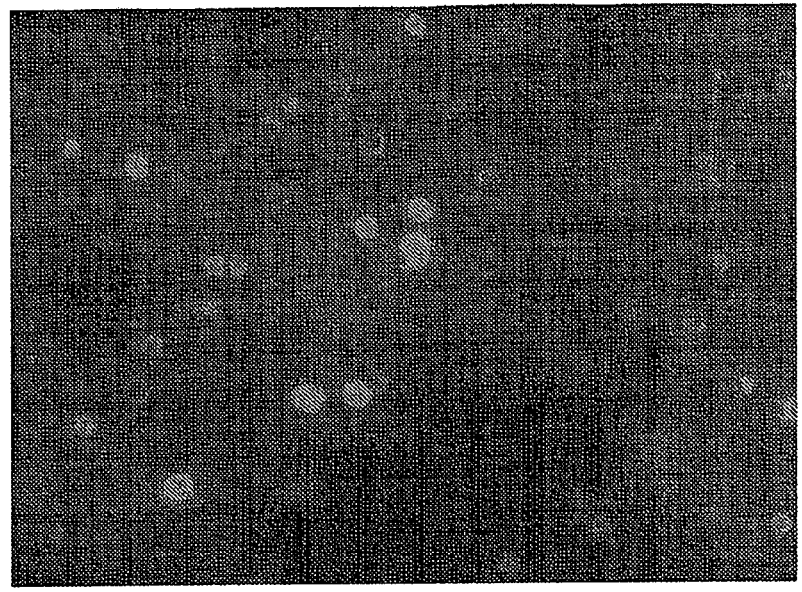
FIGS. 8A-J show fluorescent microscopy photographs of glycoengineered *Pichia pastoris* YGLY4102 overexpressing anti-Her2 Fab fragment and transformed with expression plasmids of GR2 coiled coil peptide fused to different GPI cell wall anchor protein's pGLY3015 (CWP2), pGLY3033 (ScSED1), pGLY3034 (ScSED1 truncation), pGLY3035 (PpSPI1), pGLY3036 (PpGAS1), pGLY3037 (ScGAS1), pGLY3038 (ScGAS1 truncation), pGLY3039 (HpTIP) and pGLY3040 (HpTIP truncation).
Figure 8B:
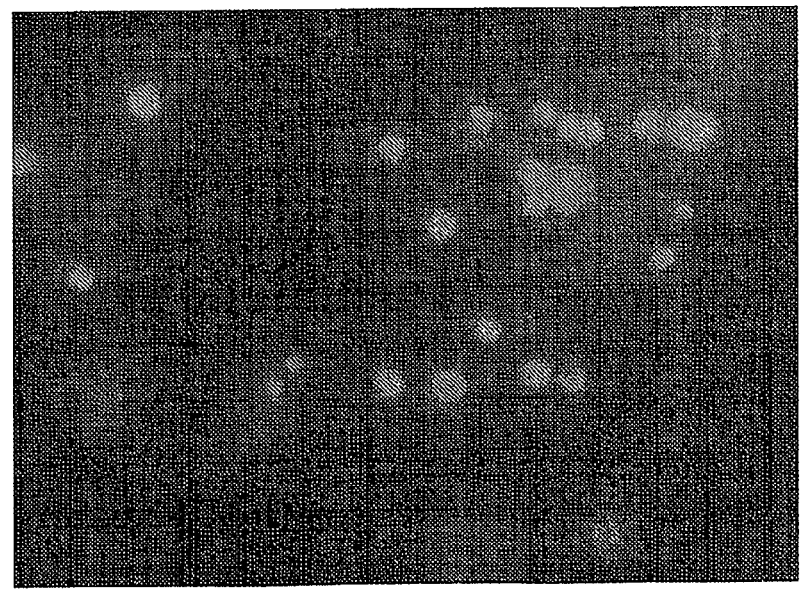
Figure 8C:
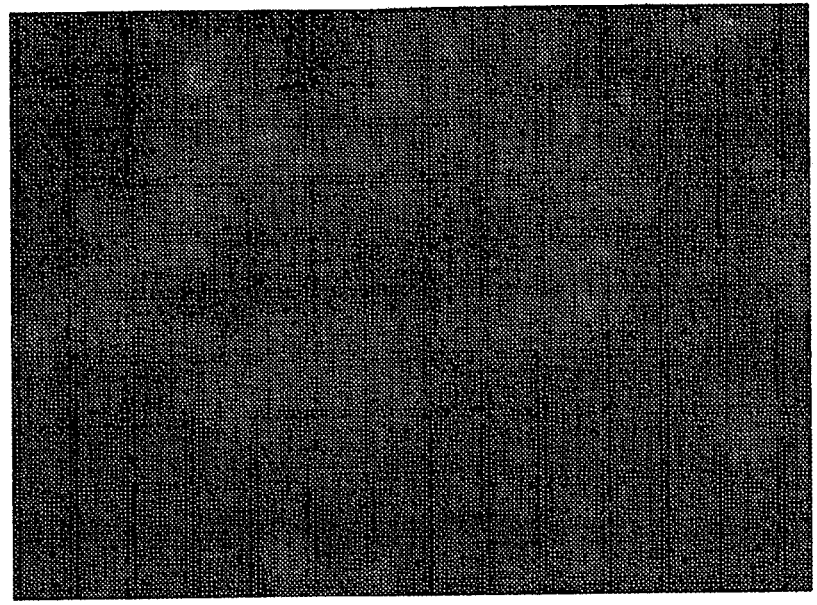
Figure 8D:
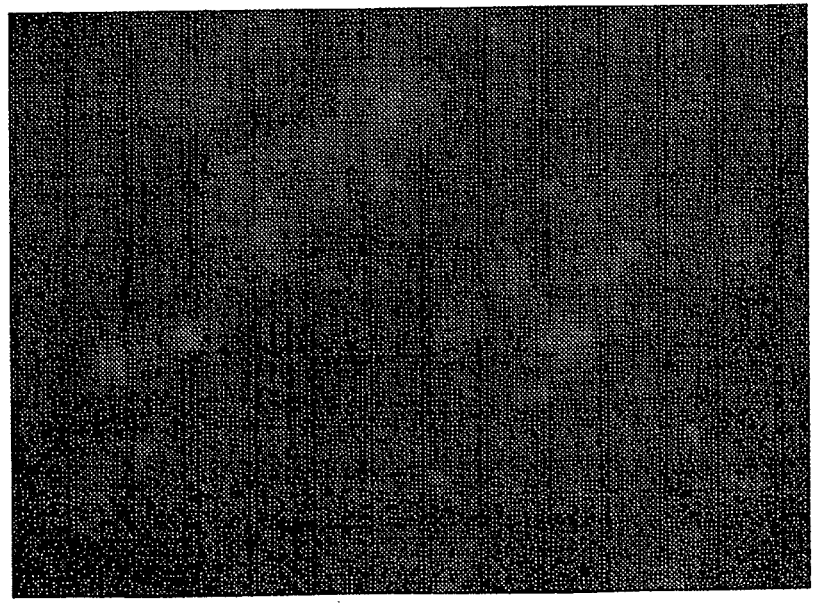
Figure 8E:
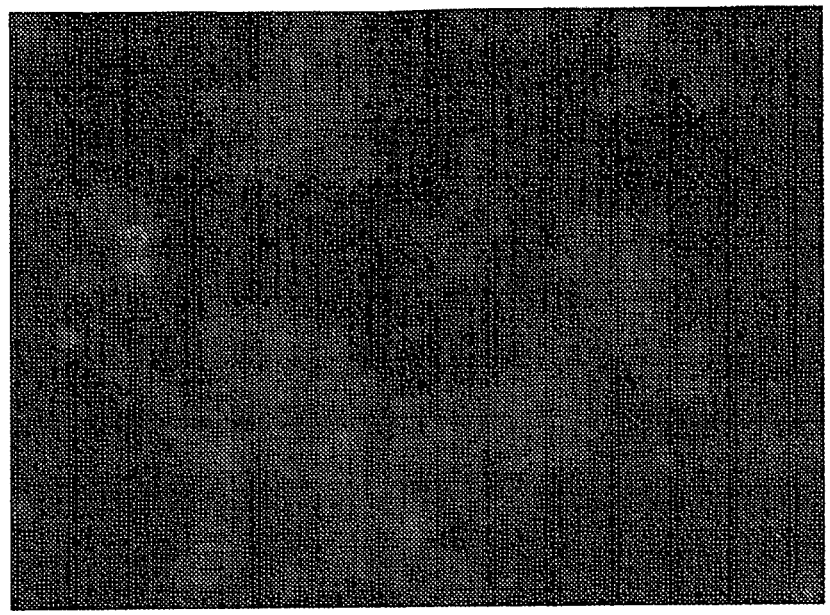
Figure 8F:
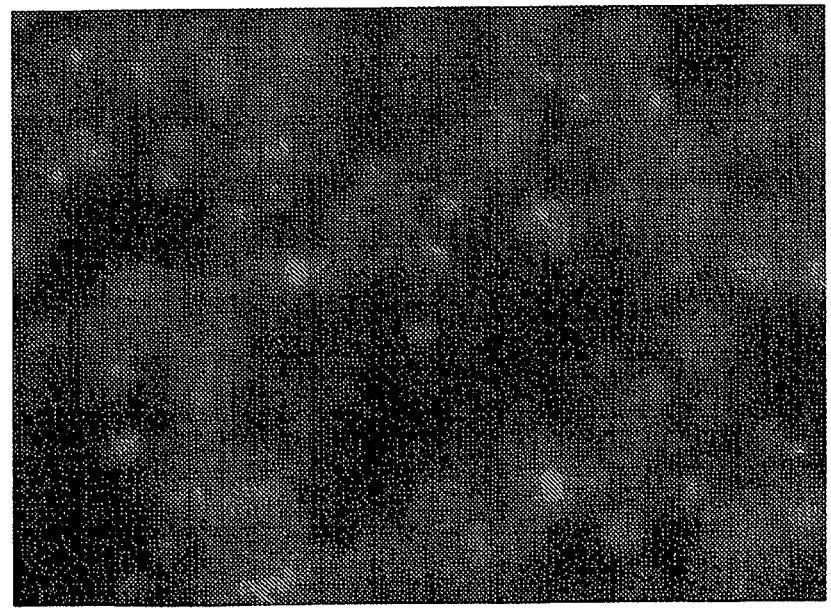
Figure 8G:
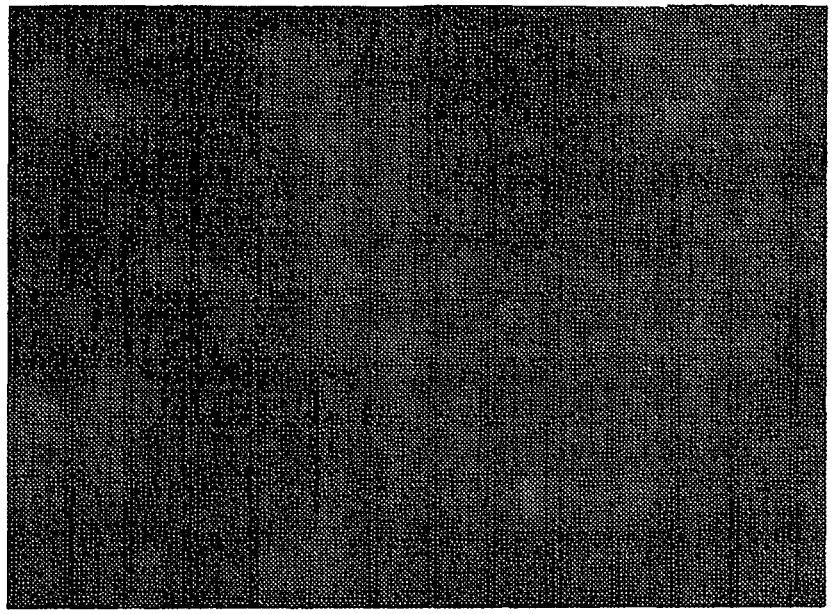
Figure 8H:
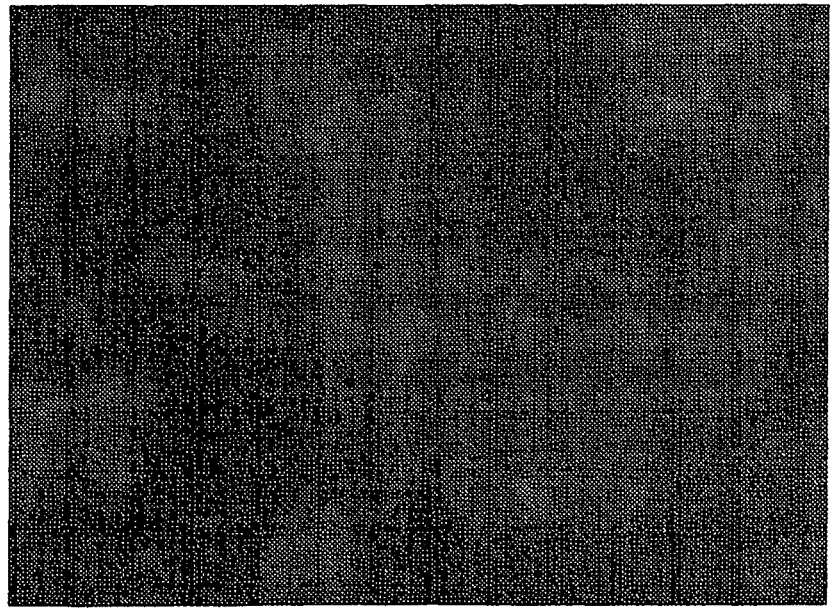
Figure 8I:
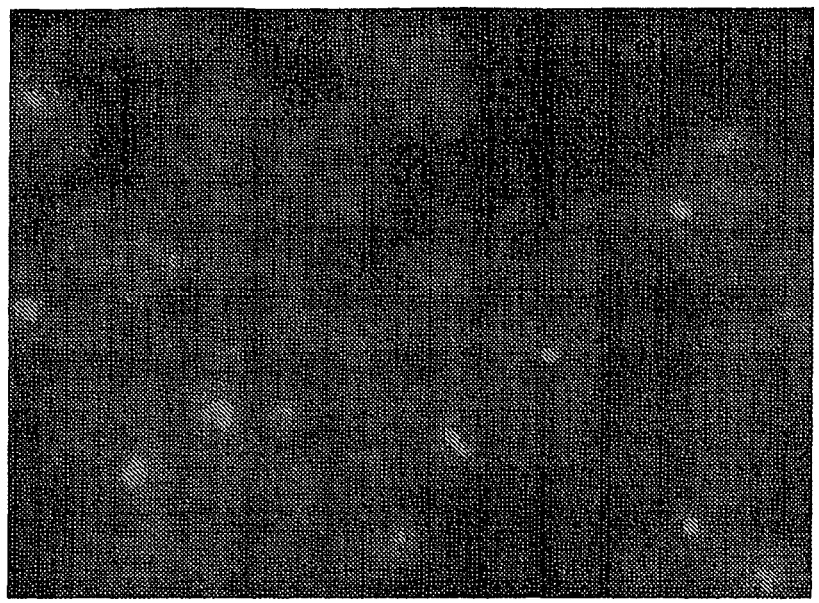
Figure 8J:
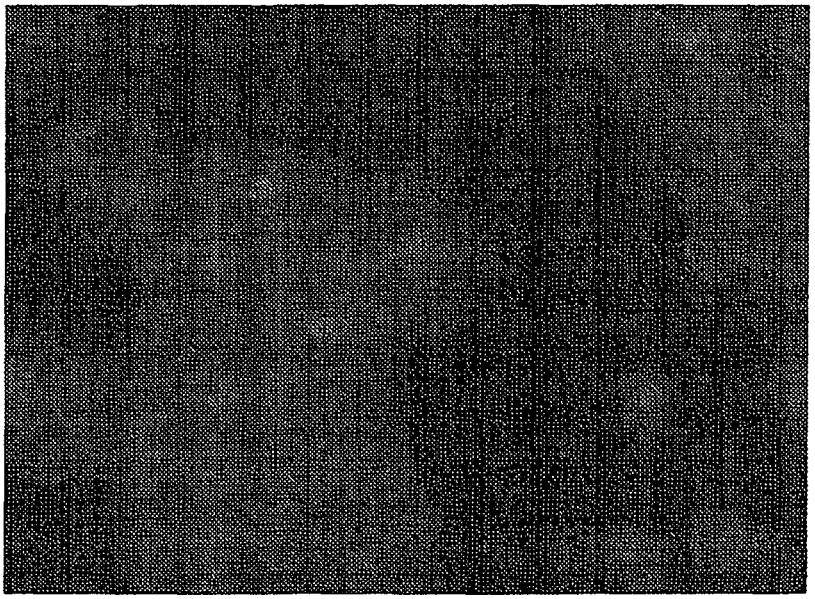

Induced cells were labeled with goat anti-human heavy and light chain (H+L) Alexa 488 conjugated antibody and viewed using fluorescence microscopy (as illustrated in FIG. 7). After induction, 0.5-1 OD600 cells were collected by centrifugation in a 1.5-mL tube. The cells were rinsed twice with 1 mL PBS and 0.5 mL goat anti-human IgG (H+L)-Alexa 488 (1:500 in 1% BSA in PBS) is added. Alternatively, fluoresin labeled secondary antibody can be used to detect the antigen. The tubes were rotated for one hour at 37° C., centrifuged, and rinsed 3× with 1 mL PBS to remove the detection antibody. About 50-100 μL of PBS was added to the tube, the cells were mixed, and a 10 μL aliquot viewed with a fluorescence microscope and photographed (See FIG. 7).

Following the above in which the expression cassette encoded the anti-Her2 Fab-GR1 fusion protein, it was determined that of the nine GPI anchored proteins in the library, cells that expressed the full length *Saccharomyces cerevisiae* SED1 had the most intense signal followed by *S. cerevisiae* CWP2 (See FIG. 8A-J). FIGS. 15 A-D shows that YGLY5149, YGLY5152, YGLY6693, and YGLY6694 all expressed anti-CD20 Fab which was captured to the cell surface using GR2 fused to SED1 anchor. Thus, SED1-GR2 fusion protein was selected the cell surface anchoring protein for the remainder of the examples.

Example 2

Expression Levels of Two Different Fab-GR1 Fusion Proteins Displayed on the Surface of Glycoengineered *Pichia pastoris* Correlated with the Expression Levels of their Full Length Counterparts Expression levels of Anti-Her2 full length monoclonal antibodies are generally five times greater than anti-DKK1 full length monoclonal antibodies when both are expressed in glycoengineered *Pichia pastoris*. *Pichia pastoris* expressing full-length anti-Her2 antibodies can produce about 1.3 g/L of antibody whereas *Pichia pastoris* expressing full-length anti-DKK1 antibodies produces about 200 mg/L in 3 L fermentors. In this Example, anti-Her2 Fab-GR1 fusion protein and anti-DKK1-GR1 fusion protein Fab were expressed and displayed on the surface of glycoengineered *Pichia pastoris* strain 2.0 expressing the SED1-GR2 fusion protein as described in Example 1. The amino acid sequences of the anti-her2 heavy and light chains are shown in SEQ ID NOs:22 and 23, respectively. The amino acid sequences of the anti-DKK1 heavy and light chains are shown in SEQ ID NOs:24 and 25, respectively.

Figure 9A:
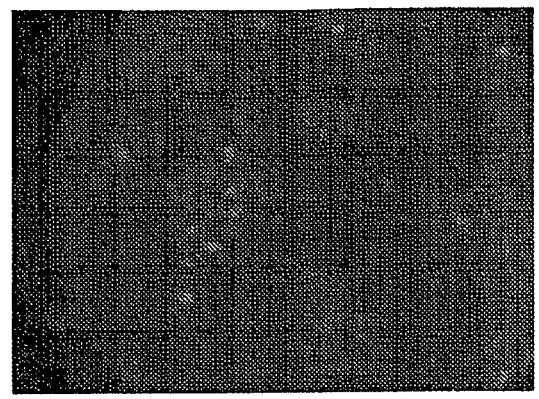
FIGS. 9A-C show fluorescent microscope images of glycoengineered *Pichia pastoris* displaying different Fab fragment.
Figure 9B:
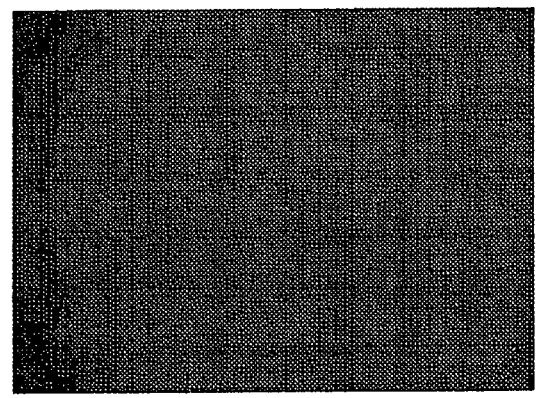
Figure 9C:
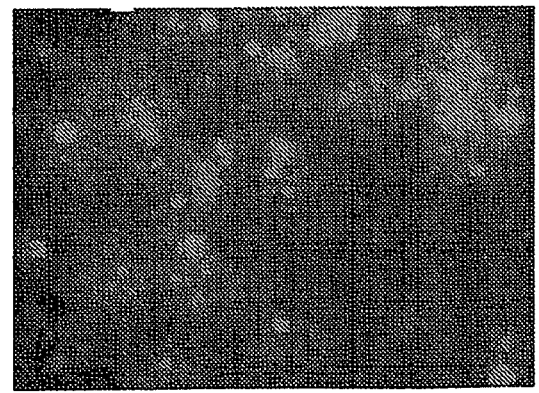

To determine the expression levels of the two Fabs, cells were labeled with goat anti-Human H+L Alexa 488 and photographed according to the method described in the Example 2. FIG. 9 shows the difference in fluorescence intensity between the anti-Her2 Fab and anti-DKK1 Fab. The cells expressing the anti-Her2 Fab displayed a much stronger signal on the surface of the cells than the cells expressing the anti-DKK1 Fab. In FIG. 9A shows a *Pichia pastoris* GS2.0 strain expressing both SED1-GR2 fusion protein and anti-DKK1 Fab-GR1 fusion protein. FIG. 9B shows a *Pichia pastoris* GS2.0 strain expressing the anti-Her2 Fab. but not the SED1-GR2 fusion protein. FIG. 9C shows a *Pichia pastoris* GS2.0 strain expressing both SED1-GR2 fusion protein and anti-Her2 Fab-GR1 fusion protein. All these cells were labeled with anti-human H&L Alexa 488 and photographed using the same exposure time. FIG. 9B clearly shows that without the GPI protein anchor, cells cannot display the Fab. FIGS. 9A-C also show that the intensity of the fluorescent signal reflects the expression level of the Fab: the weakly expressed anti-DKK1 Fab had a weak signal and the higher expression antibody has a stronger signal. This result correlates with the expression levels observed for full-length anti-DKK1 and anti-Her2 monoclonal antibodies.

Example 3

Figure 10:
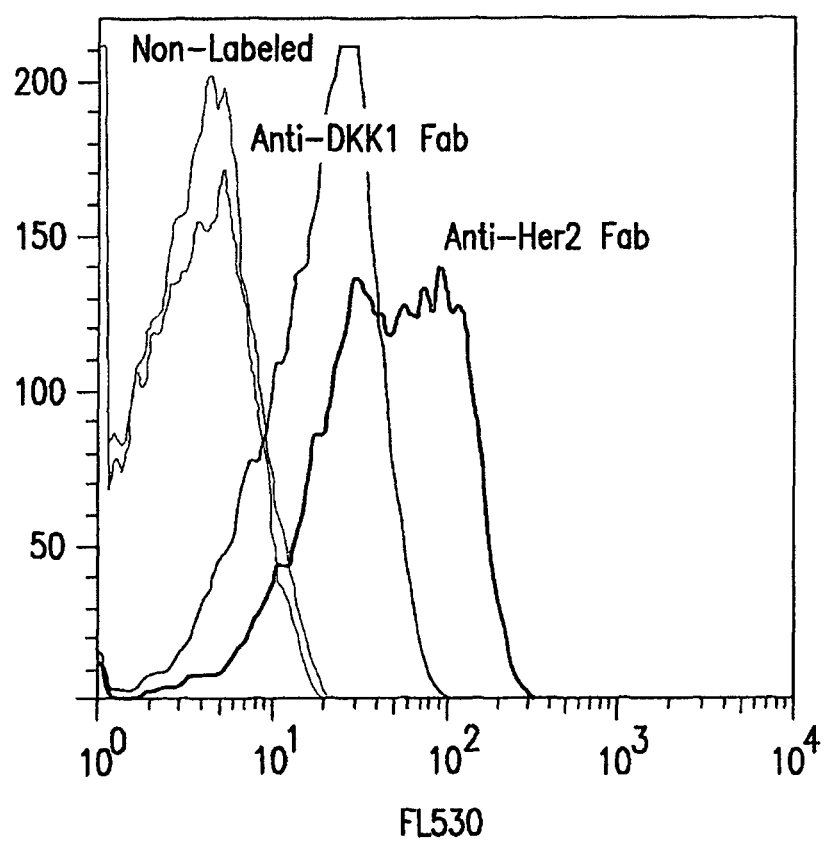
FIG. 10 shows an overlay of several fluorescence-activated cell sorting (FACS) experiments. Flow cytometry analysis was conducted using fluorescently labeled cells expressing anti-Her2 Fab fragment and α-DKK1 Fab fragment. X axis: Fluorescence intensity, Y axis: Number of sorted events. The fluorescence mean of the anti-Her2 Fab fragment is significantly higher than that of the anti-DKK1 population. Non-labeled cells are to the left marking the area of background detection.

Flow cytometry analysis was conducted using the cells expressing anti-Her2 Fab and anti-DKK1 Fab displayed on the surface of the cells. Glycoengineered yeast displaying fluorescently labeled anti-Her2 or anti-DKK1 Fab respectively were prepared as described in Examples 1 and 2. Controls were prepared in which both cell types were not labeled with the detection antibody. Using flow cytometry analysis, anti-Her2 Fab displaying cells were found to have a stronger fluorescence intensity compared to anti-DKK1 Fab displaying cells and both cell types had a stronger signal compared to the signal produced in their corresponding unlabeled controls. In FIG. 10, the fluorescent intensities from these experiments were combined. The Figure shows the difference of fluorescence intensity between the anti-Her2 Fab displaying cells and the anti-DKK1 Fab displaying cells and the same cells in the absence of detection label: anti-Her2 Fab displaying cells showed significantly higher fluorescence intensity than the anti-DKK1 Fab displaying cells. These results are in congruence with fluorescence microscopy observations in Example 3.

Figure 11:
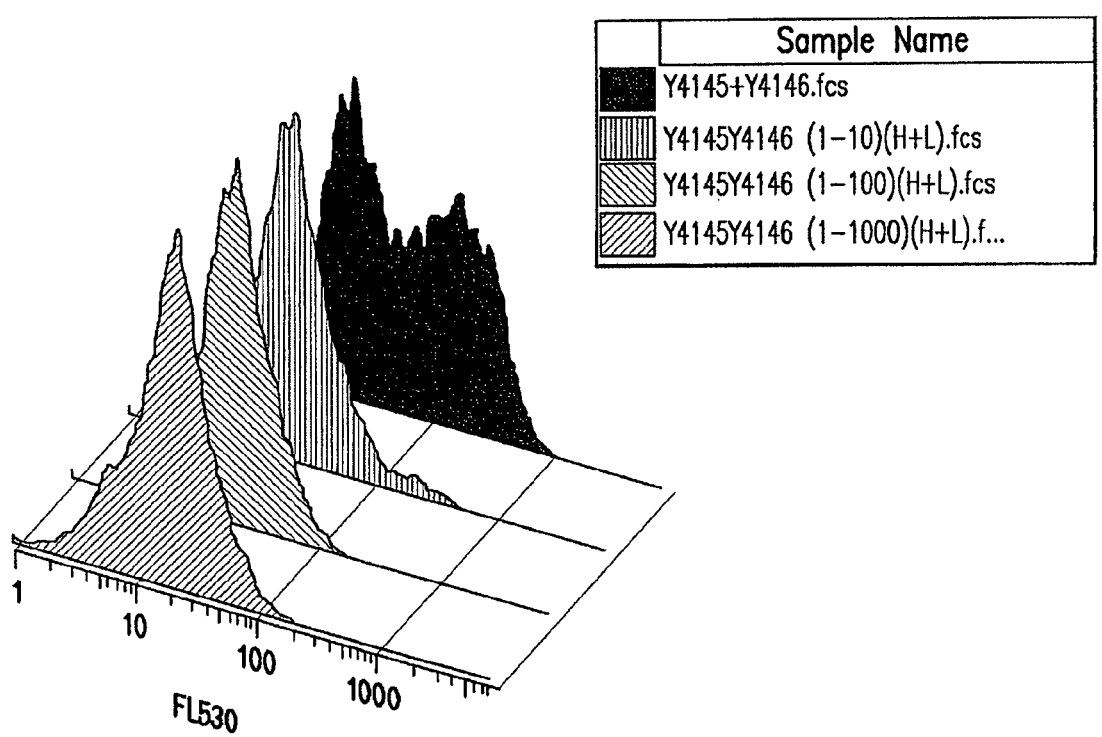
FIG. 11 shows FACS analysis of different population ratios expressing cell-surface displayed anti-Her2 and anti-DKK1, respectively. Only the ratios of anti-Her2:☐ anti-DKK1 of 1:1 (red) and 1:10 (green) allow for the detection of two distinct populations. At the higher ratios of 1:100 (blue) and 1:1000 (brown) no distinct subpopulations can be observed.

Fluorescence-activated cell sorting (FACS) profile of a mixture of cells displaying anti-Her2 Fab (strain YGLY4145) and anti-DKK1 Fab (strain YGLY4146) was performed as follows. The cells displaying anti-Her2 Fab and cells displaying anti-DKK1 Fab were mixed together in the following ratios: 1:1, 1:10, 1:100 and 1:1000. Cells were labeled with goat anti-human H+L Alexa 488 prior to mixing. FIG. 11 shows that at a 1:1 ratio there are two separate populations of cells visible: anti-Her2 Fab displaying cells and anti-DKK1 Fab displaying cells. As the mixing ratio goes up, the florescent intensity of the anti-Her2 Fab population decreases. At the higher ratios of 1:100 and 1:1000, there are no longer two separate populations of cells visible.

Figure 12A:
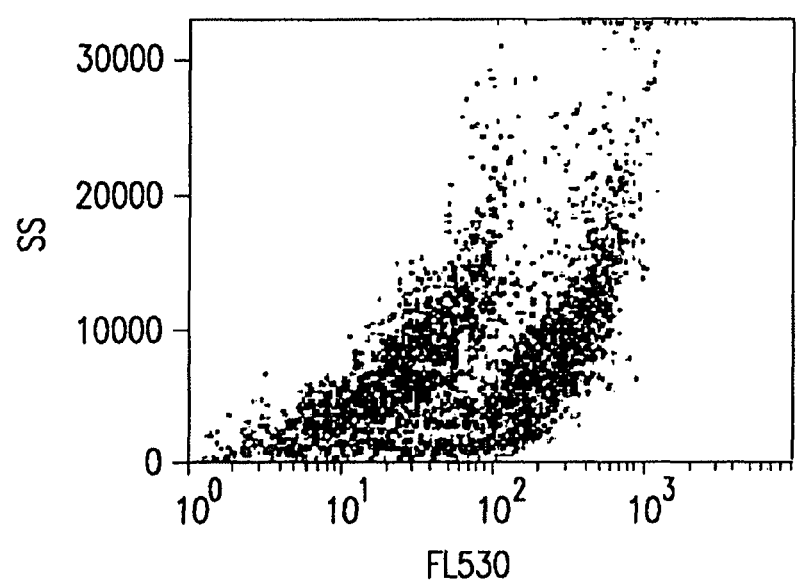
FIGS. 12A-C show the distribution of anti-Her2 and anti-DKK1 expressing cells.
Figure 12B:
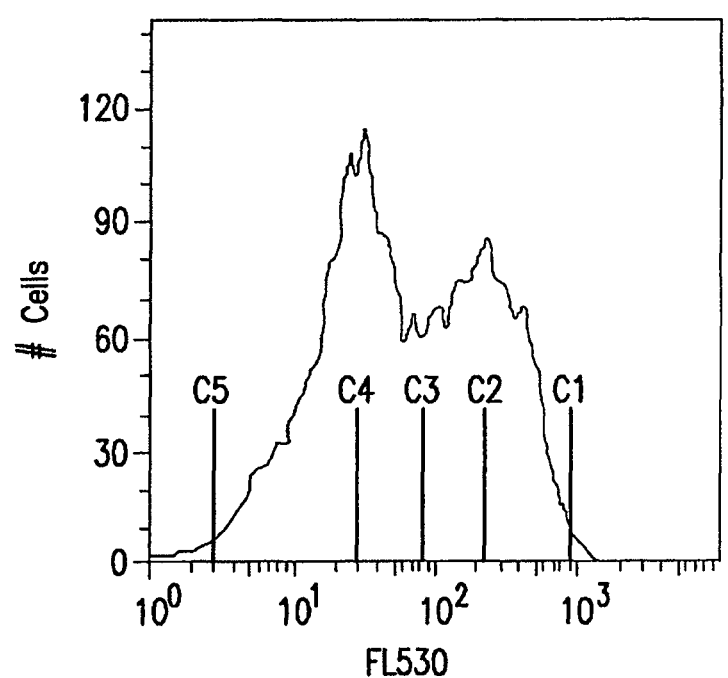
Figure 12C:
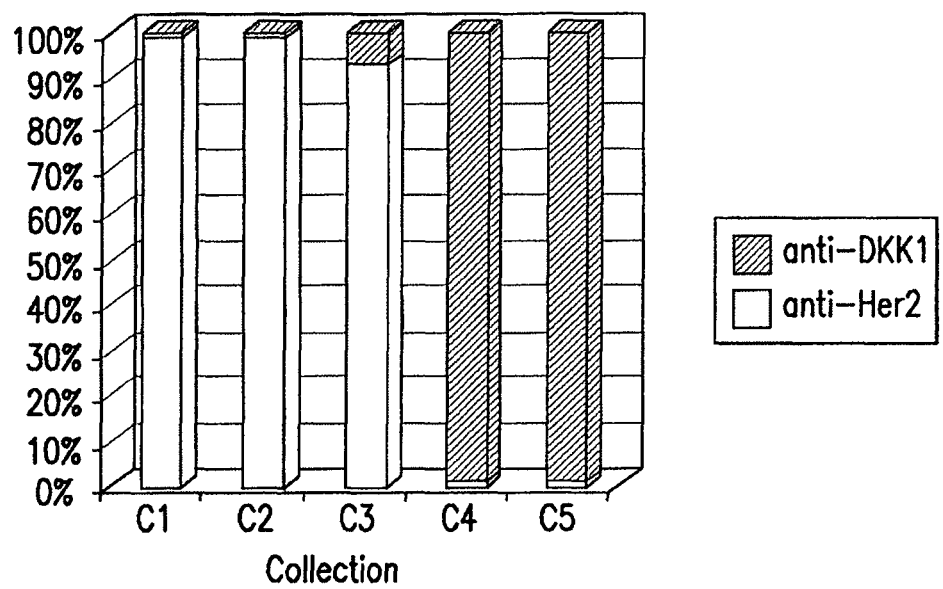

A second experiment was performed to gain better insight into cell diversity across the observed distribution of high to low levels of fluorescence. Anti-Her2 Fab and anti-DKK1 Fab displaying cells (strains YGLY4145 and YGLY4146, respectively) were mixed at a ratio of 1:1 (See FIG. 12A). Across the intensity spectrum, cell populations were isolated from five areas of decreasing fluorescence (FIG. 12B: areas C1 through C5) and plated. For each population of cells, 96 colonies were analyzed by colony PCR using PCR primers specific for each antibody to determine the predominant Fab in the area. The results obtained confirmed that sorting for high-fluorescence signal will almost exclusively result in enrichment of high-expressing anti-Her2 Fab cells, whereas isolating for low-fluorescence will result in enrichment of low expressing cells, here anti □-DKK1 Fab expressing cells (FIG. 12C).

Example 4

This example illustrates the use of FACS to isolate and enrich for a population of high Fab producing cells from a larger population of low level Fab producing cells.

Figure 13:
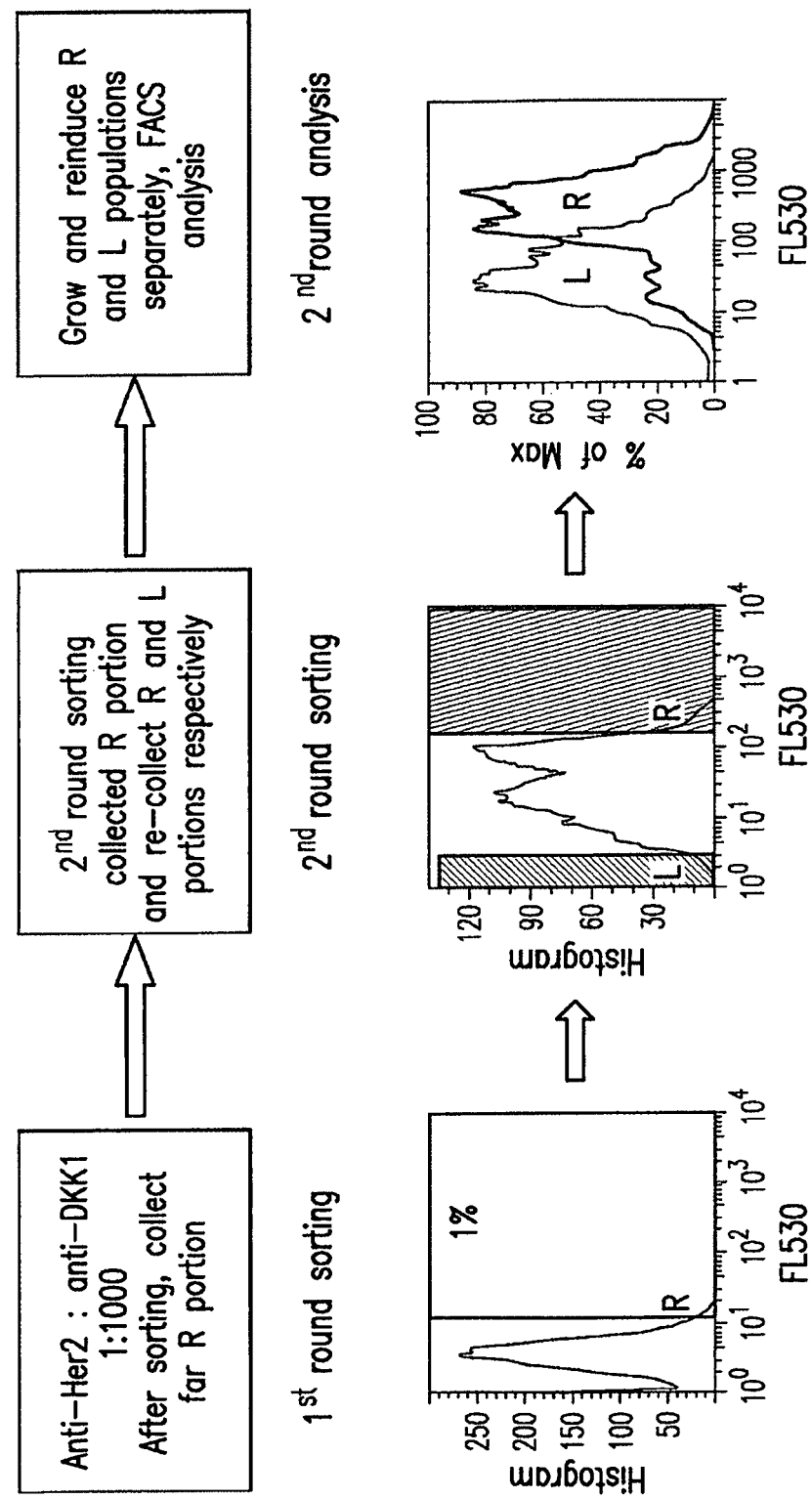
FIG. 13 illustrates enrichment of anti-Her2 Fab fragment expressing cells over three rounds of FACS.
Figure 14A:
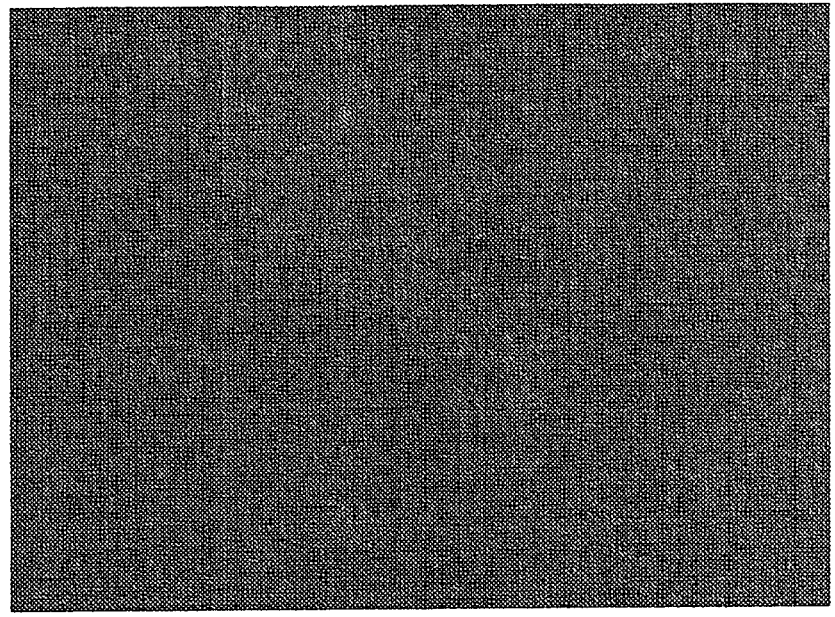
FIGS. 14A-F show fluorescence microscopy and FACS analysis of *P. pastoris* strain YGLY6724, displaying anti-Her2 full length mAb using a read-through stop codon construct and YGLY6722, displaying anti-Her2 full length mAb. Cells are labeled with goat anti-human H&L Alexa 488. G418 is an antibiotic which increases stop codon read-through. YGLY6732 is a non-displaying non-labeled yeast used to determine the level of background fluorescence.
Figure 14B:
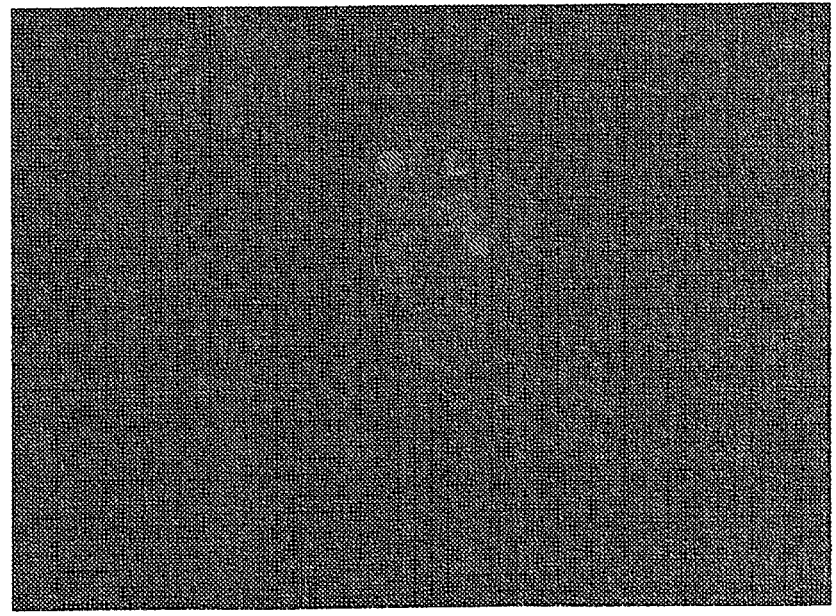
Figure 14C:
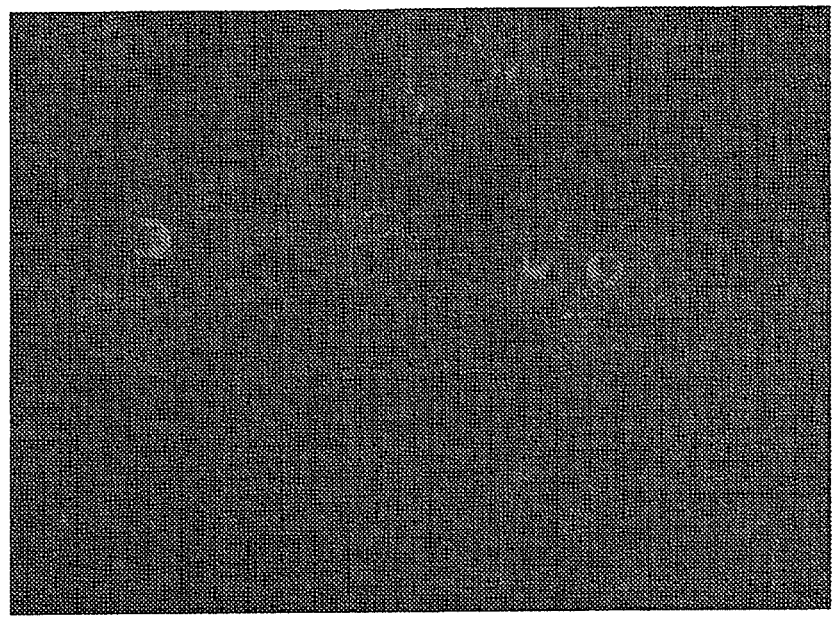
Figure 14D:
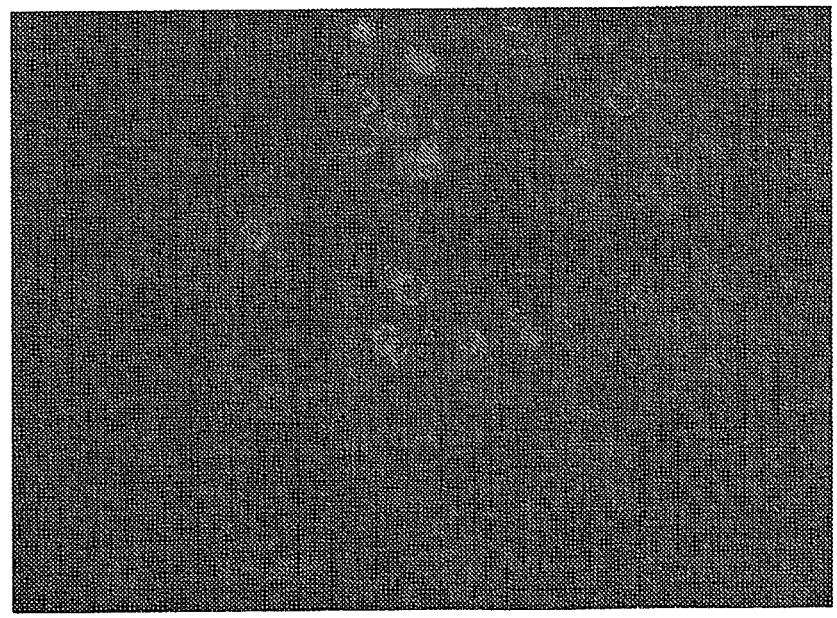
Figure 14E:
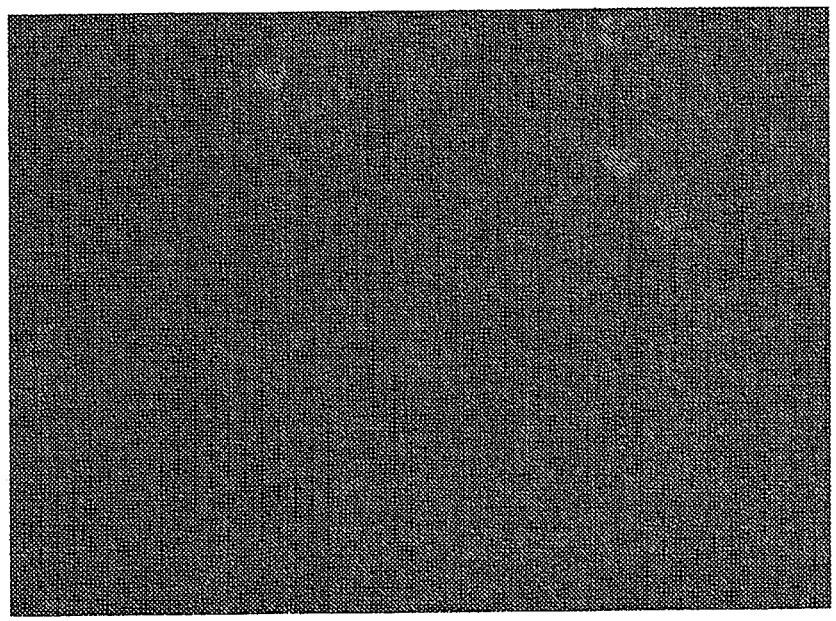
Figure 14F:
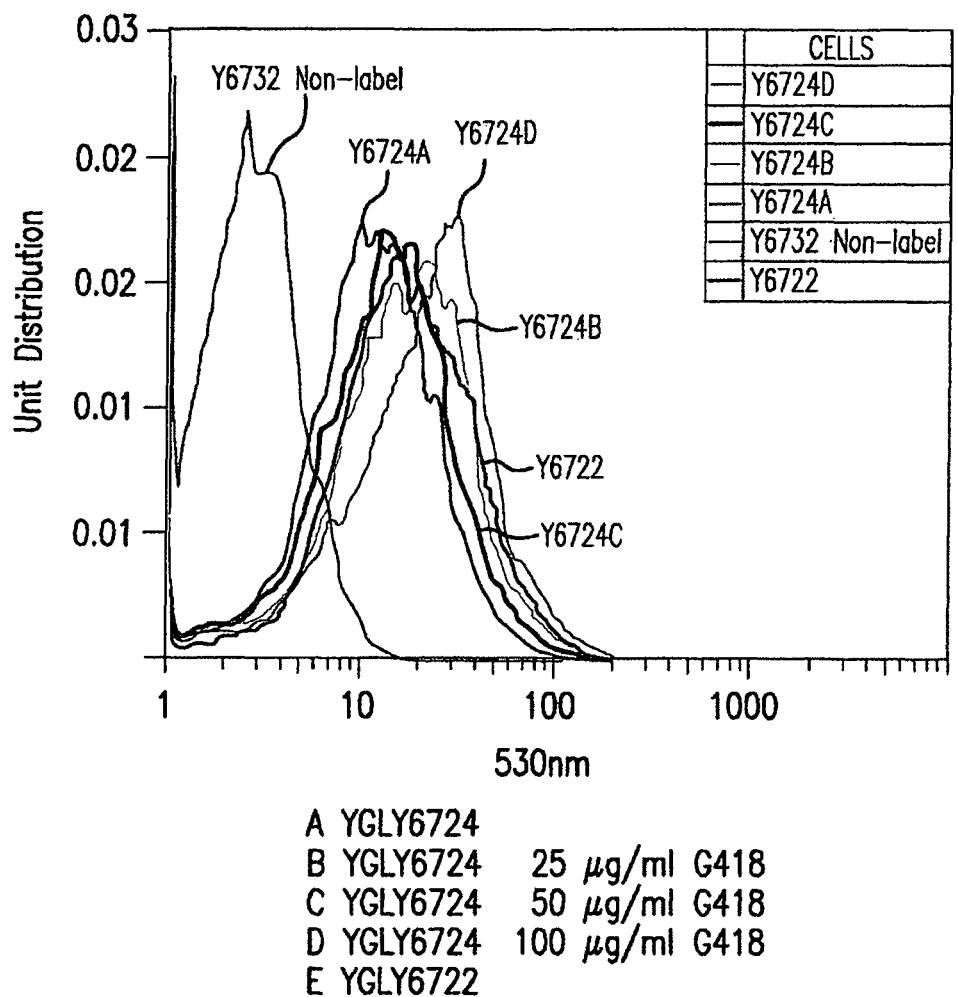
Figure 15A:
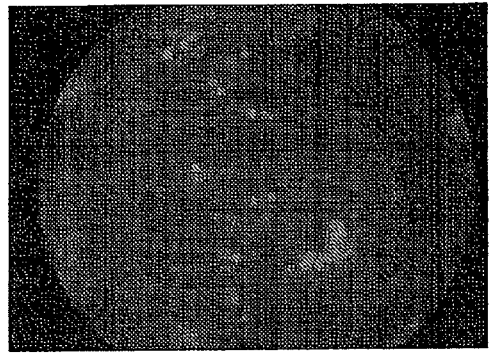
FIGS. 15A-D show fluorescence of several clones of host cells of the YGLY2696 background co-expressing SED1-GR2 fusion protein and anti-CD20 Fab fragment (heavy chain fused to GR1) and labeled with goat anti-human IgG (H+L)-Alexa 488. YGLY5149 15 second exposure (FIG. 15A), YGLY5152 15 second exposure (FIG. 15B), YGLY6693 30 second exposure (FIG. 15C), and YGLY6694 30 second exposure (FIG. 15D).
Figure 15B:
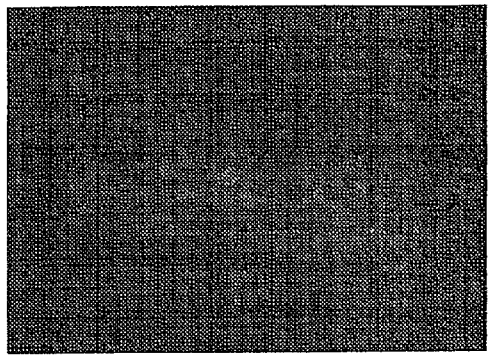
Figure 15C:
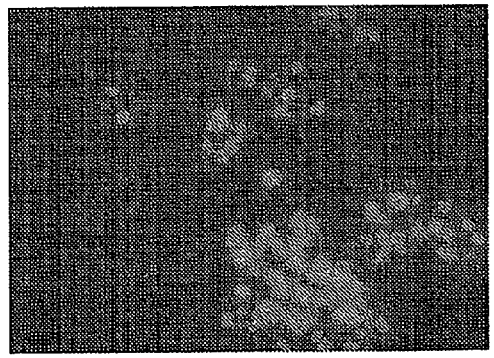
Figure 15D:
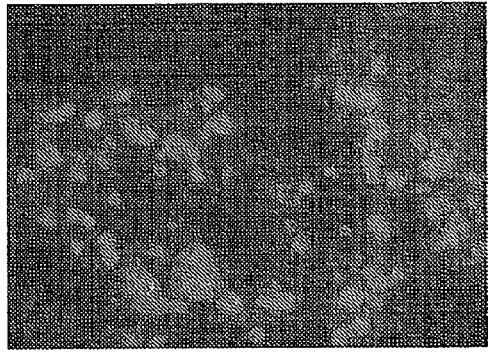

Fluorescently labeled anti-Her2 Fab and anti-DKK1 Fab displaying cells were labeled, mixed at a ratio of 1:1000, and analyzed by flow cytometry. The cells of highest 1% of fluorescence were isolated (far right of left histogram in FIG. 13). The cells were plated out on selection media and incubated three to four days. The cells were then collected by washing the plate with BMGY media and re-induced with BMMY. The re-induced cells were labeled and subsequently sorted. This second round of sorting resulted in two distinct populations of cells (FIG. 13, center histogram). Cells with the highest and lowest fluorescence were isolated and, as in the first round of sorting, grown, collected, induced, and labeled again. These two population were again analyzed using flow cytometry (FIG. 13, histogram on right). Cells from extremes of high and low fluorescence intensity were then isolated and grown up. The higher fluorescence signal population gave rise to a typical anti-Her2 Fab fragment profile whereas the lower fluorescence intensity population displayed an anti-DKK1 Fab fragment-profile very similar to that shown in FIG. 12B. Thus, in three rounds of sorting, we were able to isolate and enrich out of a 1:1000 (anti-Her2 Fab fragment:anti-DKK1 Fab fragment) dilution a distinct population of cells expressing high levels of anti-Her2 Fab fragments. These experiments clearly demonstrate the versatility and power of a cell-sorting based approach to isolate and enrich for particular population of Fab fragments. The methods herein can be used to isolate and enrich for cells expressing particular populations of antibodies.

Example 5

This example illustrates surface display of full-length antibodies using the methods disclosed herein.

FIG. 6 shows plasmid pGLY3941 which comprises an expression cassette encoding anti-Her2 antibody fused to GR1 wherein there is a single stop codon inserted in frame after the last codon encoding the full-length anti-Her2 antibody and which can be used to a display full-length antibody on the yeast cell surface using stop codon readthrough method as discussed in Example 1 for expression cassette C.

Pichia pastoris strain YGLY6724 containing pGLY3941 displays a full length anti-Her2 antibody-GR1 coiled coil fusion protein when the protein is produced under conditions that results in translational readthrough of the stop codon (See SEQ ID 32). Pichia pastoris strain YGLY6722 containing pGLY3939 (no stop codon between the coding sequences for the Her2 antibody and the GR1 peptide) also displays a full length anti-Her2 antibody-GR1 coiled coil fusion. YGLY6724 was grown with increasing amounts of the antibiotic G418 in the medium. G418 inhibits translational termination, thereby increasing stop codon readthrough and increasing fluorescence intensity. To determine the expression levels of the two antibodies, cells were labeled with goat anti-Human H+L Alexa 488 and photographed according to the method described in Example 2. FIGS. 14A-F show by microscopy observation and FACS that anti-Her2 full length antibody can be displayed on the surface and detected using fluorescence and FACS analysis.

Example 6

In strain YGLY2696, the gene encoding the endogenous PD1 replaced with a nucleic acid molecule encoding the human PD1 and a nucleic acid molecule encoding the human GRP94 protein inserted into the PEP4 locus. The strain was further engineered to alter the endogenous glycosylation pathway to produce glycoproteins that have predominantly $Man_5GlcNAc_2$ N-glycans. Strain YGLY2696 has been disclosed in co-pending application Ser. Nos. 61/066,409, filed 20 Feb. 2008, and 61/188,723, filed 12 Aug. 2008, both of which are incorporated herein in their entirety. This strain was shown to be useful for producing immunoglobulins and for producing immunoglobulins that have reduced O-glycosylation. Construction of strain yGLY2696 involved the following steps.

Construction of expression/integration plasmid vector pGLY642 comprising an expression cassette encoding the human PDI protein and nucleic acid molecules to target the plasmid vector to the *Pichia pastoris* PDI1 locus for replacement of the gene encoding the *Pichia pastoris* PDI1 with a nucleic acid molecule encoding the human PDI was as follows and is shown in FIG. 8. cDNA encoding the human PDI1 was amplified by PCR using the primers hPDI/UP1: 5' AGCGC TGACG CCCCC GAGGA GGAGG ACCAC 3' (SEQ ID NO:35) and hPDI/LP-PacI: 5' CCTTA ATTAA TTACA GTTCA TCATG CACAG CTTTC TGATC AT 3' (SEQ ID NO: 36), Pfu turbo DNA polymerase (Stratagene, La Jolla, Calif.), and a human liver cDNA (BD Bioscience, San Jose, Calif.). The PCR conditions were 1 cycle of 95° C. for two minutes, 25 cycles of 95° C. for 20 seconds, 58° C. for 30 seconds, and 72° C. for 1.5 minutes, and followed by one cycle of 72° C. for 10 minutes. The resulting PCR product was cloned into plasmid vector pCR2.1 to make plasmid vector pGLY618. The nucleotide and amino acid sequences of the human PDI1 are shown in SEQ ID NOs:37 and 38, respectively.

The nucleotide and amino acid sequences of the *Pichia pastoris* PDI1 are shown in SEQ ID NOs:39 and 40, respectively. Isolation of nucleic acid molecules comprising the *Pichia pastoris* PDI1 5' and 3' regions was performed by PCR amplification of the regions from *Pichia pastoris* genomic DNA. The 5' region was amplified using primers PB248: 5' ATGAA TTCAG GCCAT ATCGG CCATT GTTTA CTGTG CGCCC ACAGT AG 3' (SEQ ID NO: 41); PB249: 5' ATGTT TAAAC GTGAG GATTA CTGGT GATGA AAGAC 3' (SEQ ID NO: 42). The 3' region was amplified using primers PB250: 5' AGACT AGTCT ATTTG GAGAC ATTGA CGGAT CCAC 3' (SEQ ID NO: 43); PB251: 5' ATCTC GAGAG GCCAT GCAGG CCAAC CACAA GATGA ATCAA ATTTT G-3' (SEQ ID NO: 44). *Pichia pastoris* strain NRRL-11430 genomic DNA was used for PCR amplification. The PCR conditions were one cycle of 95° C. for two minutes, 25 cycles of 95° C. for 30 seconds, 55° C. for 30 seconds, and 72° C. for 2.5 minutes, and followed by one cycle of 72° C. for 10 minutes. The resulting PCR fragments, PpPDI1 (5') and PpPDI1 (3'), were separately cloned into plasmid vector pCR2.1 to make plasmid vectors pGLY620 and pGLY617, respectively. To construct pGLY678, DNA fragments PpARG3-5' and PpARG-3' of integration plasmid vector pGLY24, which targets the plasmid vector to *Pichia pastoris* ARG3 locus, were replaced with DNA fragments PpPD1 (5') and PpPD1 (3'), respectively, which targets the plasmid vector pGLY678 to the PDI1 locus and disrupts expression of the PDI1 locus.

The nucleic acid molecule encoding the human PDI was then cloned into plasmid vector pGLY678 to produce plasmid vector pGLY642 in which the nucleic acid molecule encoding the human PDI was placed under the control of the *Pichia pastoris* GAPDH promoter (PpGAPDH). Expression/integration plasmid vector pGLY642 was constructed by ligating a nucleic acid molecule encoding the *Saccharomyces cerevisiae* alpha mating factor (MF) presequence signal peptide (ScαMFpre-signal peptide) having a NotI restriction enzyme site at the 5' end and a blunt 3' end and the expression cassette comprising the nucleic acid molecule encoding the human PDI released from plasmid vector pGLY618 with AfeI and PacI to produce a nucleic acid molecule having a blunt 5' end and a PacI site at the 3' end into plasmid vector pGLY678 digested with NotI and PacI. The resulting integration/expression plasmid vector pGLY642 comprises an expression cassette encoding a human PDI1/ScαMFpre-signal peptide fusion protein operably linked to the *Pichia pastoris* promoter and nucleic acid molecule sequences to target the plasmid vector to the *Pichia pastoris* PDI1 locus for disruption of the PDI1 locus and integration of the expression cassette into the PDI1 locus. FIG. 2 illustrates the construction of plasmid vector pGLY642. The nucleotide and amino acid sequences of the ScαMFpre-signal peptide are shown in SEQ ID NOs:49 and 50, respectively.

Construction of expression/integration vector pGLY2233 encoding the human GRP94 protein was as follows and is shown in FIG. 3. The human GRP94 was PCR amplified from human liver cDNA (BD Bioscience) with the primers hGRP94/UP1: 5'-AGCGC TGACG ATGAA GTTGA TGTGG ATGGT ACAGT AG-3'; (SEQ ID NO 45); and hGRP94/LP1: 5'-GGCCG GCCTT ACAAT TCATC ATGTT CAGCT GTAGA TTC 3'; (SEQ ID NO: 46). The PCR conditions were one cycle of 95° C. for two minutes, 25 cycles of 95° C. for 20 seconds, 55° C. for 20 seconds, and 72° C. for 2.5 minutes, and followed by one cycle of 72° C. for 10 minutes. The PCR product was cloned into plasmid vector pCR2.1 to make plasmid vector pGLY2216. The nucleotide and amino acid sequences of the human GRP94 are shown in SEQ ID NOs:47 and 48, respectively.

The nucleic acid molecule encoding the human GRP94 was released from plasmid vector pGLY2216 with AfeI and FseI. The nucleic acid molecule was then ligated to a nucleic acid molecule encoding the ScαMPpre-signal peptide having NotI and blunt ends as above and plasmid vector pGLY2231 digested with NotI and FseI carrying nucleic acid molecules comprising the *Pichia pastoris* PEP4 5' and 3' regions (PpPEP4-5' and PpPEP4-3' regions, respectively) to make plasmid vector pGLY2229. Plasmid vector pGLY2229 was digested with BglII and NotI and a DNA fragment containing the PpPDI1 promoter was removed from plasmid vector pGLY2187 with BglII and NotI and the DNA fragment ligated into pGLY2229 to make plasmid vector pGLY2233. Plasmid vector pGLY2233 encodes the human GRP94 fusion protein under control of the *Pichia pastoris* PDI promoter and includes the 5' and 3' regions of the *Pichia pastoris* PEP4 gene to target the plasmid vector to the PEP4 locus of genome for disruption of the PEP4 locus and integration of the expression cassette into the PEP4 locus. FIG. 3 illustrates the construction of plasmid vector pGLY2233.

Construction of plasmid vectors pGLY1162, pGLY1896, and pGF1207t was as follows. All *Trichoderma reesei* α-1,2-mannosidase expression plasmid vectors were derived from pGF1165, which encodes the *T. reesei* α-1,2-mannosidase catalytic domain (See published International Application No. WO2007061631) fused to *S. cerevisiae* αMATpre signal peptide (ScαMPpre-signal peptide) herein expression is under the control of the *Pichia pastoris* GAP promoter and wherein integration of the plasmid vectors is targeted to the *Pichia pastoris* PRO1 locus and selection is using the *Pichia pastoris* URA5 gene. A map of plasmid vector pGF1165 is shown in FIG. 4.

Plasmid vector pGLY1162 was made by replacing the GAP promoter in pGF1165 with the *Pichia pastoris* AOX1 (PpAOX1) promoter. This was accomplished by isolating the PpAOX1 promoter as an EcoR1 (made blunt)-BglII fragment from pGLY2028, and inserting into pGF1165 that was digested with NotI (made blunt) and BglII. Integration of the plasmid vector is to the *Pichia pastoris* PRO1 locus and selection is using the *Pichia pastoris* URA5 gene. A map of plasmid vector pGLY1162 is shown in FIG. 5.

Plasmid vector pGLY1896 contains an expression cassette encoding the mouse α-1,2-mannosidase catalytic domain fused to the *S. cerevisiae* MNN2 membrane insertion leader peptide fusion protein (See Choi et al., Proc. Natl. Acad. Sci. USA 100: 5022 (2003)) inserted into plasmid vector pGFI165 (FIG. 5). This was accomplished by isolating the GAPp-ScMNN2-mouse MNSI expression cassette from pGLY1433 digested with XhoI (and the ends made blunt) and PmeI, and inserting the fragment into pGFI165 that digested with PmeI. Integration of the plasmid vector is to the *Pichia pastoris* PRO1 locus and selection is using the *Pichia pastoris* URA5 gene. A map of plasmid vector pGLY1896 is shown in FIG. 4.

Plasmid vector pGFI207t is similar to pGLY1896 except that the URA5 selection marker was replaced with the *S. cerevisiae* ARR3 (ScARR3) gene, which confers resistance to arsenite. This was accomplished by isolating the ScARR3 gene from pGFI166 digested with AscI and the AscI ends made blunt) and BglII, and inserting the fragment into pGLY1896 that digested with SpeI and the SpeI ends made blunt and BglII. Integration of the plasmid vector is to the *Pichia pastoris* PRO1 locus and selection is using the *Saccharomyces cerevisiae* ARR3 gene. A map of plasmid vector pGFI2007t is shown in FIG. 4. The ARR3 gene from *S. cerevisiae* confers arsenite resistance to cells that are grown in the presence of arsenite (Bobrowicz et al., Yeast, 13:819-828 (1997); Wysocki et al., J. Biol. Chem. 272: 30061-066 (1997)).

Yeast transfections with the above expression/integration vectors were as follows. *Pichia pastoris* strains were grown in 50 mL YPD media (yeast extract (1%), peptone (2%), dextrose (2%)) overnight to an OD of between about 0.2 to 6. After incubation on ice for 30 minutes, cells were pelleted by centrifugation at 2500-3000 rpm for 5 minutes. Media was removed and the cells washed three times with ice cold sterile 1 M sorbitol before resuspending in 0.5 ml ice cold sterile 1 M sorbitol. Ten μL linearized DNA (5-20 μg) and 100 μL cell suspension was combined in an electroporation cuvette and incubated for 5 minutes on ice. Electroporation was in a Bio-Rad GenePulser Xcell following the preset *Pichia pastoris* protocol (2 kV, 25 μF, 200Ω), immediately followed by the addition of 1 mL YPDS recovery media (YPD media plus 1 M sorbitol). The transfected cells were allowed to recover for four hours to overnight at room temperature (26° C.) before plating the cells on selective media.

Generation of Cell Lines was as follows and is shown in FIG. 6. The strain yGLY24-1 (ura5Δ::MET1 och1Δ::lacZ bmt2Δ::lacZ/K1MNN2-2/mnn4L1Δ::lacZ/MmSLC35A3 pnolΔmnn4Δ::lacZ met16Δ::lacZ), was constructed using methods described earlier (See for example, Nett and Gerngross, Yeast 20:1279 (2003); Choi et al., Proc. Natl. Acad. Sci. USA 100:5022 (2003); Hamilton et al., Science 301: 1244 (2003)). The BMT2 gene has been disclosed in Mille et al., J. Biol. Chem. 283: 9724-9736 (2008) and U.S. Published Application No. 20060211085. The PNO1 gene has been disclosed in U.S. Pat. No. 7,198,921 and the mnn4L1 gene (also referred to as mnn4b) has been disclosed in U.S. Pat. No. 7,259,007. The mnn4 refers to mnn4L2 or mnn4a. In the genotype, KIMNN2-2 is the *Kluveromyces lactis* GlcNAc transporter and MmSLC35A3 is the *Mus musculus* GlcNAc transporter. The URA5 deletion renders the yGLY24-1 strain auxotrophic for uracil (See U.S. Published application NC). 2004/0229306) and was used to construct the humanized chaperone strains that follow.

While the various expression cassettes were integrated into particular loci of the *Pichia pastoris* genome in the examples herein, it is understood that the operation of the invention is independent of the loci used for integration. Loci other than those disclosed herein can be used for integration of the expression cassettes. Suitable integration sites include those enumerated in U.S. Published application No. 20070072262 and include homologs to loci known for *Saccharomyces cerevisiae* and other yeast or fungi.

Strains yGLY702 and yGLY704 were generated in order to test the effectiveness of the human PDI1 expressed in *Pichia pastoris* cells in the absence of the endogenous *Pichia pastoris* PDI gene. Strains yGLY702 and yGLY704 (huPDI) were constructed as follows. Strain yGLY702 was generated by transfecting yGLY24-1 with plasmid vector pGLY642 containing the expression cassette encoding the human PDI under control of the constitutive PpGAPDH promoter. Plasmid vector pGLY642 also contained an expression cassette encoding the *Pichia pastoris* URA5, which rendered strain yGLY702 prototrophic for uracil. The URA5 expression cassette was removed by counterselecting yGLY702 on 5-FOA plates to produce strain yGLY704 in which, so that the *Pichia pastoris* PDI1 gene has been stably replaced by the human PDI gene and the strain is auxotrophic for uracil.

Strain yGLY733 was generated by transfecting with plasmid vector pGLY1162, which comprises an expression cassette that encodes the *Trichoderma Reesei* mannosidase (TrMNS1) operably linked to the *Pichia pastoris* AOX1 promoter (PpAOX1-TrMNS1) and the *Saccharomyces cerevisiea* αMAT pre signal sequence, into the PRO1 locus of yGLY704. This strain has the gene encoding the *Pichia pastoris* PDI replaced with the expression cassette encoding the human PDI1, has the PpAOX1-TrMNS1 expression cassette integrated into the PRO1 locus, and is a URA5 auxotroph. The PpAOX1 promoter allows overexpression when the cells are grown in the presence of methanol.

Strain yGLY762 was constructed by integrating expression cassettes encoding TrMNS1 and mouse mannosidase IA (MuMNS1A), each operably linked to the *Pichia pastoris* GAPDH promoter in plasmid vector pGFI207t into control strain yGLY733 at the 5' PRO1 locus UTR in *Pichia pastoris* genome. This strain has the gene encoding the *Pichia pastoris* PD1 replaced with the expression cassette encoding the human PDI1, has the PpGAPDH-TrMNS1 and PpGAPDH-MuMNS1A expression cassettes integrated into the PRO1 locus, and is a URA5 auxotroph.

Strain yGLY2677 was generated by counterselecting yGLY762 on 5-FOA plates. This strain has the gene encoding the *Pichia pastoris* PDI replaced with the expression cassette encoding the human PDI1, has the PpAOX1-TrMNS1 expression cassette integrated into the PRO1 locus, has the PpGAPH-TrMNS1 and PpGAPDH-MuMNS1A expression cassettes integrated into the PRO1 locus, and is a URA5 prototroph.

Figure 16:
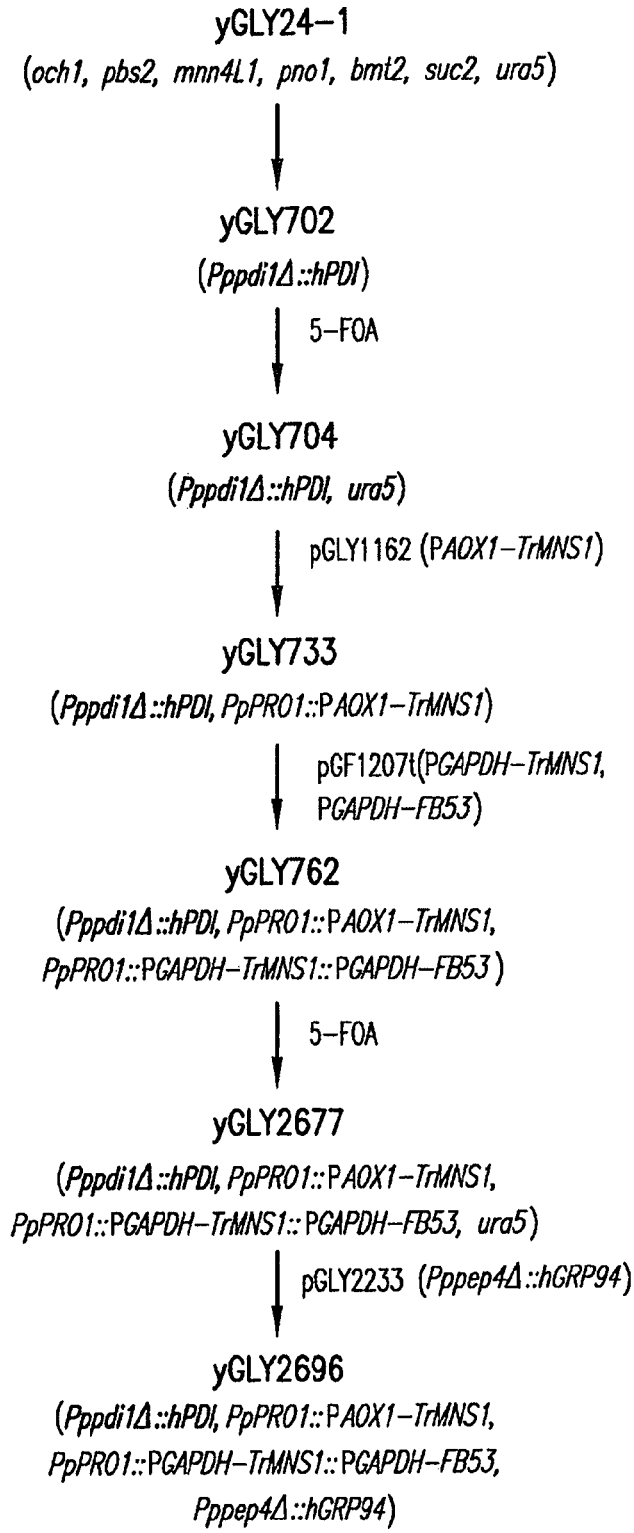
FIG. 16 shows the genealogy of humanized chaperone strain YGLY2696.

Strains yGLY2696 was generated by integrating plasmid vector pGLY2233, which encodes the human GRP94 protein, into the PEP4 locus. This strain has the gene encoding the *Pichia pastoris* PD1 replaced with the expression cassette encoding the human PDI1, has the PpAOX1-TrMNS1 expression cassette integrated into the PRO1 locus, has the PpGAPDH-TrMNS1 and PpGAPDH-MuMNS1A expression cassettes integrated into the PRO1 locus, has the human GRP64 integrated into the PEP4 locus, and is a URA5 prototroph. The genealogy of this chaperone-humanized strain is shown in FIG. 16.

Example 7

Construction of plasmid pGLY5107, pGLY5108 and pGLY5110 encoding various antibody heavy and light chains to make Fab fragments 1H23 and 1D05 (low and high affinity Fab fragments specific to PCSK9, Proprotein convertase subtilisin/kexin type 9) and anti-CD20 Fab fragment Genmab was as follows.

Figure 20:
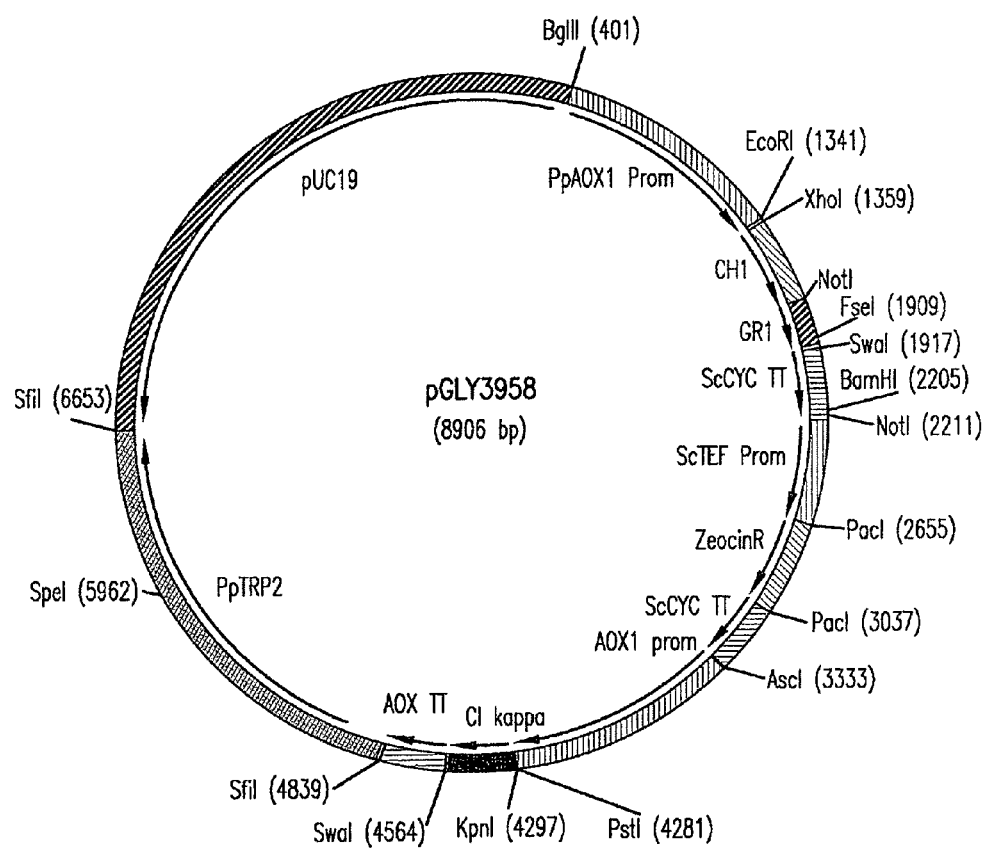
FIG. 20 shows a map of pGLY3958, which encodes light chain C1 kappa and the heavy chain CH1 fused to GR2, and which targets the plasmid to the TRP2 locus of *Pichia pastoris*. This plasmid was used to make plasmids pGLY5108, pGLY51 10, and pGLY5107.

Fab display vector pGLY3958 (FIG. 20) was constructed using Zeocin as a marker for *Pichia* transformation selection. Nucleic acid molecules encoding the $IgG_1$ CH1 domain, linker, and GR1 coiled coil peptide and the constant region of $IgG_1$ kappa light chain were codon optimized and synthesized by GeneArt according to *Pichia pastoris* codon usage. Both the nucleic acid molecules encoding the heavy chain and light chains are under *Pichia* AOX1 promoter. Unique sites EcoR1 and Xho1 were made for different antibody variable regions cloning. Likewise, Pst1 and Kpn1 sites were added between the AOX1 promoter and the constant region of light chain to facilitate variable region of light chain cloning.

Figure 21:
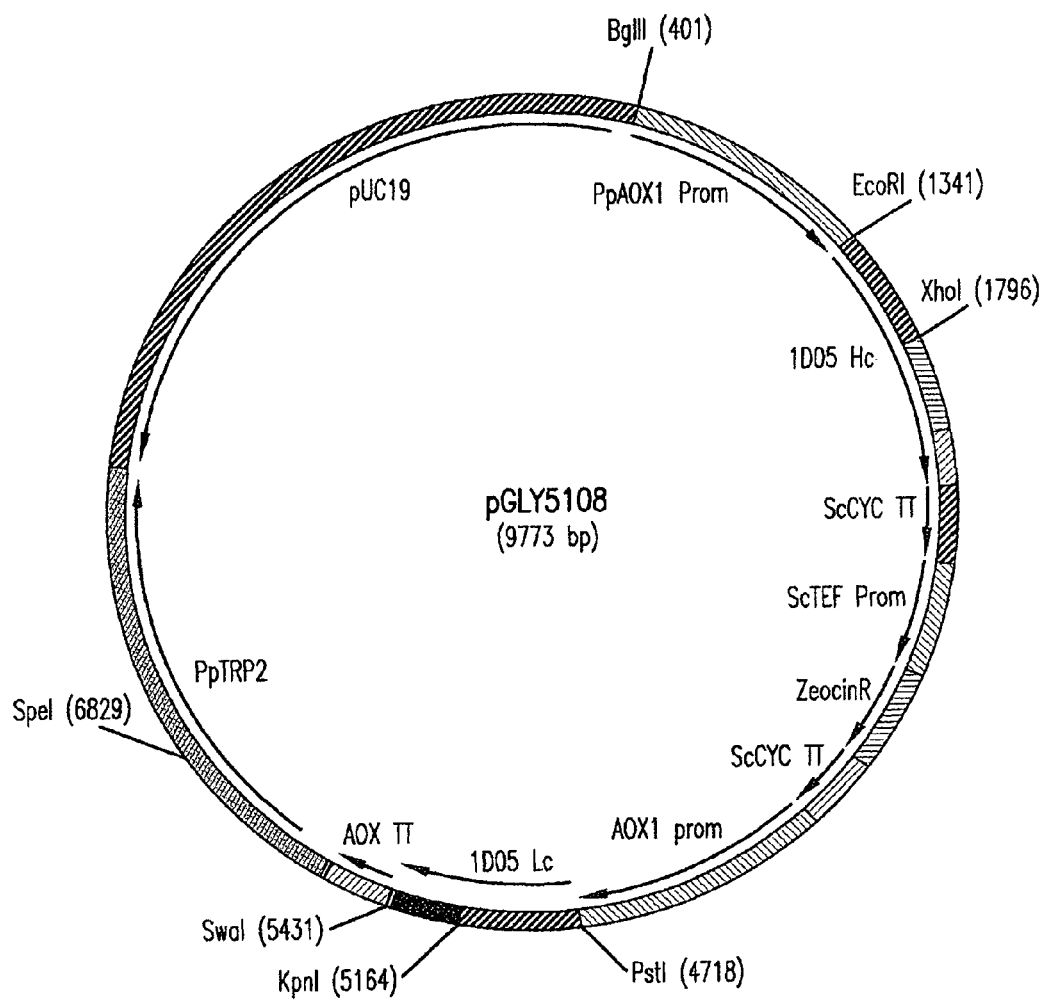
FIG. 21 shows a map of plasmid pGLY5108, which encodes the 1D05 anti-PCSK9 Fab fragment.
Figure 22:
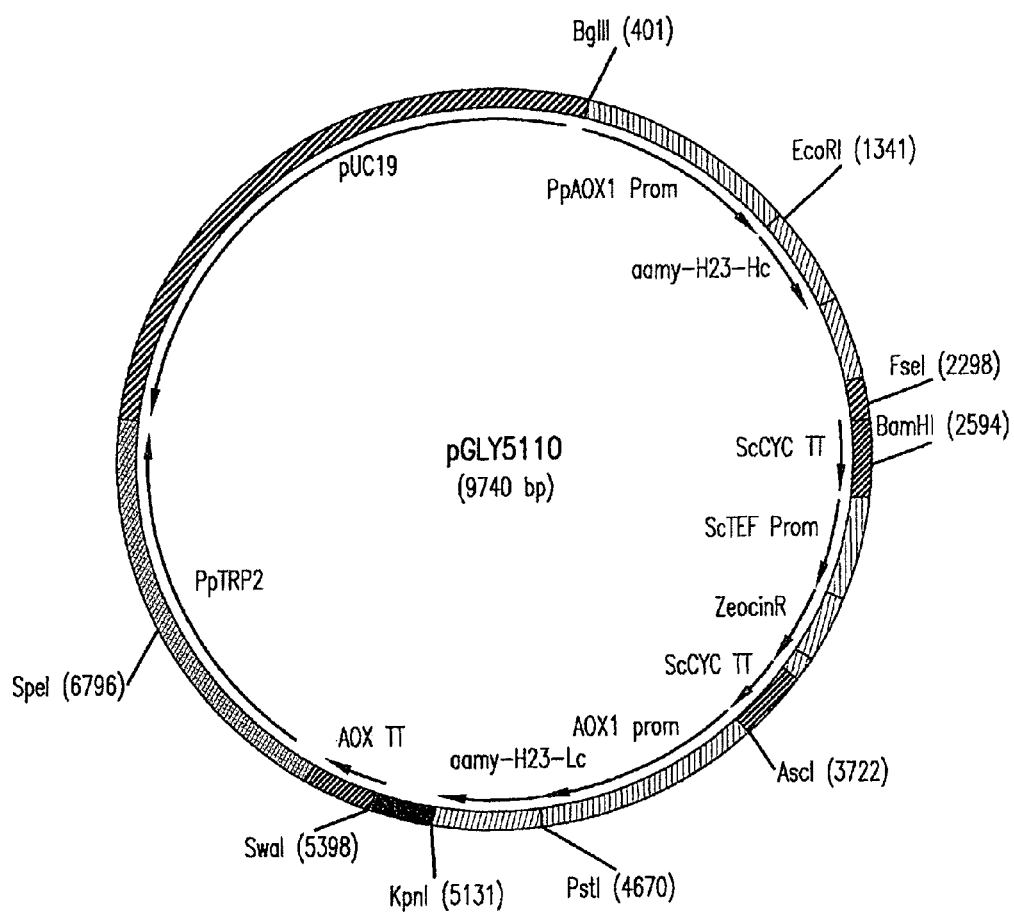
FIG. 22 shows a map of plasmid pGLY5110, which encodes the 1H23 anti-PCSK9 Fab fragment.
Figure 23:
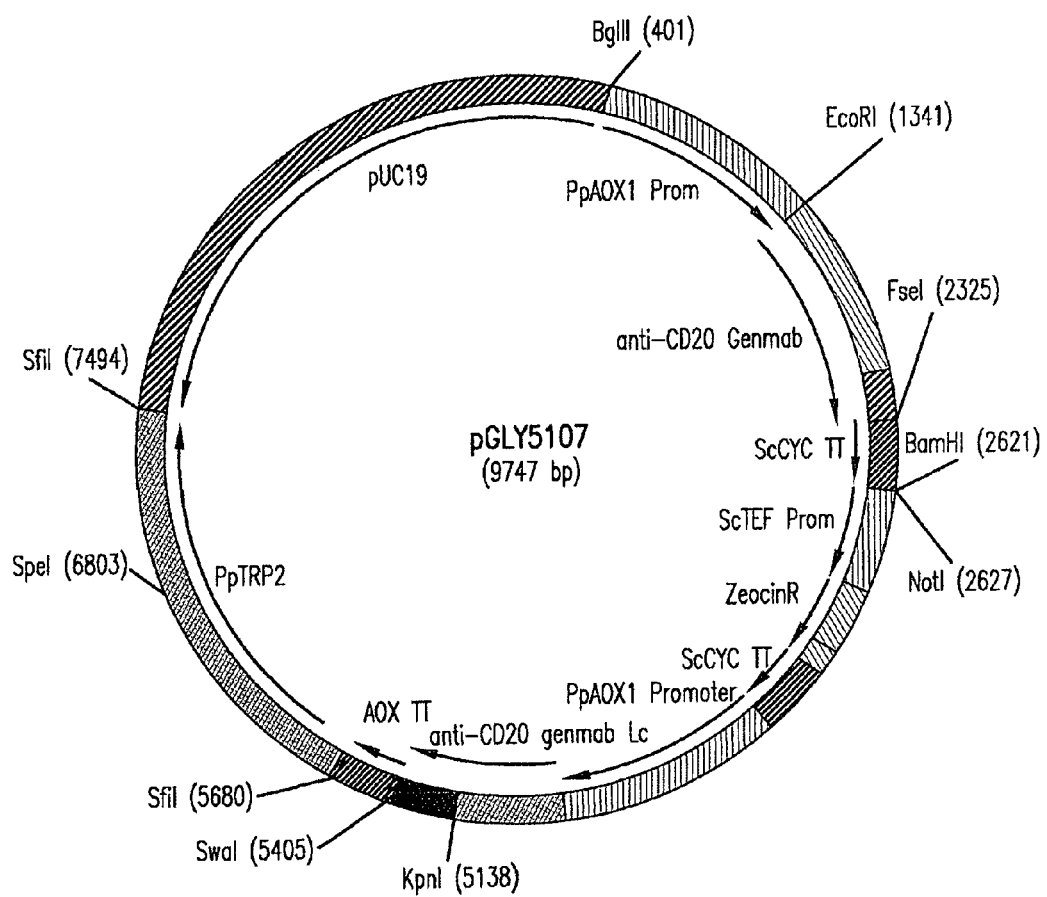
FIG. 23 shows a map of plasmid pGLY5107, which encodes the anti-CD20 Genmab antibody.

Nucleic acid molecules encoding the variable regions of the heavy and light chains of 1D05, 1H23, and anti-CD20 Genmab were codon optimized, reverse translated, and synthesized by GeneArt based on their amino acid sequences. Nucleic acid molecules encoding the *Aspergillus* amylase signal sequence (SEQ ID NO:33) was added in-frame to the 5' end of the open reading frames encoding the 1H23 heavy and light chains (SEQ ID NO:70 and 72, respectively) during the gene synthesis. The open reading frame encoding the heavy chain also included the nucleotide sequence encoding GR1. Nucleic acid molecules encoding the *Saccharomyces cerevisiae* mating factor pre-signal peptide (alpha-MAT-pro; SEQ ID NO:49) signal sequence was added in-frame to the 5' end of the open reading frames encoding the 1D05 heavy and light chains (SEQ ID NO:66 and 68, respectively) during the gene synthesis. The open reading frame encoding the heavy chain also included the nucleotide sequence encoding GR1. During synthesis, EcoR1 site was introduced at the 5' of the nucleic acid molecules encoding the heavy chains and Pst1 sites were introduced at the 5' ends of the nucleic acid molecules encoding the light chains. Xho1 and Kpn1 sites were created at the 3' ends of the heavy and light chains, respectively, using nucleic acid molecules encoding heavy chain and light chain constant regions conserved amino acids. The nucleic acid molecules encoding the variable regions of the heavy chain and light chains were cloned into pGLY3958 (FIG. 21) at the same time using four-piece ligation. Plasmids pGLY5108 encoding the 1D05 heavy and light chains (FIG. 21), pGLY5109 encoding the 1H23 heavy and light chains (FIG. 22), and pGLY5107 encoding the light and heavy chains of anti-CD20 Genmab (FIG. 23). Colony PCR, enzymatic digestion, and DNA sequencing were applied to confirm the identity of the created plasmids. The amino acid sequence of 1 D05 heavy chain with signal peptide encoded by SEQ ID NO:66 is shown in SEQ ID NO:67. The amino acid sequence of 1D05 light chain with signal peptide encoded by SEQ ID NO:68 is shown in SEQ ID NO:69. The amino acid sequence of 1H23 heavy chain with signal peptide encoded by SEQ ID NO:70 is shown in SEQ ID NO:71. The amino acid sequence of 1H23 light chain with signal peptide encoded by SEQ ID NO:72 is shown in SEQ ID NO:73. The amino acid sequence of PCSK9 is shown in SEQ ID NO:74.

Yeast transformation for making 1D05, 1H23 and anti-CD20 Genmab Fab display strains were as follows. Plasmids pGLY5107, pGLY5108 and pGLY5110 were linearized by Spe1 digestion at 37° C. and linearization was confirmed by gel electrophoresis. DNA was precipitated down using standard procedure using cold ethanol. Grew *Pichia* host YGLY5079 (expresses ScSED1-GR2 fusion protein in YGLY2696) in 50 mL BMGY media overnight to a cell density of between 1-2 of $OD_{600}$. Cells were washed three times with cold sterile water and 1 M sorbitol to render the cells competent for transformation. The linearized DNA was mixed with competent cells and shocked using the Bio-Rad electroporation machine. Then 1 mL recovery media was added to the shocked cells and the cells incubated at room temperature for 1 to 2 hours. Then the cells were plated on YPG plates with appropriate Zeocin concentration to select for transformants. The strains produced are shown in Table 5.

TABLE 5

| Strains | Fab displayed | Host | Plasmid |
|---|---|---|---|
| YGLY7761 | Anti-CD20 (Genmab) | YGLY5079 | pGLY5107 |
| YGLY7762 | 1D05 | YGLY5079 | PGLY5108 |
| YGLY7764 | 1H23 | YGLY5079 | pGLY5110 |

Example 8

It has been reported for *Saccharomyces cerevisiae* that assembly of heavy and light chains expressed in yeast can be problematic. Therefore, the ratio of heavy chain to light chain in the Fab fragments displayed on the cell surface was measured to determine the intactness of the Fab fragments displayed on the cell surface.

Strain YGLY7762 (expresses 1D05 Fab fragment heavy and light chains) and strain YGLY7764 (expresses 1H23 Fab fragment heavy and light chains) were grown in 200 mL BMGY and expression induced in a Micro24 bioreactor according to the description of Micro24 cell culture and induction. Then remove about 20-40 uL of induced yeast culture, add 1 mL of blocking solution to the sample, centrifuge at 10,000 rpm for 30 seconds and wash the cell pellet three times with 1 mL blocking solution. Measure $OD_{600}$ and calculate the volume needed to get an $OD_{600}$ of 1 in desired final volume. (Usually the final volume is about 200 uL). Blocking solution: 60 g BSA from Omni Pur, 200 mL 0.5% Tween 20, 200 mL 10×PBS (from Omni Pur), and $dH_2O$ up to two liters.

Anti-human $IgG_2$ Fd biotin-conjugated antibody (CALTAG Laboratories, code #MH1522, lot#443408A: anti-heavy chain antibody) coupled with strepavidin Alexa Fluor 488 (2 mg/mL, Invitrogen, lot#53729A) was used for detecting the displayed Fab via the Fd region of the heavy chain and anti-human kappa allophycocyanin-conjugated antibody (CALTAG Laboratories, code# MH10515, lot #358897A: anti-light chain antibody) was used for detecting the light chain. In general, three uL of anti-heavy chain antibody was incubated with the cells at room temperature for 30 minutes on a rotator kept in the dark. Then the cells were washed four times with 3% BSA-0.05% Tween 20-PBS buffer. After this, three uL of Strepavidin Alexa Fluor 488 and 3 uL of anti-light chain antibody Were added and the mixtures incubated at room temperature for 30 minutes on a rotator in the dark. Then, cells were wash three times with 3% BSA-0.05% Tween 20-PBS buffer. The cells were analyzed by FACS. Fluorescent intensity of light chain and heavy chain (Fd) were plotted using FluoJo.

Figure 17A:
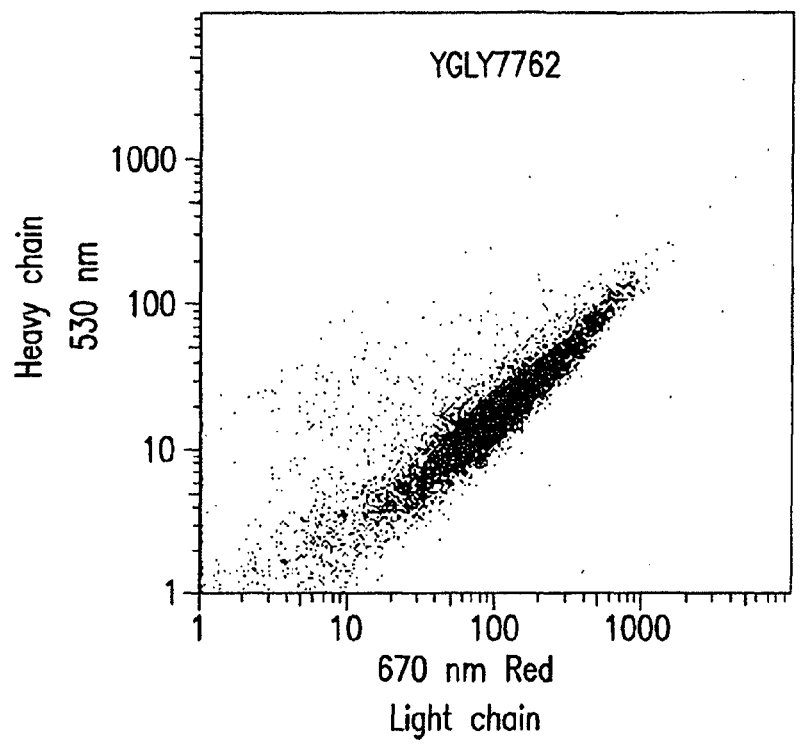
FIGS. 17A-B show that the heavy and light chains of the displayed Fab fragment in the Fab fragment-displaying cells were properly assembled. Cells displaying Fab fragments were labeled with light and heavy chain specific fluorophore-conjugated antibodies. Flow cytometric analysis shows that the displayed Fab fragment heavy chain expression corresponds with displayed light chain expression indicating proper assembly of the Fab fragments.
Figure 17B:
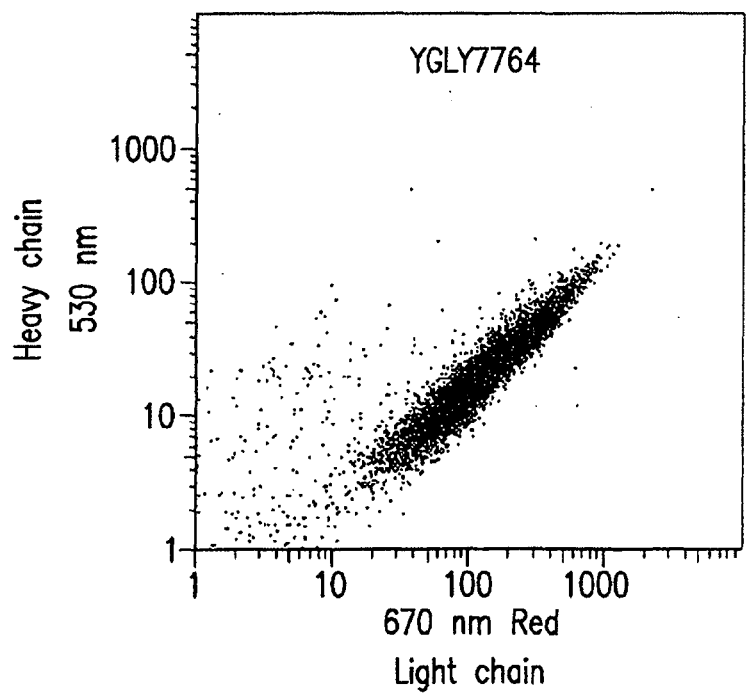

Flow cytometric analysis showed that displayed heavy chains corresponded with displayed light chains. This is shown in FIGS. 17A and 17B, which show that the cells properly assembled and displayed the heavy and light chains of the Fab fragment. In contrast to results reported for Saccharomyces cerevisiae, the nucleic acid molecules encoding the Fab fragments were integrated into a specific locus which results in constant expression f the heavy and light chains as opposed to be provided in autonomously replicating plasmids. Furthermore, the cells were grown under conditions that controlled O-glycosylation of the heavy and light chains, i.e., the presence of human chaperone proteins in place of host cell chaperone proteins and/or Pmti-3 inhibitor of O-glycosylation. The Pmti-3 inhibitor reduces the O-glycosylation occupancy, that is the number of total O-glycans on the Fab or antibody molecule. The cell further express a *T. reesei* alpha-1,2-mannsodase catalytic domain linked to the *Saccharomyces cerevisiea* αMAT pre signal peptide to control the chain length of those O-glycans that are on the Fab or antibody molecule.

Cell Culture and Induction in Micro 24

Yeast display cells are grown in 200 mL BMGY medium in regular shake flask for two days at room temperature. The yeast culture is centrifuged and the spent supernatant is decanted. The remaining cell pellet is suspended in fresh induction media (see below for recipe) to an $OD_{600}$ of between 100 and 200 depending on the experiment. About 4.5 mL of the resulting culture is inoculated into a well of an Applikon Microreactor cassette and a gas-permeable, low evaporation adhesive membrane is used to seal the cassette. The induced cells are run using a constant agitation rate of 800 rpm with a pH set-point of 6.5. Each well is aerated with a continuous flow of 1vvm (4.5 mL/min). Under these conditions the culture will typically consume 2.5% methanol in about 16-20 hours. After 16-20 hours or when a dissolved oxygen spike is observed and additional bolus of 1%-2.5% methanol will be added so the cells remain in an induction start. Once the desired length of induction is achieved the Microreactor is stopped and the culture can be removed from the well for labeling.

| BMGY Medium | |
| --- | --- |
| $KH_2PO_4$ | 11.9 g/L |
| $K_2HPO_4$ | 2.5 g/L |
| Yeast Nitrogen Base | 13.4 g/L |
| Biotin (400 mg/L stock) | 10 ml/L |
| Sorbitol | 18.2 g/L |
| Soytone | 20 g/L |
| Yeast Extract | 10 g/L |
| Methanol | 25 g/L |
| Sigma 204 | 8 drops/L |

Example 8

This example shows that the method can sort cells that display the antibody or Fab fragments of interest from cells that do not display the antibody of Fab of interest.

In a first experiment, *Pichia pastoris* cells engineered to display anti-CD20 Fab fragments (YGLY7761) were mixed with *Pichia pastoris* cells engineered to display anti-PCSK-9 Fab fragments (YGLY7762).

Strains YGLY7762, YGLY7761, and YGLY7764 were incubated at 24° C. for 24 hours and expression induced in Micro24 with BMMY and PMT inhibitor as described previously for 18 hours. Induced cells were harvested and transferred into 50 mL tubes; centrifuged at 2500 rpm for five minutes at 4° C. Supernatant fractions were decanted and the pellets resuspended in 50 mL of blocking solution. The cells were pelleted as before and the cell pellet washed once more in 50 mL of blocking solution and cells pelleted. The pellet was resuspended in blocking solution and the $OD_{600}$ was adjusted with blocking solution to give about three OD units. Then the cells were mixed in a 1:1 ratio and then labeled sequentially with fluorophore-conjugated PCSK9 antigen (Alexa 647-conjugated) for one hour at room temperature and fluorophore-conjugated generic H+L antibody (Alexa Fluor488-conjugated) for 30 minutes at room temperature. Afterwards, the cells were washed and the flow cytometric profile was determined.

FIG. 18A, shows the FACS profile of anti-CD20 Fab displaying cells and anti-PCSK-9 (1D05) Fab displaying cells when mixed at 1:1 ratio. The figure shows that method can separate the two different cell populations.

In FIG. 18B, *Pichia pastoris* cells engineered to display high affinity anti-PCSK-9 Fab fragments (1D05) and *Pichia pastoris* cells engineered to display low affinity anti-PCSK-9 Fab fragments (1H23) were each separately labeled with fluorophore-conjugated antigen and the flow cytometric profile for each was determined. FIG. 18B shows an overlay of the FACS profiles for high and low affinity Fab fragments displaying cells. The panel shows that the method can be used to sort cells on basis of affinity for an antigen.

Example 9

This example shows that the method can sort cells that display the antibody or Fab fragments of interest from a majority of cells that do not display the antibody of Fab of interest.

In a first experiment, *Pichia pastoris* cells engineered to display anti-PCSK-9 Fab fragments were mixed with *Pichia pastoris* cells engineered to display anti-CD20 Fab fragments. The cell populations were mixed at ratios of 1:1,000; 1:10,000; and 1:100,000. Each ratio of cells was then labeled sequentially with fluorophore-conjugated PCSK9 antigen (Alexa 647-conjugated) for one hour at room temperature and fluorophore-conjugated generic H+L antibody (Alexa Fluor488-conjugated) for 30 minutes at room temperature. Afterwards, the cells were washed and the flow cytometric profile was determined.

Figure 19A:
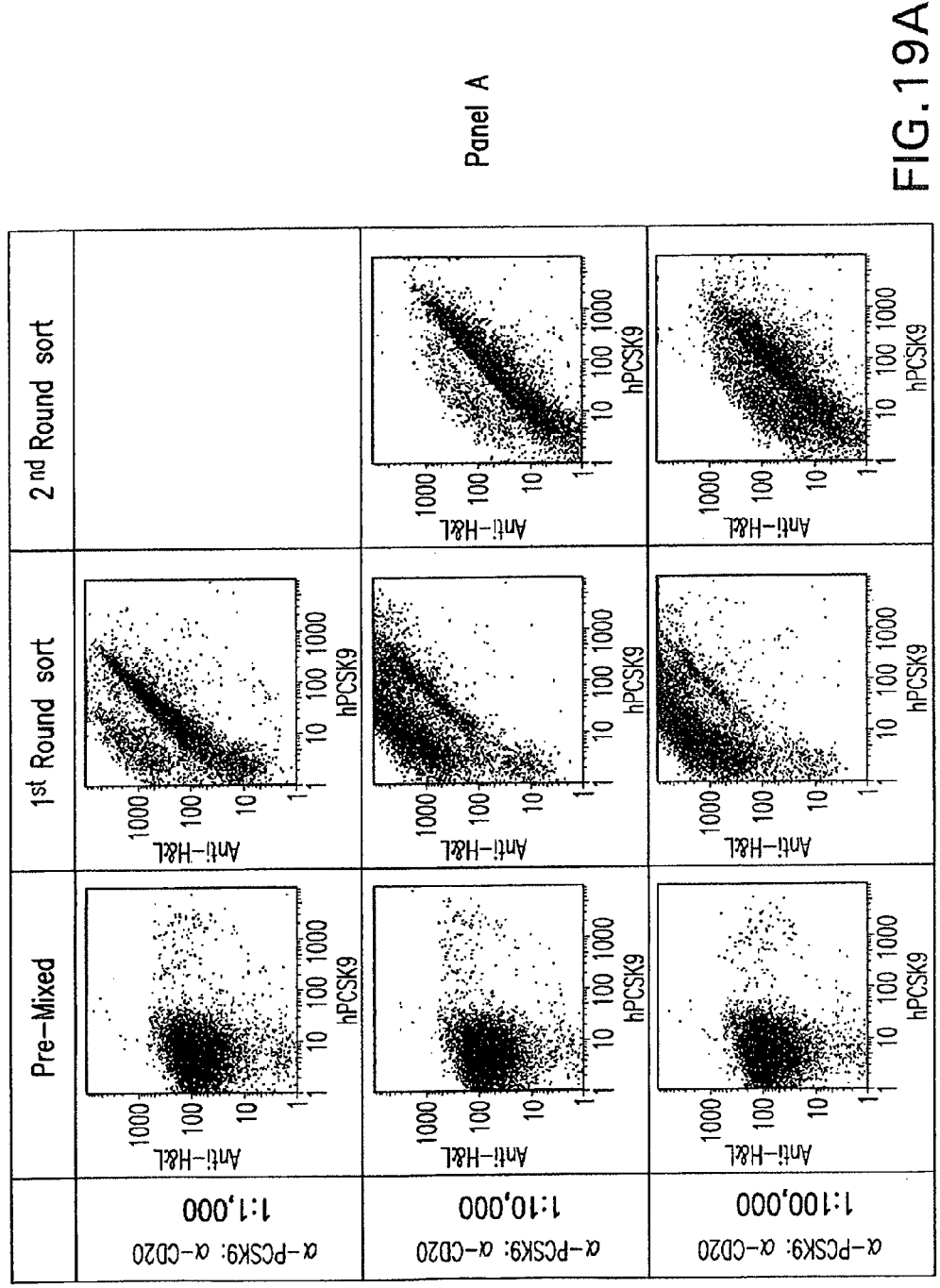
FIGS. 19A-B show FACS sorting of mixed Fab fragment displaying cell populations based on antigen affinity.

The cells from the area corresponding to the highest 1% fluorescence (area expected for the anti-PCSK-9 Fab fragments) were isolated. The cells were plated out on selection media and incubated three to four days. The cells were then collected by washing the plate with BMGY media and re-induced with BMMY. The re-induced cells were labeled and subsequently sorted. This first round of sorting resulted in two distinct populations of cells (FIG. 19A).

Figure 18:
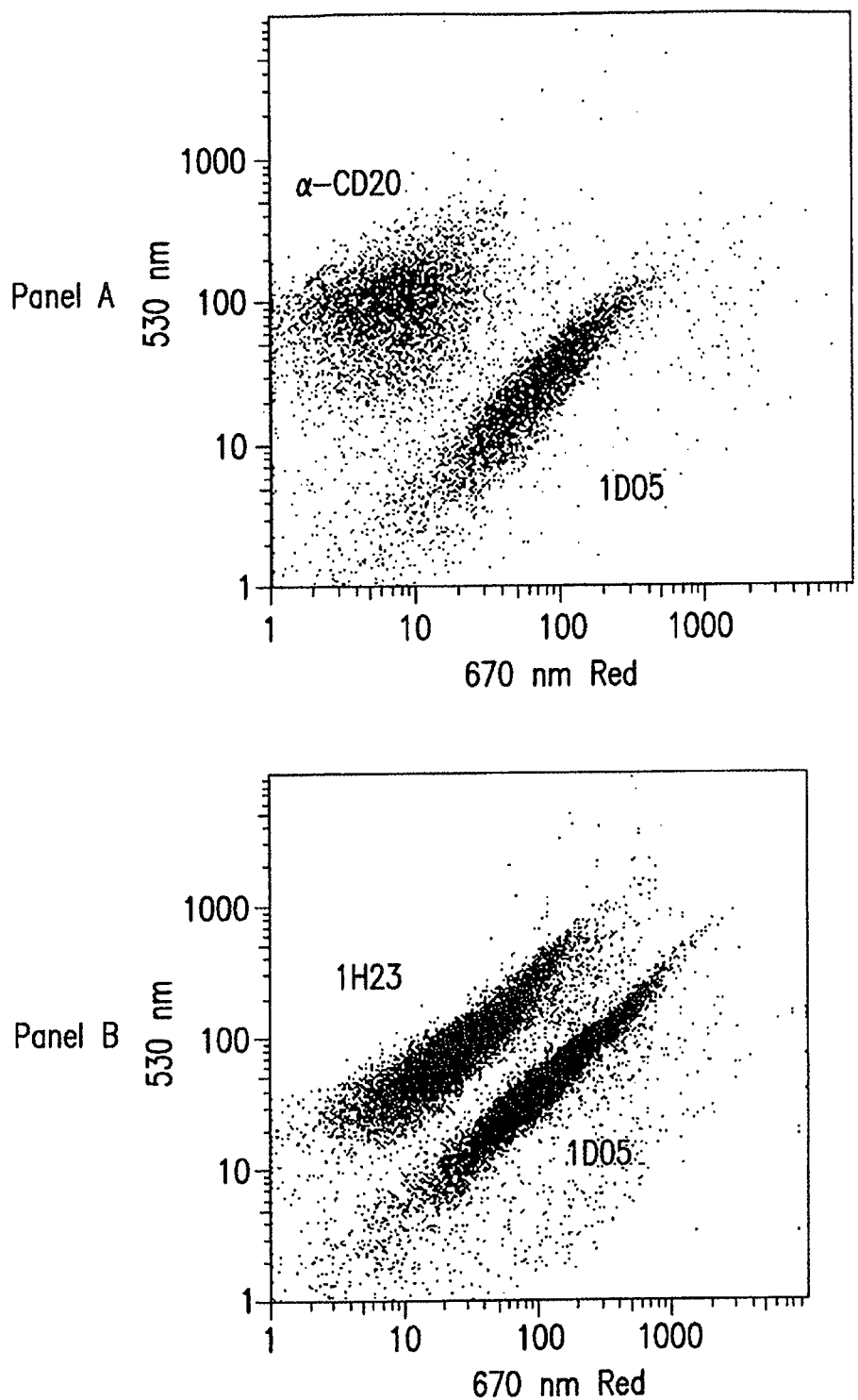
FIG. 18 shows a flow cytometric analysis of antigen-labeled cells. Anti-CD20 and anti-PCSK9 (1D05 and 1H23) Fab fragments were displayed on the yeast surface using the methods described herein. The cells were labeled by fluorophore-conjugated antigen and generic antibody detection. Panel A shows the profile of α-CD20 and anti-PCSK9 (1D05) displayed cells when mixed in a 1:1 ratio prior to labeling. In panel B, high affinity (1 D05) and low affinity (1H23) anti-PCSK9 Fab fragment expressing cells flow cytometric profiles were overlayed in the same picture.

For the 1:10,000 and 1; 100,000 dilutions, the cells with the highest fluorescence were isolated and, as in the first round of sorting, grown, collected, induced, and labeled again. These cells were again analyzed using flow cytometry (FIG. 19A). For reference, Panel A of FIG. 18 shows the FACS profile of anti-CD20 Fab fragment displaying cells and anti-PCSK-9 (1 D05) Fab fragment displaying cells when mixed at 1:1 ratio. The results show that after two rounds of sorting, cell population enriched for Fab fragments specific for PCSK-9 can be prepared.

In a second experiment, *Pichia pastoris* cells engineered to display high affinity anti-PCSK-9 Fab fragments (1D05) were mixed with *Pichia pastoris* cells engineered to display low affinity anti-PCSK-9 Fab fragments (1H23). The cell populations were mixed at ratios of 1:10,000 and 1:100,000. The cells were labeled with fluorophore-conjugated PCSK9 antigen (Alexa 647-conjugated) for one hour at room temperature. The cells were washed and the flow cytometric profile was determined.

Figure 19B:
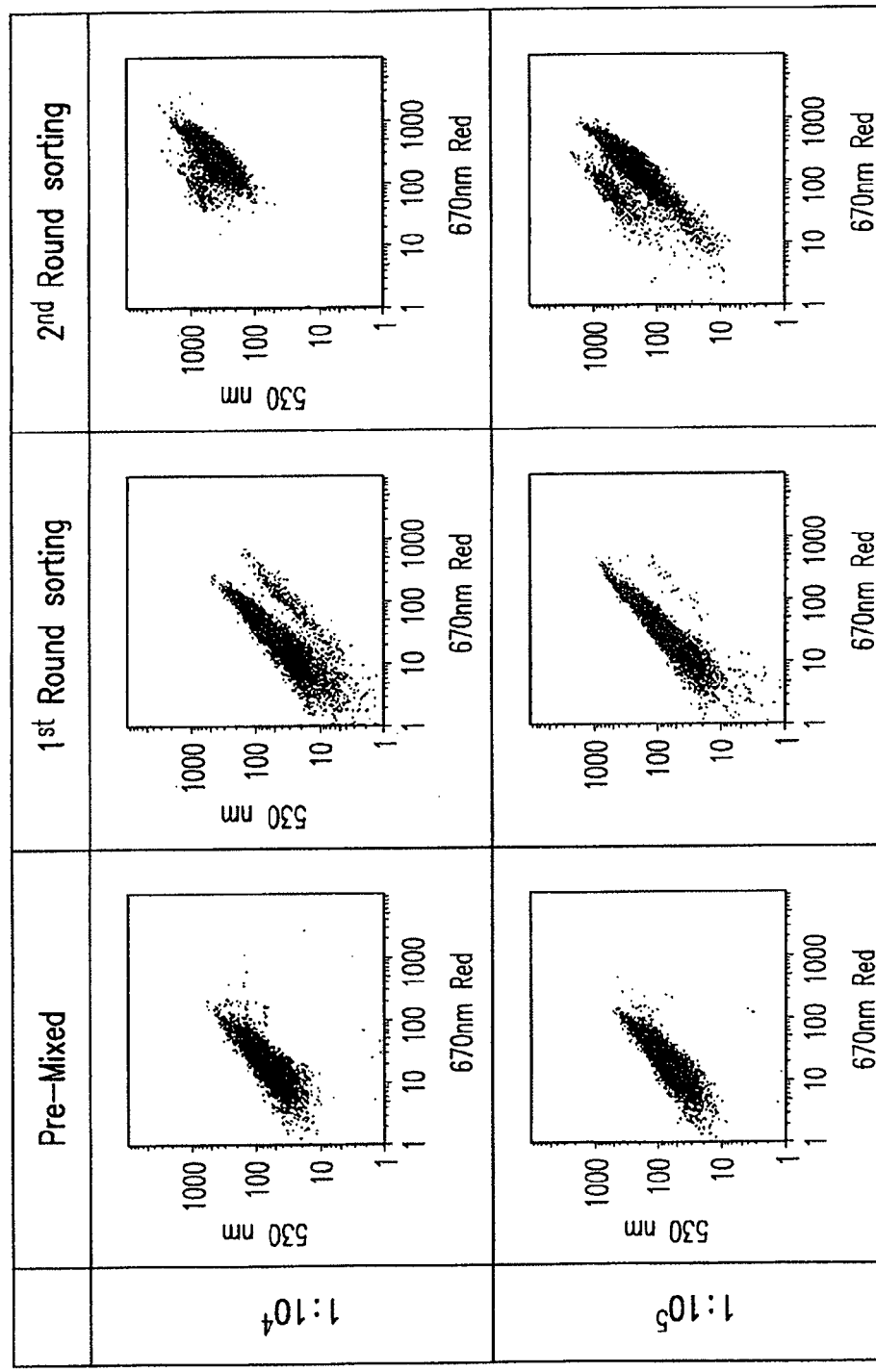

The cells from the area corresponding to the highest 1% fluorescence (area expected for high affinity 1D05 Fab fragments were isolated). The cells were plated out on selection media and incubated three to four days. The cells were then collected by washing the plate with BMGY media and re-induced with BMMY. The re-induced cells were labeled and subsequently sorted. This first round of sorting resulted in two distinct populations of cells (FIG. 19B).

For the 1:10,000 and 1; 100,000 dilutions, the cells with the highest fluorescence were isolated and, as in the first round of sorting, grown, collected, induced, and labeled again. These cells were again analyzed using flow cytometry (FIG. 19B). For reference, FIG. 18B shows an overlay of the FACS profiles for high and low affinity Fab fragment displaying cells. The results show that cells that display a high affinity Fab fragments can be separated from a vast excess of cells displaying low affinity Fab fragments.

These experiments in this example clearly demonstrate the versatility and power of a cell-sorting based approach to isolate and enrich for particular population of antibody or Fab fragments. The methods herein can be used to isolate and enrich for cells expressing particular populations of antibodies or Fab fragments.

BRIEF DESCRIPTION OF THE SEQUENCES

| SEQ ID NO: | Name | Sequence (5' to 3') |
|---|---|---|
| 1 | c-fos zipper | LQAETDQLEDEKSALQTEIANLLKEKEKL |
| 2 | c-jun zipper | LEEKVKTLKAQNSELASTANMLREQVAQL |
| 3 | c-fos zipper | LTDTLQAETDQLEDEKSALQTEIANLLKEKEKLEFILA |
| 4 | c-jun zipper | RIARLEEKVKTLKAQNSELASTANMLREQVAQLKQKVMN |
| 5 | c-jun zipper | LEEKVKTLKAQNSELASTFNMLREQFAQL |
| 6 | c-jun zipper | LEEKVKTLKAQNSELASTANMLREQVAQF |
| 7 | c-jun zipper | LEEKVKTFKAQNSELASTANMLREQVAQF |
| 8 | c-jun zipper | LEEKVKSFKAQNSEHASTANMLREQVAQL |
| 9 | S. cerevisiae CWP2 | VDESAAAISQITDGQIQATTTATTEATTTAAPSSTVETVSPSSTETISQQTENGAAKAAVGMGAGALAAAAMLL |
| 10 | S. cerevisiae CWP2 truncated version | VDTTEATTTAAPSSTVETVSPSSTETISQQTENGAAKAAVGMGAGALAAAAMLL |
| 11 | S. cerevisiae SED1 | VDQFSNSTSASSTDVTSSSSISTSSGSVTITSSEAPESDNGTSTAAPTETSTEAPTTAIPTNGTSTEAPTTAIPTNGTSTEAPTDTTTEAPTTALPTNGTSTEAPTDTTTEAPTTGLPTNGTTSAFPPTTSLPPSNTTTTPPYNPSTDYTTDYTVVTEYTTYCPEPTTFTTNGKTYTVTEPTTLTITDCPCTIEKPTTTSTTEYTVVTEYTTYCPEPTTFTTNGKTYTVTEPTTLTITDCPCTIEKSEAPESSVPVTESKGTTTKETGVTTKQTTANPSLTVSTVVPVSSSASSHSVVINSNGANVVVPGALGLAGVAMLFL |
| 12 | S. cerevisiae SED1 truncated version | VDLTVSTVVPVSSSASSHSVVINSNGANVVVPGALGLAGVAMLFL |
| 13 | Pichia pastoris SPI1 | VDLVSNSSSSVIVVPSSDATIAGNDTATPAPEPSSAAPIFYNSTATATQYEVVSEFTTYCPEPTTFVTNGATFTVTAPTTLTITNCPCTIEKPTSETSVSSTHDVETNSNAANARAIPGALGLAGAVMMLL |
| 14 | S. cerevisiae GAS1 | VDDVPAIEVVGNKFFYSNNGSQFYIRGVAYQADTANETSGSTVNDPLANYESCSRDIPYLKKLNTNVIRVYAINTTLDHSECMKALNDADIYVIADLAAPATSINRDDPTWTVDLFNSYKTVVDTFANYTNVLGFFAGNEVTNNYTNTDASAFVKAAIRDVRQYISDKNYRKIPVGYSSNDDEDTRVKMTDYFACGDDDVKADFYGINMYEWCGKSDFKTSGYADRTAEFKNLSIPVFFSEYGCNEVTPRLFTEVEALYGSNMTDVWSGGIVYMYFEETNKYGLVSIDGNDVKTLDDFNNYSSEINKISPTSANTKSYSATTSDVACPATGKYWSAATELPPTPNGGLCSCMNAANSCVVSDDVDSDDYETLFNWICNEVDCSGISANGTAGKYGAYSFCTPKEQLSFVMNLYYEKSGGSKSDCSFSGSATLQTATTQASCSSALKEIGSMGTNSASGSVDLGSGTESSTASSNASGSSSKSNSGSSGSSSSSSSSSASSSSSSKKNAATNVKANLAQVVFTSIISLSIAAGVGFALV |
| 15 | Pichia pastoris GAS1 | VDADFPTIEVTGNKFFYSNNGSQFYIKGVAYQKDTSGLSSDATFVDPLADKSTCERDIPYLEELGTNVIRVYAVDADADHDDCMQMLQDAGIYVIADLSQPNNSIITTDPEWTVDLYDGYTAVLDNLQKYDNILGFFAGNEVITNKSNTDTAPFVKAAIRDMKTYMEDKGYRSIPVGYSANDDELTRVASADYFACGDSDVKADFYGINMYEWCGKATFSNSGYKDRTAEFKNLSIPVFFSEYGCNEVQPRLFTEVQSLYGDDMTDVWSGGIVYMYFEETNNYGLVTIKSDGDVSTLEDFNNLKTELASISPSIATQSEVSATATEIDCPATGSNWKASTDLPPVPEQAACQCMADALSCVVSEDVDTDDYSDLFSYVCENVSSCDGVSADSESGEYGSYSFCSSKEKLSFLLNLYYSENGAKSSACDFSGSATLVSGTTASECSSILSAAGTAGTGSITGITGSVEAATQSGSNSGSSKSSSASQSSSSNAGVGGGASGSSWAMTGLVSISVALGMIMSF |
| 16 | Pichia pastoris GAS1 truncated version | VDSILSAAGTAGTGSITGITGSVEAATQSGSNSGSSKSSSASQSSSSNAGVGGGGASGSSWAMTGLVSISVALGMIMSF |
| 17 | H. polymorpha TIP1 | VDAAATSSVAAAASEVSSSSAAASSTQAAAAASTSAAASTEATTSAAAAATSSSEAASSSAHVHSHAAESTSAVESTSAAHSHAAESSSAAHSHAVESSSAAHVHSHAAESSSAAHSHAAGSSSAASNSSGHISTFSGAGAKLAVGAGAGIVGLAALLM |
| 18 | H. polymorpha TIP1 truncated version | VDSSAAHSHAVESSSAAHVHSHAAESSSAAHSHAAGSSSAASNSSGHISTFSGAGAKLAVGAGAGIVGLAALLM |
| 19 | Human GR2, coiled coil peptide sequence | TSRLEGLQSENHRLRMKITELDKDLEEVTMQLQDVGGC |
| 20 | SED 1 Fusion Leader GR2 cMyc SED1 | MVAWWSLFLYGLQVAAPALATSRLEGLQSENHRLRMKITELDKDLEEVTMQLQDVGGCEQKLISEEDLVDQFSNSTSASSTDVTSSSSISTSSGSVTITSSEAPESDNGTSTAAPTETSTEAPTTAIPTNGTSTEAPTTA1PTNGTSTEAPTDTT |

| SEQ ID NO: | Name | Sequence (5' to 3') |
|---|---|---|
| | | TEAPTTALPTNGTSTEAPTDTTTEAPTTGLP TNGTTSAFPPTTSLPPSNTTTTPPYNPSTDY TTDYTVVTEYTTYCPEPTTFTTNGKTYTVTE PTTLTITDCPCTIEKPTTTSTTEYTVVTEYT TYCPEPTTFTTNGKTYTVTEPTTLTITDCPC TIEKSEAPESSVPVTESKGTTTKETGVTTKQ TTANPSLTVSTVVPVSSSASSHSVVINSNGA NVVVPGALGLAGVAMLFL |
| 21 | Human GR1 coiled coil peptide sequence | EEKSRLLEKENRELEKIIAEKEERVSELRHQ LQSVGGC |
| 22 | mAb1 (anti-her2) Heavy chain | EVQLVESGGGLVQPGGSLRLSCAASGFNIKD TYIHWVRQAPGKGLEWVARIYPTNGYTRYAD SVKGRFTISADTSKNTAYLQMNSLRAEDTAV YYCSRWGGDGFYAMDYWGQGTLVTVSSASTK GPSVFPLAPSSKSTSGGTAALGCLVKDYFPE PVTVSWNSGALTSGVHTFPAVLQSSGLYSLS SVVTVPSSSLGTQTYICNVNHKPSNTKVDKK VEPKSCDKTHTCPPCPAPELLGGPSVFLFPP KPKDTLMISRTPEVTCVVVDVSHEDPEVKFN WYVDGVEVHNAKTKPREEQYNSTYRVVSVLT VLHQDWLNGKEYKCKVSNKALPAPIEKTISK AKGQPREPQVYTLPPSRDELTKNQVSLTCLV KGFYPSDIAVEWESNGQPENNYKTTPPVLDS DGSFFLYSKLTVDKSRWQQGNVFSCSVMHEA LHNHYTQKSLSLSPGK |
| 23 | mAb1 (anti-her2) Light chain | DIQMTQSPSSLSASVGDRVTITCRASQDVNT AVAWYQQKPGKAPKLLIYSASFLYSGVPSRF SGSRSGTDFTLTISSLQPEDFATYYCQQHYT TPPTFGQGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGEC |
| 24 | mAb2 (anti-DKK1) Heavy chain | EVQLVQSGAEVKKPGASVKVSCKASGYTFTD YYIHWVRQAPGQGLEWMGWIHSNSGATTYAQ KFQARVTMSRDTSSSTAYMELSRLESDDTAM YFCSREDYWGQGTLVTVSSASTK<u>GP</u>SVFPLA PCSRSTSESTAALGCLVKDYFPEPVTVSWNS GALTSGVHTFPAVLQSSGLYSLSSVVTVTSS NFGTQTYTCNVDHKPSNTKVDKTVERKCCVE CPPPCPAPPVAGPSVFLFPPKPKDTLMISRTP EVTCVVVDVSQEDPEVQFNWYVDGVEVHNAK TKPREEQFNSTFRVVSVLTVLHQDWLNGKEY KCKVSNKGLPSSIEKTISKTKGQPREPQVYT LPPSREEMTKNQVSLTCLVKGFYPSDIAVEW ESNGQPENNYKTTPPMLDSDGSFFLYSKLTV DKSRWQQGNVFSCSVMHEALHNHYTQKSLSL SPGK |
| 25 | mAb2 (anti-DKK1) Light Chain | QSVLTQPPSVSGAPGQRVTISCTGSSSNIGA GYDVHWYQQLPGTAPKLLIYGYSNRPSGVPD RFSGSKSGASASLAITGLRPDDEADYYCQSY DNSLSSYVFGGGTQLTVLSQPKANPTVTLFP PSSEE<u>LQ</u>ANKATLVCLISDFYPGAVTVAWKA DGSPVKAGVETTKPSKQSNNKYA<u>AS</u>SYLSLT PEQWKSHRSYSCQVTHEGSTVEKTVAPTEC |
| 26 | mAb3 (anti-CD20, C2B8) Heavy chain | QVQLQQPGAELVKPGASVKMSCKASGYTFTS YNMHWVKQTPGRGLEWIGAIYPGNGDTSYNQ KFKGKATLTADKSSSTAYMQLSSLTSEDSAV YYCARSTYYGGDWYFNVWGAGTTVTVSSAST KGPSVFPLAPSSKSTSGGTAALGCLVKDYFP EPVTVSWNSGALTSGVHTFPAVLQSSGLYSL SSVVTVPSSSLGTQTYICNVNHKPSNTKVDK KVEPKSCDKTHTCPPCPAPELLGGPSVFLFP PKPKDTLMISRTPEVTCVVVDVSHEDPEVKF NWYVDGVEVHNAKTKPREEQYNSTYRVVSVL TVLHQDWLNGKEYKCKVSNKALPAPIEKTIS KAKGQPREPQVYTLPPSRDELTKNQVSLTCL VKGFYPSDIAVEWESNGQPENNYKTTPPVLD SDGSFFLYSKLTVDKSRWQQGNVFSCSVMHE ALHNHYTQKSLSLSPGK |
| 27 | mAb3 (anti-CD20, C2B8) Light chain | QIVLSQSPAILSASPGEKVTMTCRASSSVSY IHWFQQKPGSSPKPWIYATSNLASGVPVRFS GSGSGTSYSLTISRVEAEDAATYYCQQWTSN PPTFGGGTKLEIKRTVAAPSVFIFPPSDEQL KSGTASVVCLLNNFYPREAKVQWKVDNALQS GNSQESVTEQDSKDSTYSLSSTLTLSKADYE KHKVYACEVTHQGLSSPVTKSFNRGEC |
| 28 | Protein mAb4 (anti-CD20, Frame grafted Heavy chain | QVQLVQSGAEVKKPGSSVKVSCKASGYTFTS YNMHWVRQAPGQGLEWMGAIYPGNGDTSYNQ KFKGRVTITADESTSTAYMELSSLRSEDTAV YYCARSTYYGGDWYFNVWGQGTLVTVSSAST KGPSVFPLAPSSKSTSGGTAALGCLVKDYFP EPVTVSWNSGALTSGVHTFPAVLQSSGLYSL SSVVTVPSSSLGTQTYICNVNHKPSNTKVDK KVEPKSCDKTHTCPPCPAPELLGGPSVFLFP PKPKDTLMISRTPEVTCVVVDVSHEDPEVKF NWYVDGVEVHNAKTKPREEQYNSTYRVVSVL TVLHQDWLNGKEYKCKVSNKALPAPIEKTIS KAKGQPREPQVYTLPPSRDELTKNQVSLTCL VKGFYPSDIAVEWESNGQPENNYKTTPPVLD SDGSFFLYSKLTVDKSRWQQGNVFSCSVMHE ALHNHYTQKSLSLSPGK |
| 29 | mAb4 (anti-CD20, Frame grafted) Light chain | EIVLTQSPATLSLSPGERATLSCRASSSVSY IHWYQQKPGQAPRLLIYATSNLASGIPARFS GSGSGTDFTLTISSLEPEDFAVYYCQQWTSN PPTFGQGTKVEIKRTVAAPSVFIFPPSDEQL KSGTASVVCLLNNFYPREAKVQWKVDNALQS GNSQESVTEQDSKDSTYSLSSTLTLSKADYE KHKVYACEVTHQGLSSPVTKSFNRGEC |
| 30 | mAb5 (anti-CD20, Genmab) Heavy chain | AVQLVESGGGLVQPGRSLRLSCAASGFTFGD YTMHWVRQAPGKGLEWVSGISWNSGSIGYAD SVKGRFTISRDNAKNSLYLQMNSLRAEDTAL YYCTKDNQYGSGSTYGLGVWGQGTLVTVSSA STKGPSVFPLAPSSKSTSGGTAALGCLVKDY FPEPVTVSWNSGALTSGVHTFPAVLQSSGLY SLSSVVTVPSSSLGTQTYICNVNHKPSNTKV DKKVEPKSCDKTHTCPPCPAPELLGGPSVFL FPPKPKDTLMISRTPEVTCVVVDVSHEDPEV KFNWYVDGVEVHNAKTKPREEQYNSTYRVVS VLTVLHQDWLNGKEYKCKVSNKALPAPIEKT ISKAKGQPREPQVYTLPPSRDELTKNQVSLT CLVKGFYPSDIAVEWESNGQPENNYKTTPPV LDSDGSFFLYSKLTVDKSRWQQGNVFSCSVM HEALHNHYTQKSLSLSPGK |
| 31 | mAb5 (anti-CD20, Genmab) Light chain | EIVLTQSPATLSLSPGERATLSCRASQSVSS YLAWYQQKPGQAPRLLIYDASNRATGIPARF SGSGSGTDFTLTISSLEPEDFAVYYCQQRSN WPLTFGGGTKVEIKRTVAAPSVFIFPPSDEQ LKSGTASVVCLLNNFYPREAKVQWKVDNALQ SGNSQESVTEQDSKDSTYSLSSTLTLSKADY EKHKVYACEVTHQGLSSPVTKSFNRGEC |
| 32 | Anti-Her2 mAb heavy chain readthrough coiled coil peptide with one stop codon X - unknown aa incorporated at stop codon | EVQLVESGGGLVQPGGSLRLSCAASGFNIKD TYIHWVRQAPGKGLEWVARIYPTNGYTRYAD SVKGRFTISADTSKNTAYLQMNSLRAEDTAV YYCSRWGGDGFYAMDYWGQGTLVTVSSASTK GPSVFPLAPSSKSTSGGTAALGCLVKDYFPE PVTVSWNSGALTSGVHTFPAVLQSSGLYSLS SVVTVPSSSLGTQTYICNVNHKPSNTKVDKK VEPKSCDKTHTCPPCPAPELLGGPSVFLFPP KPKDTLMISRTPEVTCVVVDVSHEDPEVKFN WYVDGVEVHNAKTKPREEQYNSTYRVVSVLT VLHQDWLNGKEYKCKVSNKALPAPIEKTISK AKGQPREPQVYTLPPSRDELTKNQVSLTCLV KGFYPSDIAVEWESNGQPENNYKTTPPVLDS DGSFFLYSKLTVDKSRWQQGNVFSCSVMHEA LHNHYTQKSLSLSPGKXAAAYPYDVPDYAGG |

| SEQ ID NO: | Name | Sequence (5' to 3') |
|---|---|---|
| | | HHHHHHHHHGGEEKSRLLEKENRELEKIIAE KEERVSELRHQLQSVGGC |
| 33 | Alpha amylase signal sequence (from *Aspergillus niger* α-amylase) (DNA) | ATGGTTGCTT GGTGGTCCTT GTTCTTGTAC GGATTGCAAG TTGCTGCTCC AGCTTTGGCT |
| 34 | Alpha amylase signal sequence (from *Aspergillus niger* α-amylase) | MVAWWSLFLY GLQVAAPALA |
| 35 | PCR primer hPDI/UP1 | AGCGCTGACGCCCCCGAGGAGGAGGACCAC |
| 36 | PCR primer hPDI/LP-PacI | CCTTAATTAATTACAGTTCATCATGCACAGC TTTCTGATCAT |
| 37 | human PDI Gene (DNA) | GACGCCCCCGAGGAGGAGGACCACGTCTTGG TGCTGCGGAAAAGCAACTTCGCGGAGGCGCT GGCGCACCACAAGTACCCGCCGGTGGAGTTC CATGCCCCCTGGTGTGGCCACTGCAAGGCTC TGGCCCCTGAGTATCCAAAGCCGCTGGGAAG CTGAAGGCAGAAGGTTCCGAGATCAGGTTGG CCAAGGTGGACGCCACGGAGGAGTCTGACCT AGCCCAGCAGTACGGCGTGCGCGGCTATCCC ACCATCAAGTTCTTCAGGAATGGAGACACGG CTTCCCCCAAGGAATATACAGCTGGCAGAGA GGCTGATGACATCGTGAACTGGCTGAAGAAG CGCACGGGCCCGGCTGCCACCACCCTGCCTG ACGGCGCAGCTGCAGAGTCCTTGGTGGAGTC CAGCGAGGTGGCCGTCATCGGCTTCTTCAAG GACGTGGAGTCGGACTCTGCCAAGCAGTTTT TGCAGGCAGCAGAGGCCATCGATGACATACC ATTTGGGATCACTTCCAACAGTGACGTGTTC TCCAAATACCAGCTCGACAAAGATGGGGTTG TCCTCTTTAAGAAGTTTGATGAAGGCCGGAA CAACTTTGAAGGGGAGGTCACCAAGGAGAAC CTGCTGGACTTTATCAAACACAACCAGCTGC CCCTTGTCATCGAGTTCACCGAGCAGACAGC CCCGAAGATTTTTGGAGGTGAAATCAAGACT CACATCCTGCTGTTCTTGCCCAAGAGTGTGT CTGACTATGACGGCAAATGAGCAACTTCAA AACAGCAGCCGAGAGCTTCAAGGGCAAGATC CTGTTCATCTTCATCGACAGCGACCACACCG ACAACCAGCGCATCCTGGAGTTCTTTGGCCT GAAGAAGGAAGAGTGCCCGGCCGTGCGCCTC ATCACCTTGGAGGAGGAGATGACCAAGTACA AGCCCGAATCGGAGGAGCTGACGGCAGAGAG GATCACAGAGTTCTGCCACCGCTTCCTGGAG GGCAAAATCAAGCCCCATGAGCAGCAGG AGCTGCCGGAGGACTGGGACAAGCAGCCTGT CAAGGTGCTTGTTGGGAAGAACTTTGAAGAC GTGGCTTTTGATGAGAAAAAAAACGTCTTTG TGGAGTTCTATGCCCCATGGTGTGGTCACTG CAAACAGTTGGCTCCCATTTGGGATAAACTG GGAGAGACGTACAAGGACCATGAGAACATCG TCATCGCCAAGATGGACTCGACTGCCAACGA GGTGGAGGCCGTCAAAGTGCACGGCTTCCCC ACACTCGGGTTCTTTCCTGCCAGTGCCGACA GGACGGTCATTGATTACAACGGGGAACGCAC GCTGGATGGTTTTAAGAAATTCCTAGAGAGC GGTGGCCAAGATGGGGCAGGGGATGTTGACG ACCTCGAGGACCTCGAAGAAGCAGAGGAGCC AGACATGGAGGAAGACGATGACCAGAAAGCT GTGAAAGATGAACTGTAA |
| 38 | human PDI Gene (protein) | DAPEEEDHVLVLRKSNFAEALAAHKYPPVEF HAPWCGHCKALAPEYAKAAGKLKAEGSEIRL AKVDATEESDLAQQYGVRGYPTIKFFRNGDT ASPKEYTAGREADDIVNWLKKRTGPAATTLP DGAAAESLVESSEVAVIGFFKDVESDSAKQF LQAAEAIDDIPFGITSNSDVFSKYQLDKDGV VLFKKFDEGRNNFEGEVTKENLLDFIKHNQL PLVIEFTEQTAPKIFGGEIKTHILLFLPKSV SDYDGKLSNFKTAAESFKGKILFIFIDSDHT DNQRILEFFGLKKEECPAVRLITLEEEMTKY KPESEELTAERITEFCHRFLEGKIKPHLMSQ ELPEDWDKQPVKVLVGKNFEDVAFDEKKNVF VEFYAPWCGHCKQLAPIWDKLGETYKDHENI VIAKMDSTANEVEAVKVHGFPTLGFFPASAD RTVIDYNGERTLDGFKKFLESGGQDGAGDVD DLEDLEEAEEPDMEEDDDQKAVHDEL |
| 39 | *Pichia pastoris* PDI1 Gene (DNA) | ATGCAATTCAACTGGAATATTAAAACTGTGG CAAGTATTTTGTCCGCTCTCACACTAGCACA AGCAAGTGATCAGGAGGCTATTGCTCCAGAG GACTCTCATGTCGTCAAATTGACTGAAGCCA CTTTTGAGTCTTTCATCACCAGTAATCCTCA CGTTTTGGCAGAGTTTTTTGCCCCTTGGTGT GGTCACTGTAAGAAGTTGGGGCCCTGAACTTG TTTCTGCTGCCGAGATCTTAAAGGACAATGA GCAGGTTAAGATTGCTCAAATTGATTGTACG GAGGAGAAGGAATTATGTCAAGGCTACGAAA TTAAAGGGTATCCTACTTTGAAGGTGTTCCA TGGTGAGGTTGAGGTCCCAAGTGACTATCAA GGTCAAAGACAGAGCCAAAGCATTGTCAGCT ATATGCTAAAGCAGAGTTTACCCCCTGTCAG TGAAATCAATGCAACCAAAGATTTAGACGAC ACAATCGCCGAGGCAAAAGAGCCCGTGATTG TGCAAGTACTACCGGAAGATGCATCCAACTT GGAATCTAACACCACATTTTACGGAGTTGCC GGTACTCTCAGAGAGAAATTCACTTTTGTCT CCACTAAGTCTACTGATTATGCCAAAAAATA CACTAGCGACTCGATCCTGCCTATTTGCTT GTCAGACCTGGCGAGGAACCTAGTGTTTACT CTGGTGAGGAGTTAGATGAGACTCATTTGGT GCACTGGATTGATATTGAGTCCAAACCTCTA TTTGGAGACATTGACGGATCCACCTTCAAAT CATATCTGAAGCTAACATCCCTTTAGCCTA CTATTTCTATGAGAACGAAGAACAACGTGCT GCTGCTGCCGATATTATTAAACCTTTTGCTA AAGAGCAACGTGGCAAAATTAACTTTGTTGG CTTAGATGCCGTTAAATTCGGTAAGCATGCC AAGAACTTAAACATGGATGAAGAGAAACTCC CTCTATTTGTCATTCATGATTTGGTGAGCAA CAAGAAGTTTGGAGTTCCTCAAGACCAAGAA TTGACGACAAAGATGTGACCGAGCTGATTG AGAAATTCATCGCAGGAGAGGCAGAACCAAT TGTGAAATCAGAGCCAATTCCAGAAATTCAA GAAGAGAAAGTCTTCAAGCTAGTCGGAAAGG CCCACGATGAAGTTGTCTTCGATGAATCTAA AGATGTTCTAGTCAAGTACTACGCCCCTTGG TGTGGTCACTGTAAGAGAATGGCTCCTGCTT ATGAGGAATTGGCTACTCTTTACGCCAATGA TGAGGATGCCTCTTCAAAGGTTGTGATTGCA AAACTTGATCACACTTTGAACGATGTGACAA ACGTTGATATTCAAGGTTATCCTACTTTGAT CCTTTTATCCAGCTGGTGATAAATCCAATCCT CAACTGTATGATGGATCTCGTGACCTAGAAT CATTGGTGAGTTTGTAAAGGAGAGGAAC CCACAAGTTGGATGCCCTAGCACTCAGACCA GTCGAGGAAGAAAAGGAAGCTGAAGAAGAAG CTGAAAGTGAGGCAGACGCTCACGACGAGCT TTAA |
| 40 | *Pichia pastoris* PDI1 Gene (protein) | MQFNWNIKTVASILSALTLAQASDQEAIAPE DSHVVKLTEATFESFITSNPHVLAEFFAPWC GHCKKLGPELVSAAEILKDNEQVKIAQIDCT EEKELCQGYEIKGYPTLKVFHGEVEVPSDYQ GQRSQSIVSYMLKQSLPPVSEINATKDLDD TIAEAKEPVIVQVLPEDASNLESNTTFYGVA |

| SEQ ID NO: | Name | Sequence (5' to 3') |
|---|---|---|
| | | GTLREKFTFVSTKSTDYAKKYTSDSTPAYLL VRPGEEPSVYSGEELDETHLVHWIDIESKPL FGDIDGSTFKSYAEANIPLAYYFYENEEQRA AAADIIKPFAKEQRGKINFVGLDAVKFGKHA KNLNMDEEKLPLFVIHDLVSNKKFGVPQDQE LTNKDVTELIEKFIAGEAEPIVKSEPIPEIQ EEKVFKLVGKAHDEVVFDESKDVLVKYYAPW CGHCKRMAPAYEELATLYANDEDASSKVVIA KLDHTLNDVDNVDIQGYPTLILYPAGDKSNP QLYDGSRDLESLAEFVKERGTHKVDALALRP VEEEKEAEEEAESEADAHDEL |
| 41 | PCR primer PB248 | ATGAATTCAGGC CATATCGGCCATTGTTTACTGTGCG CCCACAGTAG |
| 42 | PCR primer PB249 | ATGTTTA AACGTGAGGATTACTGGTGATGAAAGAC |
| 43 | PCR primer PB250 | AGACTAGTCTATTTGGAG ACATTGACGGATCCAC |
| 44 | PCR primer PB251 | ATCTCGAGAGGCCATGCAGGCCAACCACAAG ATGAATCAAATTTTG |
| 45 | PCR primer hGRP94/UP1 | AGCGCTGACGATGAAGTTGATGTGGATGGTA CAGTAG |
| 46 | PCR primer hGRP94/LP1 | GGCCGGCCTTACAATTCATCATG TTCAGCTGTAGATTC |
| 47 | human GRP94 Gene (DNA) | GATGATGAAGTTGACGTTGACGGTACTGTTG AAGAGGACTTGGGAAAGTCTAGAGAGGGTTC CAGAACTGACGACGAAGTTGTTCAGAGAGAG GAAGAGGCTATTCAGTTGGACGGATTGAACG CTTCCCAAATCAGAGAGTTGAGAGAGAAGTC CGAGAAGTTCGCTTTCCAAGCTGAGGTTAAC AGAATGATGAAATTGATTATCAACTCCTTGT ACAAGAACAAGAGATTTTCTTGAGAGAGTT GATCTCTAACGCTTCTGACGCTTTGGACAAG ATCAGATTGATCTCCTTGACTGACGAAAACG CTTTGTCCGGTAACGAAGAGTTGACTGTTAA GATCAAGTGTGACAAAGAGAAGAACTTGTTG CACGTTACTGACACTGGTGTTGGAATGACTA GAGAAGAGTTGGTTAAGAACTTGGGTACTAT CGCTAAGTCTGGTACTTCCGAGTTCTTGAAC AAGATGACTGAGGCTCAAGAAGATGGTCAAT CCACTTCCGAGTTGATCGGTCAGTTCGGTGT TGGTTTCTACTCCGCTTTCTTGGTTGCTGAC AAGGTTATCGTTACTTCCAAGCACAACAACG ACACTCAACACATTTGGGAATCCGATTCCAA CGAGTTCTCCGTTATTGCTGACCCAAGAGGT AACACTTTGGGTAGAGGTACTACTATCACTT TGGTTTTGAAAGAAGAGGCTTCCGACTACTT GGAGTTGGACACTATCAAGAACTTGGTTAAG AAGTACTCCCAGTTCATCAACTTCCCAATCT ATGTTTGGTCCTCCAAGACTGAGAC TGTTGAGGAACCAATGGAAGAAGAAGAGGCT GCTAAAGAAGAGAAAGAGGAATCTGACGACG AGGCTGCTGTTGAAGAAGAGGAAGAAGAAA GAAGCCAAAGACTAAGAAGGTTGAAAAGACT GTTTGGGACTGGGAGCTTATGAACGACATCA AGCCAATTTGGCAGAGACCATCCAAAGAGGT TGAGGAGGACGAGTACAAGGCTTTCTACAAG TCCTTCTCCAAAGAATCCGATGACCCAATGG CTTACATCCACTTCACTGCTGAGGGTGAAGT TACTTTCAAGTCCATCTTGTTCGTTCCAACT TCTGCTCCAAGAGGATTGTTCGACGAGTACG GTTCTAAGAAGTCCGACTACATCAAACTTTA TGTTAGAGAGTTTTCATCACTGACGACTTC CACGATATGATGCCAAAGTACTTGAACTTCG TTAAGGGTGTTGTTGATTCCGATGACTTGCC ATTGAACGTTTCCAGAGAGACTTTGCAGCAG CACAAGTTGTTGAAGGTTATCAGAAAGAAAC TTGTTAGAAAGACTTTGGACATGATCAAGAA GATCGCTGACGACAAGTACAACGACACTTTC TGGAAAGAGTTCGGAACTAACATCAAGTTGG GTGTTATTGAGGACCACTCCAACAGAACTAG ATTGGCTAAGTTGTTGAGATTCCAGTCCTCT CATCACCCAACTGACATCACTTCCTTGGACC AGTACGTTGAGAGAATGAAAGAGAAGCAGGA CAAAATCTACTTCATGGCTGGTTCCTCTAGA AAAGAGGCTGAATCCTCCCCATTCGTTGAGA GATTGTTGAAGAAGGGTTACGAGGTTATCTA CTTGACTGAGCCAGTTGACGAGTACTGTATC CAGGCTTTGCCAGAGTTTGACGGAAAGAGAT TCCAGAACGTTGCTAAAGAGGGTGTTAAGTT CGACGAATCCGAAAAGACTAAAGAATCCAGA GAGGCTGTTGAGAAAGAGTTCGAGCCATTGT TGAACTGGATGAAGGACAAGGCTTTGAAGGA CAAGATCGAGAAGGCTGTTGTTTCCCAGAGA TTGACTGAATCCCCATGTGCTTTGGTTGCTT CCCAATACGGATGGAGTGGTAACATGGAAAG AATCATGAAGGCTCAGGCTTACCAAACTGGA AAGGACATCTCCACTAACTACTACGCTTCCC AGAAGAAAACTTTCGAGATCAACCCAAGACA CCCATTGATCAGAGACATGTTGAGAAGAATC AAAGAGGACGAGGACGACAAGACTGTTTTGG ATTTGGCTGTTGTTTTGTTCGAGACTGCTAC TTTGAGATCCGGTTACTTGTTGCCAGACACT AAGGCTTACGGTGACAGAATCGAGAGAATGT TGAGATTGTCCTTGAACATTGACCCAGACGC TAAGGTTGAAGAAGAACCAGAAGAAGAGCCA GAGGAAACTGCTGAAGATACTACTGAGGACA CTGAACAAGACGAGGACGAAGAGATGGATGT TGGTACTGACGAAGAGGAAGAGCAGCAAAG GAATCCACTGCTGAACACGACGAGTTGTAA |
| 48 | human GRP94 Gene (protein) | DDEVDVDGTVEEDLGKSREGSRTDDEVVQRE EEAIQLDGLNASQIRELREKSEKFAFQAEVN RMMKLIINSLYKNKEIFLRELISNASDALDK IRLISLTDENALSGNEELTVKIKCDKEKNLL HVTDTGVGMTREELVKNLGTIAKSGTSEFLN KMTEAQEDGQSTSELIGQFGVGFYSAFLVAD KVIVTSKHNNDTQHIWESDSNEFSVIADPRG NTLGRGTTITLVLKEEASDYLELDTIKNLVK KYSQFINFPIYVWSSKTETVEEPMEEEEAAK EEKEESDDEAAVEEEEEEKKPKTKKVEKTVW DWELMNDIKPIWQRPSKEVEEDEYKAFYKSF SKESDDPMAYIHFTAEGEVTFKSILFVPTSA PRGLFDEYGSKKSDYIKLYVRRVFITDDFHD MMPKYLNFVKGVVDSDDLPLNVSRETLQQHK LLKVIRKKLVRKTLDMIKKIADDKYNDTFWK EFGTNIKLGVIEDHSNRTRLAKLLRFQSSHH PTDITSLDQYVERMKEKQDKIYFMAGSSRKE AESSPFVERLLKKGYEVIYLTEPVDEYCIQA LPEFDGKRFQNVAKEGVKFDESEKTKESREA VEKEFEPLLNWMKDKALKDKIEKAVVSQRLT ESPCALVASQYGWSGNMERIMKAQAYQTGKD ISTNYYASQKKTFEINPRHPLIRDMLRRIKE DEDDKTVLDLAVVLFETATLRSGYLLPDTKA YGDRIERMLRLSLNIDPDAKVEEEPEEEPEE TAEDTTEDTEQEDEEMDVGTDEEEETAKES TAEHDEL |
| 49 | Saccharomyces cerevisiae mating factor pre-signal peptide (DNA) | ATG AGA TTC CCA TCC ATC TTC ACT GCT GTT TTG TTC GCT GCT TCT TCT GCT TTG GCT |
| 50 | Saccharomyces cerevisiae mating factor pre-signal peptide (protein) | MRFPSIFTAVLFAASSALA |

| SEQ ID NO: | Name | Sequence (5' to 3') |
|---|---|---|
| 51 | Fab Anti-Her2 HC-GR1 fusion with Pre-pro α-mating factor signal peptide (ScαMTprepro) (DNA) | ATGAGATTCCCATCCATCTTCACTGCTGTTT<br>TGTTCGCTGCTTCTTCTGCTTTGGCTGAGGT<br>TCAGTTGGTTGAATCTGGAGGAGGATTGGTT<br>CAACCTGGTGGTTCTTTGAGATTGTCCTGTG<br>CTGCTTCCGGTTTCAACATCAAGGACACTTA<br>CATCCACTGGGTTAGACAAGCTCCAGGAAAG<br>GGATTGGAGTGGGTTGCTAGAATCTACCCAA<br>CTAACGGTTACACAAGATACGCTGACTCCGT<br>TAAGGGAAGATTCACTATCTCTGCTGACACT<br>TCCAAGAACACTGCTTACTTGCAGATGAACT<br>CCTTGAGAGCTGAGGATACTGCTGTTTACTA<br>CTGTTCCAGATGGGGTGGTGATGGTTTCTAC<br>GCTATGGACTACTGGGGTCAAGGAACTTTGG<br>TTACTGTTTCCTCCGCTTCTACTAAGGGACC<br>ATCTGTTTTCCCATTGGCTCCATCTTCTAAG<br>TCTACTTCCGGTGGTACTGCTGCTTTGGGAT<br>GTTTGGTTAAAGACTACTTCCCAGAGCCAGT<br>TACTGTTTCTTGGAACTCCGGTGCTTTGACT<br>TCTGGTGTTCACACTTTCCCAGCTGTTTTGC<br>AATCTTCCGGTTTGTACTCTTTGTCCTCCGT<br>TGTTACTGTTCCATCCTCTTCCTTGGGTACT<br>CAGACTTACATCTGTAACGTTAACCACAAGC<br>CATCCAACACTAAGGTTGACAAGAAGGTTGA<br>GCCAAAGTCCTGTGGTGGTGGTGGTAGTGGA<br>GGTGGTGGAAGTGGTGGCGGTGGTTCTGCGG<br>CCGCTTATCCATATGATGTTCCAGACTACGC<br>TGGAGGTCATCATCATCACCACCATCACCAT<br>CATGGTGGTGAAGAAGTCCAGATTGTTGG<br>AGAAAGAGAACAGAGAGTTGGAGAAGATCAT<br>CGCTGAGAAAGAAGAGAGAGTTTCCGAGTTG<br>AGACACCAATTGCAATCCGTTGGTGGTTGTT<br>AATAG |
| 52 | Anti-Her2 LC with Pre-pro α-mating factor signal peptide (ScαMTprepro) (DNA) | ATGAGATTCCCATCCATCTTCACTGCTGTTT<br>TGTTCGCTGCTTCTTCTGCTTTGGCTGACAT<br>CCAAATGACTCAATCCCCATCTTCTTTGTCT<br>GCTTCCGTTGGTGACAGAGTTACTATCACTT<br>GTAGAGCTTCCCAGGACGTTAATACTGCTGT<br>TGCTTGGTATCAACAGAAGCCAGGAAAGGCT<br>CCAAAGTTGTTGATCTACTCCGCTTCCTTCT<br>TGTACTCTGGTGTTCCATCCAGATTCTCTGG<br>TTCCAGATCCGGTACTGACTTCACTTTGACT<br>ATCTCCTCCTTGCAACCAGAAGATTTCGCTA<br>CTTACTACTGTCAGCAGCACTACACTACTCC<br>ACCAACTTTCGGACAGGGTACTAAGGTTGAG<br>ATCAAGAGAACTGTTGCTGCTCCATCCGTTT<br>TCATTTTCCCACCATCCGACGAACAGTTGAA<br>GTCTGGTACAGCTTCCGTTGTTTGTTTGTTG<br>AACAACTTCTACCCAAGAGAGGCTAAGGTTC<br>AGTGGAAGGTTGACAACGCTTTGCAATCCGG<br>TAACTCCCAAGAATCCGTTACTGAGCAAGAC<br>TCTAAGGACTCCACTTACTCCTTGTCCTCCA<br>CTTTGACTTTGTCCAAGGCTGATTACGAGAA<br>GCACAAGGTTTACGCTTGTGAGGTTACACAT<br>CAGGGTTTGTCCTCCCCAGTTACTAAGTCCT<br>TCAACAGAGGAGAGTGTTAATAG |
| 53 | Fab Anti-DKK1 HC-GR1 fusion with Alpha amylase signal peptide (from Aspergillus niger α-amylase) (DNA) | ATGGTCGCTTGGTGGTCTTTGTTTCTGTACG<br>GTCTTCAGGTCGCTGCACCTGCTTTGGCTGA<br>GGTTCAGTTGGTTCAATCTGGTGCTGAGGTT<br>AAGAAACCTGGTGCTTCCGTTAAGGTTTCCT<br>GTAAGGCTTCCGGTTACACTTTCACTGACTA<br>CTACATCCACTGGGTTAGACAAGCTCCAGGT<br>CAAGGATTGGAATGGATTGGATGGATTCACT<br>CTAACTCCGGTGCTACTACTTACGCTCAGAA<br>GTTCCAGGCTAGAGTTACTATGTCCAGAGAC<br>ACTTCTTCTTCCACTGCTTACATGGAATTGT<br>CCAGATTGGAATCCGATGACACTGCTATGTA<br>CTTTTGTGCAAGAGCTGGTTCTGGGGACAG<br>GGAACTTTGGTTACTGTTTCCTCCGCTTCTA<br>CTAAAGGGCCCTCTGTTTTTCCATTGGCTCC<br>ATGTTCTAGATCACTTCCGAATCCACTGCT<br>GCTTTGGGATGTTTGGTTAAGGACTACTTCC<br>CAGAGCCAGTTACTGTTTCTTGGAACTCCGG<br>TGCTTTGACTTCTGGTGTTCACACTTTCCCA | |
| | | GCTGTTTTGCAATCTTCCGGTTTGTACTCCT<br>TGTCCTCCGTTGTTACTGTTACTTCCTCCAA<br>CTTCGGTACTCAGACTTACACTTGTAACGTT<br>GACCACAAGCCATCCAACACTAAGGTTGACA<br>AGACTGTTGAGAGAAAGTGTGGTGGTGGTGG<br>TAGTGGAGGTGGTGGAAGTGGTGGCGGTGGT<br>TCTGCGGCCGCTTATCCATATGATGTTCCAG<br>ACTACGCTGGAGGTCATCATCATCACCACCA<br>TCACCATCATGGTGGTGAAGAGAAGTCCAGA<br>TTGTTGGAGAAAGAGAACAGAGAGTTGGAGA<br>AGATCATCGCTGAGAAAGAAGAGAGAGTTTC<br>CGAGTTGAGACACCAATTGCAATCCGTTGGT<br>GGTTGTTAATAGG |
| 54 | Anti-DKK1 LC with Alpha amylase signal peptide (from Aspergillus niger α-amylase) (DNA) | ATGGTCGCTTGGTGGTCTTTGTTTCTGTACG<br>GTCTTCAGGTCGCTGCACCTGCTTTGGCTCA<br>GTCCGTTTTGACACAACCACCATCTGTTTCT<br>GGTGCTCCAGGACAGAGAGTTACTATCTCCT<br>GTACTGGTTCCTCTTCCAACATTGGTGCTGG<br>TTACGATGTTCACTGGTATCAACAGTTGCCA<br>GGTACTGCTCCAAAGTTGTTGATCTACGGTT<br>ACTCCAACAGACCATCTGGTGTTCCAGACAG<br>ATTCTCTGGTTCTAAGTCTGGTGCTTCTGCT<br>TCCTTGGCTATCACTGGATTGAGACCAGATG<br>ACGAGGCTGACTACTACTGTCAATCCTACGA<br>CAACTCCTTGTCCTCTTACGTTTTCGGTGGT<br>GGTACTCAGTTGACTGTTTTGTCCCAGCCAA<br>AGGCTAATCCAACTGTTACTTTGTTCCCACC<br>ATCTTCCGAAGAACTGCAGGCTAATAAGGCT<br>ACTTTGGTTTGTTTGATCTCCGACTTCTACC<br>CAGGTGCTGTTACTGTTGCTTGGAAGGCTGA<br>TGGTTCTCCAGTTAAGGCTGGTGTTGAGACT<br>ACTAAGCCATCCAAGCAGTCCAATAACAAGT<br>ACGCTGCTAGCTCTTACTTGTCCTTGACACC<br>AGAACAATGGAAGTCCCACAGATCCTACTCT<br>TGTCAGGTTACACACGAGGGTTCTACTGTTG<br>AAAAGACTGTTGCTCCAACTGAGTGTTCCTA<br>ATGAG |
| 55 | Fab Anti-CD20, C2B8 HC with Alpha amylase signal peptide (from Aspergillus niger α-amylase) (DNA) | ATGGTTGCTTGGTGGTCTTTGTTCTTGTACG<br>GATTGCAAGTTGCTGCTCCAGCTTTGGCTca<br>agttcagctgcaacaaccaggtgctgaattg<br>gttaagcctggtgcttctgttaagatgtctt<br>gtaaggcttctggttacactttcacttccta<br>caacatgcactgggttaagcaaactccaggt<br>agaggattggaatggattggtgctatctacc<br>caggtaacggtgacacttcttataaccaaaa<br>gttcaagggaaaggctactttgactgctgac<br>aaatcttcttctactgcttacatgcaattgt<br>cctccttgacttctgaagattctgctgttta<br>ctactgtgctagatccacttactacggtggt<br>gactggtacttcaatgtttggggtgctggta<br>ctactgttactgtctcgagtgcttctactaa<br>gggaccatctgttttcccattggctccatct<br>tctaagtctacttccggtggtacCGCTGCTT<br>TGGGATGTTTGGTAAAGACTACTTCCCAGA<br>GCCAGTTACTGTTTCTTGGAACTCCGGTGCT<br>TTGACTTCTGGTGTTCACACTTTCCCAGCTG<br>TTTTGCAATCTTCCGGTTTGTACTCTTTGTC<br>CTCCGTTGTTACTGTTCCATCCTCTTCCTTG<br>GGTACTCAGACTTACATCTGTAACGTTAACC<br>ACAAGCCATCCAACACTAAGGTTGACAAGAA<br>GGTTGAGCCAAAGTCCTGTGGTGGTGGTGGT<br>AGTGGAGGTGGTGGAAGTGGTGGCGGTGGTT<br>CTGCGGCCGCTTATCCATATGATGTTCCAGA<br>CTACGCTGGAGGTCATCATCATCACCACCAT<br>CACCATCATGGTGGTGAAGAAGTCCAGAT<br>TGTTGGAGAAAGAGAACAGAGAGTTGGAGAA<br>GATCATCGCTGAGAAAGAAGAGAGAGTTTCC<br>GAGTTGAGACACCAATTGCAATCCGTTGGTG<br>GTTGTTAATAG |

| SEQ ID NO: | Name | Sequence (5' to 3') |
|---|---|---|
| 56 | Anti-CD20, C28B LC with Alpha amylase signal peptide (from *Aspergillus niger* α-amylase) (DNA) | <u>ATGGTTGCTTGGTGGTCCTTGTTCTTGTACG GATTGCAAGTTGCTGCTCCAGCTTTGGCT</u>ga gatcgttttgacacagtccccagctactttg tctttgtccccaggtgaaagagctacattgt cctgtagagcttcctcttccgtttcctacat ccactggtatcaacaaaagccaggacaggct ccaagattgttgatctacgctacttccaact tggcttccggtattccagctagattctctgg ttctggttccggtactgacttcactttgact atctcttccttggaaccagaggacttcgctg tttactactgtcaacagtggacttctaaccc accaactttcggacaaggtactaaggttgag atcaagcgtacggttgctgctccttccgttt tcattttcccaccatccgacgaacaattgaa gtctggtacCGCTTCCGTTGTTTGTTGTTG AACAACTTCTACCCACGTGAGGCTAAGGTTC AGTGGAAGGTTGACAACGCTTTGCAATCCGG TAACTCCCAAGAATCCGTTACTGAGCAGGAT TCTAAGGATTCCACTTACTCATTGTCCTCCA CTTTGACTTTGTCCAAGGCTGATTACGAGAA GCACAAGGTTTACGCATGCGAGGTTACACAT CAGGGTTTGTCCTCCCCAGTTACTAAGTCCT TCAACAGAGGAGAGTGTTAA |
| 57 | Fab Anti-CD20 frame grafted HC-GR1 with Alpha amylase signal peptide (from *Aspergillus niger* α-amylase) (DNA) | <u>ATGGTTGCTTGGTGGTCCTTGTTCTTGTACG GATTGCAAGTTGCTGCTCCAGCTTTGGCT</u>ca agttcagctggttcaatctggtgctgaggtt aagaagcctggttcctccgttaaggtttcct gtaaggcttccggttacactttcacttccta caacatgcactgggttagacaagctccaggt caagattggaatggatgggtgctatctacc caggtaacggtgacacttcttacaaccagaa gttcaagggtagagttactatcactgctgac gaatccacttccactgcttacatggaattgt cctcattgagatccgaggacactgctgttta ctactgctagatccacttactacgttggt gactggtactttaatgtttggggacagggaa ctttggttactgtctcgagtgcttctactaa gggaccatccgttttttccattggctccatcc tctaagtctacttccggtggtacCGCTGCTT TGGGATGTTTGGTTAAAGACTACTTCCCAGA GCCAGTTACTGTTTCTTGGAACTCCGGTGCT TTGACTTCTGGTGTTCACACTTTCCCAGCTG TTTTTGCAATCTTCCGGTTTGTACTCTTTGTC CTCCGTTGTTACTGTTCCATCCTCTTCCTTG GGTACTCAGACTTACATCTGTAACGTTAACC ACAAGCCATCCAACACTAAGGTTGACAAGAA GGTTGAGCCAAAGTCCTGTGGTGGTGGTGGT AGTGGAGGTGGTGGAAGTGGTGGCGGTGGTT CTGCGGCCGCTTATCCATATGATGTTCCAGA CTACGCTGGAGGTCATCATCACCACCAT CACCATCATGGTGG<u>TGAAGAGAAGTCCAGAT TGTTGGAGAAAGAGAACAGAGAGTTGGAGAA GATCATCGCTGAGAAAGAAGAGAGAGTTTCC GAGTTGAGACACCAATTGCAATCCGTTGGTG GTTGTTAATAG</u> |
| 58 | Anti-CD20 frame grafted LC with Alpha amylase signal peptide (from *Aspergillus niger* α-amylase) (DNA) | <u>ATGGTTGCTTGGTGGTCCTTGTTCTTGTACG GATTGCAAGTTGCTGCTCCAGCTTTGGCT</u>ga gatcgttttgacacagtccccagctactttg tctttgtccccaggtgaaagagctacattgt cctgtagagcttcctcttccgtttcctacat ccactggtatcaacaaaagccaggacaggct ccaagattgttgatctacgctacttccaact tggcttccggtattccagctagattctctgg ttctggttccggtactgacttcactttgact atctcttccttggaaccagaggacttcgctg tttactactgtcaacagtggacttctaaccc accaactttcggacaaggtactaaggttgag atcaagcgtacggttgctgctccttccgttt tcattttcccaccatccgacgaacaattgaa gtctggtacCGCTTCCGTTGTTTGTTGTTG AACAACTTCTACCCACGTGAGGCTAAGGTTC AGTGGAAGGTTGACAACGCTTTGCAATCCGG TAACTCCCAAGAATCCGTTACTGAGCAGGAT TCTAAGGATTCCACTTACTCATTGTCCTCCA CTTTGACTTTGTCCAAGGCTGATTACGAGAA GCACAAGGTTTACGCATGCGAGGTTACACAT CAGGGTTTGTCCTCCCCAGTTACTAAGTCCT TCAACAGAGGAGAGTGTTAA |
| 59 | Anti-Her2 full length HC with GR1 ORF and Pre-pro α-mating factor signal peptide (ScαMTprepro) (DNA) | <u>ATGAGATTCCCATCCATCTTCACTGCTGTTT TGTTCGCTGCTTCTTCTGCTTTGGCT</u>GAGGT TCAGTTGGTTGAATCTGGAGGAGGATTGGTT CAACCTGGTGGTTCTTTGAGATTGTCCTGTG CTGCTTCCGGTTTCAACATCAAGGACACTTA CATCCACTGGGTTAGACAAGCTCCAGGAAAG GGATTGGAGTGGGTTGCTAGAATCTACCCAA CTAACGGTTACACAAGATACGCTGACTCCGT TAAGGGAAGATTCACTATCTCTGCTGACACT TCCAAGAACACTGCTTACTTGCAGATGAACT CCTTGAGAGCTGAGGATACTGCTGTTTACTA CTGTTCCAGATGGGGTGGTGATGGTTTCTAC GCTATGGACTACTGGGGTCAAGGAACTTTGG TTACTGTTTCCTCCGCTTCTACTAAGGGACC ATCTGTTTTCCCATTGGCTCCATCTTCTAAG TCTACTTCCGGTGGTACTGCTGCTTTGGGAT GTTTGGTTAAAGACTACTTCCCAGAGCCAGT TACTGTTTCTTGGAACTCCGGTGCTTTGACT TCTGGTGTTCACACTTTCCCAGCTGTTTTGC AATCTTCCGGTTTGTACTCTTTGTCCTCCGT TGTTACTGTTCCATCCTCTTCCTTGGGTACT CAGACTTACATCTGTAACGTTAACCACAAGC CATCCAACACTAAGGTTGACAAGAAGGTTGA GCCAAAGTCCTGTGACAAGACTCATACTTGT CCACCATGTCCAGCTCCAGAATTGTTGGGTG GTCCTTCCGTTTTTTTGTTCCCACCAAAGCC AAAGGACACTTTGATGATCTCCAGAACTCCA GAGGTTACATGTGTTGTTGTTGACGTTTCTC ACGAGGACCCAGAGGTTAAGTTCAACTGGTA CGTTGACGGTGTTGAAGTTCACAACGCTAAG ACTAAGCCAAGAGAGGAGCAGTACAACTCCA CTTACAGAGTTGTTTCCGTTTTGACTGTTTT GCACCAGGATTGGTTGAACGGAAAGGAGTAC AAGTGTAAGGTTTCCAACAAGGCTTTGCCAG CTCCAATCGAAAAGACTATCTCCAAGGCTAA GGGTCAACCAAGAGAGCCACAGGTTTACACT TTGCCACCATCCAGAGATGAGTTGACTAAGA ACCAGGTTTCCTTGACTTGTTTGGTTAAGGG ATTCTACCCATCCGACATTGCTGTTGAATGG GAGTCTAACGGTCAACCAGAGAACAACTACA AGACTACTCCACCTGTTTTGGACTCTGACGG TTCCTTTTTCTTGTACTCCAAGTTGACTGTT GACAAGTCCAGATGGCAACAGGGTAACGTTT TCTCCTGTTCCGTTATGCATGAGGCTTTGCA CAACCACTACACTCAAAAGTCCTTGTCTTTG TCCCCTGGTAAGGCGGCCGCTTATCCATATG ATGTTCCAGACTACGCTGGAGGTCATCATCA TCACCACCATCACCATCATGGTGG<u>TGAAGAG AAGTCCAGATTGTTGGAGAAAGAGAACAGAG AGTTGGAGAAGATCATCGCTGAGAAAGAAGA GAGAGTTTCCGAGTTGAGACACCAATTGCAA TCCGTTGGTGGTTGTTAATAG</u> |
| 60 | Anti-Her2 full length HC with single stop codon between Ab ORF and GR1 ORF with Pre-pro α-mating factor signal peptide (ScαMTprepro) (DNA) | <u>ATGAGATTCCCATCCATCTTCACTGCTGTTT TGTTCGCTGCTTCTTCTGCTTTGGCT</u>GAGGT TCAGTTGGTTGAATCTGGAGGAGGATTGGTT CAACCTGGTGGTTCTTTGAGATTGTCCTGTG CTGCTTCCGGTTTCAACATCAAGGACACTTA CATCCACTGGGTTAGACAAGCTCCAGGAAAG GGATTGGAGTGGGTTGCTAGAATCTACCCAA CTAACGGTTACACAAGATACGCTGACTCCGT TAAGGGAAGATTCACTATCTCTGCTGACACT TCCAAGAACACTGCTTACTTGCAGATGAACT CCTTGAGAGCTGAGGATACTGCTGTTTACTA CTGTTCCAGATGGGGTGGTGATGGTTTCTAC GCTATGGACTACTGGGGTCAAGGAACTTTGG TTACTGTTTCCTCCGCTTCTACTAAGGGACC ATCTGTTTTCCCATTGGCTCCATCTTCTAAG TCTACTTCCGGTGGTACTGCTGCTTTGGGAT |

| SEQ ID NO: | Name | Sequence (5' to 3') |
|---|---|---|
| | | GTTTGGTTAAAGACTACTTCCCAGAGCCAGTTACTGTTTCTTGGAACTCCGGTGCTTTGACTTCTGGTGTTCACACTTTCCCAGCTGTTTTGCAATCTTCCGGTTTGTACTCTTTGTCCTCCGTTGTTACTGTTCCATCCTCTTCCTTGGGTACTCAGACTTACATCTGTAACGTTAACCACAAGCCATCCAACACTAAGGTTGACAAGAAGGTTGAGCCAAAGTCCTGTGACAAGACTCATACTTGTCCACCATGTCCAGCTCCAGAATTGTTGGGTGGTCCTTCCGTTTTTTGTTCCCACCAAAGCCAAAGGACACTTTGATGATCTCCAGAACTCCAGAGGTTACATGTGTTGTTGTTGACGTTTCTCACGAGGACCCAGAGGTTAAGTTCAACTGGTACGTTGACGGTGTTGAAGTTCACAACGCTAAGACTAAGCCAAGAGAGGAGCAGTACAACTCCACTTACAGAGTTGTTTCCGTTTTGACTGTTTTGCACCAGGATTGGTTGAACGGAAAGGAGTACAAGTGTAAGGTTTCCAACAAGGCTTTGCCAGCTCCAATCGAAAAGACTATCTCCAAGGCTAAGGGTCAACCAAGAGAGCCACAGGTTTACACTTTGCCACCATCCAGAGATGAGTTGACTAAGAACCAGGTTTCCTTGACTTGTTTGGTTAAGGGATTCTACCCATCCGACATTGCTGTTGAATGGGAGTCTAACGGTCAACCAGAGAACAACTACAAGACTACTCCACCTGTTTTGGACTCTGACGGTTCCTTTTTCTTGTACTCCAAGTTGACTGTTGACAAGTCCAGATGGCAACAGGGTAACGTTTTCTCCTGTTCCGTTATGCATGAGGCTTTGCACAACCACTACACTCAAAGTCCTTGTCTTTGTCCCCTGGTAAGTAGGCGGCCGCTTATCCATATGATGTTCCAGACTACGCTGGAGGTCATCATCATCACCACCATCACCATCATGGTGGTGAAGAGAAGTCCAGATTGTTGGAGAAAGAGAACAGAGAGTTGGAGAAGATCATCGCTGAGAAAGAAGAGAGAGTTTCCGAGTTGAGACACCAATTGCAATCCGTTGGTGGTTGTTAATAGGGCCGGCCATTTAA |
| 61 | Anti-CD20 C2B8 full length HC with stop codon between Ab ORF and GR1 ORF with Alpha amylase signal peptide (from *Aspergillus niger* α-amylase) (DNA) | ATGGTTGCTTGGTGGTCTTTGTTCTTGTACGGATTGCAAGTTGCTGCTCCAGCTTTGGCTcagttcagctgcaacaaccaggtgctgaattggttaagctggtgcttctgttaagatgtcttgtaaggcttctggttacacttttcacttcctacaacatgcactgggttaagcaaactccaggtagaggattggaatggattggtgctatctaccaggtaacggtgacacttcttataaccaaagttcaagggaaaggctactttgactgctgacaaatcttcttctactgcttacatgcaattgtcctccttgacttctgaagattctgctgtttactactgtgctagatccacttactacggtggtgactggtactttaatgtttggggtgctggtactgttactgtctcgagtgcttctactaagggaccatctgttttccattggctccatctctctaagtctacttccggtggtacCGCTGCTTTGGGATGTTTGGTTAAAGACTACTTCCCAGAGCCAGTTACTGTTTCTTGGAACTCCGGTGCTTTGACTTCTGGTGTTCACACTTTCCCAGCTGTTTTGCAATCTTCCGGTTTGTACTCTTTGTCCTCCGTTGTTACTGTTCCATCCTCTTCCTTGGGTACTCAGACTTACATCTGTAACGTTAACCACAAGCCATCCAACACTAAGGTTGACAAGAAGGTTGAGCCAAAGTCCTGTGACAAGACTCATACTTGTCCACCATGTCCAGCTCCAGAATTGTTGGGTGGTCCTTCCGTTTTTTGTTCCCACCAAAGCCAAAGGACACTTTGATGATCTCCAGAACTCCAGAGGTTACATGTGTTGTTGTTGACGTTTCTCACGAGGACCCAGAGGTTAAGTTCAACTGGTACGTTGACGGTGTTGAAGTTCACAACGCTAAGACTAAGCCAAGAGAGGAGCAGTACAACTCCACTTACAGAGTTGTTTCCGTTTTGACTGTTTTGCACCAGGATTGGTTGAACGGAAAGGAGTACAAGTGTAAGGTTTCCAACAAGGCTTTGCCAGCTCCAATCGAAAAGACTATCTCCAAGGCTAAGGGTCAACCAAGAGAGCCACAGGTTTACACTTTGCCACCATCCAGAGATGAGTTGACTAAGAACCAGGTTTCCTTGACTTGTTTGGTTAAGGGATTCTACCCATCCGACATTGCTGTTGAATGGGAGTCTAACGGTCAACCAGAGAACAACTACAAGACTACTCCACCTGTTTTGGACTCTGACGGTTCCTTTTTCTTGTACTCCAAGTTGACTGTTGACAAGTCCAGATGGCAACAGGGTAACGTTTTCTCCTGTTCCGTTATGCATGAGGCTTTGCACAACCACTACACTCAAAGTCCTTGTCTTTGTCCCCTGGTAAGTAGGCGGCCGCTTATCCATATGATGTTCCAGACTACGCTGGAGGTCATCATCATCACCACCATCACCATCATGGTGGTGAAGAGAAGTCCAGATTGTTGGAGAAAGAGAACAGAGAGTTGGAGAAGATCATCGCTGAGAAAGAAGAGAGAGTTTCCGAGTTGAGACACCAATTGCAATCCGTTGGTGGTTGTTAATAG |
| 62 | Anti-CD20 Genmab full length HC with single stop codon between Ab ORF and GR1 ORF with Alpha amylase signal peptide (from *Aspergillus niger* α-amylase) (DNA) | ATGGTTGCTTGGTGGTCCTTGTTCTTGTACGGATTGCAAGTTGCTGCTCCAGCTTTGGCTgctgttcagctggttgaatcggtggtggattggttcaacctggtagatccttgagattgtcctgtgctgcttccggattactttcggtgactacactatgcactgggttagacaagtccaggaaagggattggaatgggtttccggtatttcttgaactccggttccattggttacgctgattccgttaagggaagattcactatctccagagacaacgctaagaactccttgtacttgcagatgaactccttgagagctgaggatactgctttgtactactgtactaaggacaaccaatacggttctgttccacttacggattgggagtttggggacagggaactttggttactgtctcgagtgcttctactaagggaccatccgttttccattggctccatcctcaagtctacttccggtggtacCGCTGCTTTGGGATGTTTGGTTAAAGACTACTTCCCAGAGCCAGTTACTGTTTCTTGGAACTCCGGTGCTTTGACTTCTGGTGTTCACACTTTCCCAGCTGTTTTGCAATCTTCCGGTTTGTACTCTTTGTCCTCCGTTGTTACTGTTCCATCCTCTTCCTTGGGTACTCAGACTTACATCTGTAACGTTAACCACAAGCCATCCAACACTAAGGTTGACAAGAAGGTTGAGCCAAAGTCCTGTGACAAGACTCATACTTGTCCACCATGTCCAGCTCCAGAATTGTTGGGTGGTCCTTCCGTTTTTTGTTCCCACCAAAGCCAAAGGACACTTTGATGATCTCCAGAACTCCAGAGGTTACATGTGTTGTTGTTGACGTTTCTCACGAGGACCCAGAGGTTAAGTTCAACTGGTACGTTGACGGTGTTGAAGTTCACAACGCTAAGACTAAGCCAAGAGAGGAGCAGTACAACTCCACTTACAGAGTTGTTTCCGTTTTGACTGTTTTGCACCAGGATTGGTTGAACGGAAAGGAGTACAAGTGTAAGGTTTCCAACAAGGCTTTGCCAGCTCCAATCGAAAAGACTATCTCCAAGGCTAAGGGTCAACCAAGAGAGCCACAGGTTTACACTTTGCCACCATCCAGAGATGAGTTGACTAAGAACCAGGTTTCCTTGACTTGTTTGGTTAAGGGATTCTACCCATCCGACATTGCTGTTGAATGGGAGTCTAACGGTCAACCAGAGAACAACTACAAGACTACTCCACCTGTTTTGGACTCTGACGGTTCCTTTTTCTTGTACTCCAAGTTGACTGTTGACAAGTCCAGATGGCAACAGGGTAACGTTTTCTCCTGTTCCGTTATGCATGAGGCTTTGCACAACCACTACACTCAAAGTCCTTGTCTTTGTCCCCTGGTAAGTAGGCGGCCGCTTATCCATATGATGTTCCAGACTACGCTGGAGGTCATCATCATCACCACCATCACCATCATGGTGGTGAAGAAGTCCAGATTGTTGGAGAAAGAGAACAGAGAGTTGGAGAAGATCATCGCTGAGAAAGAAGAGAGAGTTTCCGAGTTGAGACACCAATTGCAATCCGTTGGTGGTTGTTAATAG |

| SEQ ID NO: | Name | Sequence (5' to 3') |
|---|---|---|
| 63 | Anti-CD20 Genmab LC Alpha amylase signal peptide (from *Aspergillus niger* α-amylase) (DNA) | ATGGTTGCTTGGTGGTCCTTGTTCTTGTACG GATTGCAAGTTGCTGCTCCAGCTTTGGCTga gatcgtttgacacagtccccagctactttg tctttgtccccaggtgaaagagctacattgt cctgtagagcttcccaatctgtttcctcta cttggcttggtatcaacaaaagccaggacag gctccaagattgttgatctacgacgcttcca atagagctactggtatcccagctagattctc tggttctggttccggtactgacttcactttg actatctcttccttggaaccagaggacttcg ctgtttactactgtcagcagagatccaattg gccattgactttcggtggtggtactaaggtt gagatcaagcgtacggttgctgctccttccg ttttcattttcccaccatccgacgaacaatt gaagtctggtaccCGTTCCGTTGTTTGTTTG TTGAACAACTTCTACCCACGTGAGGCTAAGG TTCAGTGGAAGGTTGACAACGCTTTGCAATC CGGTAACTCCCAAGAATCCGTTACTGAGCAG GATTCTAAGGATTCCACTTACTCATTGTCCT CCACTTTGACTTTGTCCAAGGCTGATTACGA AGAACACAAGGTTTACGCATGCGAGGTTACA CATCAGGGTTTGTCCTCCCCAGTTACTAAGT CCTTCAACAGAGGAGAGTGTTAA |
| 64 | Anti-CD20 full length HC with stop codon between Ab ORF and GR1 ORF with Alpha amylase signal peptide (from *Aspergillus niger* α-amylase) (DNA) | ATGGTTGCTTGGTGGTCCTTGTTCTTGTACG GATTGCAAGTTGCTGCTCCAGCTTTGGCTca agttcagctggttcaatctggtgctgaggtt aagaagcctggttcctccgttaaggtttcct gtaaggcttccggttacacttcacttccta caacatgcactgggttagacaagctccaggt caaggattggaatggatgggtgctatctacc caggtaacggtgacacttcttacaaccagaa gttcaagggtagagttactatcactgctgac gaatccacttccactgcttacatggaattgt cctcattgagatccgaggacactgctgttta ctactgtgctagatccacttactacggtggt gactggtactttaatgtttggggacagggaa ctttggttactgtctcgagtgcttctactaa gggaccatccgttttccattggctccatcc tctaagtctacttccggtggtacCGCTGCTT TGGGATGTTTGGTTAAAGACTACTTCCCAGA GCCAGTTACTGTTTCTTGGAACTCCGGTGCT TTGACTTCTGGTGTTCACACTTTCCCAGCTG TTTTTGCAATCTTCCGGTTTGTACTCTTTGTC CTCCGTTGTTACTGTTCCATCCTCTTCCTTG GGTACTCAGACTTACATCTGTAACGTTAACC ACAAGCCATCCAACACTAAGGTTGACAAGAA GGTTGAGCCAAAGTCCTGTGACAAGACTCAT ACTTGTCCACCATGTCCAGCTCCAGAATTGT TGGGTGGTCCTTCCGTTTTTTGTTCCACCA AAGCCAAAGGACACTTTGATGATCTCCAGAA CTCCAGAGGTTACATGTGTTGTTGTTGACGT TTCTCACGAGGACCCAGAGGTTAAGTTCAAC TGGTACGTTGACGGTGTTGAAGTTCACAACG CTAAGACTAAGCCAAGAGAGGAGCAGTACAA CTCCACTTACAGAGTTGTTTCCGTTTTGACT GTTTTGCACCAGGATTGGTTGAACGGAAAGG AGTACAAGTGTAAGGTTTCCAACAAGGCTTT GCCAGCTCCAATCGAAAAGACTATCTCCAAG GCTAAGGGTCAACCAAGAGAGCCACAGGTTT ACACTTTGCCACCATCCAGAGATGAGTTGAC TAAGAACCAGGTTTCCTTGACTTGTTTGGTT AAGGGATTCTACCCATCCGACATTGCTGTTG AATGGGAGTCTAACGGTCAACCAGAGAACAA CTACAAGACTACTCCACCTGTTTTGGACTCT GACGGTTCCTTTTTCTTGTACTCCAAGTTGA CTGTTGACAAGTCCAGATGGCAACAGGGTAA CGTTTTCTCCTGTTCCGTTATGCATGAGGCT TTGCACAACCACTACACTCAAAAGTCCTTGT CTTTGTCCCCTGGTAAGTAGGCGGCCGCTTA TCCATATGATGTTCCAGACTACGCTGGAGGT CATCATCATCACCACCATCACCATCATGGTG | |
| 65 | Anti-CD20 LC with Alpha amylase signal peptide (from *Aspergillus niger* α-amylase) (DNA) | GTGAAGAGAAGTCCAGATTGTTGGAGAAAGA GAACAGAGAGTTGGAGAAGATCATCGCTGAG AAAGAAGAGAGAGTTTCCGAGTTGAGACACC AATTGCAATCCGTTGGTGGTTGTTAATAG<br>ATGGTTGCTTGGTGGTCCTTGTTCTTGTACG GATTGCAAGTTGCTGCTCCAGCTTTGGCTga gatcgtttgacacagtccccagctactttg tctttgtccccaggtgaaagagctacattgt cctgtagagcttcccaatctgtttcctcta ccactggtatcaacaaaagccaggacaggct ccaagattgttgatctacgctacttccaact tggcttccggtattccagctagattctctgg ttctggttccggtactgacttcactttgact atctcttccttggaaccagaggacttcgctg tttactactgtcaacagtggacttctaaccc accaactttcggacaaggtactaaggttgag atcaagcgtacggttgctgctccttccgttt tcattttcccaccatccgacgaacaattgaa gtctggtaccCGTTCCGTTGTTTGTTTGTTG AACAACTTCTACCCACGTGAGGCTAAGGTTC AGTGGAAGGTTGACAACGCTTTGCAATCCGG TAACTCCCAAGAATCCGTTACTGAGCAGGAT TCTAAGGATTCCACTTAUCATTGTCCTCCAC TTTGACTTTGTCCAAGGCTGATTACGAGAAG CACAAGGTTTACGCATGCGAGGTTACACATC AGGGTTTGTCCTCCCCAGTTACTAAGTCCTT CAACAGAGGAGAGTGTTAA |
| 66 | DNA sequence of 1D05 Heavy chain with *Saccharomyces cerevisiae* mating factor pre-signal peptide and GR1 | ATGAGATTCCCATCCATCTTCACTGCTGTTT TGTTCGCTGCTTCTTCCGCTTTGGCTCAGGT TCAATTGGTTCAATCCGGTGCTGAAGTTAAG AAGCCTGGTTCCTCCGTTAAGGTTTCCTGTA AGGCTTCTGGTGGTACTTTTAACTCCCACGC TATCTCTTGGGTTAGACAAGCTCCAGGTCAA GGATTGGAATGGATGGGTGGTATCAACCCAA TTTTGGGTATCGCTAACTACGCTCAAAAGTT CCAGGGTAGAGTTACTATTACTGCTGACGAA TCCACTTCCACTGCTTACATGGAATTGTCCT CATTGAGATCCGAGGACACTGCTGTTTACTA CTGTGCTAGACACTACGAGATCCAGATCGGT AGATACGGAATGAACGTTTACTACTTGATGT ACAGATTCGCTTCTTGGGGACAGGGAACTTT GGTTACTGTCTCGAGTGCTTCTACTAAGGGG CCCTCTGTTTTTCCATTGGCTCCATGTTCTA GATCCACTTCCGAATCCACTGCTGCTTTGGG ATGTTTGGTTAAGGACTACTTCCCAGAGCCA GTTACTGTTTCTTGGAACTCCGGTGCTTTGA CTTCTGGTGTTCACACTTTCCCAGCTGTTTT GCAATCTTCCGGTTTGTACTCTTTGTCCTCC GTTGTTACTGTTCCTCCAACTTCGGTA CTCAGACTTACACTTGTAACGTTGACCACAA GCCATCCAACACTAAGGTTGACAAGACTGTT GAGAGAAAGGGTGGTGGTGGTAGTGGAGGTG GTGGAAGTGGTGGCGGTGGTTCTGCGGCCGC TTATCCATATGATGTTCCAGACTACGCTGGA GGTCATCATCATCACCACCATCACCATCATG GTGGTGAAGAGAAGTCCAGATTGTTGGAGAA AGAACAGAGAGTTGGAGAAGATCATCGCT GAGAAAGAAGAGAGAGTTTCCGAGTTGAGAC ACCAATTGCAATCCGTTGGTGGTTGTTAATA G |
| 67 | Amino acid sequence of 1D05 HC with *Saccharomyces cerevisiae* mating factor pre-signal peptide | MRFPSIFTAVLFAASSALAQVQLVQSGAEVK KPGSSVKVSCKASGGTFNSHAISWVRQAPGQ GLEWMGGINPILGIANYAQKFQGRVTITADE STSTAYMELSSLRSEDTAVYYCARHYEIQIG RYGMNVYYLMYRFASWGQGTLVTVSSASTKG PSVFPLAPCSRSTSESTAALGCLVKDYFPEP VTVSWNSGALTSGVHTFPAVLQSSGLYSLSS VVTVTSSNFGTQTYTCNVDHKPSNTKVDKTV ERK |

| SEQ ID NO: | Name | Sequence (5' to 3') |
|---|---|---|
| 68 | DNA sequence of 1D05 light chain with Saccharomyces cerevisiae mating factor pre-signal peptide | ATGAGATTCCCATCCATCTTCACTGCTGTTT TGTTCGCTGCTTCTTCTGCTTTGGCTGACAT CCAAATGACACAATCCCCATCTTCCTTGTCT GCTTCCGTTGGTGACAGAGTTACTATCACTT GTAGAGCTTCCCAAGGTATCAGATCCGCTTT GAACTGGTATCAACAGAAGCCAGGAAAGGCT CCAAAGTTGTTGATCTACAACGGTTCCACTT TGCAATCTGGTGTTCCATCTAGATTCTCTGG TTCCGGTTCTGGTACTGACTTCACTTTGACT ATCTCTTCCTTGCAACCAGAGGACTTCGCTG TTTACTACTGTCAACAGTTCGATGGTGACCC AACTTTTGGACAGGGTACTAAGGTTGAGATC AAGAGAACTGTTGCTGCTCCATCCGTTTTCA TTTTCCCACCATCCGACGAACAATTGAAGTC TGGTACCGCTTCCGTTGTTTGTTGTTGAAC AACTTCTACCCACGTGAGGCTAAGGTTCAGT GGAAGGTTGACAACGCTTTGCAATCCGGTAA CTCCCAAGAATCCGTTACTGAGCAGGATTCT AAGGATTCCACTTACTCATTGTCCTCCACTT TGACTTTGTCCAAGGCTGATTACGAGAAGCA CAAGGTTTACGCTTGCGAGGTTACACATCAG GGTTTGTCCTCCCCAGTTACTAAGTCCTTCA ACAGAGGAGAGTGTTAATAG |
| 69 | Amino acid sequence of 1D05 LC with Saccharomyces cerevisiae mating factor pre-signal peptide | MRFPSIFTAVLFAASSALADIQMTQSPSSLS ASVGDRVTITCRASQGIRSALNWYQQKPGKA PKLLIYNGSTLQSGVPSRFSGSGSGTDFTLT ISSLQPEDFAVYYCQQFDGDPTFGQGTKVEI KRTVAAPSVFIFPPSDEQLKSGTASVVCLLN NFYPREAKVQWKVDNALQSGNSQESVTEQDS KDSTYSLSSTLTLSKADYEKHKVYACEVTHQ GLSSPVTKSFNRGEC |
| 70 | DNA sequence of 1H23 heavy chain with Aspergillus amylase signal sequence, linker and GR1 | ATGGTTGCTTGGTGGTCCTTGTTCTTGTACG GATTGCAAGTTGCTGCTCCAGCTTTGGCTCA AGTTCAGTTGGTTGAATCCGGTGGTGGATTG GTTCAACCTGGTGGTTCTTTGAGATTGTCCT GTGCTGCTTCCGGTTTTACTTTCTCCGACTA CTACATGCACTGGGTTAGACAAGCACCTGGA AAGGGATTGGAATGGGTTTCCAACATTTCTG GTTCCGGTTCCACTACTTACTACGCTGATTC CGTTAAGGGAAGATTCACTATCTCCAGAGAC AACTCCAAGAACACTTTGTACTTGCAGATGA ACTCCTTGAGAGCTGAGGATACTGCTGTTTA CTACTGTGCTAGAGGAATGTTTGACTTCTGG GGACAGGGAACTTTGGTTACTGTCTCGAGTG CTTCTACTAAGGGGCCCTCTGTTTTTCCATT GGCTCCATGTTCTAGATCCACTTCCGAATCC ACTGCTGCTTTGGGATGTTTGGTTAAGGACT ACTTCCCAGAGCCAGTTACTGTTTCTTGGAA CTCCGGTGCTTTGACTTCTGGTGTTCACACT TTCCCAGCTGTTTTGCAATCTTCCGGTTTGT ACTCCTTGTCCTCCGTTGTTACTGTTACTTC CTCCAACTTCGGTACTCAGACTTACACTTGT AACGTTGACCACAAGCCATCCAACACTAAGG TTGACAAGACTGTTGAGAGAAAGGGTGGTGG TGGTAGTGGAGGTGGTGGAAGTGGTGGCGGT GGTTCTGCGGCCGCTTATCCATATGATGTTC CAGACTACGCTGGAGGTCATCATCATCACCA CCATCACCATCATGGTGGTGAAGAGAAGTCC AGATTGTTGGAGAAAGAGAACAGAGAGTTGG AGAAGATCATCGCTGAGAAGAAGAAGAGAGT TTCCGAGTTGAGACACCAATTGCAATCCGTT GGTGGTTGTTAATAG |
| 71 | Amino acid sequence of 1H23 HC with Aspergillus amylase signal sequence | MVAWWSLFLYGLQVAAPALAQVQLVESGGGL VQPGGSLRLSCAASGFTFSDYYMHWVRQAPG KGLEWVSNISGSGSTTYYADSVKGRFTISRD NSKNTLYLQMNSLRAEDTAVYYCARGMFDFW GQGTLVTVSSASTKGPSVFPLAPCSRSTSES TAALGCLVKDYFPEPVTVSWNSGALTSGVHT FPAVLQSSGLYSLSSVVTVTSSNFGTQTYTC NVDHKPSNTKVDKTVERK |
| 72 | DNA sequence of 1H23 light chain with Aspergillus amylase signal sequence | ATGGTTGCTTGGTGGTCCTTGTTCTTGTACG GATTGCAAGTTGCTGCTCCAGCTTTGGCTGA CATCGTTTTGACACAGTCCCCAGCTACTTTG TCTTTGTCCCCAGGTGAAAGAGCTACATTGT CCTGTAGAGCTTCCCAATCCGTTAACTCCAA CTACTTGGCTTGGTATCAACAAAAGCCAGGA CAGGCTCCAAGATTGTTGATCTACGGTGCTT CTTCTAGAGCTACTGGTGTTCCAGCTAGATT CTCTGGTTCTGGTTCCGGTACTGACTTCACT TTGACTATCTCTTCCTTGGAACCAGAGGACT TCGCTGTTTACTACTGTCAACAGTGGGGTGA CGTTCCAATTACTTTCGGACAGGGTACTAAG GTTGAGATCAAGAGAACTGTTGCTGCTCCTT CCGTTTTCATTTTCCCACCATCCGACGAACA ATTGAAGTCTGGTACCGGTACCGCTTCCGTT GTTTGTTTGTTGAACAACTTCTACCCACGTG AGGCTAAGGTTCAGTGGAAGGTTGACAACGC TTTGCAATCCGGTAACTCCCAAGAATCCGTT ACTGAGCAGGATTCTAAGGATTCCACTTACT CATTGTCCTCCACTTTGACTTTGTCCAAGGC TGATTACGAGAAGCACAAGGTTTACGCTTGC GAGGTTACACATCAGGGTTTGTCCTCCCCAG TTACTAAGTCCTTCAACAGAGGAGAGTGTTA ATAG |
| 73 | Amino acid sequence of 1H23 light chain with Aspergillus amylase signal sequence | MVAWWSLFLYGLQVAAPALADIVLTQSPATL SLSPGERATLSCRASQSVNSNYLAWYQQKPG QAPRLLIYGASSRATGVPARFSGSGSGTDFT LTISSLEPEDFAVYYCQQWGDVPITFGQGTK VEIKRTVAAPSVFIFPPSDEQLKSGTGTASV VCLLNNFYPREAKVQWKVDNALQSGNSQESV TEQDSKDSTYSLSSTLTLSKADYEKHKVYAC EVTHQGLSSPVTKSFNRGEC |
| 74 | amino acid sequence of PCSK9 without 30 amino acid signal peptide | QEDEDGDYEELVLALRSEEDGLAEAPEHGTT ATFHRCAKDPWRLPGTYVVVLKEETHLSQSE RTARRLQAQAARRGYLTKILHVFHGLLPGFL VKMSGDLLELALKLPHVDYIEEDSSVFAQSI PWNLERITPPRYRADEYQPPDGGSLVEVYLL DTSIQSDHREIEGRVMVTDFENVPEEDGTRF HRQASKCDSHGTHLAGVVSGRDAGVAKGASM RSLRVLNCQGKGTVSGTLIGLEFIRKSQLVQ PVGPLVVLLPLAGGYSRVLNAACQRLARAGV VLVTAAGNFRDDACLYSPASAPEVITVGATN AQDQPVTLGTLGTNFGRCVDLFAPGEDIIGA SSDCSTCFVSQSGTSQAAAHVAGIAAMMLSA EPELTLAELRQRLIHFSAKDVINEAWFPEDQ RVLTPNLVAALPPSTHGAGWQLFCRTVWSAH SGPTRMATAIARCAPDEELLSCSSFSRSGKR RGERMEAQGGKLVCRAHNAFGGEGVYAIARC CLLPQANCSVHTAPPAEASMGTRVHCHQQGH VLTGCSSHWEVEDLGTHKPPVLRPGQPNQC VGHREASIHASCCHAPGLECKVKEHGIPAPQ EQVTVACEEGWTLTGCSALPGTSHVLGAYAV DNTCVVRSRDVSTTGSTSEEAVTAVAICCRS RHLAQASQELQ |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. An expression vector comprising a nucleic acid encoding a fusion protein comprising an antibody heavy chain immunoglobulin fused at its C-terminus to the N-terminus of a polypeptide that includes a binding moiety which is selected from the group consisting of:

GABAB-R1;
GABAB-R2;
GR1;
GR2;
a leucine zipper comprising the amino acid sequence set forth in SEQ ID NO: 1;
a leucine zipper comprising the amino acid sequence set forth in SEQ ID NO: 2;
a leucine zipper comprising the amino acid sequence set forth in SEQ ID NO: 3;
a leucine zipper comprising the amino acid sequence set forth in SEQ ID NO: 4;
a leucine zipper comprising the amino acid sequence set forth in SEQ ID NO: 5;

a leucine zipper comprising the amino acid sequence set forth in SEQ ID NO: 6;
a leucine zipper comprising the amino acid sequence set forth in SEQ ID NO: 7;
a leucine zipper comprising the amino acid sequence set forth in SEQ ID NO: 8;
wherein the nucleic acid includes a single stop codon in frame between the nucleotide sequence encoding the antibody heavy chain immunoglobulin and the nucleotide sequence encoding the polypeptide that includes a binding moiety,
   wherein the expression vector is capable of expressing the fusion protein in a host cell, wherein the host cell is *Pichia pastoris*.

2. The vector of claim 1 wherein the polypeptide that includes a binding moiety is GABAB-R1.

3. The vector of claim 1 wherein the polypeptide that includes a binding moiety is GABAB-R2.

4. The vector of claim 1 wherein the polypeptide that includes a binding moiety is GR1.

5. The vector of claim 1 wherein the polypeptide that includes a binding moiety is GR2.

6. The vector of claim 1 wherein the polypeptide that includes a binding moiety is a leucine zipper comprising the amino acid sequence set forth in SEQ ID NO: 1.

7. The vector of claim 1 wherein the polypeptide that includes a binding moiety is a leucine zipper comprising the amino acid sequence set forth in SEQ ID NO: 2.

8. The vector of claim 1 wherein the polypeptide that includes a binding moiety is a leucine zipper comprising the amino acid sequence set forth in SEQ ID NO: 3.

9. The vector of claim 1 wherein the polypeptide that includes a binding moiety is a leucine zipper comprising the amino acid sequence set forth in SEQ ID NO: 4.

10. The vector of claim 1 wherein the polypeptide that includes a binding moiety is a leucine zipper comprising the amino acid sequence set forth in SEQ ID NO: 5.

11. The vector of claim 1 wherein the polypeptide that includes a binding moiety is a leucine zipper comprising the amino acid sequence set forth in SEQ ID NO: 6.

12. The vector of claim 1 wherein the polypeptide that includes a binding moiety is a leucine zipper comprising the amino acid sequence set forth in SEQ ID NO: 7.

13. The vector of claim 1 wherein the polypeptide that includes a binding moiety is a leucine zipper comprising the amino acid sequence set forth in SEQ ID NO: 8.

* * * * *